United States Patent
Bi et al.

(10) Patent No.: US 8,969,565 B2
(45) Date of Patent: Mar. 3, 2015

(54) IMIDAZO[1,2-B]PYRIDAZINE-BASED COMPOUNDS, COMPOSITIONS COMPRISING THEM, AND METHODS OF THEIR USE

(71) Applicants: Yingzhi Bi, Plainsboro, NJ (US); Kenneth Gordon Carson, Princeton, NJ (US); Giovanni Cianchetta, Waltham, MA (US); Michael Alan Green, Easton, PA (US); Godwin Kumi, Belle Mead, NJ (US); Zhi Liang, Lawrenceville, NJ (US); Ying Jade Liu, Lawrenceville, NJ (US); Alan Main, Far Hills, NJ (US); Yulian Zhang, Acton, MA (US); Gregory Glenn Zipp, Robbinsville, NJ (US)

(72) Inventors: Yingzhi Bi, Plainsboro, NJ (US); Kenneth Gordon Carson, Princeton, NJ (US); Giovanni Cianchetta, Waltham, MA (US); Michael Alan Green, Easton, PA (US); Godwin Kumi, Belle Mead, NJ (US); Zhi Liang, Lawrenceville, NJ (US); Ying Jade Liu, Lawrenceville, NJ (US); Alan Main, Far Hills, NJ (US); Yulian Zhang, Acton, MA (US); Gregory Glenn Zipp, Robbinsville, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 13/785,271

(22) Filed: Mar. 5, 2013

(65) Prior Publication Data

US 2013/0245021 A1    Sep. 19, 2013

Related U.S. Application Data

(60) Provisional application No. 61/608,758, filed on Mar. 9, 2012.

(51) Int. Cl.
| | | |
|---|---|---|
| *C07D 241/04* | (2006.01) |
| *C07D 401/14* | (2006.01) |
| *C07D 403/14* | (2006.01) |
| *C07D 487/04* | (2006.01) |
| *A61K 31/5025* | (2006.01) |

(52) U.S. Cl.
CPC ............ *C07D 487/04* (2013.01); *C07D 241/04* (2013.01); *C07D 401/14* (2013.01); *C07D 403/14* (2013.01); *A61K 31/5025* (2013.01)
USPC .......................................... 546/121; 514/248

(58) Field of Classification Search
CPC ............................ C07D 241/04; C07D 403/14
USPC .............................. 514/248, 252.02; 544/236
See application file for complete search history.

(56) References Cited

U.S. PATENT DOCUMENTS

| | | | |
|---|---|---|---|
| 7,750,000 B2 * | 7/2010 | Prien et al. .................. | 514/233.2 |
| 2007/0049591 A1 | 3/2007 | Pinkerton et al. | |
| 2007/0078136 A1 | 4/2007 | Vaccaro et al. | |
| 2010/0041662 A1 | 2/2010 | Ferrand et al. | |
| 2011/0021513 A1 | 1/2011 | Durand-Reville et al. | |
| 2011/0166122 A1 | 7/2011 | Andrews et al. | |
| 2011/0312934 A1 * | 12/2011 | Garcia et al. ............. | 514/210.21 |
| 2013/0253194 A1 | 9/2013 | Bi et al. | |
| 2014/0080834 A1 | 3/2014 | Lanthorn et al. | |

OTHER PUBLICATIONS

International Search Report for Corresponding Patent Application No. PCT/US2013/029043, mailed Jul. 6, 2013.
Nantermet, P.G. and Henze, D.A.., *Ann. Rep. Med. Chem.* 46:19-32 (2011).

* cited by examiner

*Primary Examiner* — Sarah Pihonak
(74) *Attorney, Agent, or Firm* — Max Bachrach

(57) ABSTRACT

Imidazo[1,2-b]pyridazine-based compounds of the formula:

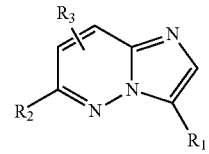

are disclosed, wherein $R_1$, $R_2$ and $R_3$ are defined herein. Compositions comprising the compounds and methods of their use to treat, manage and/or prevent diseases and disorders mediated by mediated by adaptor associated kinase 1 activity are also disclosed.

5 Claims, 1 Drawing Sheet

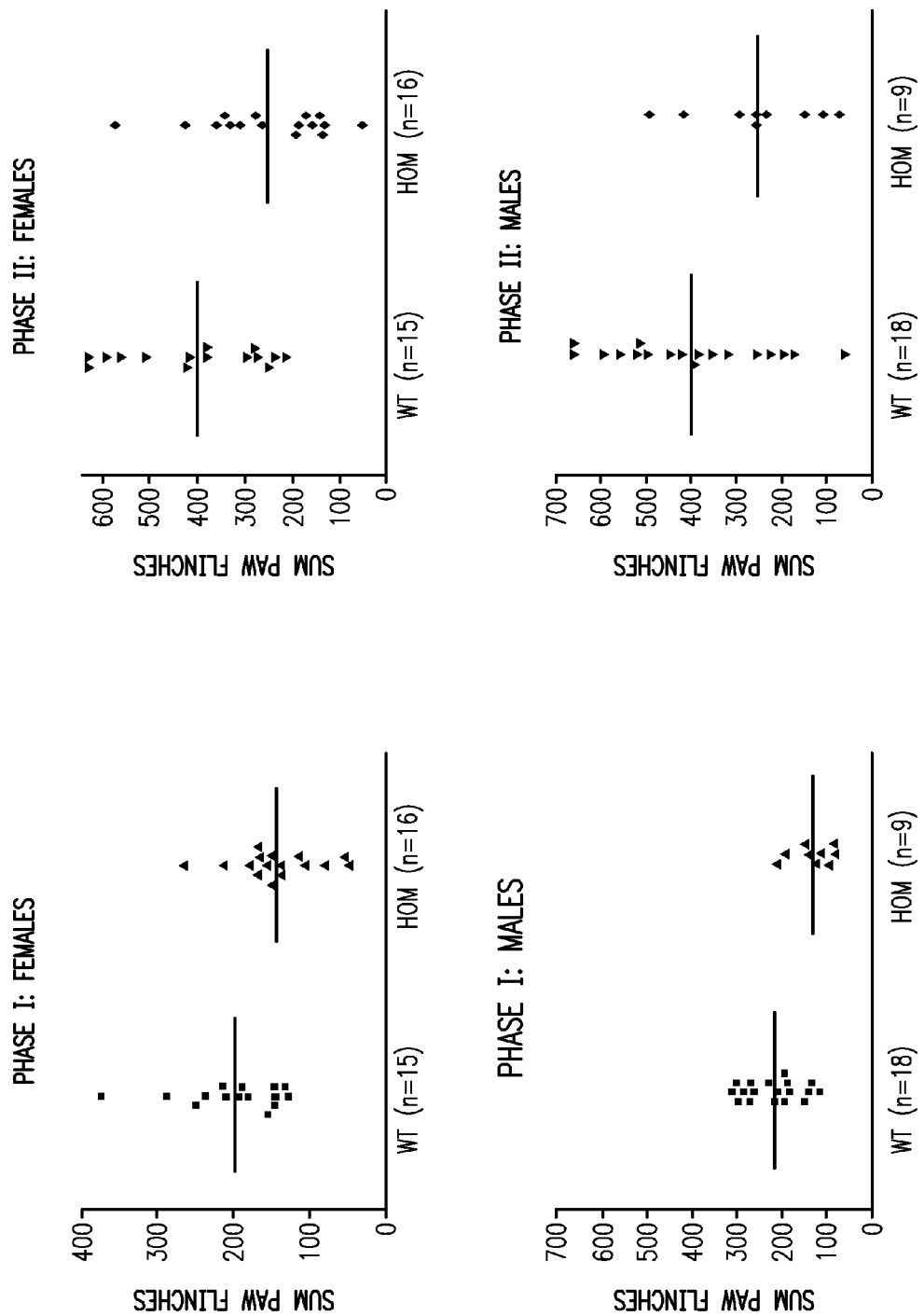

IMIDAZO[1,2-B]PYRIDAZINE-BASED COMPOUNDS, COMPOSITIONS COMPRISING THEM, AND METHODS OF THEIR USE

This application claims priority to U.S. provisional patent application No. 61/608,758, filed Mar. 9, 2012, the entirety of which is incorporated herein by reference.

1. FIELD OF THE INVENTION

This invention is directed to imidazo[1,2-b]pyridazine-based compounds useful as inhibitors of adaptor associated kinase 1 (AAK1), compositions comprising them, and methods of their use.

2. BACKGROUND OF THE INVENTION

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., *Proc. Natl. Acad. Sci. USA.* 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, bipolar disorder, and Alzheimer's disease.

3. SUMMARY OF THE INVENTION

This invention is directed, in part, to AAK1 inhibitors of the formula:

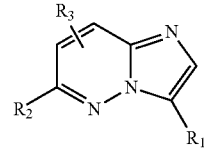

and pharmaceutically acceptable salts thereof, wherein: $R_1$ is $R_{1A}$ or optionally substituted $C_{1-12}$ hydrocarbyl or 2-12-membered heterocarbyl, which optional substitution is with one or more $R_{1A}$; each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$; each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo; each $R_{1C}$ is independently hydrogen or optionally substituted $C_{1-12}$ hydrocarbyl or 2-12-membered heterocarbyl, which optional substitution is with one or more of cyano, halo or hydroxyl; $R_2$ is —$NR_{2A}R_{2B}$, wherein $R_{2A}$ is hydrogen and $R_{2B}$ is optionally substituted $C_{1-12}$ hydrocarbyl or 2-12-membered heterocarbyl, which optional substitution is with one or more $R_{2C}$; or $R_{2A}$ and $R_{2B}$ are taken together to form a 4-7-membered heterocycle optionally substituted with one or more $R_{2C}$; each $R_{2C}$ is independently —$OR_{2D}$, —$N(R_{2D})_2$, —$C(O)R_{2D}$, —$C(O)OR_{2D}$, —$C(O)N(R_{2D})_2$, —$N(R_{2D})C(O)OR_{2D}$, cyano, halo, or optionally substituted $C_{1-12}$ hydrocarbyl or 2-12-membered heterocarbyl, which optional substitution is with one or more with one or more $R_{2D}$; each $R_{2D}$ is independently hydrogen or optionally substituted $C_{1-12}$ hydrocarbyl or 2-12-membered heterocarbyl, which optional substitution is with one or more of cyano, halo or hydroxyl; and $R_3$ is hydrogen or $C_{1-6}$ alkyl optionally substituted with one or more of cyano, halo or hydroxyl.

One embodiment of the invention encompasses pharmaceutical compositions and dosage forms comprising a compound disclosed herein (i.e., a compound of the invention).

Another embodiment of this invention encompasses methods of inhibiting adaptor associated kinase 1 (AAK1), both in vitro and in vivo, which comprise contacting AAK1 with a compound of the invention.

Another embodiment encompasses methods of treating and managing diseases and disorders mediated by AAK1 activity. Examples of such diseases and disorders are believed to include Alzheimer's disease, bipolar disorder, pain, Parkinson's disease, and schizophrenia (including cognitive deficits in schizophrenia).

4. BRIEF DESCRIPTION OF THE FIGURES

Aspects of the invention are illustrated in FIG. 1, which shows results obtained from a formalin pain model using AAK1 homozygous (−/−) knockout mice and their wild-type (+/+) littermates. The AAK1 homozygous (−/−) knockout mice show a clear reduction in both acute and tonic pain response as compared to their wild-type (+/+) littermates.

5. DETAILED DESCRIPTION OF THE INVENTION

This invention is based, in part, on the discovery that AAK1 knockout mice exhibit a high resistance to pain. That discovery prompted research that ultimately led to the discovery of AAK1 inhibitors, compositions comprising them, and methods of their use.

5.1. DEFINITIONS

Unless otherwise indicated, the phrases "compounds of the invention," "compounds of the present disclosure," and the like refer to the compounds disclosed herein.

Unless otherwise indicated, the term "hydrocarbyl" means an aliphatic or alicyclic moiety having an all-carbon backbone and consisting of carbon and hydrogen atoms. Examples of hydrocarbyl groups include those having 1-20, 1-12, 1-6, and 1-4 carbon atoms (referred to as $C_{1-20}$ hydrocarbyl, $C_{1-12}$ hydrocarbyl, $C_{1-6}$ hydrocarbyl, and $C_{1-4}$ hydrocarbyl, respectively). Particular examples include alkyl, alkenyl, alkynyl, aryl, benzyl, cycloalkyl, cycloalkenyl, cycloalkylalkyl, cycloalkenylalkyl, napthyl, phenyl, and phenylethyl.

Examples of alkyl moieties include straight-chain and branched moieties having 1-20, 1-12, 1-6, 1-4 and 1-3 carbon atoms (referred to as $C_{1-20}$ alkyl, $C_{1-12}$ alkyl, $C_{1-6}$ alkyl, $C_{1-4}$ alkyl and $C_{1-3}$ alkyl, respectively). Particular examples include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl.

Examples of alkenyl moieties include straight-chain and branched $C_{2-20}$, $C_{2-12}$ and $C_{2-6}$ alkenyl. Particular examples include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Examples of alkynyl moieties include straight-chain and branched $C_{2-20}$, $C_{2-12}$ and $C_{2-6}$ alkynyl. Particular examples include ethynyl and 2-propynyl (propargyl).

Examples of aryl moieties include anthracenyl, azulenyl, fluorenyl, indan, indenyl, naphthyl, phenyl and phenanthrenyl.

Examples of cycloalkyl moieties include $C_{3-12}$, $C_{3-7}$, $C_{4-6}$ and $C_6$ cycloalkyl. Particular examples include cyclopropyl, cyclobutyl, cyclopentyl, cyclohexyl and adamantyl.

Unless otherwise indicated, the term "halo" encompass fluoro, chloro, bromo, and iodo.

Unless otherwise indicated, the term "heterocarbyl" refers to a moiety having a backbone made up of one or more carbon atoms and one or more heteroatoms. Particular heteroatoms are nitrogen, oxygen and sulfur. A heterocarbyl moieties can be thought of as a hydrocarbyl moiety wherein at least one carbon atom, CH, $CH_2$, or $CH_3$ group is replaced with one or more heteroatoms and the requisite number of hydrogen atoms to satisfy valencies. Examples of heterocarbyl include 2-20, 2-12, 2-8, 2-6 and 2-4 membered heterocarbyl moieties, wherein the number range refers to the sum total of carbon, nitrogen, oxygen, and/or sulfur atoms in the moiety. The term "2-12 membered heterocarbyl" thus refers to a heterocarbyl moiety having a total of 2-12 carbon, nitrogen, oxygen, and/or sulfur atoms. Particular heterocarbyl moieties include straight chain and branched heteroalkyl, heteroalkenyl, and heteroalkynyl, as well as heterocycle and heteroaryl.

Examples of heteroalkyl moieties include 2-8-membered, 2-6-membered and 2-4-membered heteroalkyl moieties. Particular examples include alkoxyl, acyl (e.g., formyl, acetyl, benzoyl), alkylamino (e.g., di-($C_{1-3}$-alkyl)amino), aryl-amino, aryloxime, carbamates, carbamides, alkylcarbonyl, arylcarbonyl, aminocarbonyl, alkylaminocarbonyl, alkylsulfanyl, arylsulfanyl, alkylsulfinyl, arylsulfinyl, alkylsulfonyl, arylsulfonyl, alkylsulfonylamino, and arylsulfonylamino.

Unless otherwise indicated, the term "heterocycle" refers to a cyclic (monocyclic or polycyclic) heterocarbyl moiety which may be aromatic, partially aromatic or non-aromatic. Heterocycles include heteroaryls. Examples include 4-10-membered, 4-7-membered, 6-membered, and 5-membered heterocycles. Particular examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl. Because the term "heterocycle" refers to a ring, standing alone it does not encompass moieties such as oxazolidinone and imidazolidinone: such moieties are considered substituted heterocycles, viz. heterocycles substituted with oxo.

Examples of heteroaryl moieties include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

5.2. COMPOUNDS

This invention encompasses compounds of the formula:

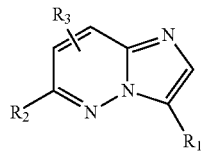

and pharmaceutically acceptable salts thereof, wherein: $R_1$ is $R_{1A}$ or optionally substituted $C_{1-12}$ hydrocarbyl or 2-12-membered heterocarbyl, which optional substitution is with one or more $R_{1A}$; each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$; each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo; each $R_{1C}$ is independently hydrogen or optionally substituted $C_{1-12}$ hydrocarbyl or 2-12-membered heterocarbyl, which optional substitution is with one or more of cyano, halo or hydroxyl; $R_2$ is —$NR_{2A}R_{2B}$, wherein $R_{2A}$ is hydrogen and $R_{2B}$ is optionally substituted $C_{1-12}$ hydrocarbyl or 2-12-membered heterocarbyl, which optional substitution is with one or more $R_{2C}$; or $R_{2A}$ and $R_{2B}$ are taken together to form a 4-7-membered heterocycle optionally substituted with one or more $R_{2C}$; each $R_{2C}$ is independently —$OR_{2D}$, —$N(R_{2D})_2$, —$C(O)R_{2D}$, —$C(O)OR_{2D}$, —$C(O)N(R_{2D})_2$, —$N(R_{2D})C(O)OR_{2D}$, cyano, halo, or optionally substituted $C_{1-12}$ hydrocarbyl or 2-12-membered heterocarbyl, which optional substitution is with one or more amino, cyano, halo, hydroxyl, or $R_{2D}$; each $R_{2D}$ is independently hydrogen or optionally substituted $C_{1-12}$ hydrocarbyl or 2-12-membered heterocarbyl, which optional substitution is with one or more amino, cyano, halo, or hydroxyl; and $R_3$ is hydrogen or $C_{1-6}$ alkyl optionally substituted with one or more of cyano, halo or hydroxyl.

In particular compounds, $R_1$ is $R_{1A}$. In particular compounds, $R_1$ is optionally substituted $C_{1-12}$ hydrocarbyl. In particular compounds, $R_1$ is optionally substituted phenyl. In particular compounds, $R_1$ is optionally substituted 2-12-membered heterocarbyl (e.g., 2-8 membered heterocarbyl, 2-6 membered heterocarbyl, 2-6 membered heterocarbyl). In particular compounds, $R_1$ is optionally substituted pyridinyl, thiophen, or imidazol.

In some compounds, $R_{1A}$ is halo. In some, $R_{1A}$ is —$OR_{1C}$, —$N(R_{1C})_2$, —$C(O)R_{1C}$, —$C(O)OR_{1C}$, or —$C(O)N(R_{1C})_2$. In some, $R_{1A}$ is —$OR_{1C}$. In some, $R_{1B}$ is —$N(R_{1C})_2$, —$OR_{1C}$, halo.

In particular compounds, $R_{2A}$ and $R_{2B}$ are taken together to form a 4-7-membered heterocycle optionally substituted with one or more $R_{2C}$.

In particular compounds, $R_{1C}$ is hydrogen. In some, $R_{1C}$ is $C_{1-12}$ hydrocarbyl (e.g., $C_{1-6}$ hydrocarbyl, $C_{1-4}$ hydrocarbyl such as methyl, ethyl, propyl).

In particular compounds, $R_{2C}$ is —$C(O)OR_{2D}$, —$C(O)N(R_{2D})_2$, or —$N(R_{2D})C(O)OR_{2D}$.

In particular compounds, $R_{2D}$ is hydrogen. In some, $R_{2D}$ is $C_{1-12}$ hydrocarbyl (e.g., $C_{1-6}$ hydrocarbyl, $C_{1-4}$ hydrocarbyl such as methyl, ethyl, propyl).

In particular compounds, $R_3$ is hydrogen.

One embodiment of the invention encompasses compounds of the formula:

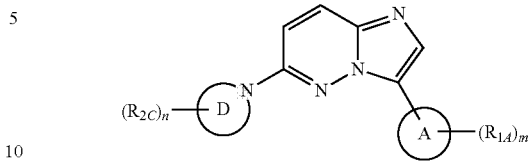

and pharmaceutically acceptable salt thereof, wherein: A is cyclic $C_{1-12}$ hydrocarbyl or 4-7-membered heterocycle; D is 4-7-membered heterocycle; each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$; each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo; each $R_{1C}$ is independently hydrogen or optionally substituted $C_{1-12}$ hydrocarbyl or 2-12-membered heterocarbyl, which optional substitution is with one or more of cyano, halo or hydroxyl; each $R_{2C}$ is independently —$OR_{2D}$, —$N(R_{2D})_2$, —$C(O)R_{2D}$, —$C(O)OR_{2D}$, —$C(O)N(R_{2D})_2$, —$N(R_{2D})C(O)OR_{2D}$, cyano, halo, or optionally substituted $C_{1-12}$ hydrocarbyl or 2-12-membered heterocarbyl, which optional substitution is with one or more with one or more amino, cyano, halo, hydroxyl, or $R_{2D}$; each $R_{2D}$ is independently hydrogen or optionally substituted $C_{1-12}$ hydrocarbyl or 2-12-membered heterocarbyl, which optional substitution is with one or more amino, cyano, halo, or hydroxyl; n is 1-3; and m is 0-3.

In particular compounds, $R_{2C}$ is not hydroxyl or optionally substituted phenyl or pyridinyl.

In particular compounds, when D is diazapine and A is pyridinyl, $R_{2C}$ is not —$C(O)O$-tert-butyl.

In particular compounds, when D is piperazin, A is phenyl and $R_{1A}$ is chloro, $R_{2C}$ is not —$C(O)O$-tert-butyl.

In particular compounds, when D is piperidinyl, A is pyridinyl and $R_{1A}$ is chloro, $R_{2C}$ is not —$NHC(O)O$-tert-butyl.

In particular compounds, when D is piperidinyl, A is pyridinyl and $R_{1A}$ is —$NHCH_2CH_2CH(CH_3)_2$, $R_{2C}$ is not $NH_2$.

One embodiment of the invention encompasses compounds of the formula:

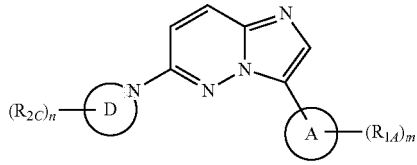

and pharmaceutically acceptable salt thereof, wherein: A is cyclic $C_{1-12}$ hydrocarbyl or 4-7-membered heterocycle; D is 4-7-membered heterocycle; each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$; each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo; each $R_{1C}$ is independently hydrogen or optionally substituted $C_{1-12}$ hydrocarbyl or 2-12-membered heterocarbyl, which optional substitution is with one or more of cyano, halo or hydroxyl; each $R_{2C}$ is independently —$OR_{2D}$, —$N(R_{2D})_2$, —C(O)R$_{2D}$, —C(O)OR$_{2D}$, —C(O)N(R$_{2D}$)$_2$, —N(R$_{2D}$)C(O)OR$_{2D}$, cyano, halo, or optionally substituted C$_{1-12}$ hydrocarbyl or 2-12-membered heterocarbyl, which optional substitution is with one or more with one or more amino, cyano, halo, hydroxyl, or R$_{2D}$; each R$_{2D}$ is independently hydrogen or optionally substituted C$_{1-12}$ hydrocarbyl or 2-12-membered heterocarbyl, which optional substitution is with one or more of amino, cyano, halo, or hydroxyl; n is 1-3; and m is 0-3.

In particular compounds encompassed by this embodiment: 1) R$_{2C}$ is not hydroxyl or optionally substituted phenyl or pyridinyl; 2) when D is diazapine and A is pyridinyl, R$_{2C}$ is not —C(O)O-tert-butyl; 3) when D is piperazin, A is phenyl and R$_{1A}$ is chloro, R$_{2C}$ is not —C(O)O-tert-butyl; 4) when D is piperidinyl, A is pyridinyl and R$_{1A}$ is chloro, R$_{2C}$ is not —NHC(O)O-tert-butyl; and 5) when D is piperidinyl, A is pyridinyl and R$_{1A}$ is —NHCH$_2$CH$_2$CH(CH$_3$)$_2$, R$_{2C}$ is not NH$_2$.

In particular compounds, D is piperazin or pyrrolidin.
In particular compounds, n is 1.
In particular compounds, m is 1 or 2.
In particular compounds, A is pyridinyl, thiophen, or imidazol.

Particular compounds of the invention are of the formula:

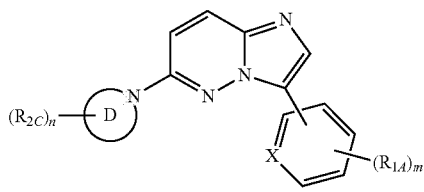

wherein X is CH or N. In one embodiment, X is N and m is 1 or 2.

One embodiment of the invention encompasses compounds of the formula:

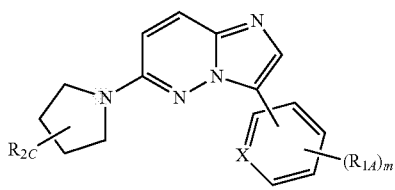

and pharmaceutically acceptable salt thereof, wherein: X is CH or N; each R$_{1A}$ is independently —OR$_{1C}$, —N(R$_{1C}$)$_2$, —C(O)R$_{1C}$, —C(O)OR$_{1C}$, —C(O)N(R$_{1C}$)$_2$, —N(R$_{1C}$)C(O)OR$_{1C}$, cyano, halo, or optionally substituted C$_{1-12}$ hydrocarbyl or 2-12-membered heterocarbyl, which optional substitution is with one or more R$_{1B}$; each R$_{1B}$ is independently —OR$_{1C}$, —N(R$_{1C}$)$_2$, —C(O)R$_{1C}$, —C(O)OR$_{1C}$, —C(O)N(R$_{1C}$)$_2$, —N(R$_{1C}$)C(O)OR$_{1C}$, cyano or halo; each R$_{1C}$ is independently hydrogen or optionally substituted C$_{1-12}$ hydrocarbyl or 2-12-membered heterocarbyl, which optional substitution is with one or more of cyano, halo or hydroxyl; each R$_{2C}$ is independently —OR$_{2D}$, —N(R$_{2D}$)$_2$, —C(O)R$_{2D}$, —C(O)OR$_{2D}$, —C(O)N(R$_{2D}$)$_2$, —N(R$_{2D}$)C(O)OR$_{2D}$, cyano, halo, or optionally substituted C$_{1-12}$ hydrocarbyl or 2-12-membered heterocarbyl, which optional substitution is with one or more with one or more amino, cyano, halo, hydroxyl, or R$_{2D}$; each R$_{2D}$ is independently hydrogen or optionally substituted C$_{1-12}$ hydrocarbyl or 2-12-membered heterocarbyl, which optional substitution is with one or more amino, cyano, halo, or hydroxyl; and m is 0-3.

In some compounds of this embodiment, R$_{2C}$ is not optionally substituted phenyl or pyridinyl.

Particular compounds of the invention are of the formula:

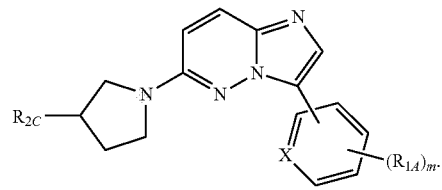

Particular compounds of the invention are of the formula:

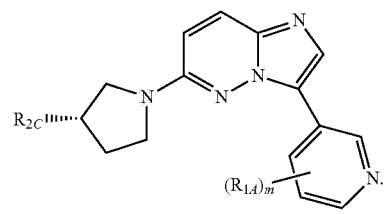

Particular compounds of the invention are of the formula:

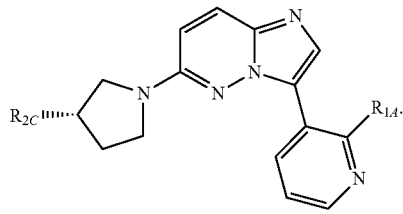

Particular compounds of the invention are of the formula:

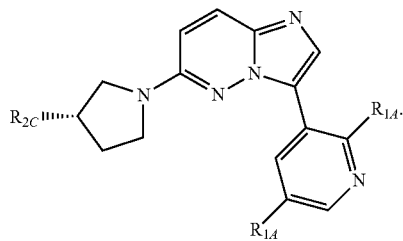

One embodiment of the invention encompasses compounds of the formula:

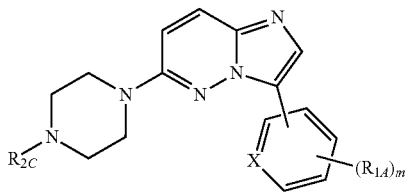

and pharmaceutically acceptable salt thereof, wherein: X is CH or N; each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$; each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo; each $R_{1C}$ is independently hydrogen or optionally substituted $C_{1-12}$ hydrocarbyl or 2-12-membered heterocarbyl, which optional substitution is with one or more of cyano, halo or hydroxyl; each $R_{2C}$ is independently —$OR_{2D}$, —$N(R_{2D})_2$, —$C(O)R_{2D}$, —$C(O)OR_{2D}$, —$C(O)N(R_{2D})_2$, —$N(R_{2D})C(O)OR_{2D}$, cyano, halo, or optionally substituted $C_{1-12}$ hydrocarbyl or 2-12-membered heterocarbyl, which optional substitution is with one or more with one or more amino, cyano, halo, hydroxyl, or $R_{2D}$; each $R_{2D}$ is independently hydrogen or optionally substituted $C_{1-12}$ hydrocarbyl or 2-12-membered heterocarbyl, which optional substitution is with one or more amino, cyano, halo, or hydroxyl; and n is 0-3.

In some compounds of this embodiment, when X is CH, m is 1 and $R_{1A}$ is chloro, $R_{2D}$ is not t-butyl.

In some compounds of this embodiment, $R_{2C}$ is not optionally substituted phenyl or pyridinyl.

Particular compounds of the invention are of the formula:

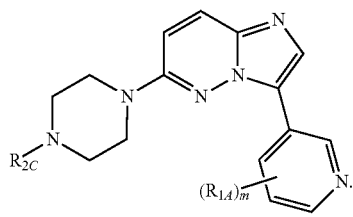

In some, m is 1 or 2.
Particular compounds of the invention are of the formula:

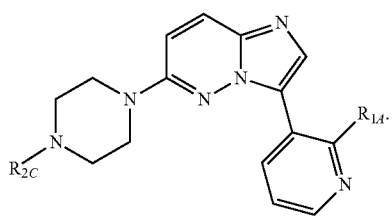

Others are of the formula:

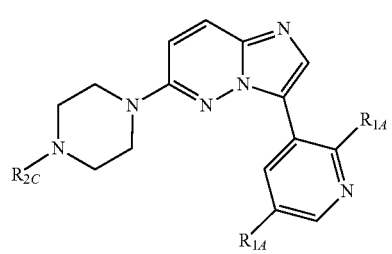

In particular compounds, $R_{1A}$ is —$OR_{1C}$.
In particular compounds, $R_{1C}$ is optionally substituted $C_{1-12}$ hydrocarbyl (e.g., $C_{1-6}$ hydrocarbyl, $C_{1-4}$ hydrocarbyl).

In particular compounds, $R_{2C}$ is —$C(O)OR_{2D}$, —$C(O)N(R_{2D})_2$, or —$N(R_{2D})C(O)OR_{2D}$. In others, $R_{2C}$ is —$C(O)R_{2D}$.

In particular compounds, each $R_{2D}$ is independently hydrogen or $C_{1-12}$ hydrocarbyl (e.g., $C_{1-6}$ hydrocarbyl, $C_{1-4}$ hydrocarbyl). In others, $R_{2D}$ is 2-12-membered heterocarbyl comprising at least one nitrogen atom.

Compounds of the invention can have one or more asymmetric centers. Unless otherwise indicated, this invention encompasses all stereoisomers of the compounds, as well as mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthalenesulfonate, nicotinate, 2-naphthalenesulfonate, oxalate, palmoate, pectinate, persulfate, 3-phenylpropionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

Particular compounds of the invention inhibit AAK1 with an $IC_{50}$ of less than 0.1, 0.01 or 0.001 μM as measured in the P81 filter plate assay described below in the Examples. Particular compounds of the invention inhibit AAK1 with an $IC_{50}$ of less than 0.1, 0.01 or 0.001 μM as measured in the HEK281 cell-based assay described below in the Examples.

5.3. METHODS OF SYNTHESIS

Compounds of the invention can be prepared using methods known to those skilled in the art. Particular compounds are of the general formula:

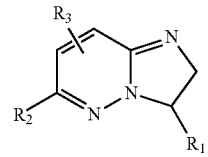

wherein $R_1$, $R_2$ and $R_3$ are defined herein. These compounds can prepared by the methods outlined below.

In Scheme 1, the chlorine or fluorine of a compound of formula 1 is displaced with an amine to produce 2. For some examples, the halogen in 1 can be hydrolyzed to give 3, and then reacted with amine to afford 2. Suzuki coupling of 2 with an appropriate boronic acid or ester $[R_3B(OR)_2]$ affords compounds of formula 4. Compound 2 can also be converted to its corresponding boronic acid 5, which can be coupled with appropriate bromide to afford 4. Alternatively, Suzuki coupling of 1 with an appropriate boronic acid or ester $[R_3B(OR)_2]$ affords compounds of formula 6, the halogen for which can be displaced to produce 4.

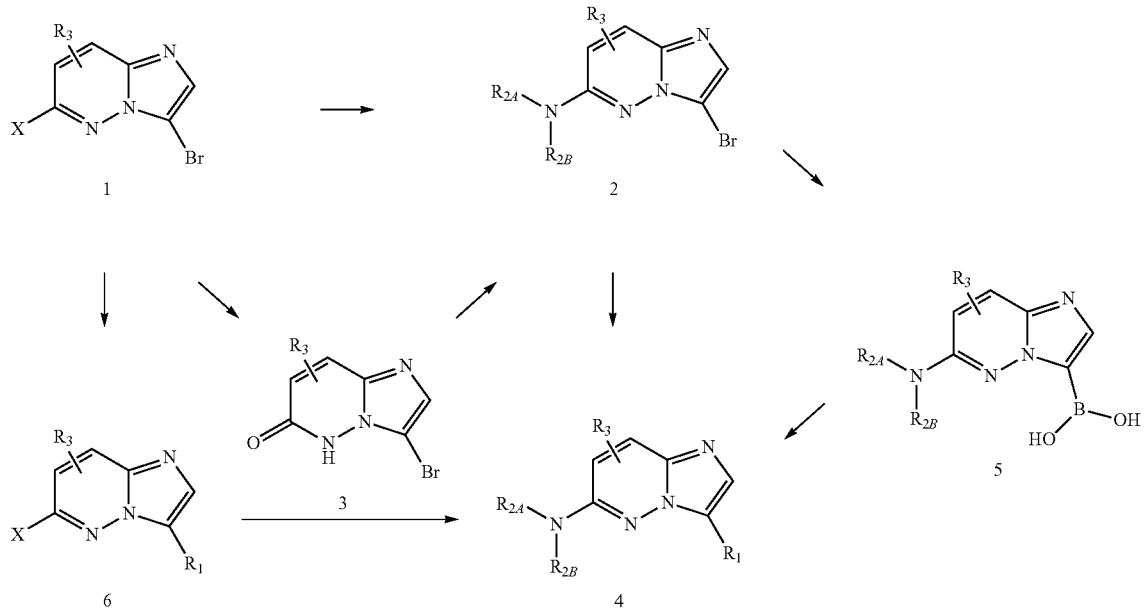

Scheme 1

Scheme 2 represents an approach useful in preparing 3-bromo-6-fluoroimidazo[1,2-b]pyridazine compound s of formula 1a. The 3,6-dichloropyridazine 7 is converted to 3,6-difluoropyridazine 8 by reacting 7 with spray dried KF in DMSO at 135° C. Displacement of one of the fluorines from 8 by $NH_4OH$ in a heated sealed tube generates 9. Cyclization of 9 with chloroacetaldehyde gives intermediate 10. Bromination of 10 affords 1a.

Scheme 2

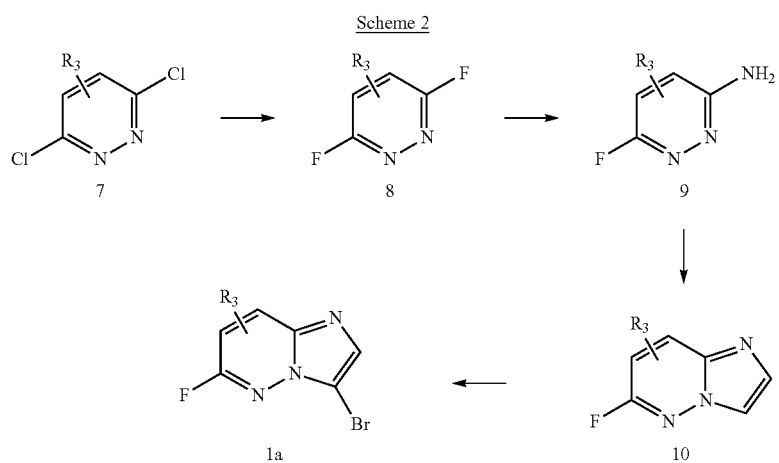

Scheme 3 shows a method of preparing 4- or 5-substituted 3-bromo-6-chloroimidazo[1,2-b]pyridazine compounds of formula 1b. Displacement of one of the chlorines from 11 by 2,4-dimethoxybenzylamine generates a mixture of regio-isomers of 12, which are separated. Removal of the 2,4-dimethoxybenzyl group produces 13. Cyclization of 13 with chloroacetaldehyde gives intermediate 14. Bromination of 14 affords 1b.

Scheme 3

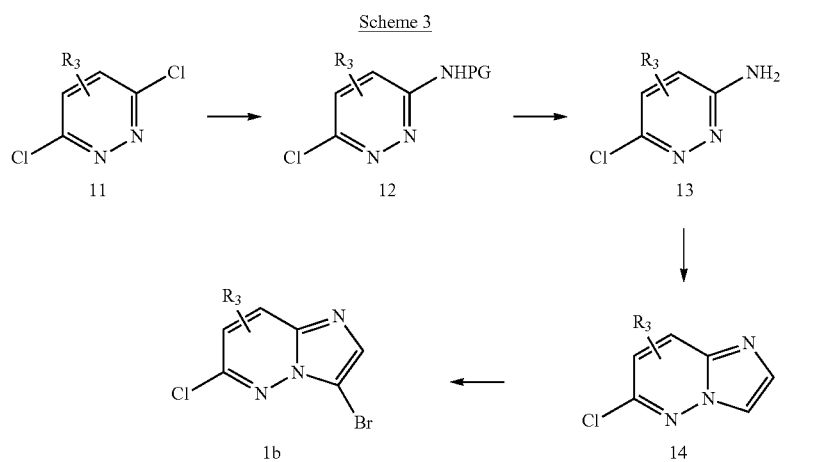

Scheme 4 shows an approach useful in preparing compounds of the invention wherein $R_2$ is aryl. Here, the Suzuki coupling of compound 15 with an appropriate boronic acid or ester $[R_3B(OR)_2]$ provides 16. Bromination of 16 affords intermediate 17. Second Suzuki coupling gives compound 18.

Scheme 5 describes the preparation of compounds of formula 20. The chlorine or fluorine of a compound of formula 1 is displaced with a thiol to produce 19. Suzuki coupling of 19 with an appropriate boronic acid or ester $[R_{1B}(OR)_2]$ affords compounds of formula 20.

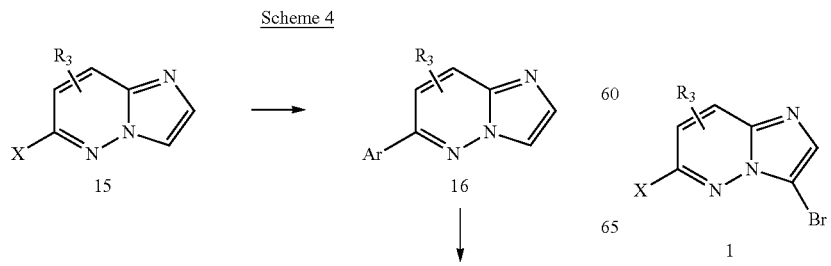

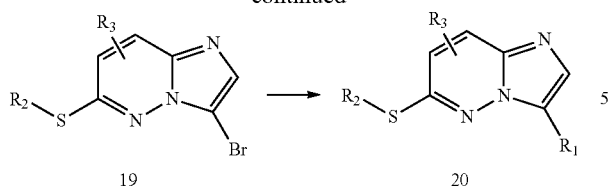

Compounds of formula 21, 22 and 23 can be prepared by the methods outlined in Scheme 6. The bromine of a compound of formula 2 is displaced with a cyano group to produce 21. Hydrolysis of the cyano group in 21 affords the acid 22. Regular amide coupling of the acid 22 gives amide 23.

Scheme 6

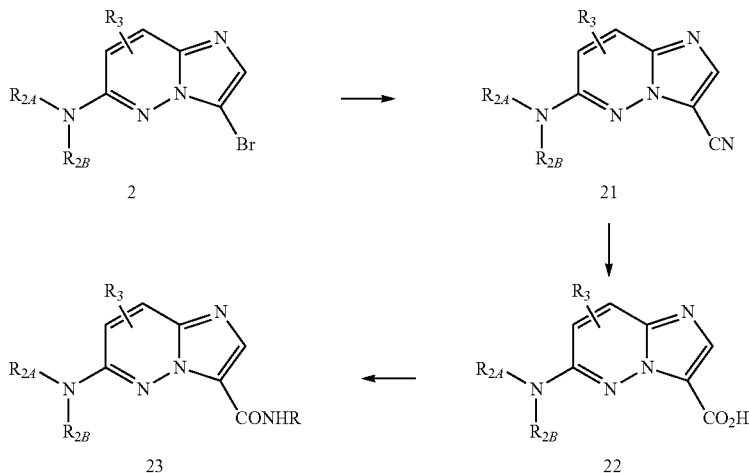

Scheme 7 describes a method of preparing compounds 26, 27 and 30. In this approach, the amine group of a compound of formula 24 is reacted with acetyl chloride in basic conditions to provide 25. Amine displacement of the chlorine in 25 affords compounds with formula 26 and 27. The amine group in 24 can also reacted with an acyl chloride bearing a terminal leaving group, such as bromine, to give 28. Intra-molecular cyclyzation of 28 under strong basic conditions provides intermediate 29. Amine displacement of the chlorine in 29 affords compounds of formula 30.

Scheme 7

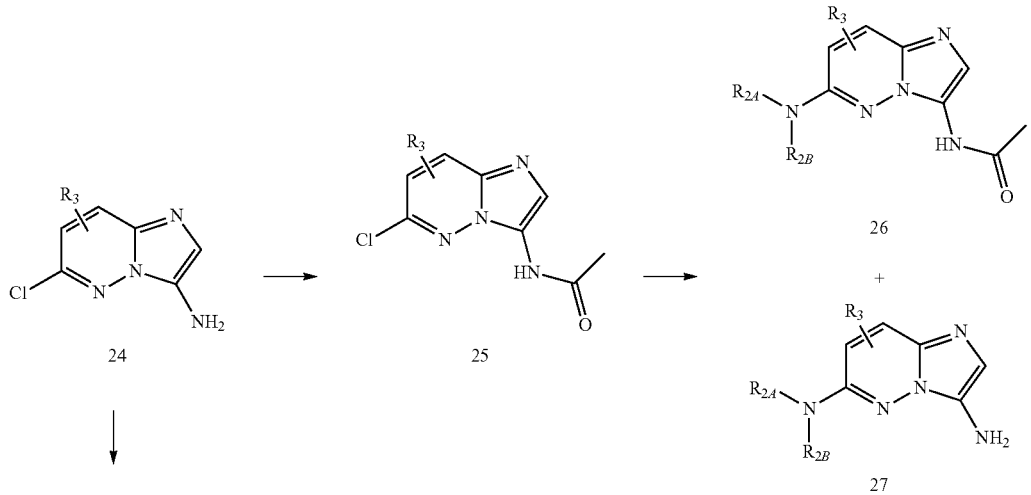

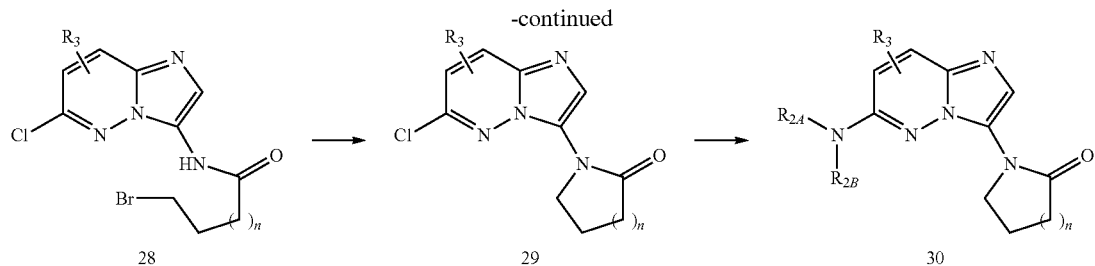

Outlined in Scheme 8 are approaches useful in preparing compounds of formulae 33 and 35. Here, reduction of the aldehyde function in compound 31 gives alcohol 32. Displacement of the chlorine in 32 affords compounds of formula 33. Conversion of the carbonyl of 31 into difluoromethyl gives 34. Displacement of the chlorine in 34 affords compounds with formula 35.

Scheme 8

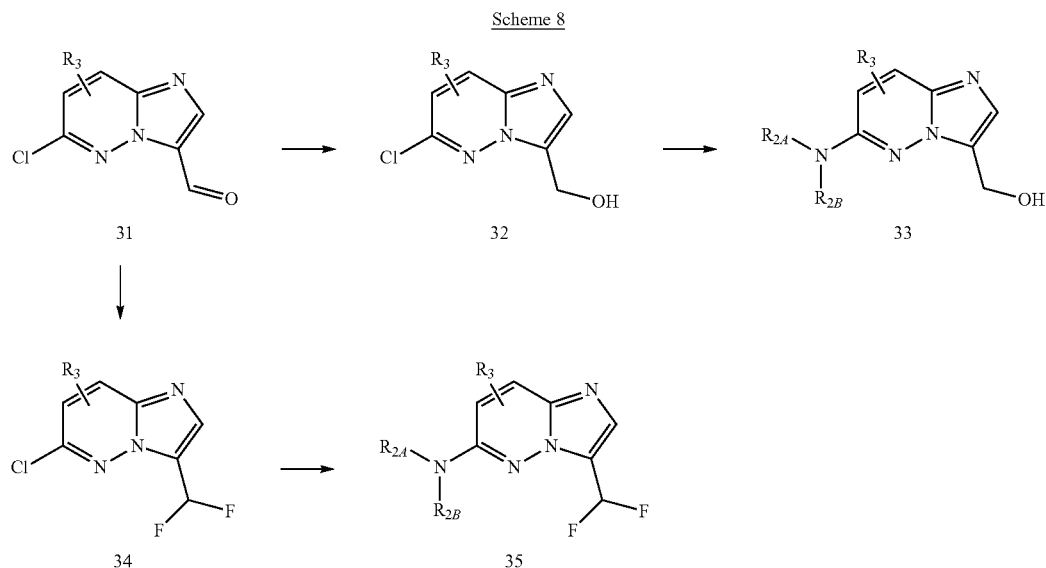

Macrocyclic compounds can be prepared according to Scheme 9. Displacement of the fluorine in 1a with a carefully assembled amine that possesses a terminal aryl bromide gives compound 36. Intra-molecular Suzuki type coupling of 36 affords the macrocyclic compound 37.

Scheme 9

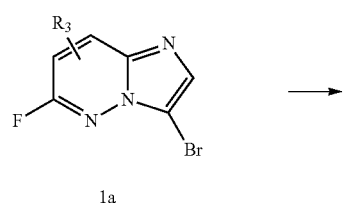

-continued

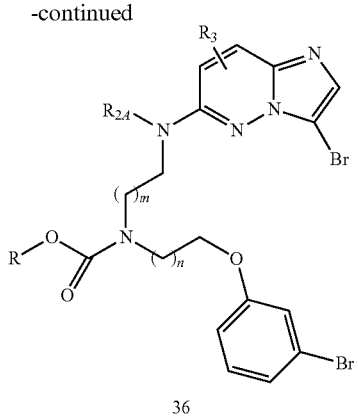

-continued

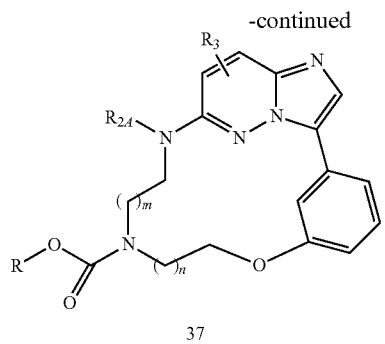

37

5.4. METHODS OF USE

One embodiment of this invention encompasses methods of inhibiting adaptor associated kinase 1 (AAK1), both in vitro and in vivo, which comprise contacting AAK1 with a compound of the invention.

Another embodiment encompasses methods of treating and managing diseases and disorders mediated by AAK1 activity. Diseases and disorders mediated by AAK1 activity are diseases and disorders that have at least one symptom, the severity or manifestation of which is affected by AAK1 activity. Examples of such diseases and disorders are believed to include Alzheimer's disease, bipolar disorder, pain, Parkinson's disease, and schizophrenia (including cognitive deficits in schizophrenia). Particular methods comprise administering to a patient (a human or other mammal) in need thereof a therapeutically or prophylactically effective amount of an AAK1 inhibitor (e.g., a compound disclosed herein).

Another embodiment of this invention encompasses a method of treating or managing a disease or disorder, which comprises administering to a patient in need thereof a therapeutically or prophylactically effective amount of an AAK1 inhibitor, wherein the disease or disorder is Alzheimer's disease, bipolar disorder, pain, Parkinson's disease, or schizophrenia (including cognitive deficits in schizophrenia). Particular types of pain include chronic pain, acute pain, and neuropathic pain. Particular types of neuropathic pain include fibromyalgia and peripheral neuropathy (e.g., diabetic neuropathy).

When used to treat or manage a disease or disorder, compounds of the invention are preferably administered as part of a pharmaceutical composition comprising one or more pharmaceutically acceptable carriers, diluents or excipients.

Pharmaceutical compositions, or formulations, may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

Compounds of the invention may be administered in combination with one or more additional therapeutic or prophylactic agents. For example, when used for the treatment of pain, possible additional agents include immunosuppressive and anti-inflammatory agents.

Immunosuppressants suitable for use in the methods and compositions of this invention include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Additional examples include inosine monophosphate dehydrogenase inhibitors, such as mycophenolate mofetil (CellCept®) and mycophenolic acid (Myfortic®).

Anti-inflammatory drugs suitable for use in the methods and compositions of this invention include those known in the art. Examples include glucocorticoids and NSAIDs.

Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the invention may be administered in combination with one or more additional therapeutic or prophylactic agents directed at the underlying disease or condition. For example, when used to treat diabetic neuropathy, compounds of the invention may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

5.5. PHARMACEUTICAL COMPOSITIONS

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

5.6. EXAMPLES

Certain aspects of the invention can be understood from the following examples.

5.6.1. AAK1 Knockout Mice

Mice homozygous (−/−) for the disruption of the AAK1 gene were prepared by two methods; gene trapping and homologous recombination.

Gene trapping is a method of random insertional mutagenesis that uses a fragment of DNA coding for a reporter or selectable marker gene as a mutagen. Gene trap vectors have been designed to integrate into introns or genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells from derived murine strain A129), were mutated by a process involving the insertion of at least a portion of a genetically engineered vector sequence into the gene of interest, the mutated embryonic stem cells were microinjected into blastocysts which were subsequently introduced into pseudopregnant female hosts and carried to term using established methods. See, e.g., "Mouse Mutagenesis", 1998, Zambrowicz et al., eds., Lexicon Press, The Woodlands, Tex. The resulting chimeric animals were subsequently bred to produce offspring capable of germline transmission of an allele containing the engineered mutation in the gene of interest.

AAK1-gene disrupted mice were also made by homologous recombination. In this case, the second coding exon of the murine AAK1 gene (see GenBank Accession Number NM_177762) was removed by methods known in the art. See, e.g., U.S. Pat. Nos. 5,487,992, 5,627,059, and 5,789,215.

Mice homozygous (−/−) for the disruption of the AAK1 gene were studied in conjunction with mice heterozygous (+/−) for the disruption of the AAK1 gene, and wild-type (+/+) litter mates. During this analysis, the mice were subject to a medical work-up using an integrated suite of medical diagnostic procedures designed to assess the function of the major organ systems in a mammalian subject. Homozygous (−/−) "knockout" mice were studied in conjunction with their heterozygous (+/−) and wild-type (+/+) litter mates. Disruption of the AAK1 gene was confirmed by Southern analysis. Expression of the murine homolog of AAK1 was detected by RT-PCR in murine brain; spinal cord; eye; thymus; spleen; lung; kidney; liver; skeletal muscle; bone; stomach, small intestine and colon; heart; adipose; asthmatic lung; LPS liver; blood; banded heart; aortic tree; prostate; and mammary gland (5 week virgin, mature virgin, 12 DPC, 3 day postpartum (lactating), 3 day post-weaning (early involution), and 7 day post-weaning (late involution)).

AAK1 homozygous (−/−) and their wild-type (+/+) littermates were tested using the formalin paw test in order to assess their acute and tonic nociceptive responses. For these tests, Automatic Nociception Analyzers (purchased from the Ozaki lab at University of California, San Diego) were used. A metal band was placed around the left hind paw of each mouse 30 minutes prior to testing. After the 30-minute acclimation period, 20 µl of 5% formalin is subcutaneously injected in the dorsal surface of the left hind paw. Mice were individually housed in cylindrical chambers for 45 minutes. A computer recorded flinches per minute, total flinches for phase I (acute phase=first 8 minutes), and total flinches for phase II (tonic phase=time between minutes 20-40) through an electromagnetic field. See Yaksh T L, Ozaki G, McCumber D, Rathbun M, Svensson C, Malkmus S, Yaksh M C. An automated flinch detecting system for use in the formalin nociceptive bioassay. *J Appl Physiol.*, 2001; 90:2386-402.

As shown in FIG. 1, phase 1 and phase 2 data were obtained using homozygous (−/−) mice females (n=16), wild-type females (n=15), homozygous (−/−) mice males (n=9), and wild-type males (n=18). In all groups and in both phases, the AAK1 homozygous (−/−) mice exhibited significantly less recorded paw flinching than their wild-type (+/+) littermates.

5.6.2. Synthesis of 1-[5-(6-Butylamino-imidazo[1,2-b]pyridazin-3-yl)-thiophen-2-yl]-ethanone

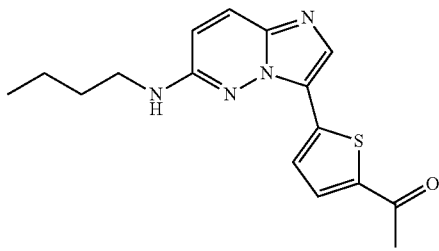 [SMILES: CCCCNc1ccc2ncc(-c3ccc(C(C)=O)s3)n2n1]

Part A. 6-Fluoro-imidazo[1,2-b]pyridazine

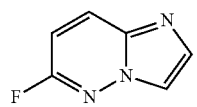

6-Fluoro-pyridazin-3-ylamine [108784-42-5] (10 g, 89 mmol) was combined with a 50% (w/v) aqueous solution of chloroacetaldehyde [107-20-0] (23 mL, 177 mmol) in n-butanol (150 mL) and stirred at reflux for 1 h. The cooled reaction solution was reduced in volume and diluted with diethyl ether to precipitate a brown solid, which was collected by filtration, to yield 12.0 g. LRMS (ESI) m/z 138.0 [(M+H)]$^+$, calc'd for $C_6H_4FN_3$: 137.12.

Part B. 3-Bromo-6-fluoro-imidazo[1,2-b]pyridazine

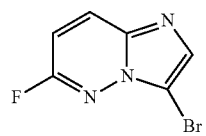

To an ambient temperature, stirred solution of 6-fluoro-imidazo[1,2-b]pyridazine (2.1 g, 15.3 mmol) in glacial acetic acid (20 mL) was slowly added bromine (2.5 g, 15.3 mmol). Upon completion of this addition the reaction solution was poured into water and extracted with ethyl acetate. The extract was dried (MgSO$_4$) and flash chromatographed (silica gel, eluted with 30% (v/v) ethyl acetate/hexanes) to provide 0.9 g of 3-bromo-6-fluoro-imidazo[1,2-b]pyridazine. LRMS (ESI) m/z 215.9/217.9 [(M+H)]$^+$, calc'd for $C_6H_3BrFN_3$: 216.01.

Part C. 1-[5-(6-Fluoro-imidazo[1,2-b]pyridazin-3-yl)-thiophen-2-yl]-ethanone

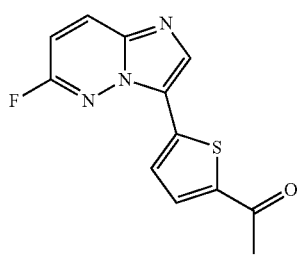 [SMILES: CC(=O)c1ccc(-c2cnc3ccc(F)nn23)s1]

A mixture of 3-bromo-6-fluoro-imidazo[1,2-b]pyridazine (620 mg, 2.9 mmol), 5-acetyl-2-thiopheneboronic acid [206551-43-1] (634 mg, 3.7 mmol), potassium carbonate [584-08-7] (792 mg, 5.7 mmol), and bis(triphenylphosphine)palladium(II) dichloride [13965-03-2] (100 mg, 0.1 mmol) was suspended in a microwave reaction vial with a 25% (v/v) solution of water in acetonitrile (4.5 mL) then stirred and irradiated to an internal temperature of 145° C. for 15 minutes. The cooled reaction mixture was diluted with ethyl acetate, filtered, and partitioned between 1N aqueous sodium hydroxide and additional ethyl acetate. The organic extract was flash chromatographed (silica gel, eluted with 20% (v/v) ethyl acetate/hexanes) to provide 1-[5-(6-fluoro-imidazo[1,2-b]pyridazin-3-yl)-thiophen-2-yl]-ethanone as 300 mg of yellow solid. $^1$H NMR (400 MHz, CHLOROFORM-d) δ ppm 2.63 (s, 3H) 7.00 (d, J=9.35 Hz, 1H) 7.75 (d, J=4.04 Hz, 1H) 7.83 (d, J=4.04 Hz, 1H) 8.13 (dd, J=9.60, 7.07 Hz, 1H) 8.21 (s, 1H). LRMS (ESI) m/z 262.1 [(M+H)]$^+$, calc'd for $C_{12}H_8FN_3OS$: 261.28.

Part D. 1-[5-(6-Butylamino-imidazo[1,2-b]pyridazin-3-yl)-thiophen-2-yl]-ethanone

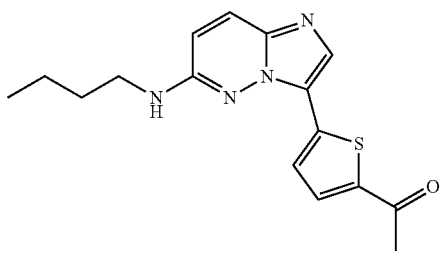 [SMILES: CCCCNc1ccc2ncc(-c3ccc(C(C)=O)s3)n2n1]

1-[5-(6-Fluoro-imidazo[1,2-b]pyridazin-3-yl)-thiophen-2-yl]-ethanone (60 mg, 0.2 mmol) and butylamine [109-73-9] (0.1 mL, 10.2 mmol) was microwave irradiated to an internal temperature of 120° C. for 10 minutes. Product 1-[5-(6-butylamino-imidazo[1,2-b]pyridazin-3-yl)-thiophen-2-yl]-ethanone was purified by preparative RP-HPLC to provide 10.1 mg. $^1$H NMR (400 MHz, METHANOL-d$_4$) δ ppm 1.03 (t, J=7.33 Hz, 3H) 1.50-1.59 (m, 2H) 1.72-1.79 (m, 2H) 2.59 (s, 3H) 3.47 (t, J=7.33 Hz, 2H) 6.73 (d, J=9.60 Hz, 1H) 7.63 (d, J=9.60 Hz, 1H) 7.70 (d, J=4.04 Hz, 1H) 7.85 (d, J=4.29 Hz, 1H) 7.95 (s, 1H). LRMS (ESI) m/z 315.2 [(M+H)]$^+$, calc'd for $C_{16}H_{18}N_4OS$: 314.41.

5.6.3. Synthesis of 1-{5-[6-(2-Hydroxy-ethylamino)-imidazo[1,2-b]pyridazin-3-yl]-thiophen-2-yl}-ethanone

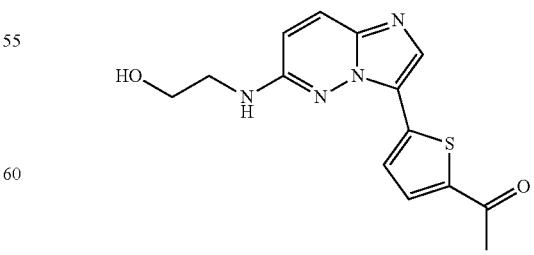

Cesium carbonate [534-17-8] (150 mg, 0.5 mmol) was added to a solution of 1-[5-(6-fluoro-imidazo[1,2-b]pyridazin-3-yl)-thiophen-2-yl]-ethanone (60 mg, 0.2 mmol)

and ethanolamine [141-43-5] (29 mg, 0.5 mmol) in N,N-dimethylformamide (3 mL). The mixture was stirred at 40° C. for 1 h then partitioned between ethyl acetate and water. Analysis of the organic extract revealed preparation ratio of the desired arylamine product to the ether to be approximately 2:1. Preparative RP-HPLC isolated 22 mg of 1-{5-[6-(2-hydroxy-ethylamino)-imidazo[1,2-b]pyridazin-3-yl]-thiophen-2-yl}-ethanone as a yellow solid. $^1$H NMR (400 MHz, DMSO-d$_6$) δ ppm 1.83 (s, 3H) 2.57 (s, 2H) 3.04 (t, J=5.68 Hz, 1H) 4.43 (t, J=5.68 Hz, 1H) 7.04 (d, J=9.60 Hz, 1H) 7.91 (d, J=4.04 Hz, 1H) 8.03 (d, J=4.04 Hz, 1H) 8.16 (d, J=9.60 Hz, 1H) 8.36 (s, 1H). LRMS (ESI) m/z 303.1 [(M+H)]$^+$, calc'd for C$_{14}$H$_{14}$N$_4$O$_2$S: 302.36.

5.6.4. Synthesis of 3-(4-(aminomethyl)phenyl)-N-(2-methoxyethyl)imidazo[1,2-b]pyridazin-6-amine

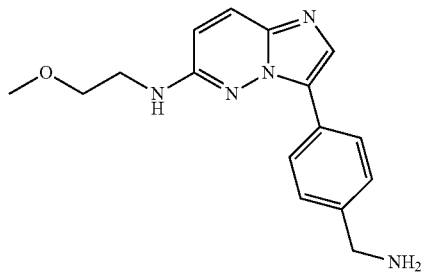

Part A. 3-bromo-N-(2-methoxyethyl)imidazo[1,2-b]pyridazin-6-amine

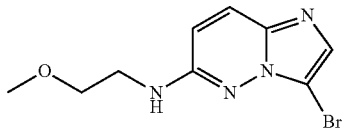

A solution of 3-bromo-6-chloroimidazo[1,2-b]pyridazine (844 mg, 3.77 mmol) and 2-methoxyethanamine (1.44 mL) was heated at 170° C. (microwave) for 30 min. The resulting mixture was cooled to room temperature and purified by preparative HPLC (neutral) to afford 3-bromo-N-(2-methoxyethyl)imidazo[1,2-b]pyridazin-6-amine (630 mg, 62% yield) as a off-white solid: $^1$H NMR (METHANOL-d$_4$) δ: 7.56 (d, J=9.9 Hz, 1H), 7.41 (s, 1H), 6.74 (d, J=9.6 Hz, 1H), 3.62-3.76 (m, 2H), 3.50-3.62 (m, 2H), 3.42 (s, 3H); LRMS (ESI) m/e 271.1 [(M+H)$^+$, calcd for C$_9$H$_{12}$BrN$_4$O 271.0]

Part B. 3-(4-(aminomethyl)phenyl)-N-(2-methoxyethyl)imidazo[1,2-b]pyridazin-6-amine

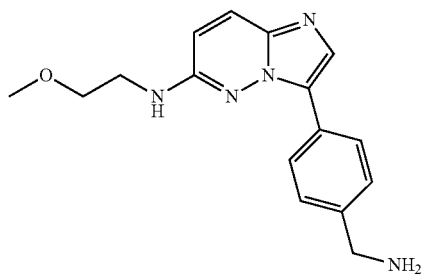

To a mixture of 3-bromo-N-(2-methoxyethyl)imidazo[1,2-b]pyridazin-6-amine (229 mg, 0.85 mmol), (4-(aminomethyl)phenyl)boronic acid (395 mg, 2.11 mmol), [1,1'-bis(diphenylphosphino)ferrocene]dichloropalladium(II) (62 mg, 0.085 mmol) and potassium phosphate (540 mg, 2.54 mmol) was added 1:1 Dimethoxyethane/water (3 mL). The resulting mixture was heated at 160° C. (microwave) for 6 min. The reaction was then filtered and diluted with a mixture of 1:1:1 methanol/water/acetonitrile, and then filtered again. The filtration was finally purified by preparative HPLC (acidic) to afford 3-(4-(aminomethyl)phenyl)-N-(2-methoxyethyl)imidazo[1,2-b]pyridazin-6-amine mono acetic acid salt as a white solid: $^1$H NMR (METHANOL-d$_4$) δ: 8.18-8.33 (m, J=8.3 Hz, 2H), 7.82 (s, 1H), 7.67 (d, J=9.6 Hz, 1H), 7.53-7.58 (m, J=8.3 Hz, 2H), 6.78 (d, J=9.6 Hz, 1H), 4.14 (s, 2H), 3.68 (t, J=5.7 Hz, 2H), 3.58 (t, J=5.4 Hz, 2H), 3.42 (s, 3H), 1.93 (s, 3H); LRMS (ESI) m/e 298.2 [(M+H)$^+$, calcd for C$_{16}$H$_{20}$N$_5$O 298.2]

5.6.5. Synthesis of 4-(6-((2-Methoxyethyl)amino)imidazo[1,2-b]pyridazin-3-yl)benzamide

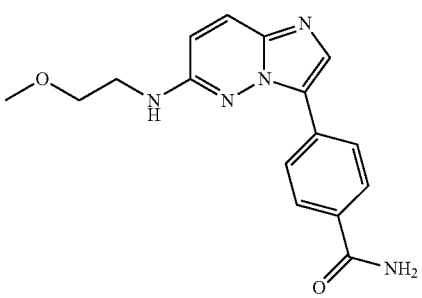

To a mixture of 3-bromo-N-(2-methoxyethyl)imidazo[1,2-b]pyridazin-6-amine (57.6 mg, 0.21 mmol), (4-carbamoylphenyl)boronic acid (87.4 mg, 0.53 mmol), [1,1'-bis(diphenylphosphino)ferrocene]dichloropalladium(II) (7.7 mg, 0.011 mmol) and potassium phosphate (134 mg, 0.63 mmol) was added 1:1 Dimethoxyethane/water (0.75 mL). The resulting mixture was heated at 160° C. (microwave) for 6 min. The reaction was then filtered and diluted with a mixture of 1:1:1 methanol/water/acetonitrile, and then filtered again. The filtration was finally purified by preparative HPLC (neutral) to afford 3-(4-(aminomethyl)phenyl)-N-(2-methoxyethyl)imidazo[1,2-b]pyridazin-6-amine (9 mg, 14% yield) as a white solid: $^1$H NMR (METHANOL-d$_4$) δ: 8.29 (d, J=8.6 Hz, 2H), 7.98 (d, J=8.6 Hz, 2H), 7.89 (s, 1H), 7.66 (d, J=9.6 Hz, 1H), 6.79 (d, J=9.9 Hz, 1H), 3.69 (t, J=5.6 Hz, 2H), 3.59 (t, J=5.4 Hz, 2H), 3.42 (s, 3H); LRMS (ESI) m/e 312.2 [(M+H)$^+$, calcd for C$_{16}$H$_{18}$N$_5$O$_2$ 312.2].

5.6.6. Synthesis of 3-(4-(Aminomethyl)phenyl)-N-butylimidazo[1,2-b]pyridazin-6-amine

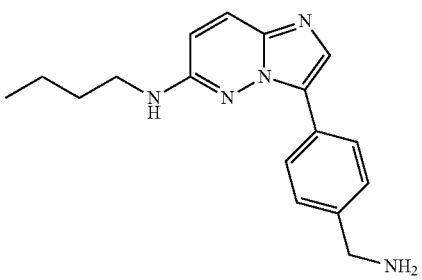 [SMILES: COCCNc1ccc2ncc(-c3ccc(CN)cc3)n2n1]

Part A.
3-bromo-N-butylimidazo[1,2-b]pyridazin-6-amine

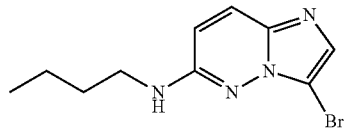

A solution of 3-bromo-6-chloroimidazo[1,2-b]pyridazine (1.2 g, 5.2 mmol) and N-butylamine (2 mL) was heated at 170° C. (microwave) for 30 min. The resulting mixture was cooled to room temperature and purified by preparative HPLC (neutral) to afford 3-bromo-N-butylimidazo[1,2-b]pyridazin-6-amine (887 mg, 63% yield) as a white solid: $^1$H NMR (METHANOL-$d_4$) δ: 7.53 (d, J=9.6 Hz, 1H), 7.39 (s, 1H), 6.69 (d, J=9.9 Hz, 1H), 3.38 (t, J=7.1 Hz, 2H), 1.59-1.73 (m, 2H), 1.41-1.53 (m, 2H), 1.01 (t, J=7.3 Hz, 3H); LRMS (ESI) m/e 269.1 [(M+H)$^+$, calcd for $C_{10}H_{14}BrN_4$ 269.0].

Part B. 3-(4-(aminomethyl)phenyl)-N-butylimidazo [1,2-b]pyridazin-6-amine

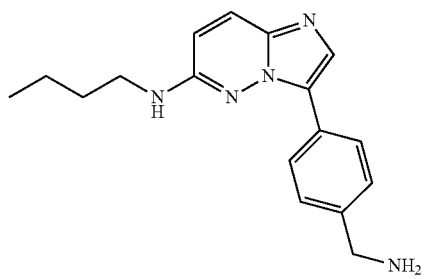 [SMILES: CCCCNc1ccc2ncc(-c3ccc(CN)cc3)n2n1]

To a mixture of 3-bromo-N-butylimidazo[1,2-b]pyridazin-6-amine (190 mg, 0.71 mmol), (4-(aminomethyl)phenyl)boronic acid (331 mg, 1.76 mmol), [1,1'-bis(diphenylphosphino)ferrocene]dichloropalladium(II) (26 mg, 0.036 mmol) and tripotassium phosphate (452 mg, 2.13 mmol) was added 1:1 dimethoxyethane/water (10 mL). The resulting mixture was heated at 160° C. (microwave) for 6 min. The reaction was then filtered and diluted with a mixture of 1:1:1 methanol/water/acetonitrile, and then filtered again. The filtration was finally purified by preparative HPLC (acidic) to afford 3-(4-(aminomethyl)phenyl)-N-butylimidazo[1,2-b]pyridazin-6-amine mono acetic acid salt (21 mg, 10% yield) as a white solid: $^1$H NMR (METHANOL-$d_4$) δ: 8.25-8.29 (m, 2H), 7.80 (s, 1H), 7.63 (d, J=9.6 Hz, 1H), 7.54 (d, J=8.3 Hz, 2H), 6.74 (s, 1H), 6.72 (s, 1H), 4.11 (s, 2H), 3.39 (t, J=7.1 Hz, 2H), 1.93 (s, 3H), 1.68-1.76 (m, 2H), 1.46-1.55 (m, 2H), 1.02 (t, J=7.5 Hz, 3H); LRMS (ESI) m/e 296.4 [(M+H)$^+$, calcd for $C_{17}H_{22}N_5$ 296.2].

5.6.7. Synthesis of {3-[3-(5-Acetyl-thiophen-2-yl)-imidazo[1,2-b]pyridazin-6-ylamino]-propyl}-methyl-carbamic acid tert-butyl ester

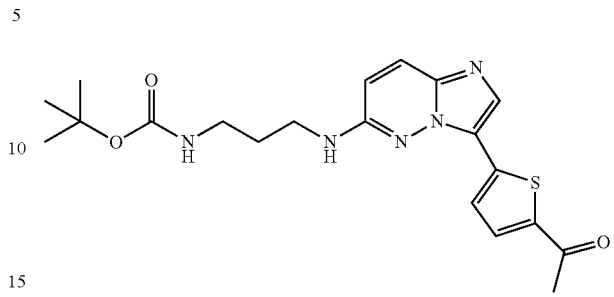

Cesium carbonate [534-17-8] (125 mg, 0.4 mmol) was added to a solution of 1-[5-(6-fluoro-imidazo[1,2-b]pyridazin-3-yl)-thiophen-2-yl]-ethanone (50 mg, 0.2 mmol) and N-(3-aminopropyl)-N-methylcarbamic acid tert-butyl ester [150349-36-3] (72 mg, 0.4 mmol) in N,N-dimethylformamide (1.5 mL) and stirred overnight at ambient temperature then partitioned between ethyl acetate and water. The organic extract was evaporated and product isolated by preparative RP-HPLC to provide {3-[3-(5-acetyl-thiophen-2-yl)-imidazo[1,2-b]pyridazin-6-ylamino]-propyl}-methyl-carbamic acid tert-butyl ester as a yellow oil. $^1$H NMR (400 MHz, METHANOL-$d_4$) δ ppm 1.33-1.49 (m, 9H) 2.04 (d, J=11.87 Hz, 2H) 2.59 (s, 3H) 2.91 (s, 3H) 3.35-3.53 (m, 4H) 4.62 (s, 1H) 6.75 (d, J=9.60 Hz, 1H) 7.64-7.75 (m, 2H) 7.87 (d, J=4.04 Hz, 1H) 7.98 (s, 1H). LRMS (ESI) m/z 430.2 [(M+H)]$^+$, calc'd for $C_{21}H_{27}N_5O_3S$: 429.55.

5.6.8. Synthesis of 4-(6-(Butylamino)imidazo[1,2-b]pyridazin-3-yl)-N-methylbenzamide

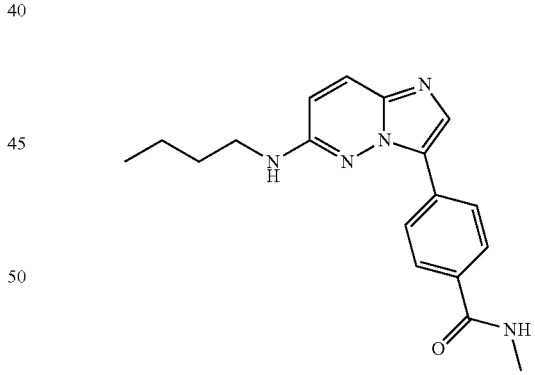

To a mixture of 3-bromo-N-butylimidazo[1,2-b]pyridazin-6-amine (100 mg, 0.37 mmol), (4-(methylcarbamoyl)phenyl)boronic acid (166 mg, 0.93 mmol), [1,1'-bis(diphenylphosphino)ferrocene]dichloropalladium(II) (15 mg, 0.02 mmol) and potassium phosphate (236 mg, 1.11 mmol) was added 1:1 Dimethoxyethane/water (5 mL). The resulting mixture was heated at 160° C. (microwave) for 6 min. The reaction was then filtered and diluted with a mixture of 1:1:1 methanol/water/acetonitrile, and then filtered again. The filtration was finally purified by preparative HPLC (acidic) to afford 4-(6-(butylamino)imidazo[1,2-b]pyridazin-3-yl)-N-methylbenzamide (32.1 mg, 27% yield) as a white solid: $^1$H NMR (METHANOL-$d_4$) δ: 8.21-8.41 (m, 2H), 7.86-7.94 (m, 3H), 7.64 (d, J=9.6 Hz, 1H), 6.74 (d, J=9.6 Hz, 1H), 3.35-3.44 (m, 5H), 2.97 (s, 3H), 1.68-1.77 (m, 2H), 1.46-1.56 (m, 2H), 1.03 (t, J=7.3 Hz, 3H); LRMS (ESI) m/e 324.4 [(M+H)$^+$, calcd for $C_{18}H_{22}N_5O$ 324.2].

5.6.9. Synthesis of [3-(4-Aminomethyl-phenyl)-imidazo[1,2-b]pyridazin-6-yl]-(tetrahydro-pyran-4-yl)-amine

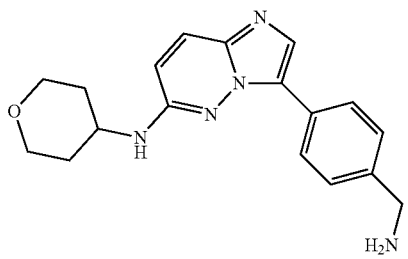 [SMILES: NCc1ccc(-c2cnc3ccc(NC4CCOCC4)nn23)cc1]

Part A. Tetrahydro-2H-pyran-4-amine

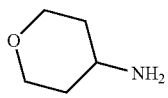

A mixture of dihydro-2H-pyran-4(3H)-one (2.3 mL, 25 mmol) and methanol (54 mL) was treated with ammonium formate (15.8 g, 250 mmol) and $H_2O$ (6 mL). The resulting mixture was maintained at RT with vigorous stirring until it became homogeneous. The mixture was then treated with palladium on carbon (2.5 g), and maintained at RT overnight. The mixture was filtered and concentrated to remove the volatile organics, then the aqueous later was exhaustively extracted with ethyl acetate. The combined organics were dried (MgSO$_4$), filtered and concentrated to afford tetrahydro-2H-pyran-4-amine (2.2 g, 88%) as an oil: $^1$H NMR (400 MHz, MeOD-$d_4$) δ 3.89-3.99 (m, 2H), 3.35-3.51 (m, 2H), 2.81-2.95 (m, 1H), 1.75-1.90 (m, 2H), 1.31-1.48 (m, 2H);

Part B. 3-bromo-N-(tetrahydro-pyran-4-yl)imidazo[1,2-b]pyridazin-6-amine

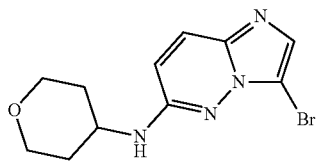 [SMILES: Brc1cnc2ccc(NC3CCOCC3)nn12]

A mixture of 3-bromo-6-fluoroimidazo[1,2-b]pyridazine (1.4 g, 6.6 mmol), tetrahydro-2H-pyran-4-amine (1.0 g, 9.9 mmol), cesium carbonate (4.3 g, 13 mmol), and DMF (10 mL) was maintained at 40° C. for 16 h, then cooled to RT and partitioned between ethyl acetate (100 mL) and $H_2O$ (100 mL). The layers were separated, and the aqueous layer was extracted with ethyl acetate (4×40 mL). The combined organic layers were washed with $H_2O$ (100 mL) and brine (100 mL), then dried (MgSO$_4$), filtered and concentrated to afford a residue that was purified by flash chromatography (SiO$_2$) to afford 3-bromo-N-(tetrahydro-pyran-4-yl)imidazo[1,2-b]pyridazin-6-amine (1.6 g, 80%) as a light yellow solid: $^1$H NMR (400 MHz, MeOD-$d_4$) δ 7.58 (d, J=9.9 Hz, 1H), 7.42 (s, 2H), 6.71 (d, J=9.9 Hz, 1H), 3.95-4.08 (m, 3H), 3.60 (td, J=11.5, 2.3 Hz, 2H), 2.16 (d, J=11.5 Hz, 2H), 1.53-1.69 (m, 2H); LCMS (ESI) m/e 297.1 [(M+H)$^+$, calcd for $C_{11}H_{13}BrN_4O$ 297.0].

Part C. [3-(4-Aminomethyl-phenyl)-imidazo[1,2-b]pyridazin-6-yl]-(tetrahydro-pyran-4-yl)-amine

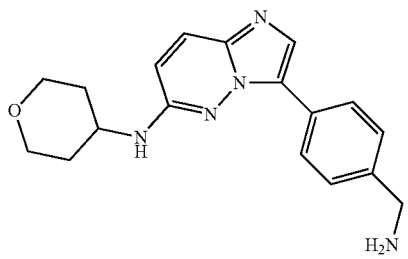

A mixture of 3-bromo-N-(tetrahydro-pyran-4-yl)imidazo[1,2-b]pyridazin-6-amine (100 mg, 0.34 mmol), 4-(aminomethyl)phenylboronic acid hydrochloride (160 mg, 0.84 mmol), dichloro[1,1'-bis(diphenylphosphino)ferrocene]palladium (II) dichloromethane adduct (25 mg, 0.034 mmol), potassium phosphate (360 mg, 1.7 mmol), DME (1.5 mL) and $H_2O$ (0.5 mL) was heated in a sealed conical vessel at 160° C. for 360 s by microwave irradiation. The organic layer was separated and the aqueous layer was extracted with ethyl acetate (2 mL). The combined organic layers were concentrated under reduced pressure to afford an oil that was purified by reverse phase HPLC to afford [3-(4-aminomethyl-phenyl)-imidazo[1,2-b]pyridazin-6-yl]-(tetrahydro-pyran-4-yl)-amine (20.5 mg, 20%) as a yellow solid: $^1$H NMR (400 MHz, MeOD) δ 8.24 (d, J=8.4 Hz, 2H), 7.82 (s, 1H), 7.55 (d, J=8.4 Hz, 1H), 6.74 (d, J=10 Hz, 1H), 4.13 (s, 2H), 4.06-3.92 (m, 3H), 3.61 (t, J=11.2 Hz, 2H), 2.15 (d, J=12.8 Hz, 2H), 1.65 (qd, J=11.2, 4.4 Hz, 2H); LCMS (ESI) m/e 324.2 [(M+H)$^+$, calcd for $C_{18}H_{22}N_5O$ 324.2].

5.6.10. Synthesis of [3-(4-Aminomethyl-phenyl)-imidazo[1,2-b]pyridazin-6-yl]-cyclohexylamine

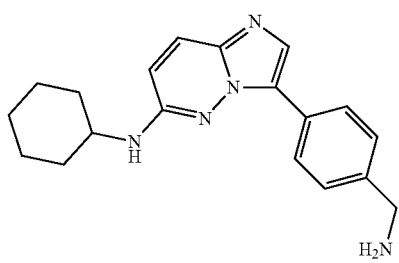 [SMILES: NCc1ccc(-c2cnc3ccc(NC4CCCCC4)nn23)cc1]

Part A. 3-bromo-N-cyclohexylimidazo[1,2-b]pyridazin-6-amine

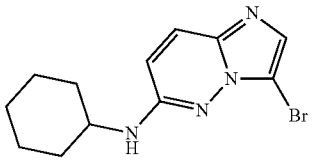 [SMILES: Brc1cnc2ccc(NC3CCCCC3)nn12]

A mixture of 3-bromo-6-fluoroimidazo[1,2-b]pyridazine (1.1 g, 5.0 mmol), cyclohexylamine (0.86 mL, 7.5 mmol), cesium carbonate (3.3 g, 10 mmol), and DMF (10 mL) was maintained at 40° C. for 6 h, then cooled to RT and partitioned between ethyl acetate (100 mL) and H$_2$O (100 mL). The layers were separated, and the aqueous layer was extracted with ethyl acetate (4×40 mL). The combined organic layers were washed with H$_2$O (100 mL) and brine (100 mL), then dried (MgSO$_4$), filtered and concentrated to afford a residue that was purified by flash chromatography (SiO$_2$) to afford 3-bromo-N-(tetrahydro-pyran-4-yl)imidazo[1,2-b]pyridazin-6-amine (1.1 g, 73%) as a light yellow solid: $^1$H NMR (400 MHz, MeOD) δ 7.53 (d, J=9.6 Hz, 1H), 7.39 (s, 1H), 6.68 (d, J=9.9 Hz, 1H), 3.68-3.87 (m, 1H), 2.14 (dd, J=12.6, 3.3 Hz, 2H), 1.82 (dt, J=13.3, 3.7 Hz, 2H), 1.70 (dt, J=12.8, 3.7 Hz, 1H), 1.38-1.52 (m, 2H), 1.23-1.38 (m, 3H); LCMS (ESI) m/e 295.2 [(M+H)$^+$, calcd for C$_{12}$H$_{15}$BrN$_4$ 295.1].

Part B. [3-(4-Aminomethyl-phenyl)-imidazo[1,2-b]pyridazin-6-yl]-cyclohexylamine

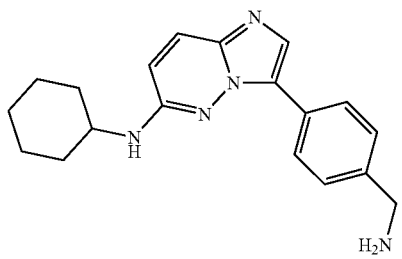 [SMILES: NCc1ccc(-c2cnc3ccc(NC4CCCCC4)nn23)cc1]

A mixture of 3-bromo-N-cyclohexylimidazo[1,2-b]pyridazin-6-amine (100 mg, 0.34 mmol), 4-(aminomethyl)phenylboronic acid hydrochloride (160 mg, 0.84 mmol), dichloro[1,1'-bis(diphenylphosphino)ferrocene]palladium (II) dichloromethane adduct (25 mg, 0.034 mmol), potassium phosphate (360 mg, 1.7 mmol), DME (1.5 mL) and H$_2$O (0.5 mL) was heated in a sealed conical vessel at 160° C. for 360 s by microwave irradiation. The organic layer was separated and the aqueous layer was extracted with ethyl acetate (2 mL). The combined organic layers were concentrated under reduced pressure to afford an oil that was purified by reverse phase HPLC to afford [3-(4-aminomethyl-phenyl)-imidazo[1,2-b]pyridazin-6-yl]-cyclohexylamine (48 mg, 44%) as a white solid: $^1$H NMR (400 MHz, MeOD-d$_4$) δ ppm 8.29 (d, J=8.6 Hz, 2H), 7.82 (s, 1H), 7.63 (d, J=9.6 Hz, 1H), 7.54 (d, J=8.6 Hz, 2H), 6.72 (d, J=9.6 Hz, 1H), 4.13 (s, 2H), 3.70-3.78 (m, 1H), 2.19 (d, J=9.1 Hz, 2H), 1.83-1.93 (m, 2H), 1.70-1.76 (m, 1H), 1.42-1.54 (m, 2H), 1.29-1.40 (m, 3H); LCMS (ESI) m/e 322.2 [(M+H)$^+$, calcd for C$_{19}$H$_{24}$N$_5$ 322.2].

5.6.11. Synthesis of 1-{5-[6-(3-Methylamino-propylamino)-imidazo[1,2-b]pyridazin-3-yl]-thiophen-2-yl}-ethanone

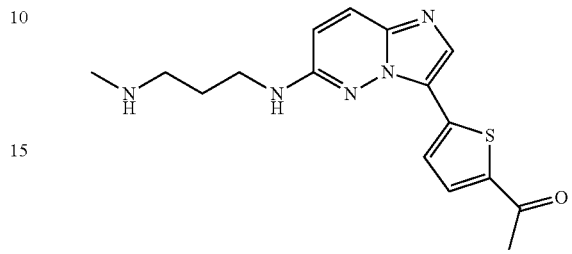

Prepared as in example 5.6.3 from 1-[5-(6-fluoro-imidazo[1,2-b]pyridazine-3-yl)-thiophen-2-yl]-ethanone (50 mg, 0.2 mmol) and N-(3-aminopropyl)-N-methylcarbamic acid tert-butyl ester [150349-36-3] (72 mg, 0.4 mmol) and deprotected with anhydrous HCl in methanol. Purification by preparative RP-HPLC provided 1-{5-[6-(3-methylamino-propylamino)-imidazo[1,2-b]pyridazin-3-yl]-thiophen-2-yl}-ethanone diacetate as a yellow solid. $^1$H NMR (400 MHz, METHANOL-d$_4$) δ ppm 1.92-1.96 (m, 5H) 2.24 (t, J=7.45 Hz, 1H) 2.62 (s, 2H) 2.80 (s, 2H) 3.23-3.31 (m, 2H) 3.61 (t, J=7.33 Hz, 1H) 6.79 (d, J=9.60 Hz, 1H) 7.70-7.74 (m, 1H) 7.92 (d, J=4.04 Hz, 1H) 8.06 (br. s., 1H). LRMS (ESI) m/z 330.1 [(M+H)]$^+$, calc'd for C$_{16}$H$_{19}$N$_5$OS: 329.43.

5.6.12. Synthesis of 3-(3-(Aminomethyl)phenyl)-N-butylimidazo[1,2-b]pyridazin-6-amine

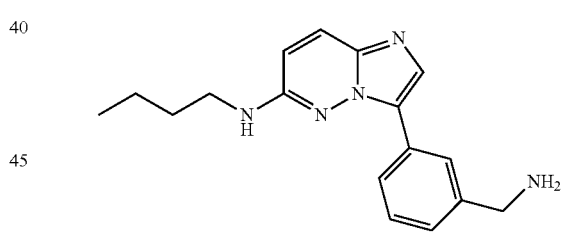

To a mixture of 3-bromo-N-butylimidazo[1,2-b]pyridazin-6-amine (62 mg, 0.23 mmol), (3-(aminomethyl)phenyl)boronic acid (108 mg, 0.58 mmol), [1,1'-bis(diphenylphosphino)ferrocene]dichloropalladium(II) (8.4 mg, 0.01 mmol) and potassium phosphate (146 mg, 0.69 mmol) was added 1:1 Dimethoxyethane/water (3 mL). The resulting mixture was heated at 160° C. (microwave) for 6 min. The reaction was then filtered and diluted with a mixture of 1:1:1 methanol/water/acetonitrile, and then filtered again. The filtration was finally purified by preparative HPLC (acidic) to afford 3-(3-(aminomethyl)phenyl)-N-butylimidazo[1,2-b]pyridazin-6-amine mono trifluoroacetic acid salt (24.1 mg, 25% yield) as a white solid: $^1$H NMR (METHANOL-d$_4$) δ: 7.53 (d, J=8.1 Hz, 1H), 7.34 (s, 1H), 7.00 (s, 1H), 6.83 (d, J=9.6 Hz, 1H), 6.73 (t, J=7.8 Hz, 1H), 6.61 (d, J=7.6 Hz, 1H), 5.93 (d, J=9.6 Hz, 1H), 3.33 (s, 2H), 2.59 (t, J=7.1 Hz, 2H), 1.12 (s, 3H), 0.87-0.96 (m, 2H), 0.64-0.74 (m, 2H), 0.20 (t, J=7.3 Hz, 3H); LRMS (ESI) m/e 296.4 [(M+H)$^+$, calcd for C$_{17}$H$_{22}$N$_5$ 296.2].

5.6.13. Synthesis of N-Butyl-3-(4-(((2-methoxy-ethyl)amino)methyl)phenyl)imidazo[1,2-b]pyridazin-6-amine

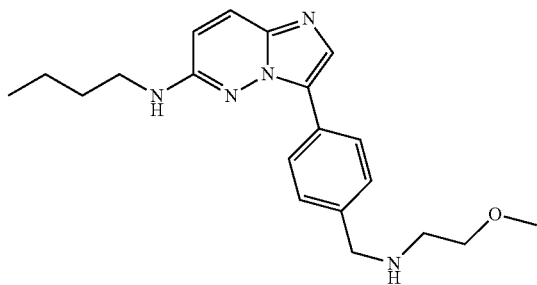 [SMILES: CCCCNc1ccc2ncc(-c3ccc(CNCCOC)cc3)n2n1]

Part A. 4-(6-(butylamino)imidazo[1,2-b]pyridazin-3-yl)benzaldehyde

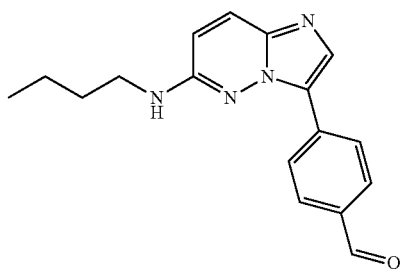 [SMILES: CCCCNc1ccc2ncc(-c3ccc(C=O)cc3)n2n1]

To a mixture of 3-bromo-N-butylimidazo[1,2-b]pyridazin-6-amine (100 mg, 0.37 mmol), (4-formylphenyl)boronic acid (139 mg, 0.93 mmol), [1,1'-bis(diphenylphosphino)ferrocene]dichloropalladium(II) (13.5 mg, 0.02 mmol) and potassium phosphate (236 mg, 1.11 mmol) was added 3:1 dimethoxyethane/water (2 mL). The resulting mixture was heated at 160° C. (microwave) for 6 min. After the reaction was cooled down and separated into two layers, the dark upper layer was then filtered and diluted with a mixture of 1:1:1 methanol/water/acetonitrile, and then filtered again. The filtration was finally purified by preparative HPLC (neutral) to afford 4-(6-(butylamino)imidazo[1,2-b]pyridazin-3-yl)benzaldehyde (78 mg, 72% yield) as a yellow solid: $^1$H NMR (METHANOL-$d_4$) δ: 10.01 (s, 1H), 8.47 (d, J=8.6 Hz, 2H), 7.98-8.03 (m, 2H), 7.97 (s, 1H), 7.66 (d, J=9.6 Hz, 1H), 6.77 (d, J=9.6 Hz, 1H), 3.42 (t, J=7.1 Hz, 2H), 1.74 (t, J=7.2 Hz, 2H), 1.52 (d, J=7.8 Hz, 2H), 1.03 (t, J=7.5 Hz, 4H); LRMS (ESI) m/e 295.2 [(M+H)$^+$, calcd for $C_{17}H_{19}N_4O$ 295.2].

Part B. N-butyl-3-(4-(((2-methoxyethyl)amino)methyl)phenyl)imidazo[1,2-b]pyridazin-6-amine

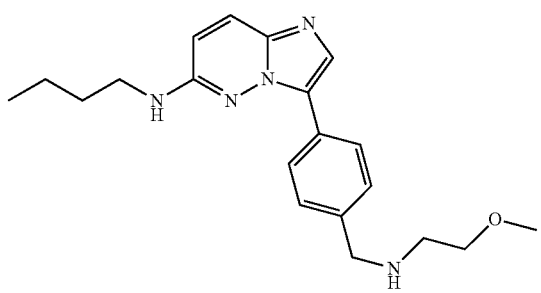 [SMILES: CCCCNc1ccc2ncc(-c3ccc(CNCCOC)cc3)n2n1]

To the solution of 4-(6-(butylamino)imidazo[1,2-b]pyridazin-3-yl)benzaldehyde (74 mg, 0.25 mmol) in 2 mL dichloroethene was added 2-methoxyethanamine (21 mg, 0.28 mmol) and allowed to stir at room temperature for 5 m. Sodium triacetoxyborohydride (106 mg, 0.5 mmol) was added and the reaction was stirred at room temperature 18 h. Then the reaction was quenched with saturated sodium bicarbonate solution and extracted with dichloromethane three times. The combined organic layers were dried over magnesium sulfate, filtered and concentrated. The crude product was finally purified by preparative HPLC (acidic) to afford N-butyl-3-(4-(((2-methoxyethyl)amino)methyl)phenyl)imidazo[1,2-b]pyridazin-6-amine mono trifluoroacetic acid salt (55.8 mg, 48% yield) as a white solid: $^1$H NMR (METHANOL-$d_4$) δ: 8.23-8.28 (m, 3H), 7.96 (d, J=9.9 Hz, 1H), 7.71 (d, J=8.3 Hz, 2H), 7.24 (d, J=9.9 Hz, 1H), 4.35 (s, 2H), 3.68-3.73 (m, 2H), 3.35-3.47 (m, 5H), 3.26-3.31 (m, 2H), 1.67-1.76 (m, 2H), 1.44-1.54 (m, 2H), 1.01 (t, J=7.3 Hz, 3H); LRMS (ESI) m/e 354.5 [(M+H)$^+$, calcd for $C_{20}H_{28}N_5$ 354.2].

5.6.14. Synthesis of 1-{5-[6-(2-Methyl-butylamino)-imidazo[1,2-b]-pyridazin-3-yl]-thiophen-2-yl}-ethanone

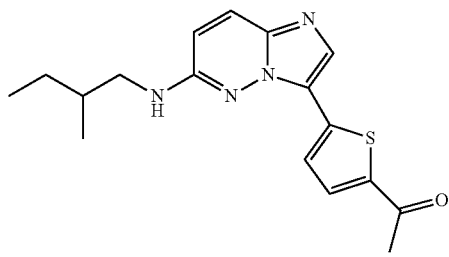 [SMILES: CCC(C)CNc1ccc2ncc(-c3ccc(C(C)=O)s3)n2n1]

Prepared as in example 5.6.3 from 1-[5-(6-fluoro-imidazo[1,2-b]pyridazine-3-yl)-thiophen-2-yl]-ethanone (50 mg, 0.2 mmol) and racemic 2-methylbutylamine [96-15-1] (42 mg, 0.5 mmol). Purification by preparative RP-HPLC provided 1-{5-[6-(2-methyl-butylamino)-imidazo[1,2-b]pyridazin-3-yl]-thiophen-2-yl}-ethanone as a yellow solid. $^1$H NMR (400 MHz, CHLOROFORM-d) δ ppm 0.88-1.01 (m, 5H) 1.19-1.30 (m, 1H) 1.50-1.61 (m, 4H) 1.89 (dq, J=13.29, 6.74 Hz, 1H) 2.54 (s, 2H) 3.26-3.33 (m, 1H) 3.40-3.49 (m, 1H) 4.57 (t, J=5.73 Hz, 1H) 6.43-6.47 (m, 1H) 7.21 (s, 1H) 7.56-7.58 (m, 1H) 7.61-7.67 (m, 2H) 7.90 (s, 1H). LRMS (ESI) m/z 329.1 [(M+H)]$^+$, calc'd for $C_{17}H_{20}N_4OS$: 328.44.

5.6.15. Synthesis of 1-{5-[6-(3-Fluoro-propylamino)-imidazo[1,2-b]pyridazin-3-yl]-thiophen-2-yl}-ethanone

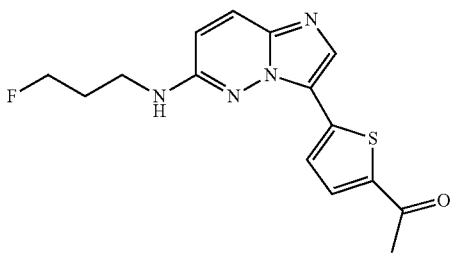 [SMILES: CC(=O)c1ccc(-c2cnc3ccc(NCCCF)nn23)s1]

Prepared as in example 5.6.3 from 1-[5-(6-fluoro-imidazo[1,2-b]pyridazine-3-yl)-thiophen-2-yl]-ethanone (50 mg, 0.2 mmol) and 3-fluoropropylamine hydrochloride [64068-31-1] (43 mg, 0.4 mmol). $^1$H NMR (400 MHz, CHLOROFORM-d) δ ppm 1.52 (s, 6H) 2.12-2.25 (m, 1H) 2.54 (s, 1H) 3.66-3.72 (m, 1H) 4.72 (t, J=5.51 Hz, 1H) 7.21 (s, 2H) 7.63-7.67 (m, 1H). LRMS (ESI) m/z 319.1 [(M+H)]$^+$, calc'd for $C_{15}H_{15}FN_4OS$: 318.38.

5.6.16. Synthesis of N-Butyl-3-(4-(pyrrolidin-1-ylmethyl)phenyl)imidazo[1,2-b]pyridazin-6-amine

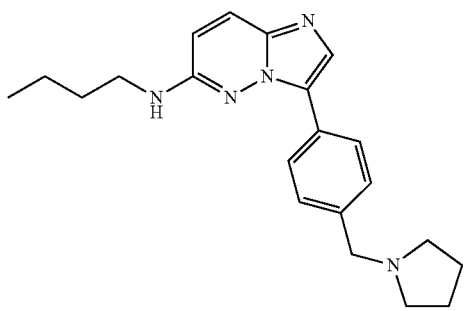 [SMILES: CCCCNc1ccc2ncc(-c3ccc(CN4CCCC4)cc3)n2n1]

To the solution of 4-(6-(butylamino)imidazo[1,2-b]pyridazin-3-yl)benzaldehyde (58 mg, 0.20 mmol) in 1.5 mL dichloroethene was added pyrrolidine (15.4 mg, 0.22 mmol) and allowed to stir at room temperature for 5 m. Sodium triacetoxyborohydride (83.5 mg, 0.4 mmol) was added and the reaction was stirred at room temperature 18 h. Then the reaction was quenched with saturated sodium bicarbonate solution and extracted with dichloromethane three times. The combined organic layers were dried over magnesium sulfate, filtered and concentrated. The crude product was finally purified by preparative HPLC (acidic) to afford N-butyl-3-(4-(pyrrolidin-1-ylmethyl)phenyl)imidazo[1,2-b]pyridazin-6-amine mono trifluoroacetic acid salt (32.2.8 mg, 35% yield) as a white solid: $^1$H NMR (METHANOL-d$_4$) δ: 8.22-8.33 (m, 3H), 7.97 (d, J=9.9 Hz, 1H), 7.73 (d, J=8.3 Hz, 2H), 7.25 (d, J=9.9 Hz, 1H), 4.49 (s, 2H), 3.57 (br. s., 2H), 3.41 (t, J=7.1 Hz, 2H), 3.26 (br. s., 2H), 2.22 (br. s., 2H), 2.07 (br. s., 2H), 1.65-1.82 (m, 2H), 1.39-1.59 (m, 2H), 1.00 (t, J=7.5 Hz, 3H); LRMS (ESI) m/e 350.5 [(M+H)$^+$, calcd for $C_{21}H_{28}N_5$ 350.2].

5.6.17. Synthesis of {3-[3-(4-Aminomethyl-phenyl)-imidazo[1,2-b]pyridazin-6-ylamino]-propyl}-methyl-carbamic acid tert-butyl ester

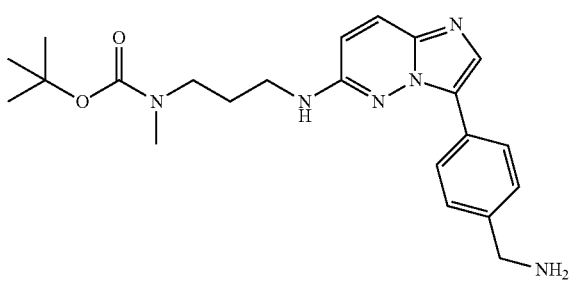 [SMILES: CN(CCCNc1ccc2ncc(-c3ccc(CN)cc3)n2n1)C(=O)OC(C)(C)C]

Part A. 3-Bromo-imidazo[1,2-b]pyridazin-6-one

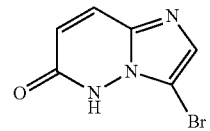

To a solution of 3-bromo-6-chloro-imidazo[1,2-b]pyridazine [13526-66-4] (425.7 mg, 1.8 mmol) in 1,2-dimethoxyethane (9 mL) was added a solution of potassium hydroxide [1310-58-3] (185.4 mg, 2.8 mmol) in water (9.0 mL) and the stirred resultant solution heated to reflux under N$_2$ for 3d, cooled and partitioned between ethyl acetate and water. The water phase was evaporated to dryness, taken up in methanol, filtered, and evaporated to yield 3-bromo-imidazo[1,2-b]pyridazin-6-one as 340 mg of yellow solid. LRMS (ESI) m/z 214.0/216.0 [(M+H)]$^+$, calc'd for $C_6H_4BrN_3O_3$: 214.02.

Part B. [3-(3-Bromo-imidazo[1,2-b]pyridazin-6-ylamino)-propyl]-methyl-carbamic acid tert-butyl ester

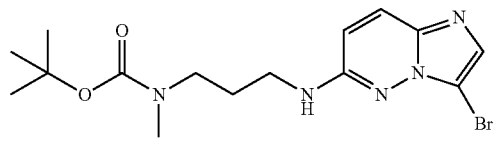 [SMILES: CN(CCCNc1ccc2ncc(Br)n2n1)C(=O)OC(C)(C)C]

Acetonitrile (16.0 mL) was added to a mixture of 3-bromo-imidazo[1,2-b]pyridazin-6-one (344.3 mg, 1.6 mmol) and (benzotriazol-1-yloxy)tris(dimethylamino)phosphonium hexafluorophosphate (BOP reagent) [56602-33-6], the mixture allowed to stir to effect dissolution. A solution of (3-amino-propyl)-methyl-carbamic acid tert-butyl ester [150349-36-3] (0.8 g, 3.98 mmol) and 1,8-diazabicyclo[5.4.0]undec-7-ene (DBU) [6674-22-2] (2.4 mL, 2.4 mmol) in DMF (4.0 mL) was added and the reaction allowed to stir at ambient temperature for 3d. The reaction solution was partitioned between brine and ethyl acetate, dried (MgSO$_4$), and flash chromatographed (silica gel, eluted with 10% (v/v) 2-propanol/ethyl acetate) to provide [3-(3-bromo-imidazo[1,2-b]pyridazin-6-ylamino)-propyl]-methyl-carbamic acid tert-butyl ester as 0.4 g of clear yellow oil. LRMS (ESI) m/z 384.1/386.1 [(M+H)]$^+$, calc'd for $C_{16}H_{22}BrN_6O_2$: 384.28.

Part C. {3-[3-(4-Aminomethyl-phenyl)-imidazo[1,2-b]pyridazin-6-ylamino]-propyl}-methyl-carbamic acid tert-butyl ester To a mixture of [3-(3-bromo-imidazo[1,2-b]pyridazin-6-ylamino)-propyl]-methyl-carbamic acid tert-butyl ester (381.0 mg, 1.0 mmol), 4-aminomethylphenylboronic acid hydrochloride [75705-21-4] (222.8 mg, 1.2 mmol), potassium phosphate tribasic monohydrate [27176-10-9] (632.4 mg, 3.0 mmol), and [1,1'-bis(diphenylphosphino)ferrocene]dichloropalladium(II), complex with dichloromethane [95464-05-4] (164.8 mg, 0.2 mmol) contained in a 50 mL round bottomed flask was added a solution of 30% (v/v) water in 1,2-dimethoxyethane (25 mL) and a magnetic stir bar. The reaction pot was fitted to a reflux condenser, lowered into an ambient temperature oil bath, and the system taken through 10 evacuation/N₂ blanket cycles while being rapidly stirred. The rapidly stirred, N₂ blanketed, reaction was heated to an oil bath temperature of 85° C. for 17 h then cooled and filtered through tightly packed filter aid and the filtrate transferred to a separatory funnel and partitioned between brine and ethyl acetate. The phase separated extract was dried (MgSO₄) and flash chromatographed (silica gel, eluted with 1% conc. NH₄OH in 10% (v/v) methanol/ethyl acetate) to provide 81.2 mg of brown oil. This product was further purified by preparative RP-HPLC to isolate {3-[3-(4-aminomethyl-phenyl)-imidazo[1,2-b]pyridazin-6-ylamino]-propyl}-methyl-carbamic acid tert-butyl ester as 4.6 mg of white solid. ¹H NMR (400 MHz, METHANOL-d₄) δ ppm 1.89-2.00 (m, 10H) 2.87 (br. s., 3H) 3.41 (q, J=7.16 Hz, 5H) 4.14 (s, 2H) 6.74 (d, J=9.60 Hz, 1H) 7.56 (m, J=8.34 Hz, 2H) 7.66 (d, J=9.60 Hz, 1H) 7.81 (s, 1H) 8.25 (m, J=8.34 Hz, 2H). LRMS (ESI) m/z 411.1 [(M+H)]⁺, calc'd for C₂₂H₃₀N₆O₂: 410.52.

5.6.18. Synthesis of [3-(4-Aminomethyl-phenyl)-imidazo[1,2-b]pyridazin-6-yl]-(3-phenyl-propyl)-amine

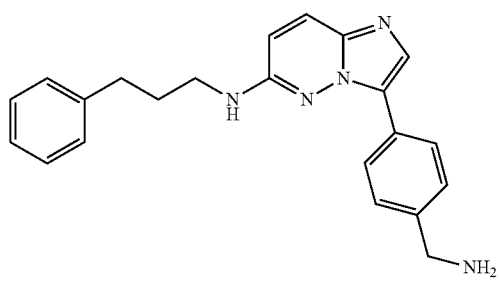 [SMILES: NCc1ccc(-c2cnc3ccc(NCCCc4ccccc4)nn23)cc1]

Part A. (3-Bromo-imidazo[1,2-b]pyridazin-6-yl)-(3-phenyl-propyl)-amine

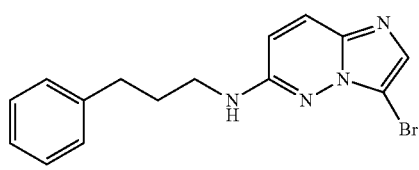 [SMILES: Brc1cnc2ccc(NCCCc3ccccc3)nn12]

A mixture of 3-bromo-6-chloro-imidazo[1,2-b]pyridazine (232 mg, 1 mmol) and phenylpropyl amine (1 ml, 7 mmol) in n-PrOH (1 mL) was heated in a microwave at 150° C. for 20 min. Additional phenylpropyl amine (0.5 ml) was added and reaction mixture heated for additional 20 min. then 30 min. in a microwave. The reaction mixture was concentrated and the residue was subjected to ISCO (40 g column, DCM 3 min. then 0-10% MeOH in DCM over 30 min.) to gave the product (380 mg ~90% pure and was used directly for next step).

Part B. [3-(4-Aminomethyl-phenyl)-imidazo[1,2-b]pyridazin-6-yl]-(3-phenyl-propyl)-amine A mixture of (3-bromo-imidazo[1,2-b]pyridazin-6-yl)-(3-phenyl-propyl)-amine (100 mg, 0.3 mmol), (4-aminomethylphenyl)boronic acid hydrochloride (67 mg, 0.36 mmol), K₂CO₃ (124 mg, 0.9 mmol) and dichlorobis(triphenylphosphine)palladium(II) (11 mg, 0.015 mmol) in MeCN/water (3.6 ml/0.9 ml) was heated in a microwave at 150° C. for 20 min. The reaction mixture was diluted with MeOH (2 ml) and filtered. The filtrate was subjected to preparative HPLC to give the titled compound as AcOH salt (29.9 mg). ¹H NMR (400 MHz, METHANOL-d₄) δ ppm 1.93 (s, 3H) 1.99-2.09 (m, 2H) 2.70-2.80 (m, 2H) 3.41 (t, J=6.95 Hz, 2H) 4.14 (s, 2H) 6.74 (d, J=9.60 Hz, 1H) 7.15-7.29 (m, 5H) 7.53 (d, J=8.34 Hz, 2H) 7.64 (d, J=9.60 Hz, 1H) 7.80 (s, 1H) 8.24 (d, J=8.59 Hz, 2H).

5.6.19. Synthesis of Pentyl-[3-(4-pyrrolidin-2-yl-phenyl)-imidazo[1,2-b]pyridazin-6-yl]-amine

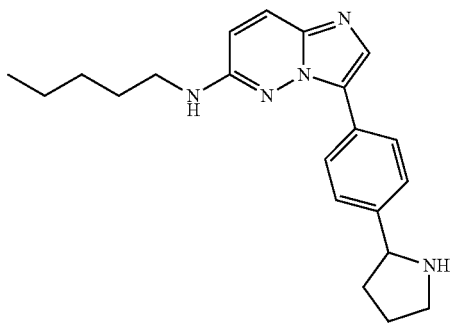 [SMILES: CCCCCNc1ccc2ncc(-c3ccc(C4CCCN4)cc3)n2n1]

Part A. Tert-butyl 2-(4-(6-(pentylamino)imidazo[1,2-b]pyridazin-3-yl)phenyl)pyrrolidine-1-carboxylate

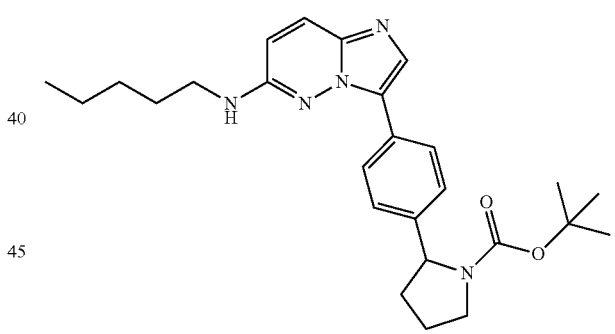

To 150 mg (0.530 mmol) of the 3-bromo-N-pentylimidazo[1,2-b]pyridazin-6-amine was added the tert-butyl 2-(4-(4,4,5,5-tetramethyl-1,3,2-dioxaborolan-2-yl)phenyl)pyrrolidine-1-carboxylate (237 mg, 0.636 mmol), K₃PO₄ (225 mg, 1.060 mmol), PdCl₂(PPh₃)₃ (37 mg, 0.053 mmol), 3 mL of DME and 1 mL of water. This mixture was microwaved for 0.5 hr at 140° C. After cooling it was diluted with 25 mL of EtOAC, and washed with about 20 mL of brine. The organic layer was dried over MgSO₄, and concentrated. The crude mixture was purified on a 12 g silica gel column (ISCO), eluting with 15-100% EtOAc/Hex to give 159 mg (67%) of the desired product.

Part B. Pentyl-[3-(4-pyrrolidin-2-yl-phenyl)-imidazo[1,2-b]pyridazin-6-yl]-amine To 45 mg of this compound, dissolved in 10 mL MeOH at 0° C. was added 1.0 ml (excess) AcCl (slowly) and the resulting mixture stirred at 0° C. for 4 hr. It was then concentrated to dryness to obtain 32 mg (100% yield) of an HCl salt of the desired compound. $^1$H NMR (400 MHz, METHANOL-d$_4$) δ ppm 0.91-0.99 (m, 3H) 1.37-1.52 (m, 4H) 1.74 (quin, J=7.01 Hz, 2H) 2.22-2.40 (m, 3H) 2.50-2.66 (m, 1H) 3.36-3.42 (m, 2H) 3.47-3.59 (m, 2H) 4.75-4.81 (m, 1H) 7.30 (d, J=9.85 Hz, 1H) 7.75 (d, J=8.08 Hz, 2H) 8.00 (d, J=9.85 Hz, 1H) 8.22-8.35 (m, 3H); LRMS (ESI) m/e 350.0 [(M+H)$^+$, calcd for C$_{21}$H$_{27}$N$_5$ 349.0].

5.6.20. Synthesis of Butyl-[3-(1H-pyrazol-4-yl)-imidazo[1,2-b]pyridazin-6-yl]amine

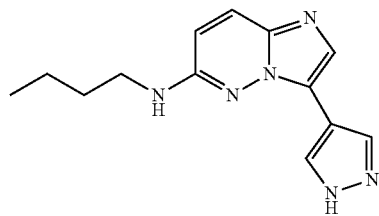 [SMILES: CCCCNc1ccc2ncc(-c3cn[nH]c3)n2n1]

A mixture of 3-bromo-N-butylimidazo[1,2-b]pyridazin-6-amine (100 mg, 0.37 mmol), (1H-pyrazol-4-yl)boronic acid (90 mg, 0.45 mmol), dichloro-bis(triphenylphosphino) palladium (II) (15 mg, 0.021 mmol), potassium phosphate (80 mg, 0.56 mmol), acetonitrile (1.5 mL) and H$_2$O (0.5 mL) was heated in a sealed conical vessel at 160° C. for 1000 s by microwave irradiation. The organic layer was separated and the aqueous layer was extracted with ethyl acetate (2 mL). The combined organic layers were concentrated under reduced pressure to afford an oil that was purified by reverse phase HPLC to afford butyl-[3-(1H-pyrazol-4-yl)-imidazo[1,2-b]pyridazin-6-yl]-amine (60 mg, 62%) as a white solid: $^1$H NMR (400 MHz, METHANOL-d$_4$) δ ppm 7.67 (s, 1H), 7.59 (d, J=9.6 Hz, 1H), 6.67 (d, J=9.6 Hz, 1H), 3.44 (t, J=7.1 Hz, 1H), 1.70-1.80 (m, 1H), 1.46-1.59 (m, 1H), 1.03 (t, J=7.3 Hz, 1H); LCMS (ESI) m/e 257.3 [(M+H)$^+$, calcd for C$_{13}$H$_{17}$N$_6$ 257.1].

5.6.21. Synthesis of Butyl-{3-[4-(tert-butylamino-methyl)-3-fluoro-phenyl]-imidazo[1,2-b]pyridazin-6-yl}-amine

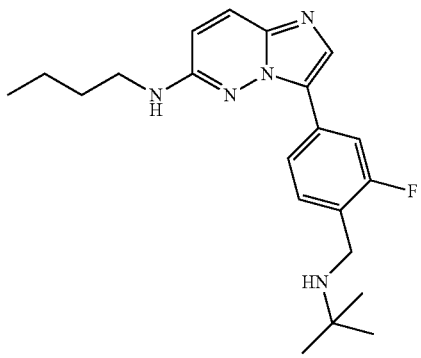 [SMILES: CCCCNc1ccc2ncc(-c3ccc(CNC(C)(C)C)c(F)c3)n2n1]

Part A. 4-(6-Butylamino-imidazo[1,2-b]pyridazin-3-yl)-2-fluorobenzaldehyde

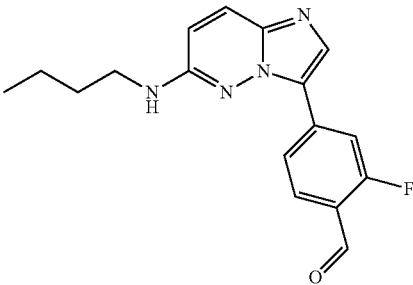 [SMILES: CCCCNc1ccc2ncc(-c3ccc(C=O)c(F)c3)n2n1]

A mixture of 3-bromo-N-butylimidazo[1,2-b]pyridazin-6-amine (300 mg, 1.1 mmol), 3-fluoro-4-formylphenylboronic acid (230 mg, 1.3 mmol), dichloro-bis(triphenylphosphino) palladium (II) (40 mg, 0.055 mmol), potassium carbonate (230 mg, 1.7 mmol), acetonitrile (1.5 mL) and H$_2$O (0.5 mL) was heated in a sealed conical vessel at 160° C. for 1000 s by microwave irradiation. The organic layer was separated and the aqueous layer was extracted with ethyl acetate (2 mL). The combined organic layers were concentrated under reduced pressure to afford an oil that was purified by reverse phase HPLC to afford 4-(6-butylamino-imidazo[1,2-b]pyridazin-3-yl)-2-fluorobenzaldehyde (240 mg, 68%) as a yellow solid: $^1$H NMR (400 MHz, CHLOROFORM-d) δ ppm 10.39 (s, 1H), 8.28 (dd, J=12.9, 1.5 Hz, 1H), 7.91-8.01 (m, 3H), 7.73 (d, J=9.6 Hz, 1H), 6.54 (d, J=9.6 Hz, 1H), 3.48 (td, J=7.2, 5.8 Hz, 2H), 1.69-1.80 (m, 2H), 1.46-1.57 (m, 2H), 1.03 (t, J=7.5 Hz, 3H); LCMS (ESI) m/e 313.2 [(M+H)$^+$, calcd for C$_{17}$H$_{18}$FN$_4$O 313.1].

Part B. Butyl-{3-[4-(tert-butylamino-methyl)-3-fluoro-phenyl]-imidazo[1,2-b]pyridazin-6-yl}-amine A mixture of 4-(6-butylamino-imidazo[1,2-b]pyridazin-3-yl)-2-fluoro-benzaldehyde (30 mg, 0.10 mmol) and dichloroethane (DCE, 1 mL) was treated with tert-butyl amine (0.011 mL, 0.11 mmol) and the resulting reaction mixture was maintained at RT for 20 min. The reaction was then treated with sodium triacetoxyborohydride (23 mg, 0.11 mmol) and the resulting mixture was maintained until LCMS indicated complete consumption of the aldehyde. The reaction was quenched with saturated aqueous sodium bicarbonate, the layers were separated, and the aqueous layer was extracted with dichloromethane (3×10 mL). The combined organic layers were washed with water (20 mL) and brine (20 mL), then dried (MgSO$_4$), filtered and concentrated to afford a residue that was purified by reverse phase HPLC to afford butyl-{3-[4-(tert-butylamino-methyl)-3-fluoro-phenyl]-imidazo[1,2-b]pyridazin-6-yl}-amine (32 mg, 86%) as a white solid: $^1$H NMR (400 MHz, METHANOL-d$_4$) δ ppm 8.21 (dd, J=12.3, 1.5 Hz, 1H), 7.93 (dd, J=8.0, 1.7 Hz, 1H), 7.82 (s, 1H), 7.58 (d, J=9.7 Hz, 1H), 7.50 (t, J=8.0 Hz, 1H), 6.68 (d, J=9.7 Hz, 1H), 4.02 (s, 2H), 3.34 (t, J=7.2 Hz, 2H), 1.60-1.73

(m, 2H), 1.39-1.51 (m, 2H), 1.24-1.35 (m, 10H), 0.91-1.00 (m, 3H); LCMS (ESI) m/e 370.2 [(M+H)$^+$, calcd for C$_{21}$H$_{29}$FN$_5$ 370.2].

5.6.22. Synthesis of N-(3-((3-(5-acetylthiophen-2-yl)imidazo[1,2-b]pyridazin-6-yl)amino)propyl)-N-isopropylacetamide

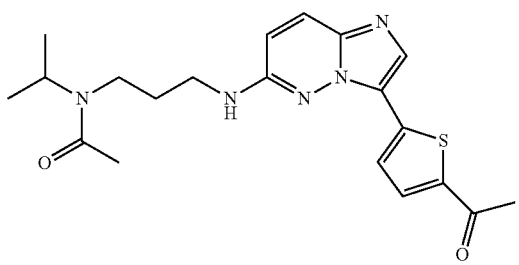 [SMILES: CC(=O)c1ccc(-c2cnc3ccc(NCCCN(C(C)=O)C(C)C)nn23)s1]

Part A. N1-(3-Bromoimidazo[1,2-b]pyridazin-6-yl)propane-1,3-diamine

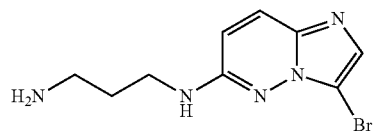 [SMILES: NCCCNc1ccc2ncc(Br)n2n1]

Propylene diamine [109-76-2] (7.5 mL, 90.3 mmol) was added to a stirred suspension of 3-bromo-6-chloro-imidazo[1,2-b]pyridazine [13526-66-4] (2.1 g, 9.0 mmol) in toluene (18.1 mL) and was heated to reflux, under N$_2$ blanket, for 7d then partitioned between aqueous 1N sodium hydroxide and ethyl acetate. The extract was washed with water then evaporated to obtain 1.1 g of yellow semi-solid. LRMS (ESI) m/z 270.0/272.0 [(M+H)]$^+$, calc'd for C$_9$H$_{12}$BrN$_5$: 270.13.

Part B. N1-(3-Bromoimidazo[1,2-b]pyridazin-6-yl)-N3-isopropylpropane-1,3-diamine

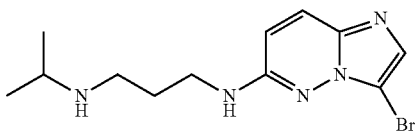 [SMILES: CC(C)NCCCNc1ccc2ncc(Br)n2n1]

Acetone [67-64-1] (2.0 mL, 43.5 mmol), then powdered, activated, 4 Angstrom molecular sieve were added to a solution of N1-(3-bromoimidazo[1,2-b]pyridazin-6-yl)propane-1,3-diamine (367.2 mg, 1.4 mmol) in methanol (4.8 mL). The reaction vessel was closed and the mixture allowed to rapidly stir, at ambient temperature, for 17 h then its content rapidly transferred into a stirring suspension of sodium borohydride [16940-66-2] (0.3 g, 6.9 mmol) in methanol (50 mL). After 1 h the mixture was gravity filtered and the filtrate evaporated. The crude product was then taken up in ethyl acetate, washed with brine, dried (MgSO$_4$) and evaporated to provide 196.9 mg of yellow solid. LRMS (ESI) m/z 312.0/314.0 [(M+H)]$^+$, calc'd for C$_{12}$H$_{18}$BrN$_5$: 312.21.

Part C. N-(3-((3-Bromoimidazo[1,2-b]pyridazin-6-yl)amino)propyl)-N-isopropylacetamide

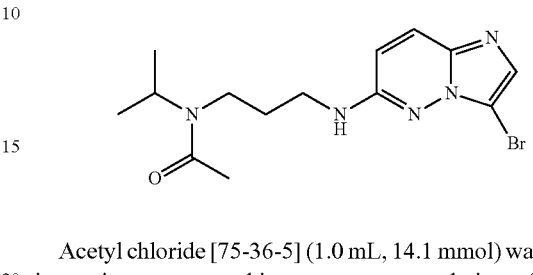

Acetyl chloride [75-36-5] (1.0 mL, 14.1 mmol) was added, in portions, to an ambient temperature solution of N1-(3-bromoimidazo[1,2-b]pyridazin-6-yl)-N3-isopropylpropane-1,3-diamine (196.9 mg, 0.6 mmol) in pyridine (6.5 mL), and stirred under N$_2$ blanket for 17 h. Pyridine was evaporated from the reaction mixture and the residue partitioned between aqueous 5% (w/v) sodium bicarbonate and ethyl acetate. The organic phase was washed with brine, dried (MgSO$_4$) and evaporated to afford 219.2 mg of dark oil. LRMS (ESI) m/z 354.1/356.1 [(M+H)]$^+$, calc'd for C$_{14}$H$_{20}$BrN$_5$O: 354.25.

Part D. N-(3-((3-(5-acetylthiophen-2-yl)imidazo[1,2-b]pyridazin-6-yl)amino)propyl)-N-isopropylacetamide To a mixture of N-(3-((3-bromoimidazo[1,2-b]pyridazin-6-yl)amino)propyl)-N-isopropylacetamide (219.2 mg, 0.6 mmol), (5-acetylthiophen-2-yl)boronic acid [206551-43-1] (128.4 mg, 0.8 mmol), potassium phosphate tribasic monohydrate [27176-10-9] (266.5 mg, 1.3 mmol), and [1,1'-bis(diphenylphosphino)ferrocene]dichloro-palladium(II), complex with dichloromethane [95464-05-4] (53.6 mg, 0.1 mmol) contained in a 25 mL round bottomed flask was added a solution of 30% (v/v) water in 1,2-dimethoxyethane (13 mL) and a magnetic stir bar. The reaction pot was fitted to a reflux condenser, lowered into an ambient temperature oil bath, and the system taken through 10 evacuation/N$_2$ blanket cycles while being rapidly stirred. The rapidly stirred, N$_2$ blanketed, reaction was heated to an oil bath temperature of 85° C. for 17 h then cooled and partitioned between brine and ethyl acetate. The phase separated extract was dried (MgSO$_4$) and evaporated to yield a dark brown solid. Product was purified by preparative RP-HPLC. Purified chromatography fractions were combined and partitioned between aqueous saturated sodium bicarbonate and ethyl acetate. The organic extract dried (CaSO$_4$) and evaporated to provide N-(3-((3-(5-acetylthiophen-2-yl)imidazo[1,2-b]pyridazin-6-yl)amino)propyl)-N-isopropylacetamide as 45.7 mg of yellow solid. $^1$H NMR (400 MHz, DMSO-d$_6$) δ ppm 1.05-1.20 (m, 4H) 1.24 (br. s., 1H) 1.86-2.03 (m, 4H) 2.49-2.56 (m, 6H) 3.24-3.48 (m, 5H) 6.76 (dd, J=9.73, 1.14 Hz, 1H) 7.33-7.43 (m, 1H) 7.79-

7.84 (m, 1H) 7.97 (d, J=4.04 Hz, 1H) 8.14 (d, J=5.05 Hz, 1H). LRMS (ESI) m/z 400.2 [(M+H)]⁺, calc'd for $C_{20}H_{25}N_5O_2S$: 399.52.

5.6.23. Synthesis of 6-(6-Butylamino-imidazo[1,2-b]pyridazin-3-yl)-3,4-dihydro-2H-isoquinolin-1-one

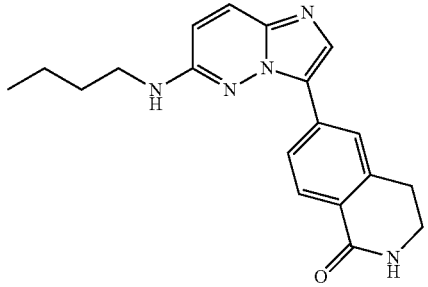 [SMILES: CCCCNc1ccc2ncc(-c3ccc4c(c3)CCNC4=O)n2n1]

A mixture of 3-bromo-N-butylimidazo[1,2-b]pyridazin-6-amine (160 mg, 0.61 mmol), (1-oxo-1,2,3,4-tetrahydroisoquinolin-6-yl)boronic acid (200 mg, 0.73 mmol), dichloro[1,1'-bis(diphenylphosphino)ferrocene]palladium (II) dichloromethane adduct (50 mg, 0.06 mmol), potassium phosphate (250 mg, 1.2 mmol), DME (1.5 mL) and $H_2O$ (0.5 mL) was heated in a sealed conical vessel at 160° C. for 360 s by microwave irradiation. The organic layer was separated and the aqueous layer was extracted with ethyl acetate (2 mL). The combined organic layers were concentrated under reduced pressure to afford an oil that was purified by reverse phase HPLC to afford 6-(6-butylamino-imidazo[1,2-b]pyridazin-3-yl)-3,4-dihydro-2H-isoquinolin-1-one (90 mg, 44%) as a white solid: ¹H NMR (400 MHz, METHANOL-d₄) δ ppm 8.11-8.20 (m, 2H), 7.94 (d, J=8.2 Hz, 1H), 7.84 (s, 1H), 7.57 (d, J=9.7 Hz, 1H), 6.67 (d, J=9.7 Hz, 1H), 3.50 (t, J=6.7 Hz, 2H), 3.34 (t, J=7.2 Hz, 2H), 3.00 (t, J=6.6 Hz, 2H), 1.60-1.75 (m, 2H), 1.36-1.50 (m, 2H), 0.95 (t, J=7.4 Hz, 3H); LCMS (ESI) m/e 336.2 [(M+H)⁺, calcd for $C_{19}H_{22}N_6O$ 336.2].

5.6.24. Synthesis of 3-(6-aminopyridin-3-yl)-N-butylimidazo[1,2-b]pyridazin-6-amine

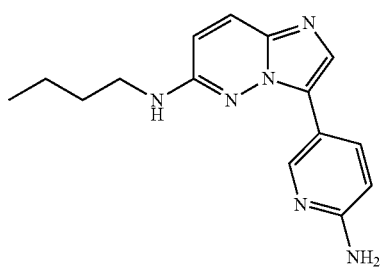 [SMILES: CCCCNc1ccc2ncc(-c3ccc(N)nc3)n2n1]

To a mixture of 3-bromo-N-butylimidazo[1,2-b]pyridazin-6-amine (75 mg, 0.28 mmol), tert-butyl(5-(4,4,5,5-tetramethyl-1,3,2-dioxaborolan-2-yl)pyridin-2-yl)carbamate (107 mg, 0.33 mmol), [1,1'-bis(diphenylphosphino)ferrocene]dichloropalladium(II) (10 mg, 0.014 mmol) and potassium phosphate (58 mg, 0.42 mmol) was added 3:1 acetonitrile/water (2 mL). The resulting mixture was heated at 145° C. (microwave) for 1000 s. The reaction was then filtered and concentrated. The residue was finally purified by preparative HPLC (neutral) to afford 3-(6-aminopyridin-3-yl)-N-butylimidazo[1,2-b]pyridazin-6-amine (50.3 mg, 47% yield) as a yellow solid: ¹H NMR (METHANOL-d₄) δ: 8.72 (d, J=1.8 Hz, 1H), 8.08 (dd, J=8.7, 2.3 Hz, 1H), 7.58 (s, 1H), 7.52 (d, J=9.7 Hz, 1H), 6.58-6.66 (m, 2H), 4.78-4.88 (m, 11H), 3.27-3.33 (m, 3H), 1.62 (d, J=7.1 Hz, 2H), 1.42 (d, J=7.9 Hz, 2H), 0.91-0.97 (m, 3H); LRMS (ESI) m/e 283.4 [(M+H)⁺, calcd for $C_{15}H_{19}N_6$ 283.2].

5.6.25. Synthesis of Butyl-{3-[4-(tert-butylamino-methyl)-2-fluoro-phenyl]-imidazo[1,2-b]pyridazin-6-yl}-amine

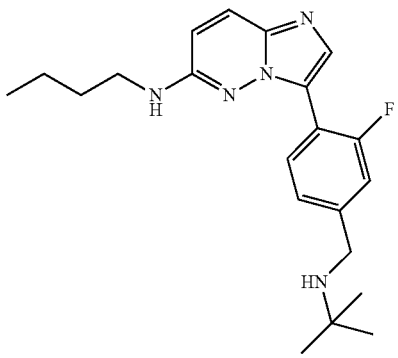 [SMILES: CCCCNc1ccc2ncc(-c3ccc(CNC(C)(C)C)cc3F)n2n1]

Part A. 4-(6-Butylamino-imidazo[1,2-b]pyridazin-3-yl)-3-fluoro-benzaldehyde

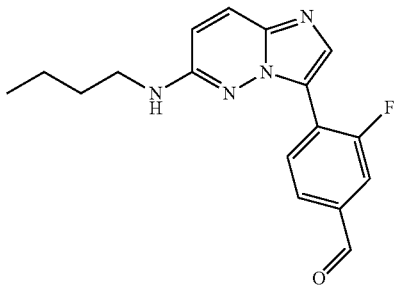 [SMILES: CCCCNc1ccc2ncc(-c3ccc(C=O)cc3F)n2n1]

A mixture of 3-bromo-N-butylimidazo[1,2-b]pyridazin-6-amine (810 mg, 3.0 mmol), 2-fluoro-4-formylphenylboronic acid (1.2 g, 7.5 mmol), dichloro[1,1'-bis(diphenylphosphino)ferrocene]palladium (II) dichloromethane adduct (200 mg, 0.30 mmol), potassium phosphate (1.9 g, 9.0 mmol), DME (9 mL) and $H_2O$ (3 mL) was maintained in a sealed vessel at 80° C. for 12 h. The organic layer was separated and concentrated under reduced pressure to afford a yellow solid that was purified by reverse phase HPLC to afford 4-(6-butylamino-imidazo[1,2-b]pyridazin-3-yl)-3-fluoro-benzaldehyde (600 mg, 64%) as a white solid: ¹H NMR (400 MHz, CDCl₃) δ ppm 10.02 (d, J=1.8 Hz, 1H), 8.84-8.93 (m, 1H), 8.12 (d, J=4.3 Hz, 1H), 7.79 (dd, J=8.1, 1.5 Hz, 1H), 7.68-7.76 (m, 2H), 6.55 (d, J=9.6 Hz, 1H), 3.43 (td, J=7.1, 5.6 Hz, 2H), 1.67-1.78 (m, 2H), 1.49 (dq, J=15.0, 7.4 Hz, 2H), 1.01 (t, J=7.3 Hz, 3H); LCMS (ESI) m/e 313.1 [(M+H)⁺, calcd for $C_{17}H_{18}FN_4O$ 313.1].

Part B. Butyl-{3-[4-(tert-butylamino-methyl)-2-fluoro-phenyl]-imidazo[1,2-b]pyridazin-6-yl}-amine A mixture of 4-(6-butylamino-imidazo[1,2-b]pyridazin-3-yl)-3-fluoro-benzaldehyde (120 mg, 0.40 mmol) and dichloroethane (DCE, 4 mL) was treated with tert-butyl amine (0.050 mL, 0.50 mmol) and the resulting reaction mixture was maintained at RT for 20 min. The reaction was then treated with sodium triacetoxyborohydride (170 mg, 0.80 mmol) and the resulting mixture was maintained until LCMS indicated complete consumption of the aldehyde. The reaction was quenched with saturated aqueous sodium bicarbonate, the layers were separated, and the aqueous layer was extracted with dichloromethane (3×20 mL). The combined organic layers were washed with water (20 mL) and brine (20 mL), then dried (MgSO$_4$), filtered and concentrated to afford a residue that was purified by reverse phase HPLC to afford butyl-{3-[4-(tert-butylamino-methyl)-2-fluoro-phenyl]-imidazo[1,2-b]pyridazin-6-yl}-amine (98 mg, 67%) as a white solid: $^1$H NMR (400 MHz, METHANOL-d$_4$) δ ppm 8.21 (dd, J=12.3, 1.5 Hz, 1H), 7.93 (dd, J=8.0, 1.7 Hz, 1H), 7.82 (s, 1H), 7.58 (d, J=9.7 Hz, 1H), 7.50 (t, J=8.0 Hz, 1H), 6.68 (d, J=9.7 Hz, 1H), 4.02 (s, 2H), 3.34 (t, J=7.2 Hz, 2H), 1.84 (s, 1H), 1.61-1.71 (m, 2H), 1.39-1.50 (m, 2H), 1.32 (s, 9H), 1.25-1.30 (m, 1H), 0.91-0.99 (m, 3H); LCMS (ESI) m/e 370.2 [(M+H)$^+$, calcd for C$_{21}$H$_{29}$FN$_5$ 370.2].

5.6.26. Synthesis of Butyl-[3-(1H-indazol-5-yl)-imidazo[1,2-b]pyridazin-6-yl]amine

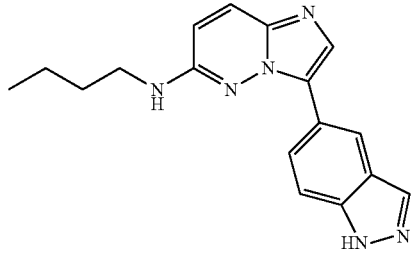 [SMILES: CCCCNc1ccc2ncc(-c3ccc4[nH]ncc4c3)n2n1]

A mixture of 3-bromo-N-butylimidazo[1,2-b]pyridazin-6-amine (140 mg, 0.50 mmol), (1H-indazole-5-boronic acid pinacol ester (150 mg, 0.60 mmol), dichloro-bis(triphenylphosphino) palladium (II) (20 mg, 0.025 mmol), potassium carbonate (110 mg, 0.75 mmol), acetonitrile (1.5 mL) and H$_2$O (0.5 mL) was heated in a sealed conical vessel at 160° C. for 1000 s by microwave irradiation. The organic layer was separated and the aqueous layer was extracted with ethyl acetate (2 mL). The combined organic layers were concentrated under reduced pressure to afford an oil that was purified by reverse phase HPLC to afford butyl-[3-(1H-indazol-5-yl)-imidazo[1,2-b]pyridazin-6-yl]-amine (100 mg, 65%) as a white solid: $^1$H NMR (400 MHz, METHANOL-d$_4$) δ ppm 8.62-8.68 (m, 1H), 8.13-8.20 (m, 2H), 8.02 (dd, J=8.8, 1.5 Hz, 1H), 7.94 (d, J=9.9 Hz, 1H), 7.72 (d, J=8.8 Hz, 1H), 7.21 (d, J=9.9 Hz, 1H), 3.43 (t, J=7.2 Hz, 2H), 1.66-1.79 (m, 2H), 1.49 (dq, J=15.1, 7.4 Hz, 2H), 0.99 (t, J=7.5 Hz, 3H); LCMS (ESI) m/e 307.2 [(M+H)$^+$, calcd for C$_{17}$H$_{19}$N$_6$ 307.2].

5.6.27. Synthesis of (3-{[3-(5-Acetyl-thiophen-2-yl)-imidazo[1,2-b]pyridazin-6-yl]-methyl-amino}-propyl)-carbamic acid tert-butyl ester

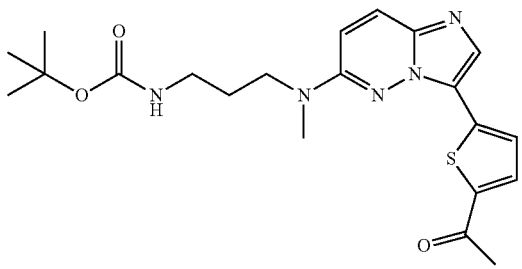 [SMILES: CC(=O)c1ccc(-c2cnc3ccc(N(C)CCCNC(=O)OC(C)(C)C)nn23)s1]

Part A. N-(3-Bromo-imidazo[1,2-b]pyridazin-6-yl)-N'-methyl-propane-1,3-diamine and N*1*-(3-bromo-imidazo[1,2-b]pyridazin-6-yl)-N*1*-methyl-propane-1,3-diamine

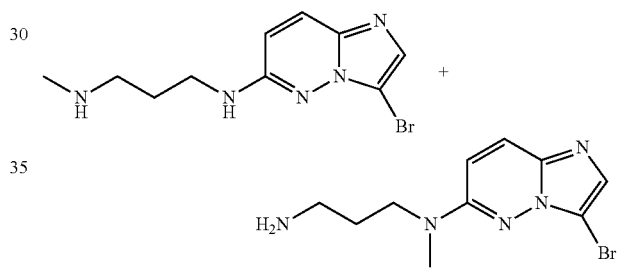

3-Bromo-6-chloro-imidazo[1,2-b]pyridazine [13526-66-4] (1.0 g, 4.5 mmol) was dissolved in N-methyl-propane-1,3-diamine [6291-84-5] (8.0 mL, 77.3 mmol) and the solution stirred at 65° C. under N$_2$ blanket for 4 h, then partitioned between saturated aqueous sodium bicarbonate and ethyl acetate. The organic extract was dried (MgSO$_4$), filtered, and evaporated to obtain 1.31 g of yellow oil as a mixture of the titled compounds. LRMS (ESI) m/z 284.0/286.0 [(M+H)]$^+$, calc'd for C$_{10}$H$_{14}$BrN$_5$: 284.16. LRMS (ESI) m/z 284.0/286.0 [(M+H)]$^+$, calc'd for C$_{10}$H$_{14}$BrN$_5$: 284.16.

Part B. N-{3-[(3-Bromo-imidazo[1,2-b]pyridazin-6-yl)-methyl-amino]-propyl}-2,2,2-trifluoro-acetamide

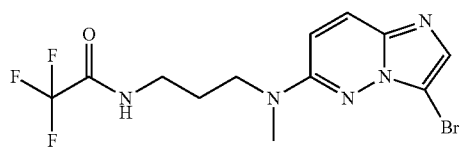 [SMILES: CN(CCCNC(=O)C(F)(F)F)c1ccc2ncc(Br)n2n1]

A mixture of N-(3-bromo-imidazo[1,2-b]pyridazin-6-yl)-N'-methyl-propane-1,3-diamine and N*1*-(3-bromo-imidazo[1,2-b]pyridazin-6-yl)-N*1*-methyl-propane-1,3-diamine (1.31 g, 4.6 mmol) was dissolved, with stirring, in ethyl acetate (46 mL). Trifluoroacetic anhydride [407-25-0] (6.4 mL, 46.1 mmol) was slowly added to the ambient temperature stirred solution and the reaction heated at 50° C. for 8 h to ensure complete trifluoroacetylation. Reaction was washed with brine, dried (MgSO$_4$), evaporated and flash chromatographed (silica gel, eluted with 50% (v/v) acetone/hexanes) to isolate two well resolved products: R$_f$=0.35 (desired mono-trifluoroacetylated product) and R$_f$=0.53 (di-trifluoroacetylated product). Chromatography fractions of component of R$_f$=0.53 were combined and evaporated to obtain 0.87 g of yellow solid. Chromatography fractions of component of R$_f$=0.35 (desired product) were combined and evaporated to obtain 0.54 g of clear yellow oil. LRMS (ESI) m/z 380.0/382.0 [(M+H)]$^+$, calc'd for C$_{12}$H$_{13}$BrF$_3$N$_5$O: 380.17

Part C. {3-[(3-Bromo-imidazo[1,2-b]pyridazin-6-yl)-methyl-amino]-propyl}-carbamic acid tert-butyl ester

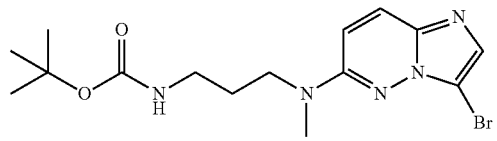 [SMILES: CN(CCCNC(=O)OC(C)(C)C)c1ccc2ncc(Br)n2n1]

Water (10 mL) was added to a mixture of N-{3-[(3-bromo-imidazo[1,2-b]pyridazin-6-yl)-methyl-amino]-propyl}-2,2,2-trifluoro-acetamide (0.5 g, 1.4 mmol) and potassium carbonate [584-08-7] (1.1 g, 8.0 mmol) in methanol (10 mL) and allowed to stir at ambient temperature for 3d. The mixture was evaporated to dryness and the residue triturated in ethyl acetate. The ethyl acetate suspension was filtered of its insoluble solids, to it was added di-tert-butyl dicarbonate [24424-99-5] (0.3 g, 1.5 mmol) and N-methylmorpholine [109-02-4] (0.5 mL, 4.3 mmol), reaction was stirred overnight, washed with brine, dried (MgSO$_4$), and evaporated to yield 0.5 g of clear yellow oil. LRMS (ESI) m/z 384.1/386.1 [(M+H)]$^+$, calc'd for C$_{16}$H$_{22}$BrN$_5$O$_2$: 384.28.

Part D. (3-{[3-(5-Acetyl-thiophen-2-yl)-imidazo[1,2-b]pyridazin-6-yl]-methyl-amino}-propyl)-carbamic acid tert-butyl ester (3-{[3-(5-Acetyl-thiophen-2-yl)-imidazo[1,2-b]pyridazin-6-yl]-methyl-amino}-propyl)-carbamic acid tert-butyl ester was prepared and isolated similarly to the procedure detailed in example 5.6.17 from a mixture of {3-[(3-bromo-imidazo[1,2-b]pyridazin-6-yl)-methyl-amino]-propyl}-carbamic acid tert-butyl ester (0.5 g, 1.3 mmol), 5-acetyl-2-thiopheneboronic acid [206551-43-1] (0.3 g, 1.5 mmol), potassium phosphate tribasic monohydrate [27176-10-9] (0.5 g, 2.5 mmol), and [1,1'-bis(diphenylphosphino)ferrocene]dichloropalladium(II), complex with dichloromethane [95464-05-4] (0.1 g, 0.1 mmol) in a solution of 30% (v/v) water in 1,2-dimethoxyethane (30 mL) to afford 0.16 g of yellow powder, mp. 148-149° C. $^1$H NMR (400 MHz, DMSO-d$_6$) δ ppm 1.37 (s, 9H) 1.78 (quin, J=6.95 Hz, 2H) 2.54 (s, 3H) 3.05 (q, J=6.57 Hz, 2H) 3.17 (s, 3H) 3.61 (t, J=7.20 Hz, 2H) 6.88 (br. s., 1H) 7.12 (d, J=9.85 Hz, 1H) 7.82 (d, J=4.29 Hz, 1H) 7.92 (d, J=9.85 Hz, 1H) 7.97 (d, J=4.04 Hz, 1H) 8.20 (s, 1H). LRMS (ESI) m/z 430.1 [(M+H)]$^+$, calc'd for C$_{21}$H$_{27}$BN$_5$O$_3$S: 429.55.

5.6.28. Synthesis of N-[3-(5-Aminomethyl-thiophen-2-yl)-imidazo[1,2-b]pyridazin-6-yl]-N'-methyl-N'-phenyl-ethane-1,2-diamine

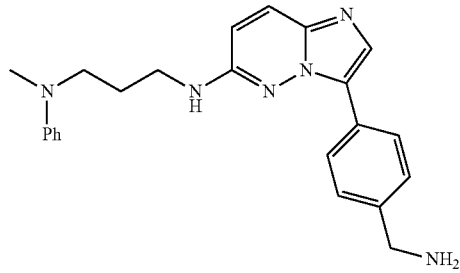 [SMILES: CN(CCCNc1ccc2ncc(-c3ccc(CN)cc3)n2n1)c1ccccc1]

Part A. N1-(3-bromoimidazo[1,2-b]pyridazin-6-yl)-N3-methyl-N3-phenylpropane-1,3-diamine

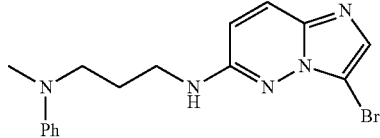 [SMILES: CN(CCCNc1ccc2ncc(Br)n2n1)c1ccccc1]

To 300 mg (1.389 mmol) of the 3-bromo-6-fluoroimidazo[1,2-b]pyridazine, was added N1-methyl-N1-phenylpropane-1,3-diamine (456 mg, 2.778 mmol) Cs$_2$CO$_3$ (903 mg, 2.778 mmol) and 10 mL DMF. This mixture is stirred overnight at rt. It was diluted with 30 mL EtOAc, and 15 mL of water. The organic layer was washed with brine and dried over MgSO$_4$. It was concentrated and purified using silica gel chromatography (ISCO) eluting with 0-10% MeOH/DCM to obtain 301 mg (60%) of product.

Part B. N-[3-(5-Aminomethyl-thiophen-2-yl)-imidazo[1,2-b]pyridazin-6-yl]-N'-methyl-N'-phenyl-ethane-1,2-diamine The isolated product obtained from part A was coupled to (4-(aminomethyl)phenyl)boronic acid by the Suzuki reaction described in example 5.6.19 to obtain the titled compound in 56% yield. $^1$H NMR (400 MHz, METHANOL-d$_4$) δ ppm 2.14 (t, J=7.06 Hz, 2H) 3.08 (s, 3H) 3.53-3.69 (m, 4H) 4.27 (s, 2H) 6.75 (t, J=7.28 Hz, 1H) 6.85-6.93 (m, 3H) 7.26 (t, J=8.05 Hz, 2H) 7.65 (d, J=8.38 Hz, 2H) 7.80 (d, J=9.70 Hz, 1H) 7.95 (s, 1H) 8.38 (d, J=8.38 Hz, 2H); LRMS (ESI) m/e 387.0 [(M+H)]$^+$, calcd for C$_{23}$H$_{26}$N$_6$ 386.0].

5.6.29. Synthesis of Butyl-[3-(1H-imidazol-4-yl)-imidazo[1,2-b]pyridazin-6-yl]amine

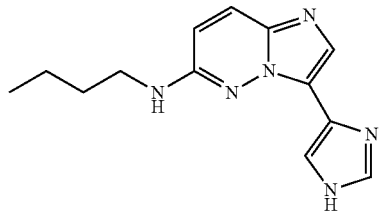 [SMILES: CCCCNc1ccc2ncc(-c3c[nH]cn3)n2n1]

Part A. (6-(butylamino)imidazo[1,2-b]pyridazin-3-yl)boronic acid

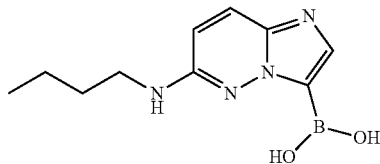 [SMILES: CCCCNc1ccc2ncc(B(O)O)n2n1]

A precooled (−78° C.) solution of 3-bromo-N-butylimidazo[1,2-b]pyridazin-6-amine (200 mg, 0.74 mmol) and tetrahydrofuran (4 mL) was treated dropwise with n-butyllithium (1.2 mL, 1.6 M, 1.9 mmol). The resulting reaction mixture was maintained at −78° C. for 5 min, then treated dropwise with tris(isopropyl)borate (0.21 mL, 0.89 mmol) and maintained at −78° C. for 2.5 h. The reaction was quenched with H$_2$O (1 mL) and allowed to warm to RT. The organic volatiles were removed under reduced pressure, and the aqueous layer was acidified with 1 N HCl until a white precipitate formed. The solid was collected by filtration to afford (6-(butylamino)imidazo[1,2-b]pyridazin-3-yl)boronic acid (100 mg, 58%) as a white solid: $^1$H NMR (400 MHz, METHANOL-d$_4$) δ ppm 7.56 (d, J=9.9 Hz, 1H), 7.39 (s, 1H), 6.66 (d, J=9.9 Hz, 1H), 3.25-3.35 (m, 2H), 1.60-1.75 (m, 1H), 1.37-1.58 (m, 1H), 0.94-1.08 (m, 1H); LCMS (ESI) m/e 235.2 [(M+H)$^+$, calcd for C$_{10}$H$_{15}$BN$_4$O$_2$ 235.1].

Part B. Butyl-[3-(1H-imidazol-4-yl)-imidazo[1,2-b]pyridazin-6-yl]-amine

A mixture of (6-(butylamino)imidazo[1,2-b]pyridazin-3-yl)boronic acid (120 mg, 0.5 mmol), 4-bromo-1H-imidazole (75 mg, 0.5 mmol), dichloro[1,1'-bis(diphenylphosphino)ferrocene]palladium (II) dichloromethane adduct (40 mg, 0.050 mmol), potassium phosphate (210 mg, 1.0 mmol), DME (1.5 mL) and H$_2$O (0.5 mL) was heated in a sealed conical vessel at 140° C. for 600 s by microwave irradiation. The organic layer was separated and the aqueous layer was extracted with ethyl acetate (2 mL). The combined organic layers were concentrated under reduced pressure to afford an oil that was purified by reverse phase HPLC to afford butyl-[3-(1H-imidazol-4-yl)-imidazo[1,2-b]pyridazin-6-yl]-amine (95 mg, 72%) as a white solid: $^1$H NMR (400 MHz, METHANOL-d$_4$) δ ppm 7.99 (br. s., 1H), 7.82 (d, J=1.0 Hz, 2H), 7.60 (d, J=9.6 Hz, 1H), 6.68 (d, J=9.6 Hz, 1H), 3.44 (t, J=7.1 Hz, 2H), 1.69-1.82 (m, 2H), 1.46-1.60 (m, 2H), 1.03 (t, J=7.3 Hz, 3H); LCMS (ESI) m/e 257.2 [(M+H)$^+$, calcd for C$_{13}$H$_{17}$N$_6$ 257.1].

5.6.30. Synthesis of 3-(4-(aminomethyl)-3-fluorophenyl)-N-butylimidazo[1,2-b]pyridazin-6-amine

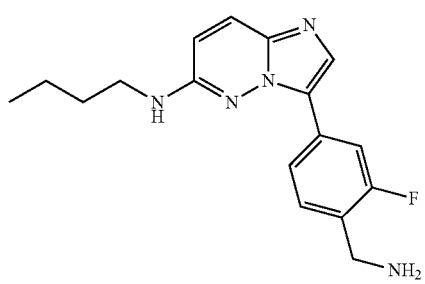 [SMILES: CCCCNc1ccc2ncc(-c3ccc(CN)c(F)c3)n2n1]

Part A. tert-butyl 4-bromo-2-fluorobenzylcarbamate

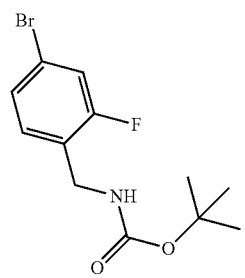 [SMILES: CC(C)(C)OC(=O)NCc1ccc(Br)cc1F]

To the solution of (4-bromo-2-fluorophenyl)methanamine mono HCl salt (336 mg, 1.4 mmol) in 1:1 1,4-dioxane/water (8 mL) was added triethyl amine (312 mg, 3.08 mmol) and di-tert-butyl dicarbonate (366 mg, 1.68 mmol). The reaction was maintained at room temperature for 2 days, and then quenched with saturated sodium bicarbonate solution (8 mL) and extracted with ethyl acetate (8 mL) three times. The combined organic layers were washed with brine (8 mL) and dried over sodium sulfate, filtered and concentrated under reduced pressure to afford tert-butyl 4-bromo-2-fluorobenzylcarbamate (419 mg 96% yield) as a white solid: $^1$H NMR (CHLOROFORM-d) δ: 7.05-7.29 (m, 3H), 3.65 (s, 2H), 1.39 (s, 9H); LRMS (ESI) m/e 304.0 [(M+H)$^+$, calcd for C$_{12}$H$_{16}$BrFNO$_2$ 304.0].

Part B. tert-butyl 2-fluoro-4-(4,4,5,5-tetramethyl-1,3,2-dioxaborolan-2-yl)benzylcarbamate

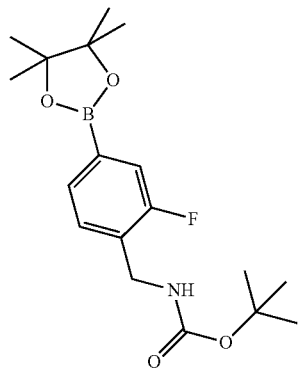 [SMILES: CC(C)(C)OC(=O)NCc1ccc(B2OC(C)(C)C(C)(C)O2)cc1F]

The mixture of tert-butyl 4-bromo-2-fluorobenzylcarbamate (419 mg, 1.38 mmol), bis(pinacolato)diboron (385 mg, 1.52 mmol), [1,1'-bis(diphenylphosphino)ferrocene]dichloropalladium(II) (101 mg, 0.138 mmol), potassium acetate (406 mg, 4.13 mmol) and 1,4-dioxane (10 mL) was stirred at 80° C. for 18 h. The reaction was then filtered and concentrated to afford a residue that was purified by column chromatography on silica gel (0-30% ethyl acetate in hexane) to afford tert-butyl 2-fluoro-4-(4,4,5,5-tetramethyl-1,3,2-dioxaborolan-2-yl)benzylcarbamate (293 mg, 61% yield) as a clear oil: $^1$H NMR (CHLOROFORM-d) δ: 7.51-7.62 (m, 1H), 7.47 (d, J=10.4 Hz, 1H), 7.35 (t, J=7.2 Hz, 1H), 4.39 (d, J=5.3 Hz, 2H), 1.46 (s, 9H), 1.33-1.38 (m, 12H).

Part C. tert-butyl 4-(6-(butylamino)imidazo[1,2-b]pyridazin-3-yl)-2-fluorobenzylcarbamate

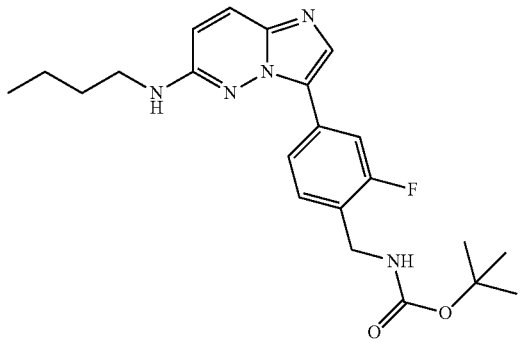 [SMILES: CCCCNc1ccc2ncc(-c3ccc(CNC(=O)OC(C)(C)C)c(F)c3)n2n1]

To a mixture of 3-bromo-N-butylimidazo[1,2-b]pyridazin-6-amine (187 mg, 0.7 mmol), tert-butyl 2-fluoro-4-(4,4,5,5-tetramethyl-1,3,2-dioxaborolan-2-yl)benzylcarbamate (293 mg, 1.2 mmol), [1,1'-bis(diphenylphosphino)ferrocene]dichloropalladium(II) (24 mg, 0.034 mmol) and tripotassium phosphate (144 mg, 1.04 mmol) was added 3:1 acetonitrile/water (3 mL). The resulting mixture was heated at 145° C. (microwave) for 800 s. The reaction was then filtered and concentrated. The residue was dissolved in methanol, and then filtered again. The filtration was finally purified by preparative HPLC (neutral) to afford tert-butyl 4-(6-(butylamino)imidazo[1,2-b]pyridazin-3-yl)-2-fluorobenzylcarbamate (110 mg, 38% yield) as a white solid: $^1$H NMR (CHLOROFORM-d) δ: 8.02 (dd, J=11.9, 1.3 Hz, 1H), 7.78-7.89 (m, 2H), 7.74 (d, J=9.6 Hz, 1H), 7.43 (t, J=8.0 Hz, 1H), 7.28 (s, 2H), 6.52 (d, J=9.6 Hz, 1H), 4.95 (br. s., 1H), 4.31-4.57 (m, 3H), 3.45 (td, J=7.1, 5.6 Hz, 2H), 1.68-1.80 (m, 2H), 1.02 (t, J=7.3 Hz, 3H); LRMS (ESI) m/e 414.3 [(M+H)$^+$, calcd for $C_{22}H_{29}FN_5O_2$ 414.2].

Part D. 3-(4-(aminomethyl)-3-fluorophenyl)-N-butylimidazo[1,2-b]pyridazin-6-amine The solution of tert-butyl 4-(6-(butylamino)imidazo[1,2-b]pyridazin-3-yl)-2-fluorobenzylcarbamate (91 mg, 0.22 mmol) was cooled to 0° C. and treated with acetyl chloride (518 mg, 6.6 mmol). The reaction was maintained at room temperature for overnight. The resulting solution was concentrated under reduced pressure to afford 3-(4-(aminomethyl)-3-fluorophenyl)-N-butylimidazo[1,2-b]pyridazin-6-amine HCl salt (75 mg, 88% yield) as a white solid: $^1$H NMR (METHANOL-d$_4$) δ: 8.38 (s, 1H), 8.23 (d, J=11.4 Hz, 1H), 8.05 (d, J=7.8 Hz, 1H), 8.00 (d, J=9.9 Hz, 1H), 7.74 (t, J=7.8 Hz, 1H), 7.30 (d, J=9.9 Hz, 1H), 4.31 (s, 2H), 3.43 (t, J=7.1 Hz, 2H), 1.65-1.84 (m, 2H), 1.42-1.59 (m, 2H), 1.01 (t, J=7.3 Hz, 3H); LRMS (ESI) m/e 314.4 [(M+H)$^+$, calcd for $C_{17}H_{21}FN_5$ 314.2].

5.6.31. Synthesis of [3-(4-Aminomethyl-phenyl)-imidazo[1,2-b]pyridazin-6-yl]-butyl-methyl-amine

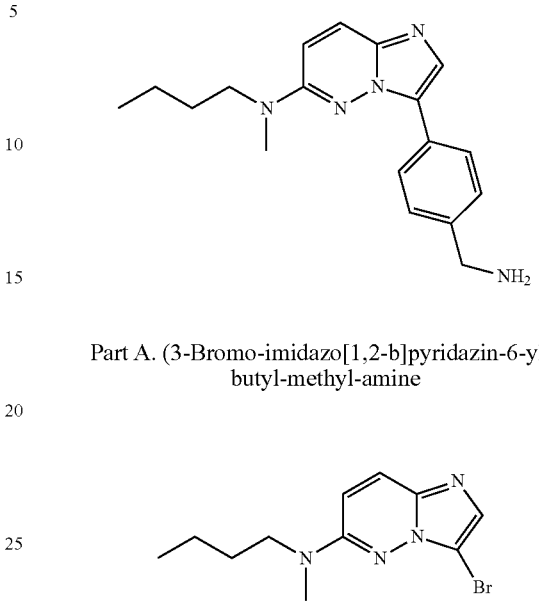

Part A. (3-Bromo-imidazo[1,2-b]pyridazin-6-yl)-butyl-methyl-amine

A neat solution of 3-bromo-6-chloro-imidazo[1,2-b]pyridazine [13526-66-4] (522.9 mg, 2.3 mmol) in N-methyl butylamine [110-68-9] (3.0 mL, 24.3 mmol) and Hunig's base [7087-68-5] (0.6 mL, 3.5 mmol) was stirred under $N_2$ blanket at 65° C. overnight then evaporated to provide 0.9 g of yellow solid, used in the next step without further purification. LRMS (ESI) m/z 283.1/285.1 [(M+H)]$^+$, calc'd for $C_{11}H_{15}BrN_4$: 283.17.

Part B. [3-(4-Aminomethyl-phenyl)-imidazo[1,2-b]pyridazin-6-yl]-butyl-methyl-amine To a mixture of (3-bromo-imidazo[1,2-b]pyridazin-6-yl)-butyl-methyl-amine (377.7 mg, 1.3 mmol), 4-aminomethylphenylboronic acid hydrochloride [75705-21-4] (302.4 mg, 1.6 mmol), potassium phosphate tribasic monohydrate [27176-10-9] (612.7 mg, 2.7 mmol), and [1,1'-bis(diphenylphosphino)ferrocene]dichloropalladium(II), complex with dichloromethane [95464-05-4] (110.4 mg, 0.1 mmol) contained in a 25 mL round bottomed flask was added a solution of 30% (v/v) water in 1,2-dimethoxyethane (15 mL) and a magnetic stir bar. The reaction pot was fitted to a reflux condenser, lowered into an ambient temperature oil bath, and the system taken through 10 evacuation/$N_2$ blanket cycles while being rapidly stirred. The rapidly stirred, $N_2$ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried (CaSO$_4$), evaporated and flash chromatographed (silica gel, eluted with 1% NH$_4$OH in 10% (v/v) methanol/ethyl acetate) to isolate a brown solid which was triturated in heptane to precipitate a brown solid. Trituration solvent was then evaporated to provide [3-(4-aminomethyl-phenyl)-imidazo[1,2-b]pyridazin-6-yl]-butyl-methyl-amine as 41.8 mg white solid, mp. 99-101° C. $^1$H NMR (400 MHz, DMSO-d$_6$) δ ppm 0.94 (t, J=7.33 Hz, 3H) 1.30-1.42 (m, 2H) 1.47-1.70 (m, 2H) 1.90 (br. s., 1H) 3.10 (s, 3H) 3.51-3.57 (m, 2H) 3.75 (s, 2H) 7.05 (d, J=9.85 Hz, 1H) 7.42 (d, J=8.34 Hz, 2H) 7.85 (d, J=10.11 Hz, 1H) 7.92 (s, 1H) 8.14 (d, J=8.34 Hz, 2H). LRMS (ESI) m/z 310.3 [(M+H)]$^+$, calc'd for $C_{18}H_{23}N_6$: 309.42.

5.6.32. Synthesis of N-butyl-3-(isoindolin-5-yl)imidazo[1,2-b]pyridazin-6-amine

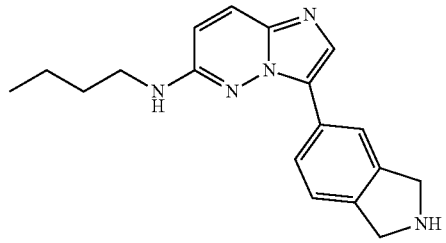 [SMILES: CCCCNc1ccc2ncc(-c3ccc4c(c3)CNC4)n2n1]

Part A. tert-butyl 5-(6-(butylamino)imidazo[1,2-b]pyridazin-3-yl)isoindoline-2-carboxylate

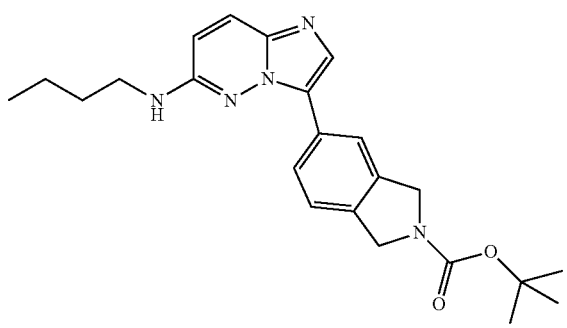 [SMILES: CCCCNc1ccc2ncc(-c3ccc4c(c3)CN(C(=O)OC(C)(C)C)C4)n2n1]

To a mixture of (6-(butylamino)imidazo[1,2-b]pyridazin-3-yl)boronic acid (47 mg, 0.2 mmol), tert-butyl 5-bromoisoindoline-2-carboxylate (47 mg, 0.16 mmol), [1,1'-bis(diphenylphosphino)ferrocene]dichloropalladium(II) (7 mg, 0.01 mmol) and tripotassium phosphate (41 mg, 0.3 mmol) was added 3:1 acetonitrile/water (3 mL). The resulting mixture was heated at 145° C. (microwave) for 800 s. The reaction was then filtered and concentrated. The residue was dissolved in methanol, and then filtered again. The filtration was finally purified by preparative HPLC (neutral) to afford tert-butyl 5-(6-(butylamino)imidazo[1,2-b]pyridazin-3-yl)isoindoline-2-carboxylate (43 mg, 66% yield) as a white solid: $^1$H NMR (METHANOL-$d_4$) δ: 8.15 (d, J=10.9 Hz, 1H), 8.00-8.08 (m, 1H), 7.75 (s, 1H), 7.59 (d, J=9.6 Hz, 1H), 7.35 (t, J=9.1 Hz, 1H), 6.68 (d, J=9.9 Hz, 1H), 4.69 (br. s., 4H), 3.37 (d, J=7.3 Hz, 2H), 1.65-1.78 (m, 2H), 1.56 (s, 9H), 1.45-1.53 (m, 2H), 1.02 (td, J=7.3, 2.3 Hz, 3H); LRMS (ESI) m/e 408.3 [(M+H)$^+$, calcd for $C_{23}H_{30}N_5O_2$ 408.2].

Part B. N-butyl-3-(isoindolin-5-yl)imidazo[1,2-b]pyridazin-6-amine

The solution of tert-butyl 5-(6-(butylamino)imidazo[1,2-b]pyridazin-3-yl)isoindoline-2-carboxylate (38 mg, 0.09 mmol) was cooled to 0° C. and treated with acetyl chloride (220 mg, 2.8 mmol). The reaction was maintained at room temperature for overnight. The resulting solution was concentrated under reduced pressure to afford N-butyl-3-(isoindol-5-yl)imidazo[1,2-b]pyridazin-6-amine hydrochloride (12 mg, 35% yield) as a white solid: $^1$H NMR (METHANOL-$d_4$) δ: 8.26 (s, 1H), 8.17-8.21 (m, 2H), 7.98 (d, J=10.1 Hz, 1H), 7.65 (d, J=8.6 Hz, 1H), 7.27 (d, J=9.9 Hz, 1H), 4.76 (s, 4H), 3.36-3.45 (m, 2H), 1.63-1.81 (m, 2H), 1.40-1.56 (m, 2H), 1.00 (t, J=7.3 Hz, 3H); LRMS (ESI) m/e 308.4 [(M+H)$^+$, calcd for $C_{18}H_{22}N_5$ 308.2].

5.6.33. Synthesis of 1-{3-[3-(4-Aminomethyl-phenyl)-imidazo[1,2-b]pyridazin-6-ylamino]-propyl}-pyrrolidin-2-one

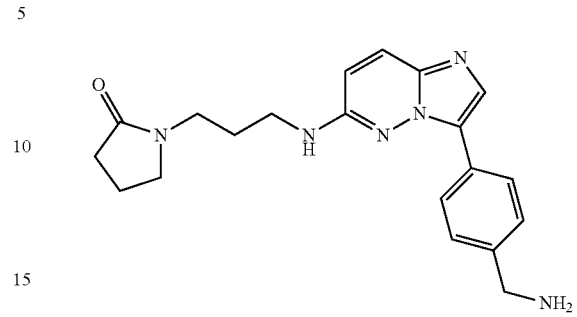

Part A. 1-(3-((3-bromoimidazo[1,2-b]pyridazin-6-ylamino)-propyl)-pyrrolidin-2-one

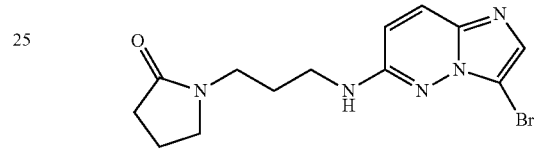

The 3-bromo-6-fluoroimidazo[1,2-b]pyridazine was alkylated with 1-(3-aminopropyl)pyrrolidin-2-one, under same reaction condition as used in the synthesis of N1-(3-bromoimidazo[1,2-b]pyridazin-6-yl)-N3-methyl-N3-phenyl-propane-1,3-diamine example 5.6.29 to obtain 68% product.

Part B. 1-{3-[3-(4-Aminomethyl-phenyl)-imidazo[1,2-b]pyridazin-6-ylamino]-propyl}-pyrrolidin-2-one The 1-(3-((3-bromoimidazo[1,2-b]pyridazin-6-yl)amino)propyl)pyrrolidin-2-one was also coupled to (4-(aminomethyl)phenyl)boronic acid using the Suzuki coupling conditions described in example 5.6.19 to obtain the titled product in 64% yield. $^1$H NMR (400 MHz, METHANOL-$d_4$) δ ppm 1.94-2.09 (m, 4H) 2.33-2.43 (m, 2H) 3.36-3.53 (m, 6H) 4.16 (s, 2H) 6.74 (d, J=9.60 Hz, 1H) 7.57 (m, J=8.34 Hz, 2H) 7.65 (d, J=9.60 Hz, 1H) 7.81 (s, 1H) 8.25 (m, J=8.34 Hz, 2H); LRMS (ESI) m/e 365.0 [(M+H)$^+$, calcd for $C_{20}H_{24}N_6O$ 364.0].

5.6.34. Synthesis of 5-(6-((3-(2-oxopyrrolidin-1-yl)propyl)amino)imidazo[1,2-b]pyridazin-3-yl)thiophene-2-carboxamide

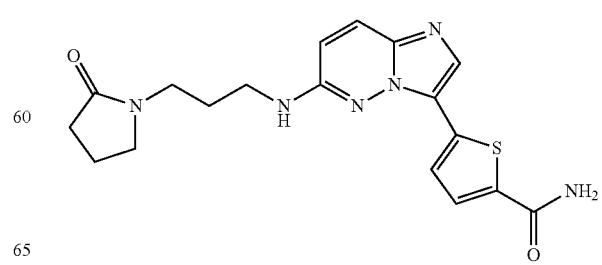

Part A. 5-(6-((3-(2-oxopyrrolidin-1-yl)propyl)amino)imidazo[1,2-b]pyridazin-3-yl)thiophene-2-carboxylic acid

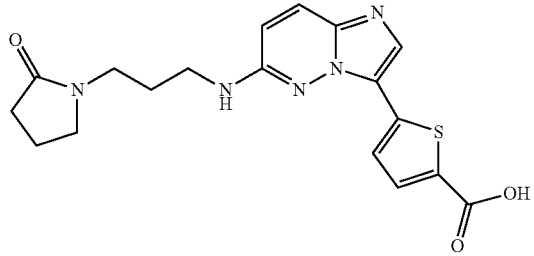 [SMILES: O=C(O)c1ccc(-c2cnc3ccc(NCCCN4CCCC4=O)nn23)s1]

The Suzuki coupling of 5-boronothiophene-2-carboxylic acid and 1-(3-((3-bromoimidazo[1,2-b]pyridazin-6-yl)amino)propyl)pyrrolidin-2-one using the procedure described in example 5.6.19 yielded 64% of the titled compound.

Part B. N-(2,4-dimethoxybenzyl)-5-(6-((3-(2-oxopyrrolidin-1-yl)propyl)amino)imidazo[1,2-b]pyridazin-3-yl)thiophene-2-carboxamide

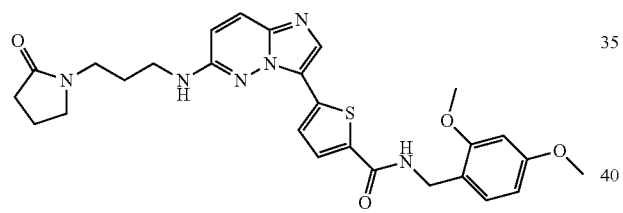

The amide coupling reaction of the carboxylic acid with 2,4-dimethoxy-benzylamine afforded 83% product.

Part C. 5-(6-((3-(2-oxopyrrolidin-1-yl)propyl)amino)imidazo[1,2-b]pyridazin-3-yl)thiophene-2-carboxamide To 50 mg (0.094 mmol) of N-(2,4-dimethoxybenzyl)-5-(6-((3-(2-oxopyrrolidin-1-yl)propyl)amino)imidazo[1,2-b]pyridazin-3-yl)thiophene-2-carboxamide dissolved in 1 mL DCM was added 5 mL of TFA. The resulting solvent was stirred at rt for 0.5 hr and then concentrated. It was purified in the PREP HPLC to obtain 26 mg (72%) of the desired product. $^1$H NMR (400 MHz, METHANOL-$d_4$) δ ppm 2.04 (quin, J=7.39 Hz, 4H) 2.33-2.41 (m, 2H) 3.45-3.60 (m, 6H) 6.76 (d, J=9.85 Hz, 1H) 7.64-7.72 (m, 2H) 7.75 (d, J=4.04 Hz, 1H) 7.94 (s, 1H); LRMS (ESI) m/e 385.0 [(M+H)$^+$, calcd for $C_{18}H_{20}N_6O_2S$ 384.0].

5.6.35. Synthesis of N-(2-aminoethyl)-4-(6-(butylamino)imidazo[1,2-b]pyridazin-3-yl)benzamide

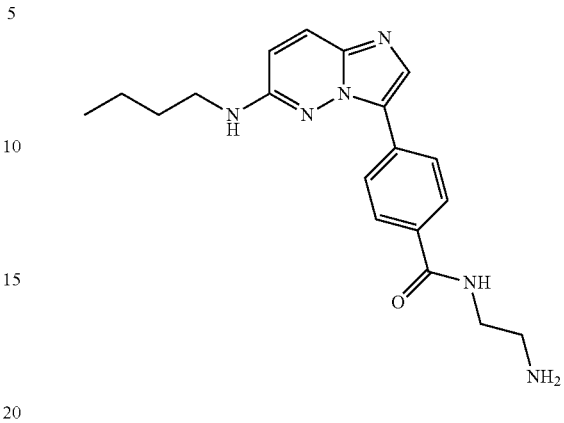

Part A. methyl 4-(6-(butylamino)imidazo[1,2-b]pyridazin-3-yl)benzoate

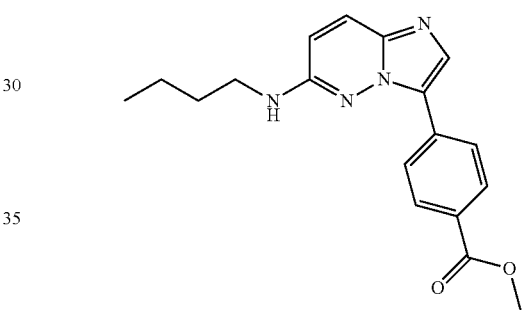

To a mixture of 3-bromo-N-butylimidazo[1,2-b]pyridazin-6-amine (386 mg, 1.43 mmol), (4-(methoxycarbonyl)phenyl)boronic acid (310 mg, 1.72 mmol), [1,1'-bis(diphenylphosphino)ferrocene]dichloropalladium(II) (50 mg, 0.07 mmol) and potassium carbonate (296 mg, 2.15 mmol) was added 3:1 acetonitrile/water (5 mL). The resulting mixture was heated at 145° C. (microwave) for 800 s. The reaction was then filtered and concentrated. The residue was dissolved in methanol, and then filtered again. The filtration was finally purified by column chromatography on silica gel (50% ethyl acetate in hexane) to afford methyl 4-(6-(butylamino)imidazo[1,2-b]pyridazin-3-yl)benzoate (312 mg, 67% yield) as a yellow solid: $^1$H NMR (CHLOROFORM-d) δ: 8.22-8.34 (m, 2H), 8.09-8.20 (m, 2H), 7.93 (s, 1H), 7.71 (d, J=9.6 Hz, 1H), 6.51 (d, J=9.6 Hz, 1H), 3.97 (s, 3H), 3.41-3.53 (m, 2H), 1.72 (t, J=7.2 Hz, 2H), 1.50 (dd, J=15.0, 7.5 Hz, 2H), 1.02 (t, J=7.5 Hz, 3H); LRMS (ESI) m/e 325.2 [(M+H)$^+$, calcd for $C_{18}H_{21}N_4O_2$ 325.2].

Part B. N-(2-aminoethyl)-4-(6-(butylamino)imidazo[1,2-b]pyridazin-3-yl)benzamide The solution of methyl aluminum (2.0 M in hexane, 0.31 mL, 0.62 mmol) in toluene (2 mL) was cooled to 0° C. Then to the stirring solution was respectively added dropwise ethane-1,2-diamine (37.4 mg, 0.62 mmol), and the solution of methyl 4-(6-(butylamino)imidazo[1,2-b]pyridazin-3-yl)benzoate (126 mg, 0.39 mmol) in toluene (1 mL). The resulting reaction was refluxed at 110° C. overnight, and then cooled to 0° C. To the solution was added dropwise water (0.05 mL), methanol (0.2 mL) and chloroform (0.2 mL). The resulting mixture was refluxed on a steam bath for 15 m, and then filtered over sodium sulfate and concentrated. The residue was purified by preparative HPLC to afford N-(2-aminoethyl)-4-(6-(butylamino)imidazo[1,2-b]pyridazin-3-yl)benzamide acetic acid salt (5.7 mg, 4% yield) as a yellow solid: $^1$H NMR (METHANOL-$d_4$) δ: 8.27-8.43 (m, J=8.6 Hz, 2H), 7.95-8.04 (m, J=8.3 Hz, 2H), 7.89 (s, 1H), 7.65 (d, J=9.6 Hz, 1H), 6.75 (d, J=9.9 Hz, 1H), 3.68 (t, J=5.9 Hz, 2H), 3.41 (t, J=7.2 Hz, 2H), 3.16 (br. s., 2H), 1.95 (br. s., 5H), 1.73 (t, J=7.1 Hz, 2H), 1.42-1.61 (m, 2H), 1.02 (t, J=7.3 Hz, 3H); LRMS (ESI) m/e 353.4 [(M+H)$^+$, calcd for $C_{19}H_{25}N_6O$ 353.2].

5.6.36. Synthesis of N-butyl-3-(4-(4,5-dihydro-1H-imidazol-2-yl)phenyl)imidazo[1,2-b]pyridazin-6-amine

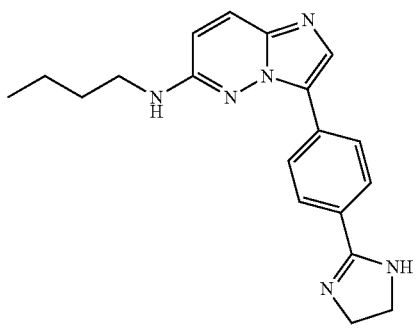 [SMILES: CCCCNc1ccc2ncc(-c3ccc(C4=NCCN4)cc3)n2n1]

The solution of methyl aluminum (2.0 M in hexane, 0.31 mL, 0.62 mmol) in toluene (2 mL) was cooled to 0° C. Then to the stirring solution was respectively added dropwise ethane-1,2-diamine (37.4 mg, 0.62 mmol), and the solution of methyl 4-(6-(butylamino)imidazo[1,2-b]pyridazin-3-yl)benzoate (126 mg, 0.39 mmol) in toluene (1 mL). The resulting reaction was refluxed at 110° C. overnight, and then cooled to 0° C. To the solution was added dropwise water (0.05 mL), methanol (0.2 mL) and chloroform (0.2 mL). The resulting mixture was refluxed on a steam bath for 15 m, and then filtered over sodium sulfate and concentrated. The residue was purified by preparative HPLC to afford N-butyl-3-(4-(4,5-dihydro-1H-imidazol-2-yl)phenyl)imidazo[1,2-b]pyridazin-6-amine acetic acid salt (3.9 mg, 3% yield) as a yellow solid: $^1$H NMR (METHANOL-$d_4$) δ: 8.46-8.59 (m, J=8.8 Hz, 2H), 8.01 (s, 1H), 7.93-7.98 (m, J=8.8 Hz, 2H), 7.67 (d, J=9.9 Hz, 1H), 6.80 (d, J=9.6 Hz, 1H), 4.13 (s, 4H), 3.42 (t, J=7.1 Hz, 2H), 1.86-2.05 (m, 6H), 1.74 (t, J=7.2 Hz, 2H), 1.39-1.61 (m, 2H), 1.03 (t, J=7.3 Hz, 3H); LRMS (ESI) m/e 335.4 [(M+H)$^+$, calcd for $C_{19}H_{23}N_6$ 335.2].

5.6.37. Synthesis of 3-(6-(aminomethyl)pyridin-3-yl)-N-butylimidazo[1,2-b]pyridazin-6-amine

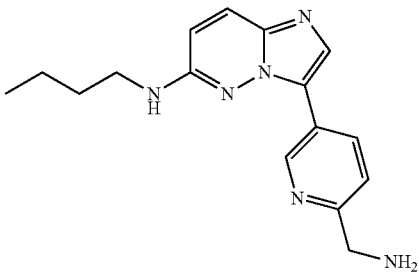

To a mixture of (6-(butylamino)imidazo[1,2-b]pyridazin-3-yl)boronic acid (36 mg, 0.15 mmol), (5-bromopyridin-2-yl)methanamine (35 mg, 0.18 mmol), [1,1'-Bis(diphenylphosphino)ferrocene]dichloropalladium(II) (5 mg, 0.01 mmol) and potassium carbonate (31 mg, 0.23 mmol) was added 3:1 acetonitrile/water (3 mL). The resulting mixture was heated at 145° C. (microwave) for 800 s. The reaction was then filtered and concentrated. The residue was dissolved in methanol, and then filtered again. The filtration was finally purified by preparative HPLC to afford 3-(6-(aminomethyl)pyridin-3-yl)-N-butylimidazo[1,2-b]pyridazin-6-amine acetic acid salt (13 mg, 29% yield) as a white solid: $^1$H NMR (METHANOL-$d_4$) δ: 8.64 (d, J=8.3 Hz, 1H), 7.91 (s, 1H), 7.66 (d, J=9.6 Hz, 1H), 6.77 (d, J=9.9 Hz, 1H), 3.39 (t, J=7.1 Hz, 2H), 1.94 (s, 4H), 1.71 (t, J=7.3 Hz, 2H), 1.41-1.58 (m, 2H), 1.01 (t, J=7.5 Hz, 3H); LRMS (ESI) m/e 297.4 [(M+H)$^+$, calcd for $C_{16}H_{21}N_6$, 297.2].

5.6.38. Synthesis of {3-[3-(4-Aminomethyl-phenyl)-imidazo[1,2-b]pyridazin-6-ylamino]-propyl}-methyl-carbamic acid isopropyl ester

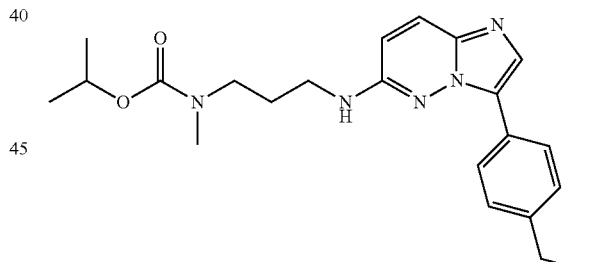

Part A.
2,2,2-Trifluoro-N-(3-methylamino-propyl)-acetamide

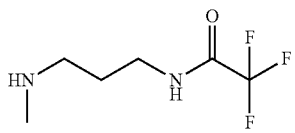

Ethyl trifluoroacetate [383-63-1] (7.5 mL, 62.9 mmol) was slowly added to an ambient temperature solution of N1-methylpropane-1,3-diamine [6291-84-5] (6.5 mL, 62.8 mmol) in anhydrous THF (100 mL) then allowed to stir, under $N_2$ blanket for 17 h. The reaction solution was then evaporated to provide 12.3 g of clear colorless liquid. LRMS (ESI) m/z 185.1 [(M+H)]$^+$, calc'd for $C_6H_{11}F_3N_2O$: 184.16.

Part B. Methyl-[3-(2,2,2-trifluoro-acetylamino)-propyl]-carbamic acid isopropyl ester

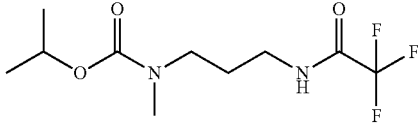 [SMILES: CC(C)OC(=O)N(C)CCCNC(=O)C(F)(F)F]

To a rapidly stirred, 0° C., N₂ blanketed, solution of 2,2,2-trifluoro-N-(3-methylamino-propyl)-acetamide (6.0 g, 32.4 mmol) and N-methylmorpholine [109-02-4] (7.1 mL, 64.6 mmol) in ethyl acetate (65 mL) was steadily added a 1.0M solution of isopropyl chloroformate in toluene (32.4 mL) over the course of 10 minutes. The reaction was allowed to stir and warm to ambient temperature over night at which time it was washed with brine, dried (MgSO₄) and evaporated to provide 9.0 g of clear yellow oil. LRMS (ESI) m/z 271.1 [(M+H)]⁺, calc'd for $C_{10}H_{17}F_3N_2O_3$: 270.25.

Part C. (3-Amino-propyl)-methyl-carbamic acid isopropyl ester

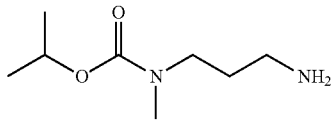

A suspension of methyl-[3-(2,2,2-trifluoro-acetylamino)-propyl]-carbamic acid isopropyl ester (9.0 g, 33.15 mmol), and potassium carbonate [584-08-7] in 50% (v/v) methanol/water (200 mL) was stirred at ambient temperature, under N₂ blanket for 17 h, filtered, and the filtrate evaporated to reduce its volume. The resultant aqueous product solution was place in a continuous extractor and extracted with ethyl acetate to 2d. The ethyl acetate extract was dried (CaSO₄) and evaporated to afford 6.3 g of clear yellow oil. LRMS (ESI) m/z 175.1 [(M+H)]⁺, calc'd for $C_8H_{18}N_2O_2$: 174.24.

Part D. [3-(3-Bromo-imidazo[1,2-b]pyridazin-6-ylamino)-propyl]-methyl-carbamic acid isopropyl ester

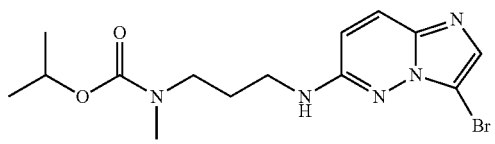 [SMILES: CC(C)OC(=O)N(C)CCCNc1ccc2ncc(Br)n2n1]

A stirred mixture of (3-amino-propyl)-methyl-carbamic acid isopropyl ester (3.0 g, 17.0 mmol), 3-bromo-6-chloro-imidazo[1,2-b]pyridazine [13526-66-4] (723.7 mg, 3.1 mmol), and Hunig's base [7087-68-5] (0.6 mL, 3.2 mmol) was heated to 85° C., under N₂ blanket, for 3d then preabsorbed on silica gel and flash chromatographed (silica gel eluted with 10% (v/v) methanol/ethyl acetate) to obtain 1.0 g of clear yellow oil. LRMS (ESI) m/z 370.2/372.2 [(M+H)]⁺, calc'd for $C_{14}H_{20}BrN_5O_2$: 370.25.

Part E. {3-[3-(4-Aminomethyl-phenyl)-imidazo[1,2-b]pyridazin-6-ylamino]-propyl}-methyl-carbamic acid isopropyl ester To a mixture of [3-(3-bromo-imidazo[1,2-b]pyridazin-6-ylamino)-propyl]-methyl-carbamic acid isopropyl ester (601.4 mg, 1.6 mmol), (4-(aminomethyl)phenyl)boronic acid hydrochloride [75705-21-4] (366.3 mg, 2.0 mmol), potassium phosphate tribasic monohydrate [27176-10-9] (1.1 g, 4.9 mmol), and [1,1'-bis(diphenylphosphino)ferrocene]dichloro-palladium(II), complex with dichloromethane [95464-05-4] (138.7 mg, 0.2 mmol) contained in a 50 mL round bottomed flask was added a solution of 30% (v/v) water in 1,2-dimethoxyethane (12 mL) and a magnetic stir bar. The reaction pot was fitted to a reflux condenser, lowered into an ambient temperature oil bath, and the system taken through 10 evacuation/N₂ blanket cycles while being rapidly stirred. The rapidly stirred, N₂ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried (MgSO₄) purified by preparative RP-HPLC. Purified chromatography fractions were combined and partitioned between aqueous saturated sodium bicarbonate and ethyl acetate. The organic extract dried (CaSO₄) and evaporated to provide {3-[3-(4-aminomethyl-phenyl)-imidazo[1,2-b]pyridazin-6-ylamino]-propyl}-methyl-carbamic acid isopropyl ester as 19.4 mg of clear yellow oil. ¹H NMR (400 MHz, METHANOL-d₄) δ ppm 1.12 (br. s., 2H) 1.17-1.28 (m, 4H) 1.84-1.98 (m, 2H) 2.90 (s, 2H) 3.10-3.21 (m, 1H) 3.32-3.43 (m, 3H) 3.88 (s, 2H) 4.78-4.87 (m, 4H) 6.69 (d, J=9.60 Hz, 1H) 7.45 (d, J=8.34 Hz, 2H) 7.61 (d, J=9.60 Hz, 1H) 7.69-7.75 (m, 1H) 8.12 (dd, J=8.21, 2.65 Hz, 2H). ¹³C NMR (100 MHz, METHANOL-d₄) δ ppm 22.58, 37.39, 40.24, 46.39, 70.29, 110.81, 114.20, 125.95, 126.19, 127.75, 127.85, 128.87, 129.41, 129.65, 129.73, 130.34, 138.67, 141.99, 155.32. LRMS (ESI) m/z 397.3 [(M+H)]⁺, calc'd for $C_{21}H_{28}N_6O_2$: 396.50.

5.6.39. Synthesis of 5-(6-Butylamino-imidazo[1,2-b]pyridazin-3-yl)indan-1-one

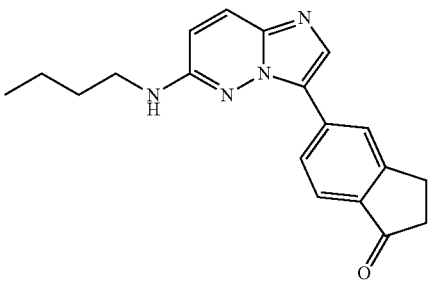 [SMILES: CCCCNc1ccc2ncc(-c3ccc4c(c3)CCC4=O)n2n1]

Part A. 5-(4,4,5,5-tetramethyl-1,3,2-dioxaborolan-2-yl)-2,3-dihydro-1H-inden-1-one

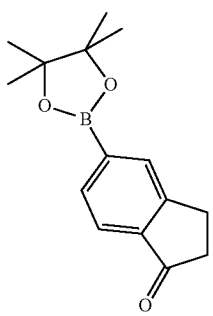 [SMILES: CC1(C)OB(c2ccc3c(c2)CCC3=O)OC1(C)C]

A mixture of 5-bromo-2,3-dihydro-1H-inden-1-one (1.1 g, 5.0 mmol), bis(pinacolato)diboron (1.9 g, 7.5 mmol), potassium acetate (2.5 g, 25 mmol), dichloro[1,1'-bis(diphenylphosphino)ferrocene]palladium (II) dichloromethane adduct (400 mg, 0.5 mmol), and DMF (25 mL) was maintained at 80° C. for 12 h. The resulting mixture was allowed to cool to RT, then partitioned between ethyl acetate (200 mL) and H$_2$O (240 mL). The layers were separated, and the aqueous layer was extracted with ethyl acetate (2×50 mL). Combined organic layers were washed with H$_2$O and brine, then dried (MgSO$_4$), filtered and concentrated to afford a dark residue that was purified by flash chromatography (SiO$_2$) to afford 5-(4,4,5,5-tetramethyl-1,3,2-dioxaborolan-2-yl)-2,3-dihydro-1H-inden-1-one $^1$H NMR (400 MHz, CHLOROFORM-d) δ ppm 7.96 (s, 1H), 7.80-7.84 (m, 1H), 7.74-7.79 (m, 1H), 3.13-3.20 (m, 2H), 2.69-2.75 (m, 2H), 1.39 (s, 12H).

Part B. 5-(6-Butylamino-imidazo[1,2-b]pyridazin-3-yl)-indan-1-one

A mixture of 3-bromo-N-butylimidazo[1,2-b]pyridazin-6-amine (400 mg, 1.5 mmol), 5-(4,4,5,5-tetramethyl-1,3,2-dioxaborolan-2-yl)-2,3-dihydro-1H-inden-1-one (770 mg, 3.0 mmol), dichloro[1,1'-bis(diphenylphosphino)ferrocene]palladium (II) dichloromethane adduct (240 mg, 0.30 mmol), potassium phosphate (1.0 g, 4.5 mmol), DME (6 mL) and H$_2$O (2 mL) was heated in a sealed vessel at 80° C. for 12 h. The reaction was cooled to RT, then the organic layer was separated and concentrated under reduced pressure to afford an oil that was purified by flash chromatography (SiO$_2$) to afford 5-(6-butylamino-imidazo[1,2-b]pyridazin-3-yl)-indan-1-one (410 mg, 85%) as a pink solid: $^1$H NMR (400 MHz, DMSO-d$_6$) δ ppm 8.52 (s, 1H), 8.22 (d, J=8.1 Hz, 1H), 8.07 (s, 1H), 7.78 (s, 1H), 7.65 (d, J=8.1 Hz, 1H), 7.17 (t, J=5.4 Hz, 1H), 6.75 (d, J=9.6 Hz, 1H), 3.22-3.42 (m, 3H), 3.05-3.18 (m, 2H), 2.58-2.71 (m, 2H), 1.58-1.73 (m, 2H), 1.34-1.51 (m, 2H), 0.89-1.00 (m, 3H); LCMS (ESI) m/e 321.2 [(M+H)$^+$, calcd for C$_{19}$H$_{21}$N$_4$O 321.2].

5.6.40. Synthesis of [3-(1-Amino-indan-5-yl)-imidazo[1,2-b]pyridazin-6-yl]-butyl-amine

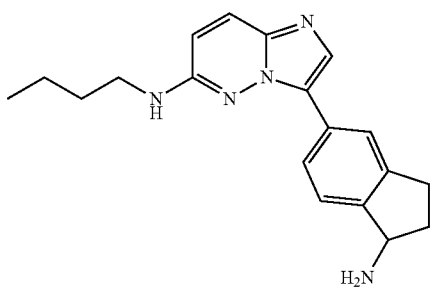 [SMILES: CCCCNc1ccc2ncc(-c3ccc4c(c3)CCC4N)n2n1]

A mixture of 5-(6-butylamino-imidazo[1,2-b]pyridazin-3-yl)-indan-1-one (50 mg, 0.16 mmol), ammonium acetate (500 mg), and methanol (5 mL) was maintained at RT for 5 min, then treated with sodium cyanoborohydride (500 mg). The resulting mixture was heated to 50° C. and maintained 16 h, then cooled to RT and concentrated under reduced pressure. The residue was partitioned between ethyl acetate and saturated aqueous sodium bicarbonate. The layers were separated and the aqueous layer was extracted with ethyl acetate (2×). The combined organic layers were washed with brine, then dried (MgSO$_4$), filtered and concentrated to afford a residue that was purified by reverse phase HPLC to afford [3-(1-amino-indan-5-yl)-imidazo[1,2-b]pyridazin-6-yl]-butyl-amine (26 mg, 52%) as a white solid: $^1$H NMR (400 MHz, METHANOL-d$_4$) δ ppm 8.22 (s, 1H), 8.12 (d, J=8.1 Hz, 1H), 7.78 (s, 1H), 7.54-7.66 (m, 2H), 6.72 (d, J=9.6 Hz, 1H), 4.77-4.83 (m, 1H), 3.38 (t, J=7.2 Hz, 2H), 3.18-3.30 (m, 1H), 3.01-3.13 (m, 1H), 2.59-2.73 (m, 1H), 2.06-2.22 (m, 1H), 1.72 (quin, J=7.4 Hz, 2H), 1.43-1.57 (m, 2H), 1.02 (t, J=7.3 Hz, 3H); LCMS (ESI) m/e 322.3 [(M+H)$^+$, calcd for C$_{19}$H$_{24}$N$_5$ 322.2].

5.6.41. Synthesis of N-butyl-3-(4-(1,4,5,6-tetrahydropyrimidin-2-yl)phenyl)imidazo[1,2-b]pyridazin-6-amine

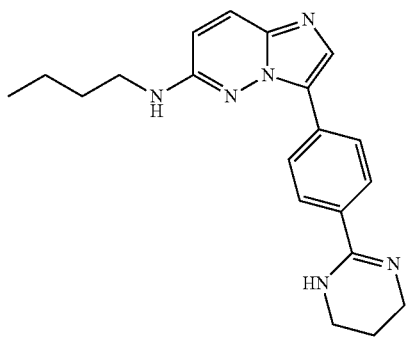 [SMILES: CCCCNc1ccc2ncc(-c3ccc(C4=NCCCN4)cc3)n2n1]

The solution of methyl aluminum (2.0 M in hexane, 0.32 mL, 0.64 mmol) in toluene (2 mL) was cooled to 0° C. Then to the stirring solution was respectively added dropwise propane-1,3-diamine (48 mg, 0.64 mmol), and the solution of methyl 4-(6-(butylamino)imidazo[1,2-b]pyridazin-3-yl)benzoate (130 mg, 0.4 mmol) in toluene (1 mL). The resulting reaction was refluxed at 110° C. overnight, and then cooled to 0° C. To the solution was added dropwise water (0.05 mL), methanol (0.2 mL) and chloroform (0.2 mL). The resulting mixture was refluxed on a steam bath for 15 m, and then filtered over sodium sulfate and concentrated. The residue was purified by preparative HPLC to afford N-butyl-3-(4-(1,4,5,6-tetrahydropyrimidin-2-yl)phenyl)imidazo[1,2-b]pyridazin-6-amine acetic acid salt (23.3 mg, 17% yield) as a white solid: $^1$H NMR (METHANOL-d$_4$) δ: 8.42-8.56 (m, J=8.6 Hz, 2H), 7.96 (s, 1H), 7.75-7.86 (m, J=8.6 Hz, 2H), 7.66 (d, J=9.6 Hz, 1H), 6.78 (d, J=9.9 Hz, 1H), 3.64 (t, J=5.8 Hz, 4H), 3.41 (t, J=7.1 Hz, 2H), 2.16 (t, J=5.7 Hz, 2H), 1.94 (s, 5H), 1.73 (t, J=7.2 Hz, 2H), 1.42-1.58 (m, 2H), 1.02 (t, J=7.3 Hz, 3H); LRMS (ESI) m/e 349.5 [(M+H)$^+$, calcd for C$_{20}$H$_{24}$N$_6$ 349.2].

5.6.42. Synthesis of 1-(5-{6-[3-(2-Methyl-piperidin-1-yl)-propylamino]-imidazo[1,2-b]pyridazin-3-yl}-thiophen-2-yl)-ethanone

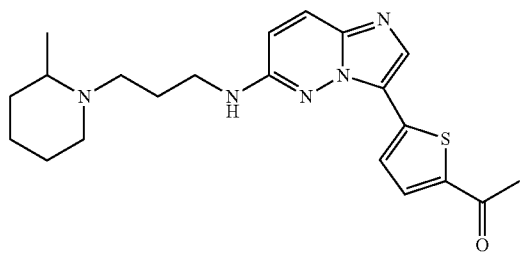 [SMILES: CC(=O)c1ccc(-c2cnc3ccc(NCCCN4CCCCC4C)nn23)s1]

Part A. 3-bromo-N-(3-(2-methylpiperidin-1-yl)propyl)imidazo[1,2-b]pyridazin-6-amine

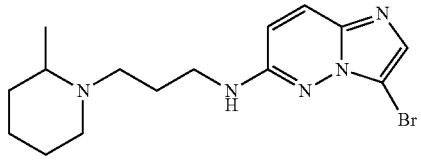 [SMILES: CC1CCCCN1CCCNc1ccc2ncc(Br)n2n1]

To 400 mg (1.852 mmol) of the aryl fluoride was added 1-(3-aminopropyl)pyrrolidin-2-one (347 mg, 2.222 mmol), 2 mL of isopropanol, and triethylamine (0.52 ml, 3.704 mmol). This mixture was microwaved at 140° C. for 0.5 hr. It was diluted with EtOAc, washed with brine and dried over MgSO$_4$. It was purified with silica gel (ISCO) eluting with 0-10 MeOH/DCM to obtain 486 mg (74%) of the aryl amine.

Part B. 1-(5-{6-[3-(2-Methyl-piperidin-1-yl)-propylamino]-imidazo[1,2-b]pyridazin-3-yl}-thiophen-2-yl)-ethanone The reaction of 3-bromo-N-(3-(2-methylpiperidin-1-yl)propyl)imidazo[1,2-b]pyridazin-6-amine with (5-acetylthiophen-2-yl)boronic acid, under the Suzuki coupling condition described in example 5.6.19, afforded the desired compound in 71% yield. $^1$H NMR (400 MHz, CHLOROFORM-d) δ ppm 1.34 (d, J=6.57 Hz, 3H) 1.45-1.59 (m, 1H) 1.67-1.96 (m, 5H) 2.13-2.31 (m, 2H) 2.60 (s, 3H) 2.74 (dd, J=10.86, 4.80 Hz, 1H) 2.83-2.95 (m, 1H) 3.11 (br. s., 1H) 3.17-3.31 (m, 1H) 3.34-3.46 (m, 1H) 3.53-3.72 (m, 2H) 6.72 (d, J=9.85 Hz, 1H) 7.56 (d, J=4.04 Hz, 1H) 7.64-7.73 (m, 2H) 7.94 (s, 1H); LRMS (ESI) m/e 398.0 [(M+H)$^+$, calcd for C$_{21}$H$_{27}$N$_5$OS 397.0].

5.6.43. Synthesis of (4-aminopiperidin-1-yl)(4-(6-(butylamino)imidazo[1,2-b]pyridazin-3-yl)phenyl)methanone

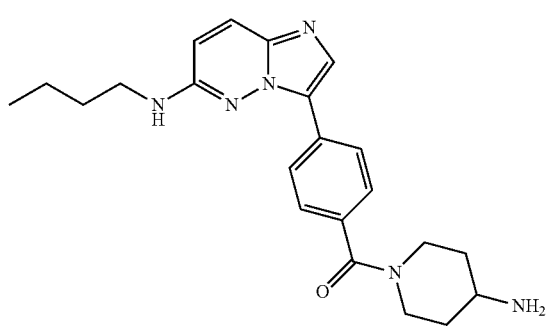 [SMILES: CCCCNc1ccc2ncc(-c3ccc(C(=O)N4CCC(N)CC4)cc3)n2n1]

Part A. 4-(6-(butylamino)imidazo[1,2-b]pyridazin-3-yl)benzoic acid

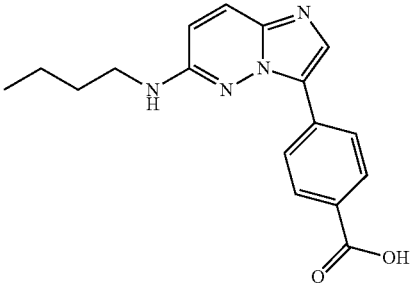 [SMILES: CCCCNc1ccc2ncc(-c3ccc(C(=O)O)cc3)n2n1]

To the mixture of 3-bromo-N-butylimidazo[1,2-b]pyridazin-6-amine (340 mg, 1.26 mmol), 4-boronobenzoic acid (210 mg, 1.26 mmol), [1,1'-bis(diphenylphosphino)ferrocene]dichloropalladium(II) (44 mg, 0.063 mmol) and potassium carbonate (261 mg, 1.89 mmol) was added 3:1 acetonitrile/water (3 mL). The resulting mixture was heated at 145° C. (microwave) for 800 s. The reaction was then filtered and concentrated to afford 4-(6-(butylamino)imidazo[1,2-b]pyridazin-3-yl)benzoic acid (886 mg, >100% yield) as a crude off-white solid: LRMS (ESI) m/e 311.2 [(M+H)$^+$, calcd for C$_{17}$H$_{19}$N$_4$O$_2$ 311.2].

Part B. tert-butyl(1-(4-(6-(butylamino)imidazo[1,2-b]pyridazin-3-yl)benzoyl)piperidin-4-yl)carbamate

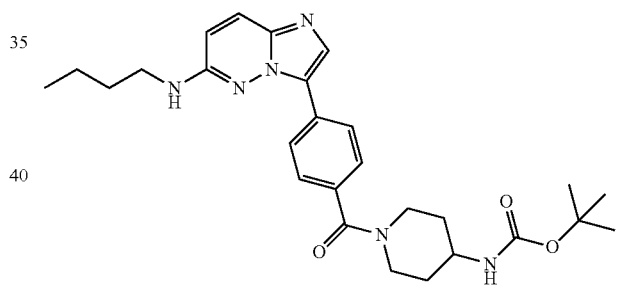

The reaction of the 4-(6-(butylamino)imidazo[1,2-b]pyridazin-3-yl)benzoic acid (93 mg, 0.3 mmol), tert-butyl piperidin-4-ylcarbamate (66 mg, 0.33 mmol), 1-ethyl-3-(3-dimethylaminopropyl)carbodiimide (63 mg, 0.33 mmol) and dichloromethane (3 mL) was maintained at room temperature overnight. The resulting solution was purified by preparative HPLC (neutral) to afford tert-butyl(1-(4-(6-(butylamino)imidazo[1,2-b]pyridazin-3-yl)benzoyl)piperidin-4-yl)carbamate (76 mg, 52% yield) as a yellow solid: $^1$H NMR (METHANOL-d$_4$) δ: 8.23-8.43 (m, J=8.3 Hz, 2H), 7.85 (s, 1H), 7.63 (d, J=9.9 Hz, 1H), 7.45-7.56 (m, 2H), 6.68-6.87 (m, 1H), 4.55 (d, J=12.1 Hz, 1H), 3.82 (br. s., 1H), 3.59-3.72 (m, 1H), 3.35-3.48 (m, 4H), 3.19 (d, J=15.2 Hz, 2H), 1.92-2.17 (m, 1H), 1.90 (br. s., 1H), 1.72 (m, 2H), 1.35-1.59 (m, 13H), 1.01 (t, J=7.3 Hz, 3H); LRMS (ESI) m/e 493.3 [(M+H)$^+$, calcd for C$_{27}$H$_{37}$N$_6$O$_3$ 493.3].

Part C. (4-aminopiperidin-1-yl)(4-(6-(butylamino)imidazo[1,2-b]pyridazin-3-yl)phenyl)methanone The solution of tert-butyl(1-(4-(6-(butylamino)imidazo[1,2-b]pyridazin-3-yl)benzoyl)piperidin-4-yl)carbamate (47 mg, 0.1 mmol) was cooled to 0° C. and treated with acetyl chloride (225 mg, 2.86 mmol). The reaction was maintained at room temperature for overnight. The resulting solution was concentrated under reduced pressure and the residue was purified by preparative HPLC (neutral) to afford (4-aminopiperidin-1-yl)(4-(6-(butylamino)imidazo[1,2-b]pyridazin-3-yl)phenyl)methanone acetic acid salt (34 mg, 79% yield) as a white solid: $^1$H NMR (METHANOL-d$_4$) δ: 8.17-8.42 (m, J=8.3 Hz, 2H), 7.86 (s, 1H), 7.63 (d, J=9.6 Hz, 1H), 7.48-7.57 (m, J=8.6 Hz, 2H), 6.74 (d, J=9.6 Hz, 1H), 3.36-3.49 (m, 3H), 1.90-1.99 (m, 9H), 1.72 (quin, J=7.3 Hz, 2H), 1.63 (br. s., 2H), 1.44-1.55 (m, 2H), 1.01 (t, J=7.5 Hz, 3H); LRMS (ESI) m/e 393.2 [(M+H)$^+$, calcd for C$_{22}$H$_{29}$N$_6$O 393.2].

5.6.44. Synthesis of (4-(6-(butylamino)imidazo[1,2-b]pyridazin-3-yl)phenyl)(piperazin-1-yl)methanone

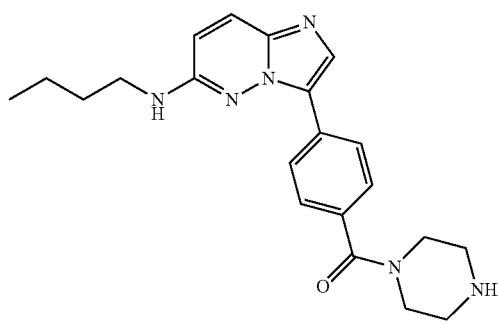 [SMILES: CCCCNc1ccc2ncc(-c3ccc(C(=O)N4CCNCC4)cc3)n2n1]

Part A. tert-butyl 4-(4-(6-(butylamino)imidazo[1,2-b]pyridazin-3-yl)benzoyl)piperazine-1-carboxylate

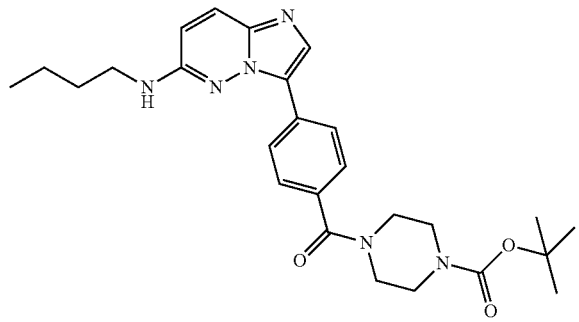 [SMILES: CCCCNc1ccc2ncc(-c3ccc(C(=O)N4CCN(C(=O)OC(C)(C)C)CC4)cc3)n2n1]

The reaction of the 4-(6-(butylamino)imidazo[1,2-b]pyridazin-3-yl)benzoic acid (124 mg, 0.4 mmol), tert-butyl piperazine-1-carboxylate (82 mg, 0.44 mmol), 1-ethyl-3-(3-dimethylaminopropyl)carbodiimide (84 mg, 0.44 mmol) and dichloromethane (3 mL) was maintained at room temperature overnight. The resulting solution was purified by preparative HPLC (neutral) to afford tert-butyl 4-(4-(6-(butylamino)imidazo[1,2-b]pyridazin-3-yl)benzoyl)piperazine-1-carboxylate (89 mg, 47% yield) as a yellow solid: $^1$H NMR (METHANOL-d$_4$) δ: 8.20-8.39 (m, J=8.3 Hz, 2H), 7.85 (s, 1H), 7.63 (d, J=9.9 Hz, 1H), 7.48-7.56 (m, 2H), 6.66-6.79 (m, 1H), 4.55 (d, J=12.1 Hz, 1H), 3.82 (br. s., 1H), 3.58-3.73 (m, 1H), 3.35-3.45 (m, 4H), 3.26 (br. s., 1H), 3.17 (d, J=15.2 Hz, 1H), 3.10 (br. s., 1H), 1.92-2.15 (m, 1H), 1.90 (br. s., 1H), 1.72 (quin, J=7.4 Hz, 2H), 1.34-1.57 (m, 14H), 1.01 (t, J=7.3 Hz, 3H); LRMS (ESI) m/e 479.3 [(M+H)$^+$, calcd for C$_{26}$H$_{35}$N$_6$O$_3$ 479.3].

Part B. (4-(6-(butylamino)imidazo[1,2-b]pyridazin-3-yl)phenyl)(piperazin-1-yl)methanone The solution of tert-butyl 4-(4-(6-(butylamino)imidazo[1,2-b]pyridazin-3-yl)benzoyl)piperazine-1-carboxylate (65 mg, 0.14 mmol) was cooled to 0° C. and treated with acetyl chloride (320 mg, 4.07 mmol). The reaction was maintained at room temperature for overnight. The resulting solution was concentrated under reduced pressure and the residue was purified by preparative HPLC (neutral) to afford (4-(6-(butylamino)imidazo[1,2-b]pyridazin-3-yl)phenyl)(piperazin-1-yl)methanone acetic acid salt (52 mg, 76% yield) as a white solid: $^1$H NMR (METHANOL-d$_4$) δ: 8.34 (d, J=8.3 Hz, 2H), 7.87 (s, 1H), 7.64 (d, J=9.6 Hz, 1H), 7.55 (d, J=8.3 Hz, 2H), 6.75 (d, J=9.6 Hz, 1H), 3.40 (t, J=7.2 Hz, 2H), 3.04 (br. s., 3H), 1.92-2.02 (m, 7H), 1.73 (t, J=7.2 Hz, 2H), 1.41-1.59 (m, 2H), 1.02 (t, J=7.3 Hz, 3H); LRMS (ESI) m/e 379.2 [(M+H)$^+$, calcd for C$_{21}$H$_{27}$O 379.2].

5.6.45. Synthesis of Butyl-{3-[4-(1H-tetrazol-5-yl)-phenyl]-imidazo[1,2-b]pyridazin-6-yl}-mine

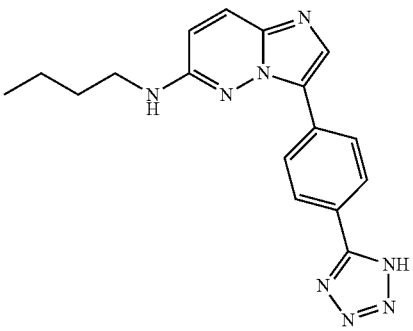 [SMILES: CCCCNc1ccc2ncc(-c3ccc(-c4nnn[nH]4)cc3)n2n1]

To a mixture of (3-bromo-imidazo[1,2-b]pyridazin-6-yl)-butyl-amine (327.5 mg, 1.2 mmol), [[4-(2H-tetrazol-5-yl)phenyl]boronic acid [179942-55-3] (287.2 mg, 1.5 mmol), potassium phosphate tribasic monohydrate [27176-10-9] (564.7 mg, 2.5 mmol), and [1,1'-bis(diphenylphosphino) ferrocene]dichloropalladium(II), complex with dichloromethane [95464-05-4] (103.7 mg, 0.1 mmol) contained in a 50 mL round bottomed flask was added a solution of 30% (v/v) water in 1,2-dimethoxyethane (20 mL) and a magnetic stir bar. The reaction pot was fitted to a reflux condenser, lowered into an ambient temperature oil bath, and the system taken through 10 evacuation/N$_2$ blanket cycles while being rapidly stirred. The rapidly stirred, N$_2$ blanketed, reaction was heated to an oil bath temperature of 85° C. for 17 h then cooled, diluted with methanol, filtered, and flash chromatographed (silica gel, eluted with 1% acetic acid in 10% (v/v) methanol/ethyl acetate) to isolate a tan solid which was recrystallized from boiling 2-propanol to yield 101.7 mg of butyl-{3-[4-(1H-tetrazol-5-yl)-phenyl]-imidazo[1,2-b]pyridazin-6-yl}-mine as an off white powder, mp. 270-271° C. $^1$H NMR (400 MHz, DMSO-d$_6$) δ ppm 0.98 (t, J=7.06 Hz, 3H) 1.38-1.53 (m, 2H) 1.59-1.73 (m, 2H) 3.34 (d, J=5.51 Hz, 2H) 6.75 (d, J=9.48 Hz, 1H) 7.17 (br. s., 1H) 7.79 (d, J=9.04 Hz, 1H) 8.06 (br. s., 1H) 8.12 (d, J=7.72 Hz, 2H) 8.47 (m, J=7.72 Hz, 2H). $^{13}$C NMR (100 MHz, DMSO-d$_6$) δ ppm 13.63, 19.77, 30.02, 40.66, 112.49, 122.39, 125.43, 125.65, 126.80, 130.59, 131.70, 153.44. LRMS (ESI) m/z 335.1 [(M+H)]$^+$, calc'd for $C_{17}H_{18}N_8$: 334.39.

5.6.46. Synthesis of [3-(4-Aminomethyl-phenyl)-imidazo[1,2-b]pyridazin-6-yl]-[2-(2-methoxy-phenoxy)-ethyl]-amine

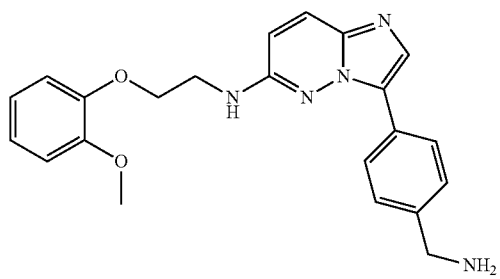 [SMILES: COc1ccccc1OCCNc1ccc2ncc(-c3ccc(CN)cc3)n2n1]

Part A. (3-Bromo-imidazo[1,2-b]pyridazin-6-yl)-[2-(2-methoxy-phenoxy)-ethyl]-amine

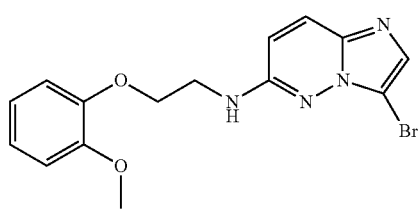 [SMILES: COc1ccccc1OCCNc1ccc2ncc(Br)n2n1]

A mixture of 3-bromo-6-chloro-imidazo[1,2-b]pyridazine (232 mg, 1 mmol) and 2-(2-methoxy-phenoxy)-ethylamine (2 g, 12 mmol) was heated in a microwave at 160° C. for 30 min. The reaction mixture was subjected to ISCO (40 g column, DCM 3 min. then 0-10% MeOH in DCM over 30 min.) to gave the product (160 mg). LRMS (ESI) m/z 363 and 365.1 [(M+H)]$^+$, calc'd for $C_{15}H_{15}BrN_4O_2$: 363.22.

Part B. [3-(4-Aminomethyl-phenyl)-imidazo[1,2-b]pyridazin-6-yl]-[2-(2-methoxy-phenoxy)-ethyl]-amine A mixture of ((3-bromo-imidazo[1,2-b]pyridazin-6-yl)-[2-(2-methoxy-phenoxy)-ethyl]-amine (75 mg, 0.21 mmol), (4-aminomethylphenyl)boronic acid hydrochloride (51 mg, 0.27 mmol), $K_2CO_3$ (87 mg, 0.63 mmol) and dichlorobis(triphenylphosphine)palladium(II) (7.4 mg, 0.011 mmol) in MeCN/water (3.2 ml/0.8 ml) was heated in a microwave at 150° C. for 15 min. The reaction mixture was diluted with MeOH (3 ml) and filtered. The filtrate was subjected to preparative HPLC to give the titled compound as AcOH salt (59.6 mg). $^1$H NMR (400 MHz, METHANOL-$d_4$) δ ppm 1.93 (s, 3H) 3.76-3.83 (m, 5H) 4.13 (s, 2H) 4.26 (t, J=5.56 Hz, 2H) 6.77 (d, J=9.60 Hz, 1H) 6.85-6.99 (m, 4H) 7.51 (d, J=8.34 Hz, 2H) 7.65 (d, J=9.60 Hz, 1H) 7.79 (s, 1H) 8.21 (d, J=8.34 Hz, 2H). LRMS (ESI) m/z 390.2 [(M+H)]$^+$, calc'd for $C_{22}H_{23}N_5O_2$: 389.46.

5.6.47. Synthesis of 3-[3-(5-Acetyl-thiophen-2-yl)-imidazo[1,2-b]pyridazin-6-ylamino]-propionic acid methyl ester

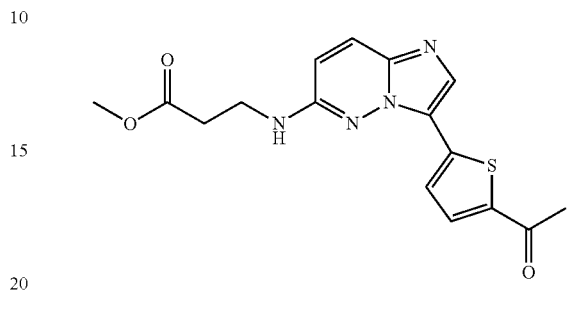

Part A. methyl 3-((3-bromoimidazo[1,2-b]pyridazin-6-yl)amino)propanoate

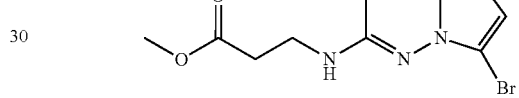

The alkylation of the aryl fluoride with methyl 3-aminopropanoate was carried out by following the amine displacement procedure described in example 5.6.42.

Part B. 3-[3-(5-Acetyl-thiophen-2-yl)-imidazo[1,2-b]pyridazin-6-ylamino]-propionic acid methyl ester The methyl 3-((3-bromoimidazo[1,2-b]pyridazin-6-yl)amino)propanoate was then subjected to Suzuki coupling reaction with (5-acetyl-thiophen-2-yl)boronic acid as described in example 5.6.19. However for this reaction, triethylamine was used as the base in place of the regular base ($K_2CO_3$). The desired product was obtained in 79% yield. $^1$H NMR (400 MHz, CHLOROFORM-d) δ ppm 2.62-2.65 (m, 3H) 2.88 (t, J=5.94 Hz, 2H) 3.77 (s, 3H) 3.88 (t, J=5.68 Hz, 2H) 7.06 (d, J=9.85 Hz, 1H) 7.70 (d, J=4.04 Hz, 1H) 7.77 (d, J=4.04 Hz, 1H) 8.15 (s, 1H) 8.33 (d, J=9.85 Hz, 1H); LRMS (ESI) m/e 345.0 [(M+H)]$^+$, calcd for $C_{16}H_{16}N_4O_3S$ 344.0].

5.6.48. Synthesis of N-butyl-3-(1H-pyrazol-3-yl)imidazo[1,2-b]pyridazin-6-amine

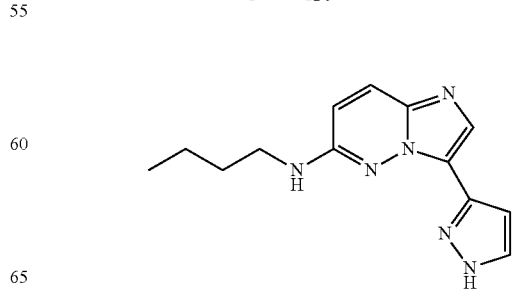

A mixture of 3-bromo-6-(butylamino)imidazo[1,2-b]pyridazine (100 mg, 0.38 mmol), (1H-pyrazol-4-yl)boronic acid (45 mg, 0.38 mmol), PdCl$_2$(PPh$_3$)$_2$ (10 mg, 0.014 mmol) and potassium carbonate (98 mg, 0.71 mmol) was dissolved in CH$_3$CN (3 mL) and water (1.5 mL). The reaction was heated at 140° C. for 30 min in the microwave. The catalyst was filtered off celite, then the filtrate was concentrated and purified by Prep HPLC (neutral) to give N-butyl-3-(1H-pyrazol-3-yl)imidazo[1,2-b]pyridazin-6-amine acetate salt as yellow solid (1.7 mg, 2% yield): $^1$H NMR (400 MHz, METHANOL-d$_4$) δ ppm 8.12 (s, 1H), 7.86-7.92 (m, 2H), 7.30 (d, J=2.53 Hz, 1H), 7.17 (d, J=9.85 Hz, 1H), 3.47 (t, J=7.20 Hz, 2H), 1.75 (quin, J=7.26 Hz, 2H), 1.52 (sxt, J=7.43 Hz, 2H), 1.02 (t, J=7.33 Hz, 3H); LRMS (ESI) m/e 257.2 [(M+H)$^+$, calcd for C$_{13}$H$_{17}$N$_6$ 257.3].

5.6.49. Synthesis of 3-[4-(6-Butylamino-imidazo[1,2-b]pyridazin-3-yl)-phenyl]-4H-[1,2,4]oxadiazol-5-one

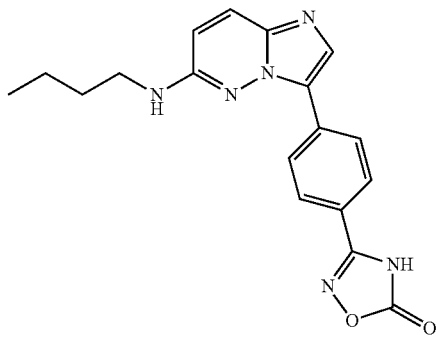 [SMILES: CCCCNc1ccc2ncc(-c3ccc(-c4noc(=O)[nH]4)cc3)n2n1]

To a mixture of 3-(4-bromophenyl)-1,2,4-oxadiazol-5(4H)-one [16672-19-8] (502.7 mg, 2.1 mmol), potassium acetate [127-08-2] (615.4 mg, 6.3 mmol), 4,4,4',4',5,5,5',5'-octamethyl-2,2'-bi(1,3,2-dioxaborolane) [73183-34-3] (582.6 mg, 2.3 mmol), and [1,1'-bis(diphenylphosphino)ferrocene]dichloropalladium(II), complex with dichloromethane [95464-05-4] (53.4 mg, 0.1 mmol) was added anhydrous dimethylsulfoxide. The mixture was stirred at ambient temperature for 17 h then poured into stirred water to precipitate the product. Crude 3-(4-(4,4,5,5-tetramethyl-1,3,2-dioxaborolan-2-yl)phenyl)-1,2,4-oxadiazol-5(4H)-one was isolated by filtration, washed with water, allowed to dry and used in the next step without further purification. LRMS (ESI) m/z 287.3 [(M–H)]$^-$, calc'd for C$_{14}$H$_{17}$BN$_2$O$_4$: 288.11.

Following the Suzuki coupling conditions described in example 5.6.45 from (3-bromo-imidazo[1,2-b]pyridazin-6-yl)-butyl-amine (213.1 mg, 0.8 mmol), and 3-(4-(4,4,5,5-tetramethyl-1,3,2-dioxaborolan-2-yl)phenyl)-1,2,4-oxadiazol-5(4H)-one (308.2 mg, 1.1 mmol) to provide 70.9 mg of 3-[4-(6-butylamino-imidazo[1,2-b]pyridazin-3-yl)-phenyl]-4H-[1,2,4]oxadiazol-5-one as white crystalline powder, mp. 253-254° C. (dec.). $^1$H NMR (400 MHz, DMSO-d$_6$) δ ppm 0.96 (t, J=7.33 Hz, 3H) 1.44 (sxt, J=7.38 Hz, 2H) 1.65 (quin, J=7.26 Hz, 2H) 3.26-3.35 (m, 2H) 6.75 (d, J=9.85 Hz, 1H) 7.15 (t, J=5.31 Hz, 1H) 7.77 (d, J=9.60 Hz, 1H) 7.88 (m, J=8.84 Hz, 2H) 8.05 (s, 1H) 8.44 (m, J=8.59 Hz, 2H). $^{13}$C NMR (100 MHz, DMSO-d$_6$) δ ppm 13.73, 19.89, 30.15, 40.81, 112.82, 120.91, 125.38, 125.50, 126.11, 131.05, 133.01, 137.80, 153.62, 157.06, 159.94. LRMS (ESI) m/z 351.2 [(M+H)]$^+$, calc'd for C$_{18}$H$_{18}$N$_6$O$_2$: 350.38.

5.6.50. Synthesis of N-butyl-3-(2,4-dimethylthiazol-5-yl)imidazo[1,2-b]pyridazin-6-amine

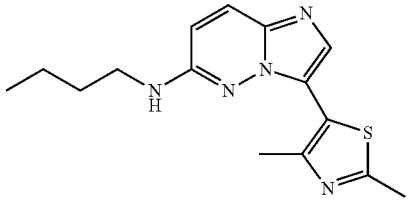 [SMILES: CCCCNc1ccc2ncc(-c3sc(C)nc3C)n2n1]

Using the Suzuki coupling conditions described in example 5.6.48 afforded the titled compound in 16% yield as a white solid. $^1$H NMR (400 MHz, METHANOL-d$_4$) δ ppm 7.59-7.69 (m, 2H), 6.70-6.74 (m, 1H), 3.39 (t, J=7.20 Hz, 2H), 2.70 (s, 3H), 2.57 (s, 3H), 1.67-1.75 (m, 2H), 1.45-1.54 (m, 2H), 1.01 (t, J=7.45 Hz, 3H); LRMS (ESI) m/e 302.2 [(M+H)]$^+$, calc'd for C$_{15}$H$_{20}$N$_5$S 302.4].

5.6.51. Synthesis of 4-[3-(5-Acetyl-thiophen-2-yl)-imidazo[1,2-b]pyridazin-6-ylamino]-butyric acid

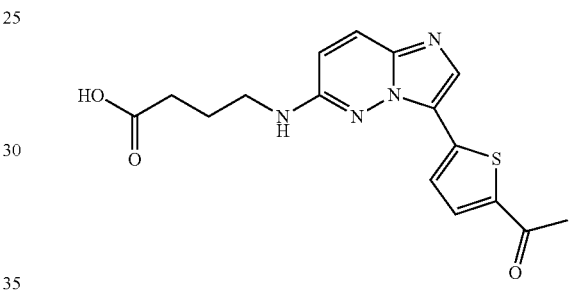

Part A. Ethyl 4-((3-bromoimidazo[1,2-b]pyridazin-6-yl)amino)butanoate

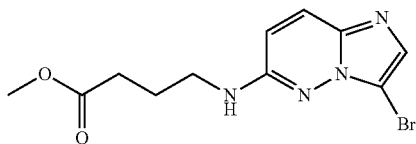 [SMILES: COC(=O)CCCNc1ccc2ncc(Br)n2n1]

The alkylation of the aryl fluoride with ethyl 4-aminobutanoate proceeded under the conditions described in example 5.6.46 to afford the titled compound.

Part B. Ethyl 4-((3-(5-acetylthiophen-2-yl)imidazo[1,2-b]pyridazin-6-yl)amino)butanoate

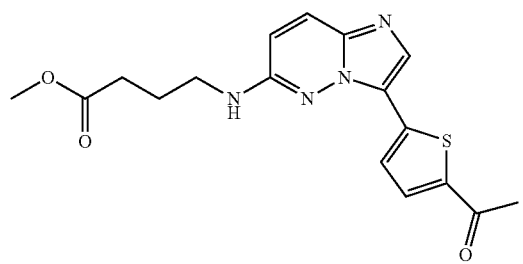 [SMILES: COC(=O)CCCNc1ccc2ncc(-c3ccc(C(C)=O)s3)n2n1]

The ethyl 4-((3-bromoimidazo[1,2-b]pyridazin-6-yl)amino)butanoate was subjected to Suzuki coupling with (5-acetylthiophen-2-yl)boronic acid, using triethylamine as the base and the procedure described in example 5.6.19 to give 74% yield of the product.

Part C. 4-[3-(5-Acetyl-thiophen-2-yl)-imidazo[1,2-b]pyridazin-6-ylamino]-butyric acid

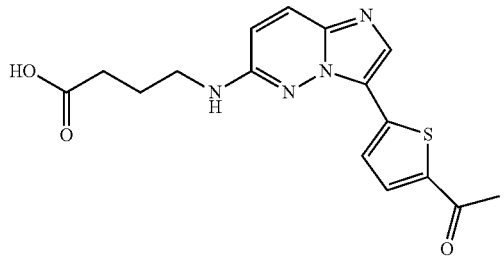 [SMILES: CC(=O)c1ccc(-c2cnc3ccc(NCCCC(=O)O)nn23)s1]

To 200 mg (0.566 mmol) of this ester was added LiOH.H$_2$O (71.4 mg, 1.700 mmol), 10 mL of THF and 3 mL of water and then stirred at rt for 4 hr. The reaction mixture was acidified to pH of about 3, and the product extracted with EtOAc. The organic solvents was washed with brine and dried over MgSO$_4$. It was concentrated to obtain 148 mg (76%) of the desired product. No purification was required. $^1$H NMR (400 MHz, METHANOL-d$_4$) δ ppm 2.60 (s, 3H) 2.73 (t, J=6.73 Hz, 2H) 3.68 (t, J=6.73 Hz, 2H) 4.23 (s, 2H) 7.26 (d, J=9.92 Hz, 1H) 7.67 (d, J=8.16 Hz, 2H) 7.99 (d, J=9.70 Hz, 1H) 8.27 (s, 1H); LRMS (ESI) m/e 345.0 [(M+H)$^+$, calcd for C$_{16}$H$_{16}$N$_4$O$_3$S 344.0].

5.6.52. Synthesis of Butyl-(3-isoquinolin-6-yl-imidazo[1,2-b]pyridazin-6-yl)amine

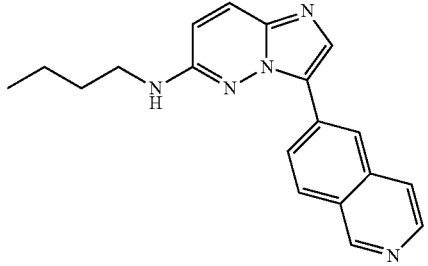 [SMILES: CCCCNc1ccc2ncc(-c3ccc4cnccc4c3)n2n1]

Part A. 6-(4,4,5,5-Tetramethyl-[1,3,2]dioxaborolan-2-yl)-isoquinoline

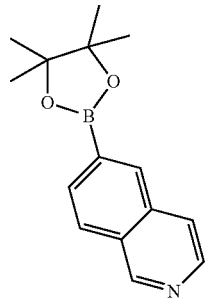 [SMILES: CC1(C)OB(c2ccc3cnccc3c2)OC1(C)C]

A mixture of 6-bromoisoquinoline (208 mg, 1 mmol), bis(pinacolato)diboron (279 mg, 1.1 mmol), KOAc (323 mg, 3.3 mmol) and Pd(dppf)$_2$Cl$_2$ (73 mg, 0.1 mmol) in DMSO (3 ml) was heated in a microwave for 10 min at 160° C. The mixture was diluted with water (20 ml) and extracted with EtOAc (4×20 ml). The combined EtOAc was washed with water (15 ml) and brine (15 ml) then dried (Na$_2$SO$_4$). The solvent was removed to give the titled compound which was used directly for next step.

Part B. Butyl-(3-isoquinolin-6-yl-imidazo[1,2-b]pyridazin-6-yl)-amine

A mixture of (3-bromo-imidazo[1,2-b]pyridazin-6-yl)-butyl-amine (100 mg, 0.37 mmol), 6-(4,4,5,5-tetramethyl-[1,3,2]dioxaborolan-2-yl)-isoquinoline (from part A, ~1 mmol), K$_2$CO$_3$ (153 mg, 1.11 mmol) and dichlorobis(triphenylphosphine)palladium(II) (13 mg, 0.019 mmol) in MeCN/water (4 ml/1 ml) was heated in a microwave at 150° C. for 15 min. The water layer was removed and the reaction mixture was diluted with MeCN (3 ml) and filtered. The filtrate was subjected to preparative HPLC to give the titled compound (80.8 mg). $^1$H NMR (400 MHz, CHLOROFORM-d) δ ppm 1.03 (t, J=7.33 Hz, 3H) 1.53 (dq, J=14.97, 7.39 Hz, 2H) 1.74-1.81 (m, 2H) 3.48-3.54 (m, 2H) 4.58 (t, J=5.05 Hz, 1H) 6.54 (d, J=9.60 Hz, 1H) 7.68 (d, J=5.56 Hz, 1H) 7.75 (d, J=9.60 Hz, 1H) 8.01-8.05 (m, 2H) 8.25 (dd, J=8.72, 1.64 Hz, 1H) 8.55 (d, J=5.81 Hz, 1H) 8.86 (s, 1H) 9.25 (s, 1H). LRMS (ESI) m/z 318.2 [(M+H)]$^+$, calc'd for C$_{19}$H$_{19}$N$_5$: 317.40.

5.6.53. Synthesis of 4-[3-(4-Aminomethyl-phenyl)-imidazo[1,2-b]pyridazin-6-ylamino]-N,N-dimethyl-butyramide

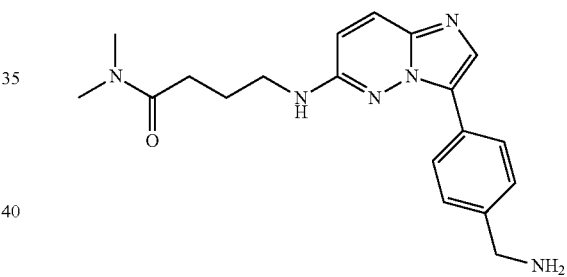

Part A. 4-((3-(4-(((tert-butoxycarbonyl)amino)methyl)phenyl)imidazo[1,2-b]pyridazin-6-yl)amino)butanoic acid

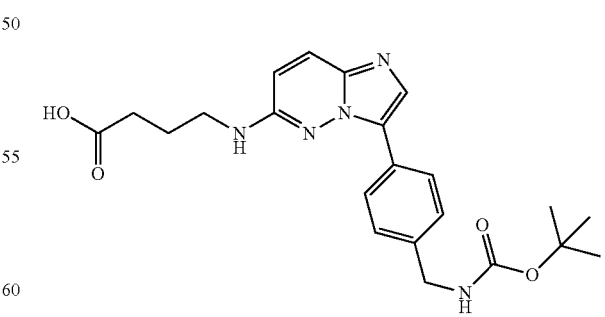

The ethyl 4-((3-bromoimidazo[1,2-b]pyridazin-6-yl)amino)butanoate was subjected to Suzuki coupling with N-Boc-benzyl amine boronic acid, using 4.0 equivalents of K$_2$CO$_3$ as the base and procedure described in example 5.6.19 to give the titled compound.

Part B. tert-Butyl 4-(6-((4-(dimethylamino)-4-oxobutyl)amino)imidazo[1,2-b]pyridazin-3-yl)benzylcarbamate

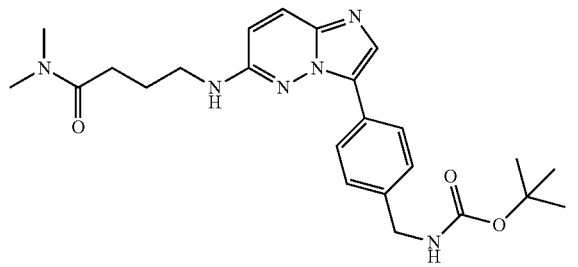 [SMILES: CN(C)C(=O)CCCNc1ccc2ncc(-c3ccc(CNC(=O)OC(C)(C)C)cc3)n2n1]

The carboxylic acid was reacted with dimethylamine, under the regular amide coupling conditions to afford 59% product.

Part C. 4-[3-(4-Aminomethyl-phenyl)-imidazo[1,2-b]pyridazin-6-ylamino]-N,N-dimethyl-butyramide The purified amide (20.4 mg, 0.045 mmol) was dissolved in 2 mL of DCM and 3 mL of TFA was added and stirred for 2 hr. It was concentrated to give 100% (21 mg) yield TFA salt of the titled product. $^1$H NMR (400 MHz, METHANOL-$d_4$) δ ppm 2.01 (quin, J=7.06 Hz, 2H) 2.52 (t, J=7.39 Hz, 2H) 2.93 (s, 3H) 3.05 (s, 3H) 3.46 (t, J=6.84 Hz, 2H) 4.24 (s, 2H) 7.26 (d, J=9.70 Hz, 1H) 7.68 (d, J=8.16 Hz, 2H) 7.99 (d, J=9.92 Hz, 1H) 8.22 (d, J=8.38 Hz, 2H) 8.26 (s, 1H); LRMS (ESI) m/e 353.0 [(M+H)$^+$, calcd for $C_{19}H_{24}N_6O$ 352.0].

5.6.54. Synthesis of N-(4-(aminomethyl)phenyl)-6-(butylamino)imidazo[1,2-b]pyridazine-3-carboxamide

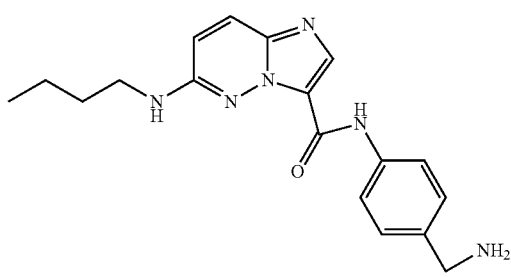 [SMILES: CCCCNc1ccc2ncc(C(=O)Nc3ccc(CN)cc3)n2n1]

Part A. 6-(butylamino)imidazo[1,2-b]pyridazine-3-carbonitrile

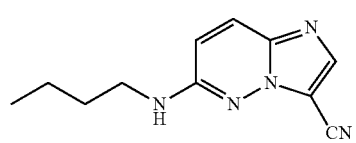 [SMILES: CCCCNc1ccc2ncc(C#N)n2n1]

A solution of 6-(butylamino)imidazo[1,2-b]pyridazine-3-bromide (820 mg, 2.34 mmol), NaCN (137 mg, 2.8 mmol), CuI (45 mg, 0.23 mmol), KI (78 mg, 0.47 mmol) and N1,N2-dimethylethane-1,2-diamine (0.25 mL, 2.34 mmol) in toluene (3 mL) was stirred at 110° C. for 12 h. The reaction was cooled, concentrated, taken up with EtOAc and water, extracted and dried organic layer with MgSO$_4$. The organic layer was concentrated and purified by ISCO (0-5% MeOH/DCM) to give 6-(butylamino)imidazo[1,2-b]pyridazine-3-carbonitrile as a light yellow solid (460 mg, 92% yield). LRMS (ESI) m/e 216.1 [(M+H)$^+$, calcd for $C_{11}H_{14}N_5$ 216.3].

Part B. 6-(butylamino)imidazo[1,2-b]pyridazine-3-carboxylic acid

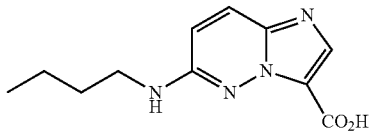 [SMILES: CCCCNc1ccc2ncc(C(=O)O)n2n1]

A solution of 6-(butylamino)imidazo[1,2-b]pyridazine-3-carbonitrile (250 mg, 1.16 mmol) in 10% aqueous solution of NaOH (15 mL) was refluxed for overnight. The reaction mixture was cooled down to room temperature, neutralized to pH=5-7 using 1N HCl, extracted with DCM, dried and concentrated to give 6-(butylamino)imidazo[1,2-b]pyridazine-3-carboxylic acid as white solid (150 mg, 60%). LRMS (ESI) m/e 235.1 [(M+H)$^+$, calcd for $C_{11}H_{15}N_4O_2$ 235.3].

Part C. tert-butyl 4-(6-(butylamino)imidazo[1,2-b]pyridazine-3-carboxamido)benzylcarbamate

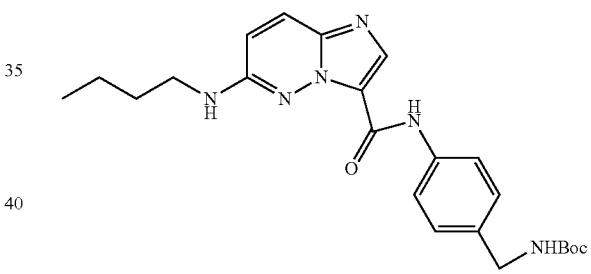

To a solution of 6-(butylamino)imidazo[1,2-b]pyridazine-3-carboxylic acid (150 mg, 0.64 mmol) in CH$_3$CN (1 mL) were added BOP reagent (567 mg, 1.28 mmol), triethyl amine (0.26 mL, 1.92 mmol) and tert-butyl 4-aminobenzylcarbamate (143 mg, 0.64 mmol). The reaction was stirred for overnight. Then the reaction was purified ISCO column chromatography on silica gel (10% MeOH/DCM) to give tert-butyl 4-(6-(butylamino)imidazo[1,2-b]pyridazine-3-carboxamido)benzylcarbamate as white solid (280 mg, 100% yield). 20 mg was further purified by prep HPLC (neutral) to afford tert-butyl 4-(6-(butylamino)imidazo[1,2-b]pyridazine-3-carboxamido)benzylcarbamate (5 mg) as white solid. $^1$H NMR (400 MHz, METHANOL-$d_4$) δ ppm 8.10 (s, 1H), 7.76 (d, J=9.70 Hz, 1H), 7.67 (d, J=8.38 Hz, 2H), 7.32 (d, J=8.38 Hz, 2H), 6.90 (d, J=9.70 Hz, 1H), 4.62 (s, 1H), 4.24 (s, 2H), 3.47 (t, J=7.28 Hz, 2H), 1.79 (t, J=7.39 Hz, 2H), 1.46-1.57 (m, 10H), 1.02 (t, J=7.39 Hz, 3H); LRMS (ESI) m/e 439.9 [(M+H)$^+$, calcd for $C_{23}H_{31}N_6O_3$ 439.5].

Part D. N-(4-(aminomethyl)phenyl)-6-(butylamino)imidazo[1,2-b]pyridazine-3-carboxamide To a solution of tert-butyl 4-(6-(butylamino)imidazo[1,2-b]pyridazine-3-carboxamido)benzylcarbamate (230 mg, 0.53 mmol) in methanol (15 mL) was added acetyl chloride (0.37 mL, 5.25 mmol) dropwise. The reaction mixture was stirred for overnight, concentrated and purified by Prep HPLC (neutral) to give N-(4-(aminomethyl)phenyl)-6-(butylamino)imidazo[1,2-b]pyridazine-3-carboxamide (25 mg, 20% yield). $^1$H NMR (400 MHz, METHANOL-$d_4$) δ ppm 8.54 (s, 1H), 8.11 (s, 1H), 7.80 (d, J=8.38 Hz, 2H), 7.77 (d, J=9.92 Hz, 1H), 7.50 (d, J=8.38 Hz, 2H), 6.92 (d, J=9.70 Hz, 1H), 4.12 (s, 2H), 3.48 (t, J=7.17 Hz, 2H), 1.79 (quin, J=7.33 Hz, 2H), 1.55 (dq, J=15.02, 7.41 Hz, 2H), 1.02 (t, J=7.39 Hz, 3H); LRMS (ESI) m/e 339.2 [(M+H)$^+$, calcd for $C_{18}H_{23}N_6O$ 339.4].

5.6.55. Synthesis of [3-(4-Aminomethyl-phenyl)-7-methyl-imidazo[1,2-b]pyridazin-6-yl]-butyl-amine

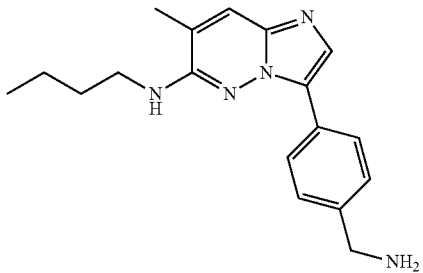 [SMILES: CCCCNc1nn2c(-c3ccc(CN)cc3)cnc2cc1C]

Part A. 6-Chloro-5-methyl-pyridazin-3-ylamine

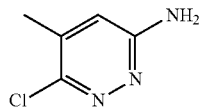

A mixture of 3,6-dichloro-4-methylpyridazine (1.35 g, 8.28 mmol) and 2,4-dimethoxybenzylamine (11.1 g, 66.3 mmol) in i-PrOH (5 ml) was heated in a microwave at 100° C. for 50 min. (30+20 min.). The mixture was concentrated and the residue was subjected to ISCO (120 g column, hexane 5 min., 0-55% EtOAc in hexane over 90 min. to give (6-chloro-5-methyl-pyridazin-3-yl)-(2,4-dimethoxy-benzyl)-amine (680 mg) plus the 6-methyl analog (320 mg).

To a solution of (6-chloro-5-methyl-pyridazin-3-yl)-(2,4-dimethoxy-benzyl)-amine from above (680 mg) in DCM (8 ml) was added TFA (8 ml). The resulting solution was allowed to stand for overnight. The mixture was concentrated to give the titled compound which was used directly for next step.

Part B.
3-Bromo-6-chloro-7-methyl-imidazo[1,2-b]pyridazine

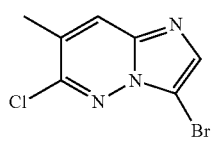

A mixture of 6-chloro-5-methyl-pyridazin-3-ylamine from Part A (~2.3 mmol) and chloroacetaldehyde water solution (50% water, 880 ul, ~7 mmol) in n-BuOH was refluxed for overnight. After cooled to rt, the mixture was diluted with MeOH (15 ml) and filtered. The filtrate was concentrated and treated with Et$_2$O (15 ml). The solid product was collected by filtration.

To a suspension of above product in AcOH (6 ml) was added Br$_2$ (358 ul, 6.96 mmol) slowly at rt. The resulting mixture was stirred at rt for 3 h. The reaction mixture was concentrated and the residue was suspended in Et$_2$O (80 ml) and stirred overnight. The solid product (~800 mg) was collected by filtration and used directly for next step.

Part C. (3-Bromo-7-methyl-imidazo[1,2-b]pyridazin-6-yl)-butyl-amine

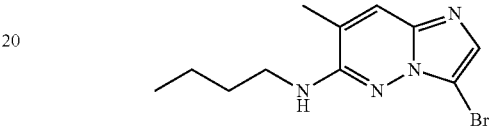

To the 3-bromo-6-chloro-7-methyl-imidazo[1,2-b]pyridazine from Part B was added n-BuNH$_2$ (10 ml). The mixture was heated in a microwave at 160° C. for 60 min (30+30 min.). The mixture was concentrated and the residue was subjected to ISCO (40 g column, hexane 3 min., 0-100% EtOAc in hexane over 25 min. the EtOAc 10 min.) to five the titled compound (348 mg). $^1$H NMR (400 MHz, CHLOROFORM-d) δ ppm 0.97 (t, J=7.39 Hz, 3H) 1.29-1.50 (m, 2H) 1.61-1.71 (m, 2H) 2.14 (s, 3H) 3.44 (q, J=6.62 Hz, 2H) 4.39 (br. s., 1H) 7.34 (s, 1H) 7.37 (s, 1H). LRMS (ESI) m/z 283 and 285 [(M+H)]$^+$, calc'd for $C_{11}H_{15}BrN_4$: 283.17.

Part D. [3-(4-Aminomethyl-phenyl)-7-methyl-imidazo[1,2-b]pyridazin-6-yl]-butyl-amine A mixture of (3-bromo-7-methyl-imidazo[1,2-b]pyridazin-6-yl)-butyl-amine (115 mg, 0.41 mmol), (4-aminomethylphenyl)boronic acid hydrochloride (99.9 mg, 0.53 mmol), K$_2$CO$_3$ (170 mg, 1.23 mmol) and dichlorobis(triphenylphosphine)palladium(II) (14.4 mg, 0.021 mmol) in MeCN/water (3.2 ml/0.8 ml) was heated in a microwave at 150° C. for 15 min. The reaction mixture was diluted with MeCN and filtered. The filtrate was subjected to preparative HPLC to give the titled compound as AcOH salt (66.5 mg). $^1$H NMR (400 MHz, METHANOL-$d_4$) δ ppm 1.01 (t, J=7.39 Hz, 3H) 1.42-1.52 (m, 2H) 1.73 (t, J=7.28 Hz, 2H) 2.23 (s, 3H) 3.41 (t, J=7.28 Hz, 2H) 4.16 (s, 2H) 7.44 (s, 1H) 7.52 (d, J=8.38 Hz, 2H) 7.75 (s, 1H) 8.25 (d, J=8.38 Hz, 2H) 8.54 (s, 1H). LRMS (ESI) m/z 310.2 [(M+H)]$^+$, calc'd for $C_{18}H_{23}N_5$: 309.42.

5.6.56. Synthesis of [2-(3-Bromo-imidazo[1,2-b]pyridazin-6-ylamino)-ethyl]-methyl-carbamic acid tert-butyl ester

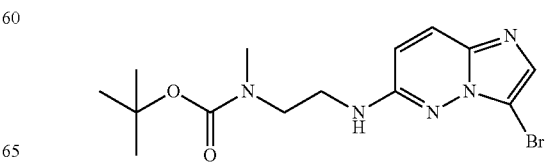

A solution of 3-bromo-6-fluoro-imidazo[1,2-b]pyridazine (1.4 g, 6.3 mmol), N-(2-aminoethyl)-n-methyl carbamic acid tert-butyl ester [121492-06-6] (961 mg, 5.5 mmol), and Hunig's base [7087-68-5] (1.1 mL, 6.4 mmol) in 2-propanol (28 mL) was heated to reflux for 4d, cooled, preloaded onto silica gel and flash chromatographed (silica gel eluted with 10% (v/v) methanol/ethyl acetate). The isolated light yellow solid product was recrystallized (ethyl acetate/heptane) to yield 1.2 g of [2-(3-bromo-imidazo[1,2-b]pyridazin-6-ylamino)-ethyl]-methyl-carbamic acid tert-butyl ester as a white powder, mp. 128-129° C. $^1$H NMR (400 MHz, DMSO-$d_6$) δ ppm (rotamers present) 1.16 (s, 6H) 1.33 (br. s., 3H) 2.84 (s, 2H) 2.90 (br. s., 1H) 3.34-3.44 (m, 3H) 3.45-3.52 (m, 1H) 6.68 (d, J=9.60 Hz, 1H) 7.31 (br. s., 1H) 7.49 (s, 1H) 7.72 (d, J=9.35 Hz, 1H). $^{13}$C NMR (100 MHz, DMSO-$d_6$) δ ppm 28.22, 28.45, 34.02, 35.07, 39.02, 39.97, 46.23, 47.06, 78.52, 78.87, 99.57, 113.35, 125.92, 130.80, 137.01, 154.37, 155.39. LRMS (ESI) m/z 370.1/372.1 [(M+H)]$^+$, calc'd for $C_{14}H_{20}BrN_6O_2$: 370.25.

5.6.57. Synthesis of Isopropyl-carbamic acid 4-(6-butylamino-imidazo[1,2-b]pyridazin-3-yl)-benzyl ester

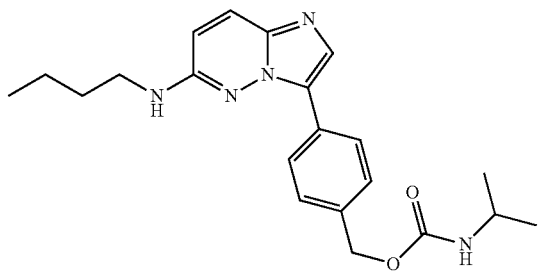 [SMILES: CCCCNc1ccc2ncc(-c3ccc(COC(=O)NC(C)C)cc3)n2n1]

Part A. Isopropyl-carbamic acid 4-(4,4,5,5-tetramethyl-[1,3,2]dioxaborolan-2-yl)-benzyl ester

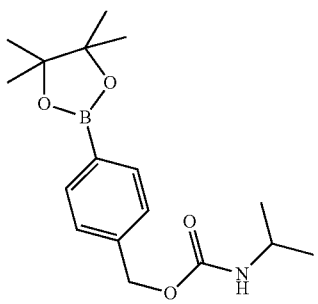 [SMILES: CC(C)NC(=O)OCc1ccc(B2OC(C)(C)C(C)(C)O2)cc1]

To a solution of [4-(4,4,5,5-tetramethyl-[1,3,2]dioxaborolan-2-yl)-phenyl]-methanol (2.34 g, 10 mmol) and pyridine (890 ul, 11 mmol) in THF (50 ml) at rt was added dropwise a solution of 4-nitrophenyl chloroformate (2.22 g, 11 mmol) in THF (10 ml). The reaction mixture was stirred at rt for overnight. The precipitate was removed by filtration. The filtrate was concentrated to give the desired compound (4.2 g, may contain some pyridine HCl salt).

To a solution of above product (400 mg, 1 mmol) in THF (3 ml) was added isopropyl amine (1.5 ml). The mixture was stirred at it for 3 h then concentrated to give the titled compound. LRMS (ESI) m/z 320.2 [(M+H)]$^+$, calc'd for $C_{17}H_{26}BNO_4$: 319.21

Part B. Isopropyl-carbamic acid 4-(6-butylamino-imidazo[1,2-b]pyridazin-3-yl)-benzyl ester A mixture of (3-bromo-imidazo[1,2-b]pyridazin-6-yl)-butyl-amine (50 mg, 0.19 mmol), isopropyl-carbamic acid 4-(4,4,5,5-tetramethyl-[1,3,2]dioxaborolan-2-yl)-benzyl ester (from part A, ~0.5 mmol), $K_2CO_3$ (77 mg, 0.56 mmol) and dichlorobis(triphenylphosphine)palladium(II) (6.5 mg, 0.01 mmol) in MeCN/water (2 ml/0.5 ml) was heated in a microwave at 140° C. for 10 min. The reaction was repeated with another half of the bronic ester from Part A. The two reactions were combined for purification. The water layer was removed and the reaction mixture was diluted with MeCN (3 ml) and filtered. The filtrate was subjected to preparative HPLC to give the titled compound (100 mg). $^1$H NMR (400 MHz, CHLOROFORM-d) δ ppm 1.00 (t, J=7.39 Hz, 3H) 1.19 (d, J=6.62 Hz, 6H) 1.43-1.52 (m, 2H) 1.66-1.73 (m, 2H) 3.41 (td, J=7.06, 5.73 Hz, 2H) 3.87 (d, J=6.84 Hz, 1H) 4.49 (t, J=5.29 Hz, 1H) 5.14 (m, 1H) 6.45 (d, J=9.70 Hz, 1H) 7.46 (d, J=8.16 Hz, 2H) 7.66 (d, J=9.48 Hz, 1H) 7.81 (s, 1H) 8.14 (d, J=8.38 Hz, 2H). LRMS (ESI) m/z 382.2 [(M+H)]$^+$, calc'd for $C_{21}H_{27}N_5O_2$: 381.48.

5.6.58. Synthesis of 2-[4-(6-Butylamino-imidazo[1,2-b]pyridazin-3-yl)-phenoxy]-acetamide

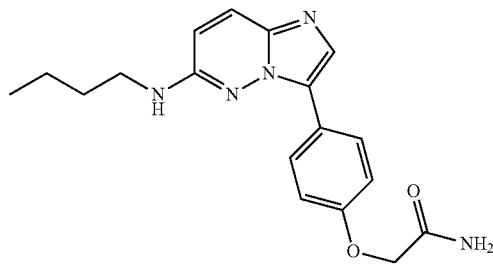 [SMILES: CCCCNc1ccc2ncc(-c3ccc(OCC(N)=O)cc3)n2n1]

Part A. 2-(4-(4,4,5,5-tetramethyl-1,3,2-dioxaborolan-2-yl)phenoxy)acetic acid

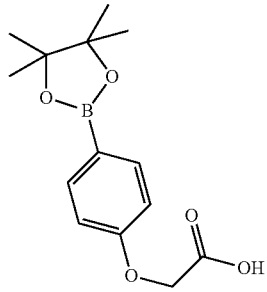 [SMILES: CC1(C)OB(c2ccc(OCC(=O)O)cc2)OC1(C)C]

To 135 mg (0.441 mmol) of the commercially available ester, was added 99 mg (1.765 mmol) of KOH, and 8 mL of 3:1 MeOH/$H_2O$ solution, and stirred for 2 hr of at rt. The pH was adjusted to 4 using 2M HCl solution. Three extractions were done using EtOAc. The combined organic layer was washed with brine and dried over MgSO$_4$. It was filtered and the solvents were evaporated to obtain 72 mg (59%) of the desired carboxylic acid.

Part B. 2-(4-(4,4,5,5-tetramethyl-1,3,2-dioxaborolan-2-yl)phenoxy)acetamide

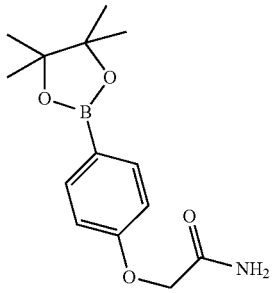 [SMILES: CC1(C)OB(c2ccc(OCC(N)=O)cc2)OC1(C)C]

To the 72 mg of carboxylic acid was added 8 mL (excess) of SOCl$_2$ and stirred at rt for 2 hr, and then concentrated to dryness. To the solid acid chloride intermediate obtained was slowly added 2.6 mL of 0.5 M NH$_3$/dioxane solution and stirred for another 2 hr. The reaction mixture was concentrated to obtain the desired primary amide.

Part C. 2-[4-(6-Butylamino-imidazo[1,2-b]pyridazin-3-yl)-phenoxy]-acetamide

The Suzuki coupling of the boronic ester and the aryl bromide under the same conditions as described for example 5.6.19 afforded the titled compound in 78% yield. $^1$H NMR (400 MHz, METHANOL-d$_4$) δ ppm 1.01 (t, J=7.45 Hz, 3H) 1.44-1.55 (m, 2H) 1.65-1.76 (m, 2H) 3.40 (t, J=7.20 Hz, 2H) 4.62 (s, 2H) 7.15-7.25 (m, 3H) 7.93 (d, J=9.85 Hz, 1H) 8.04-8.16 (m, 3H); LRMS (ESI) m/e 340.0 [(M+H)$^+$, calcd for C$_{18}$H$_{21}$N$_5$O$_5$ 339.0.

5.6.59. Synthesis of 3-(2-aminopyrimidin-5-yl)-N-butylimidazo[1,2-b]pyridazin-6-amine

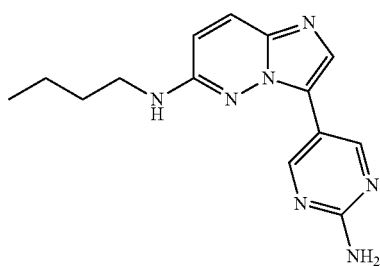

Using the Suzuki coupling conditions described in example 5.6.48 afforded the titled compound in 63% yield as white solid. $^1$H NMR (400 MHz, METHANOL-d$_4$) δ ppm 9.03 (s, 2H), 7.73 (s, 1H), 7.61 (d, J=9.85 Hz, 1H), 6.71 (d, J=9.60 Hz, 1H), 4.64 (s, 1H), 3.36 (t, J=7.07 Hz, 2H), 1.66-1.73 (m, 2H), 1.45-1.54 (m, 2H), 1.00 (t, J=7.33 Hz, 3H); LRMS (ESI) m/e 284.2 [(M+H)$^+$, calcd for C$_{14}$H$_{18}$N$_7$ 284.3].

5.6.60. Synthesis of {2-[3-(5-Acetyl-thiophen-2-yl)-imidazo[1,2-b]pyridazin-6-ylamino]ethyl}-methyl-carbamic acid tert-butyl ester

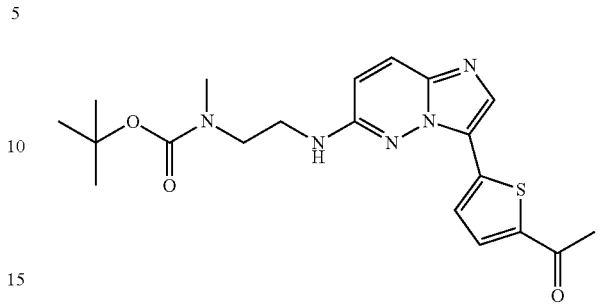

To a mixture of [2-(3-bromo-imidazo[1,2-b]pyridazin-6-ylamino)-ethyl]-methyl-carbamic acid tert-butyl ester (285.5 mg, 0.8 mmol), (5-acetylthiophen-2-yl)boronic acid [206551-43-1] (157.3 mg, 0.9 mmol), potassium phosphate tribasic monohydrate [27176-10-9] (354.8 mg, 1.5 mmol), and [1,1'bis(diphenylphosphino)ferrocene]dichloropalladium(II), complex with dichloromethane [95464-05-4] (63.4 mg, 0.1 mmol) contained in a 25 mL round bottomed flask was added a solution of 30% (v/v) water in 1,2-dimethoxyethane (12.5 mL) and a magnetic stir bar. The reaction pot was fitted to a reflux condenser, lowered into an ambient temperature oil bath, and the system taken through 10 evacuation/N$_2$ blanket cycles while being rapidly stirred. The rapidly stirred, N$_2$ blanketed, reaction was heated to an oil bath temperature of 85° C. for 17 h then cooled and partitioned between brine and ethyl acetate. The phase separated extract was dried (MgSO$_4$), evaporated, flash chromatographed (silica gel eluted with 100% ethyl acetate) and crystallized (ethyl acetate/heptane) to provide {2-[3-(5-acetyl-thiophen-2-yl)-imidazo[1,2-b]pyridazin-6-ylamino]-ethyl}-methyl-carbamic acid tert-butyl ester as 121.3 mg of yellow powder, mp. 174-175° C. $^1$H NMR (400 MHz, DMSO-d$_6$) δ ppm (rotamers present) 1.11 (br. s., 6H) 1.39 (br. s., 3H) 2.54 (s, 3H) 2.87 (br. s., 2H) 2.92 (br. s., 1H) 3.32 (s, 1H) 3.52 (br. s., 3H) 3.62 (br. s., 1H) 7.78-7.85 (m, 2H) 7.96 (d, J=4.29 Hz, 1H) 8.14 (s, 1H). $^{13}$C NMR (100 MHz, DMSO-d$_6$) δ ppm 26.95, 28.16, 28.50, 34.07, 46.09, 78.50, 113.14, 123.02, 124.18, 126.13, 130.89, 134.37, 137.71, 138.38, 141.77, 154.32, 155.43, 191.11. LRMS (ESI) m/z 416.2 [(M+H)]$^+$, calc'd for C$_{14}$H$_{20}$BrN$_6$O$_2$: 415.52.

5.6.61. Synthesis of 2-[4-(6-Butylamino-imidazo[1,2-b]pyridazin-3-yl)-phenoxy]-N-methylacetamide

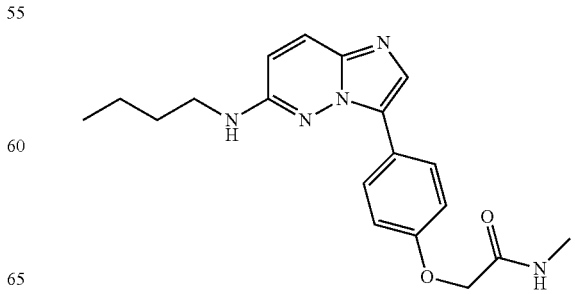

Part A. Ethyl 2-(4-(6-(butylamino)imidazo[1,2-b]pyridazin-3-yl)phenoxy)acetate

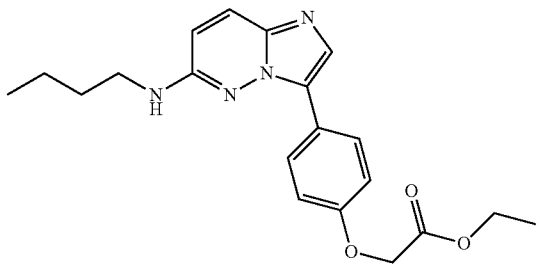 [SMILES: CCCCNc1ccc2ncc(-c3ccc(OCC(=O)OCC)cc3)n2n1]

The ethyl 2-(4-(6-(butylamino)imidazo[1,2-b]pyridazin-3-yl)phenoxy)acetate, was synthesized by the Suzuki coupling reaction of the boronic ester and the aryl bromide under the same conditions as described for example 5.6.19.

Part B. 2-(4-(6-(butylamino)imidazo[1,2-b]pyridazin-3-yl)phenoxy)acetic acid

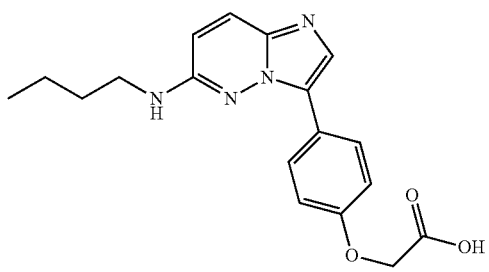 [SMILES: CCCCNc1ccc2ncc(-c3ccc(OCC(=O)O)cc3)n2n1]

To 368 mg (1.00 mmol) of the ester dissolved in 15 mL of THF was added, LiOH.H$_2$O (82 mg, 2.00 mmol) and 5 mL of water. This was stirred overnight at 50° C. It was cooled to rt, concentrated to dryness, and then suspended in water. The pH was adjusted to about 3 using 1N HCl. EtOAc was used for the extraction. The organic layer was washed with brine, dried over MgSO$_4$, and concentrated to carboxylic acid in 100% yield (340 mg).

Part C. 2-[4-(6-Butylamino-imidazo[1,2-b]pyridazin-3-yl)-phenoxy]-N-methyl-acetamide To 50 mg (0.147 mmol) of carboxylic acid was added 20 mg (0.294 mmol) methyl amine (HCl salt), followed by HOBt (30 mg, 0.221 mmol), EDC (42 mg, 0.221 mmol), triethylamine (0.30 mg, 0.294 mmol) and 5 mL DMF. The resulting mixture was stirred overnight at rt. It was diluted with EtOAc, and then washed with brine and dried over MgSO$_4$. It was concentrated and purified on the PREP HPLC to obtain 27 mg (52%) of the titled compound. $^1$H NMR (400 MHz, METHANOL-d$_4$) δ ppm 0.97-1.05 (m, 3H) 1.44-1.56 (m, 2H) 1.67-1.79 (m, 2H) 2.83-2.89 (m, 3H) 3.40 (t, J=7.20 Hz, 2H) 4.62 (s, 2H) 7.17-7.27 (m, 3H) 7.93 (d, J=9.85 Hz, 1H) 8.06-8.18 (m, 3H); LRMS (ESI) m/e 354.0 (M+H)$^+$, calcd for C$_{19}$H$_{23}$N$_5$O$_2$ 353.0.

5.6.62. Synthesis of (R)-2-Amino-4-methyl-pentanoic acid 4-(6-butylamino-imidazo[1,2-b]pyridazin-3-yl)-benzylamide

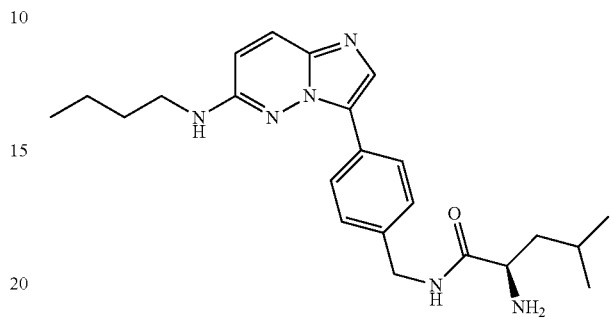

Part A. (R)-tert-butyl(1-((4-(6-(butylamino)imidazo[1,2-b]pyridazin-3-yl)benzyl)amino)-4-methyl-1-oxopentan-2-yl)carbamate

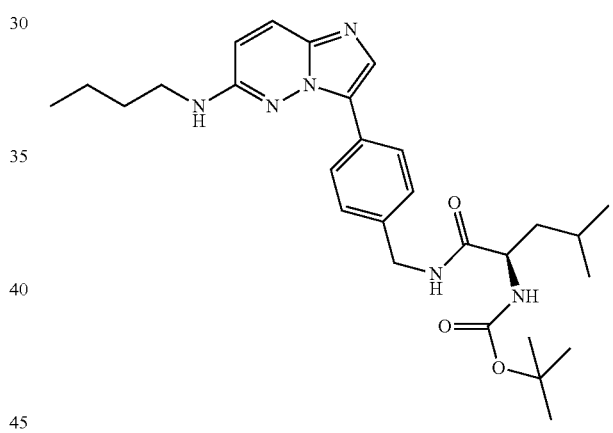

The (4-(4,4,5,5-tetramethyl-1,3,2-dioxaborolan-2-yl)phenyl)methanamine and the (R)-2-((tert-butoxy-carbonyl)amino)-4-methylpentanoic acid were both commercially available, and they were subjected to the regular amide coupling reaction, and yielded 94% product (No purification was needed). This product is coupled by Suzuki reaction with the aryl bromide under the conditions described in example 5.6.19. The crude mixture was purified on the ISCO (silica gel) eluting with 2-10% MeOH/DCM.

Part B. (R)-2-Amino-4-methyl-pentanoic acid 4-(6-butylamino-imidazo[1,2-b]pyridazin-3-yl)-benzylamide To 100 mg (0.197 mmol) of (R)-tert-butyl(1-((4-(6-(butylamino)imidazo[1,2-b]pyridazin-3-yl)benzyl)-amino)-4-methyl-1-oxopentan-2-yl)carbamate was added 10 mL of 4 M HCl/dioxane, and stirred at rt for 4 hr and then concentrated to dryness to 102 mg (100%) of the TFA salt of the desired product. $^1$H NMR (400 MHz, METHANOL-d$_4$) δ ppm 0.97-1.03 (m, 9H) 1.48 (dq, J=15.02, 7.41 Hz, 2H) 1.69-1.79 (m, 5H) 3.40 (t, J=7.06 Hz, 2H) 3.92 (t, J=6.95 Hz, 1H) 4.49 (dd, J=15.10, 4.08 Hz, 1H) 4.56-4.63 (m, 1H) 7.23 (d, J=9.92 Hz, 1H) 7.52 (m, J=8.38 Hz, 2H) 7.95 (d, J=9.92 Hz, 1H) 8.12 (m, J=8.38 Hz, 2H) 8.20 (s, 1H); LRMS (ESI) m/e 409.0 (M+H)$^+$, calcd for $C_{23}H_{32}N_6O$ 408.0.

5.6.63. Synthesis of {2-[3-(4-Carbamoyl-phenyl)-imidazo[1,2-b]pyridazin-6-ylamino]-ethyl}-methyl-carbamic acid tert-butyl ester

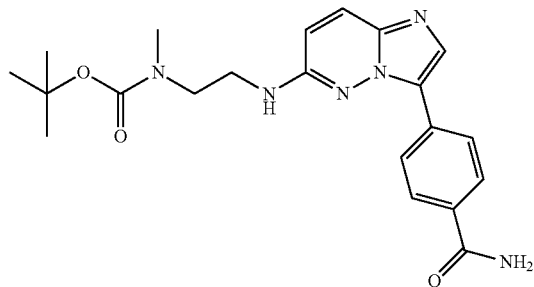 [SMILES: CN(CCNc1ccc2ncc(-c3ccc(C(N)=O)cc3)n2n1)C(=O)OC(C)(C)C]

{2-[3-(4-Carbamoyl-phenyl)-imidazo[1,2-b]pyridazin-6-ylamino]-ethyl}-methyl-carbamic acid tert-butyl ester was prepared similarly to the procedure for example 5.6.60 from [2-(3-bromo-imidazo[1,2-b]pyridazin-6-ylamino)-ethyl]-methyl-carbamic acid tert-butyl ester (367.4 mg, 1.0 mmol), (4-carbamoylphenyl)boronic acid [123088-59-5] (196.7 mg, 1.2 mmol), potassium phosphate tribasic monohydrate [27176-10-9] (418.4 mg, 1.8 mmol), and [1,1'-bis(diphenylphosphino)ferrocene]dichloropalladium(II), complex with dichloromethane [95464-05-4] (82.1 mg, 0.1 mmol) in 30% (v/v) water in 1,2-dimethoxyethane (25 mL) at 85° C. for 17 h. White powder from ethyl acetate/heptane, mp. 190-191° C. (dec.). $^1$H NMR (400 MHz, DMSO-d$_6$) δ ppm (rotamers present) 1.15 (br. s., 5H) 1.28 (br. s., 1H) 1.38 (br. s., 3H) 2.85 (br. s., 3H) 3.32 (br. s., 1H) 3.54 (br. s., 1H) 6.73 (d, J=9.35 Hz, 1H) 7.27 (br. s., 1H) 7.34 (br. s., 1H) 7.79 (d, J=9.60 Hz, 1H) 7.94-8.03 (m, 4H) 8.28 (d, J=8.08 Hz, 2H). LRMS (ESI) m/z 411.2 [(M+H)]$^+$, calc'd for $C_{21}H_{26}N_6O_3$: 410.48.

5.6.64. Synthesis of [3-(4-Aminomethyl-cyclohex-1-enyl)-imidazo[1,2-b]pyridazin-6-yl]-butyl-amine

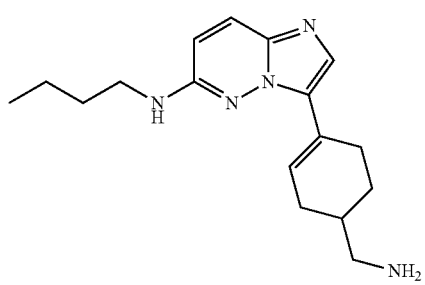 [SMILES: CCCCNc1ccc2ncc(C3=CCC(CN)CC3)n2n1]

Part A. Methyl 4-(6-(butylamino)imidazo[1,2-b]pyridazin-3-yl)cyclohex-3-enecarboxylate

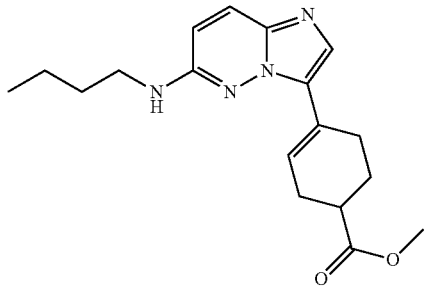 [SMILES: CCCCNc1ccc2ncc(C3=CCC(C(=O)OC)CC3)n2n1]

The Suzuki coupling of aryl bromide and commercially available boronic ester under the same conditions as described in example 5.6.19 afforded the titled compound in 97% yield.

Part B. (4-(6-(butylamino)imidazo[1,2-b]pyridazin-3-yl)cyclohex-3-en-1-yl)methanol

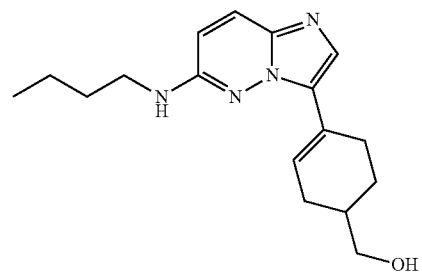 [SMILES: CCCCNc1ccc2ncc(C3=CCC(CO)CC3)n2n1]

To 200 mg (0.610 mmol) of the isolated product dissolved in 15 mL of THF at 0° C. was added 2.44 mL (2.439 mmol) of 1M Lithium aluminum hydride THF solution. After 15 minutes of stirring, the reaction was completed. It was diluted with 40 mL of THF, and 2.0 g of Na$_2$SO$_4$.10H$_2$O was slowly added and stirred for another 1 hr. It was then filtered and the filtrate concentrated to obtain 182 mg (99%) of the desired alcohol.

Part C. 2-((4-(6-(butylamino)imidazo[1,2-b]pyridazin-3-yl)cyclohex-3-en-1-yl)methyl)isoindoline-1,3-dione

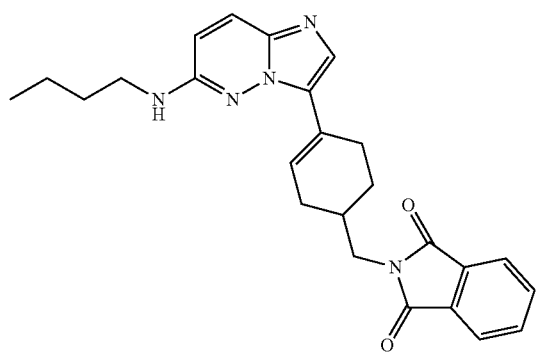 [SMILES: CCCCNc1ccc2ncc(C3=CCC(CN4C(=O)c5ccccc5C4=O)CC3)n2n1]

To 150 mg (0.500 mmol) of the alcohol dissolved in 15 mL THF at 0° C., was added phthalimide (80.9 mg, 0.55 mmol), DIAD (121 mg, 0.599 mmol) and triphenylphosphine (157 mg, 0.599 mmol). After 0.5 hr of stirring at 0° C., the ice bath was removed, and stirring was continued at rt for about 16 hr. It was then diluted with 20 mL EtOAc, and quenched with 10 mL water. The organic layer was separated and washed with brine, dried over MgSO$_4$, and purified on the ISCO (silica gel) eluting with 0-10% MeOH/DCM to give 163 mg (76%) product.

Part D. [3-(4-Aminomethyl-cyclohex-1-enyl)-imidazo[1,2-b]pyridazin-6-yl]-butyl-amine To 130 mg (0.303 mmol) of the phthalimide protected amine, dissolved in 10 mL of EtOH was added 45.5 mg (0.909 mmol) of hydrazine monohydrate. The resulting mixture was refluxed for 4 hr, cooled to rt, filtered to remove the solids, and the filtrate was concentrated to obtain 88 mg (97%) of the desired compound. $^1$H NMR (400 MHz, METHANOL-d$_4$) δ ppm 1.01 (t, J=7.45 Hz, 3H) 1.44-1.61 (m, 3H) 1.66-1.76 (m, 2H) 2.03-2.20 (m, 3H) 2.50-2.76 (m, 3H) 3.00 (d, J=6.57 Hz, 2H) 3.39 (t, J=7.07 Hz, 2H) 7.19 (d, J=9.85 Hz, 1H) 7.24-7.31 (m, 1H) 7.82-7.86 (m, 1H) 7.88-7.93 (m, 1H); LRMS (ESI) m/e 300.0 (M+H)$^+$, calcd for C$_{17}$H$_{25}$N$_5$ 299.0.

5.6.65. Synthesis of Methyl-[2-(3-phenyl-imidazo[1,2-b]pyridazin-6-ylamino)-ethyl]-carbamic acid tert-butyl ester

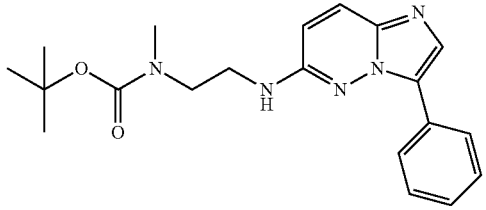 [SMILES: CN(CCNc1ccc2ncc(-c3ccccc3)n2n1)C(=O)OC(C)(C)C]

Methyl-[2-(3-phenyl-imidazo[1,2-b]pyridazin-6-ylamino)-ethyl]-carbamic acid tert-butyl ester was prepared similarly to the procedure for example 5.6.60 from [2-(3-bromo-imidazo[1,2-b]pyridazin-6-ylamino)-ethyl]-methyl-carbamic acid tert-butyl ester (370.3 mg, 1.0 mmol), phenylboronic acid [98-80-6] (146.4 mg, 1.2 mmol), potassium phosphate tribasic monohydrate [27176-10-9] (460.2 mg, 2.0 mmol), and [1,1′-bis(diphenylphosphino)ferrocene]dichloropalladium(II), complex with dichloromethane [95464-05-4] (81.9 mg, 0.1 mmol) in 30% (v/v) water in 1,2-dimethoxyethane (12.5 mL) at 85° C. for 17 h. Off white powder from ethyl acetate/heptane, mp. 150-151° C. $^1$H NMR (400 MHz, DMSO-d$_6$) δ ppm (rotamers present) 1.16 (br. s., 5H) 1.20-1.33 (m, 1H) 1.37 (br. s., 3H) 2.49-2.54 (m, 1H) 2.83 (br. s., 3H) 3.43 (br. s., 2H) 3.51 (br. s., 1H) 6.69 (d, J=8.84 Hz, 1H) 7.22 (br. s., 1H) 7.29-7.38 (m, 1H) 7.43-7.54 (m, 2H) 7.76 (d, J=8.84 Hz, 1H) 7.89 (br. s., 1H) 8.16 (d, J=6.82 Hz, 2H). $^{13}$C NMR (100 MHz, DMSO-d$_6$) δ ppm 14.39, 22.55, 28.24, 28.49, 31.71, 34.17, 35.10, 46.33, 47.00, 78.60, 112.58, 126.28, 127.46, 128.93, 130.40, 134.52, 153.69, 155.40. LRMS (ESI) m/z 368.1 [(M+H)]$^+$, calc'd for C$_{20}$H$_{25}$N$_5$O$_2$: 367.45.

5.6.66. Synthesis of 4-{6-[2-(3-tert-Butyl-1-methyl-ureido)-ethylamino]-imidazo[1,2-b]pyridazin-3-yl}-benzamide

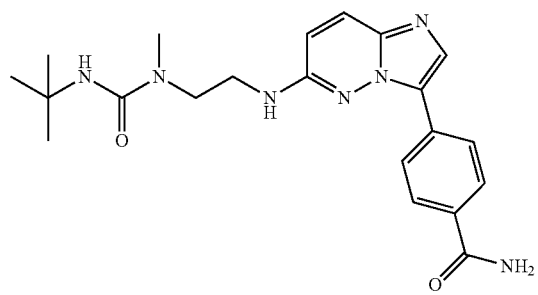 [SMILES: CN(CCNc1ccc2ncc(-c3ccc(C(N)=O)cc3)n2n1)C(=O)NC(C)(C)C]

Part A. 4-[6-(2-Methylamino-ethylamino)-imidazo[1,2-b]pyridazin-3-yl]-benzamide dihydrochloride

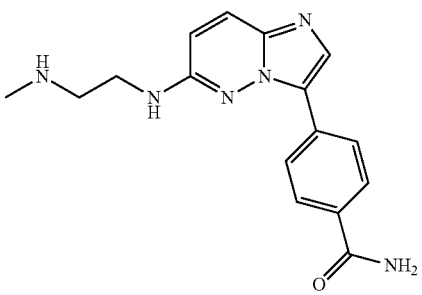 [SMILES: CNCCNc1ccc2ncc(-c3ccc(C(N)=O)cc3)n2n1]

Concentrated hydrochloric acid was added to an ambient temperature solution of 2-[3-(4-carbamoyl-phenyl)-imidazo[1,2-b]pyridazin-6-ylamino]-ethyl}-methyl-carbamic acid tert-butyl ester (784.1 mg, 1.9 mmol) in methanol (130 mL) and allowed to stir under N$_2$ blanket for 2d. The reaction mixture was cooled and filtered to provide 4-[6-(2-methyl amino-ethylamino)-imidazo[1,2-b]pyridazin-3-yl]-benzamide di-hydrochloride as an off white powder, mp. 322-323° C. (dec.). $^1$H NMR (400 MHz, DEUTERIUM OXIDE) δ ppm 2.68 (s, 3H) 3.34 (t, J=5.81 Hz, 2H) 3.74 (t, J=5.68 Hz, 2H) 7.24 (d, J=9.85 Hz, 1H) 7.88 (d, J=8.59 Hz, 2H) 7.96-8.02 (m, 3H) 8.08 (s, 1H). LRMS (ESI) m/z 311.1 [(M+H)]$^+$, calc'd for C$_{16}$H$_{18}$N$_6$O: 310.36.

Part B. 4-{6-[2-(3-tert-Butyl-1-methyl-ureido)-ethylamino]-imidazo[1,2-b]pyridazin-3-yl}-benzamide 2-Isocyanato-2-methylpropane was slowly added to a stirred, 0° C., suspension of 4-[6-(2-methylamino-ethylamino)-imidazo[1,2-b]pyridazin-3-yl]-benzamide dihydrochloride (177.3 mg, 0.5 mmol), and Hunig's base [7087-68-5] (0.3 mL, 1.8 mmol) in dichloromethane (4.6 mL) and the mixture allowed to stir and warm to ambient temperature over 17 h. The reaction mixture was then partitioned between brine and ethyl acetate, dried (MgSO$_4$), flash chromatographed (silica gel eluted with 10% (v/v) methanol/ethyl acetate), and

5.6.67. Synthesis of 6-(butylamino)-N-(1H-pyrazol-3-yl)imidazo[1,2-b]pyridazine-3-carboxamide

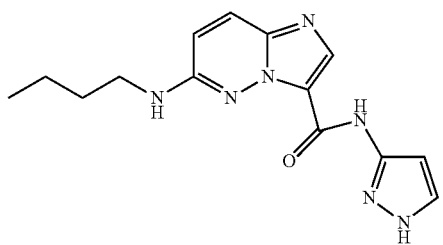 [SMILES: CCCCNc1ccc2ncc(C(=O)Nc3cc[nH]n3)n2n1]

Using the amide coupling reaction conditions described in example 5.6.54 afforded the titled compound as colored solid in 43% yield. $^1$H NMR (400 MHz, METHANOL-d$_4$) δ ppm 8.01-8.07 (m, 2H), 7.70 (d, J=9.92 Hz, 1H), 7.63 (br. s., 1H), 6.84 (d, J=9.92 Hz, 1H), 4.56 (s, 1H), 3.41 (t, J=7.06 Hz, 2H), 1.69-1.76 (m, 2H), 1.48 (dq, J=15.05, 7.48 Hz, 2H), 0.96 (t, J=7.39 Hz, 3H); LRMS (ESI) m/e 300.0 [(M+H)$^+$, calcd for C$_{14}$H$_{18}$N$_7$O 300.3].

5.6.68. Synthesis of 3-(4-(aminomethyl)phenyl)-N-(2-(tert-butoxy)ethyl)imidazo[1,2-b]pyridazin-6-amine

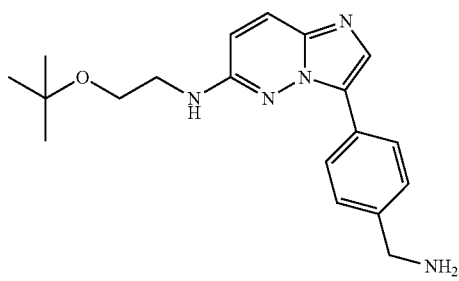 [SMILES: CC(C)(C)OCCNc1ccc2ncc(-c3ccc(CN)cc3)n2n1]

Part A. 3-bromo-N-(2-(tert-butoxy)ethyl)imidazo[1,2-b]pyridazin-6-amine

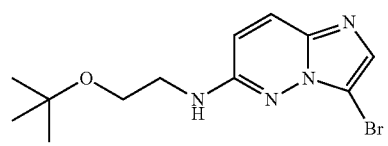 [SMILES: CC(C)(C)OCCNc1ccc2ncc(Br)n2n1]

A solution of 3-bromo-6-fluoroimidazo[1,2-b]pyridazine (216 mg, 1.0 mmol), triethyl amine (0.35 mL, 2.5 mmol) and 2-(tert-butoxy)ethanamine (180 mg, 1.5 mmol) in isopropanol (2 mL) was heated at 65° C. for overnight. The mixture was cooled, diluted with ethyl acetate and washed with water. The organic layer was dried over MgSO$_4$ and concentrated to give brown solid as crude in quantitative yield for further synthesis. 20 mg was further purified by Prep HPLC to give pure 3-bromo-N-(2-(tert-butoxy)ethyl)imidazo[1,2-b]pyridazin-6-amine as white solid (8 mg). $^1$H NMR (400 MHz, METHANOL-d$_4$) δ ppm 7.57 (d, J=9.85 Hz, 1H), 7.42 (s, 1H), 6.76 (d, J=9.60 Hz, 1H), 4.56 (s, 1H), 3.67 (t, J=5.94 Hz, 2H), 3.53 (t, J=5.94 Hz, 2H), 1.24 (s, 9H) LRMS (ESI) m/e 315.0 [(M+H)$^+$, calcd for C$_{12}$H$_{18}$BrN$_4$O 314.2].

Part B. 3-(4-(aminomethyl)phenyl)-N-(2-(tert-butoxy)ethyl)imidazo[1,2-b]pyridazin-6-amine Using the Suzuki coupling conditions described in example 5.6.48 provided the titled compound as white solid in 40% yield. $^1$H NMR (400 MHz, METHANOL-d$_4$) δ ppm 8.53 (s, 1H), 8.24-8.28 (m, 2H), 7.82 (s, 1H), 7.66 (d, J=9.60 Hz, 1H), 7.57 (d, J=8.59 Hz, 2H), 6.79 (d, J=9.85 Hz, 1H), 4.18 (s, 2H), 3.67 (t, J=5.81 Hz, 2H), 3.53 (t, J=5.94 Hz, 2H), 1.23 (s, 9H); LRMS (ESI) m/e 340.1 [(M+H)$^+$, calcd for C$_{19}$H$_{26}$N$_5$O 340.4].

5.6.69. Synthesis of 4-((3-(4-(aminomethyl)phenyl)imidazo[1,2-b]pyridazin-6-yl)amino)-2-methylbutan-2-ol

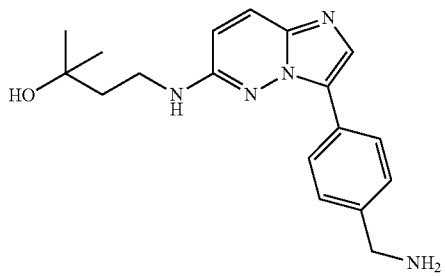 [SMILES: CC(C)(O)CCNc1ccc2ncc(-c3ccc(CN)cc3)n2n1]

Part A. 4-((3-bromoimidazo[1,2-b]pyridazin-6-yl)amino)-2-methylbutan-2-ol

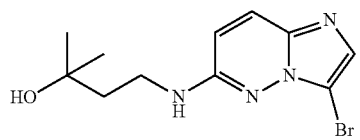 [SMILES: CC(C)(O)CCNc1ccc2ncc(Br)n2n1]

The 3-bromo-6-fluoroimidazo[1,2-b]pyridazine was reacted with 4-amino-2-methylbutan-2-ol using the same reaction conditions as described in example 5.6.42, Part A to obtain 82% product.

Part B. 4-((3-(4-(aminomethyl)phenyl)imidazo[1,2-b]pyridazin-6-yl)amino)-2-methylbutan-2-ol The 4-((3-bromoimidazo[1,2-b]pyridazin-6-yl)amino)-2-methylbutan-2-ol was coupled with (4-(aminomethyl)phenyl)boronic acid as described in example 5.6.19 to afford the titled compound in 78% yield. $^1$H NMR (400 MHz, METHA- NOL-d$_4$) δ ppm 1.29 (s, 6H) 1.84-1.94 (m, 2H) 3.49-3.58 (m, 2H) 4.24 (s, 2H) 7.25 (d, J=9.85 Hz, 1H) 7.67 (d, J=8.59 Hz, 2H) 7.97 (d, J=9.85 Hz, 1H) 8.22-8.29 (m, 3H); LRMS (ESI) m/e 326.0 [(M+H)$^+$, calcd for C$_{18}$H$_{23}$N$_5$O 325.0].

5.6.70. Synthesis of N-allyl-4-(6-(allylamino)imidazo[1,2-b]pyridazin-3-yl)benzamide

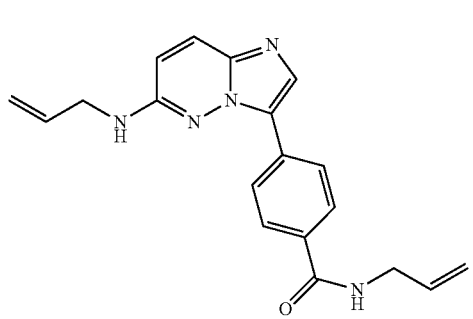 [SMILES: C=CCNC(=O)c1ccc(-c2cnc3ccc(NCC=C)nn23)cc1]

Part A.
N-allyl-3-bromoimidazo[1,2-b]pyridazin-6-amine

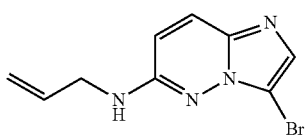

A solution of 3-bromo-6-chloroimidazo[1,2-b]pyridazine (1000 mg, 4.32 mmol) and allylamine (6.0 mL, 80 mmol) was heated at 80° C. (sealed tube) for 6 h. The resulting mixture was cooled to room temperature and purified on silica gel (eluting with ethyl acetate) to afford N-allyl-3-bromoimidazo [1,2-b]pyridazin-6-amine (550 mg, 51% yield) as a yellow solid: LRMS (ESI) m/z 253.0, 255.0 [(M+H)$^+$, calcd for C$_9$H$_9$BrN$_4$ 252.0]

Part B. N-allyl-4-(6-(allylamino)imidazo[1,2-b]pyridazin-3-yl)benzamide

To a mixture of N-allyl-3-bromoimidazo[1,2-b]pyridazin-6-amine (365 mg, 1.44 mmol), (4-(allylcarbamoyl)phenyl) boronic acid (615 mg, 3.0 mmol), [1,1'-bis(diphenylphosphino)ferrocene]dichloropalladium(II) (62 mg, 0.085 mmol) was added n-butanol (3 mL) and 2 M aqueous sodium carbonate (2 mL). The resulting mixture was heated at 100° C. for 5 h. The reaction was then diluted with water, extracted with ethyl acetate, and purified by silica gel column (10% methanol in ethyl acetate) followed by preparative HPLC (acetonitrile/aqueous ammonium formate, Sunfire column) to afford N-allyl-4-(6-(allylamino)imidazo[1,2-b]pyridazin-3-yl)benzamide as a white solid: $^1$H NMR (METHANOL-d$_4$) δ: 8.30-8.33 (d, J=8.4 Hz, 2H), 7.94 (d, J=8.4 Hz, 2H), 7.67 (d, J=9.6 Hz, 1H), 6.78 (d, J=9.6 Hz, 1H), 5.9-6.2 (m, 2H), 5.1-5.4 (m, 4H), 4.00 (m, 4H); LRMS (ESI) m/z 334.2 [(M+H)$^+$, calcd for C$_{19}$H$_{19}$N$_5$O 333.4]

5.6.71. Synthesis of 3-(4-(aminomethyl)phenyl)-N-(3-(tert-butoxy)propyl)imidazo[1,2-b]pyridazin-6-amine

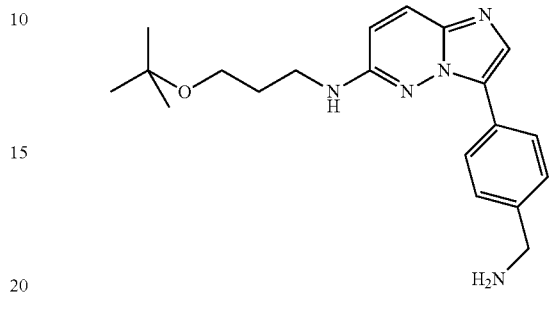

Using a process similar to that described in example 5.6.68 provided the titled compound. $^1$H NMR (400 MHz, METHANOL-d$_4$) δ ppm 8.51 (s, 2H), 8.30 (d, J=8.38 Hz, 2H), 7.83 (s, 1H), 7.65 (d, J=9.48 Hz, 1H), 7.56 (d, J=8.38 Hz, 2H), 6.76 (s, 1H), 6.73 (s, 1H), 4.17 (s, 2H), 3.56 (t, J=6.17 Hz, 2H), 3.47 (t, J=6.73 Hz, 2H), 1.93 (t, J=6.50 Hz, 2H), 1.22 (s, 9H); LRMS (ESI) m/e 354.1 [(M+H)$^+$, calcd for C$_{20}$H$_{28}$N$_5$O 354.4].

5.6.72. Synthesis of [2-(3-Bromo-imidazo[1,2-b]pyridazin-6-ylamino)-ethyl]-isopropyl-carbamic acid tert-butyl ester

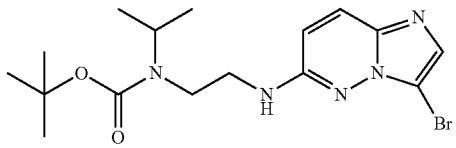 [SMILES: CC(C)N(CCNc1ccc2ncc(Br)n2n1)C(=O)OC(C)(C)C]

Part A. N1-(3-bromoimidazo[1,2-b]pyridazin-6-yl)ethane-1,2-diamine

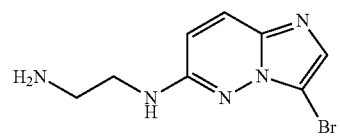 [SMILES: NCCNc1ccc2ncc(Br)n2n1]

A stirred suspension of 3-bromo-6-chloro-imidazo[1,2-b] pyridazine [13526-66-4] (5.0 g, 21.5 mmol) in ethylenediamine [107-15-3] (25.0 mL, 373.1 mmol) was heated to 65° C. under nitrogen blanket. Once on temperature, the mixture became a clear yellow solution. These conditions were maintained for 17 h, at which time, the hot reaction solution poured into water, and the bulk extracted exhaustively with ethyl acetate. The combined extracts were combined, dried (CaSO$_4$), and evaporated to obtain 1.79 g of yellow solid. This solid was recrystallized from ethyl acetate/heptane to provide 1.4 g of N1-(3-bromoimidazo[1,2-b]pyridazin-6-yl)ethane-1,2-diamine as a white powder, mp. 158-159° C. $^1$H NMR (400 MHz, DMSO-d$_6$) δ ppm 1.49 (br. s., 1H) 2.79 (t, J=6.19 Hz, 2H) 3.27 (q, J=5.89 Hz, 2H) 6.73 (d, J=9.60 Hz, 1H) 7.10 (t, J=5.05 Hz, 1H) 7.47 (s, 1H) 7.68 (d, J=9.60 Hz, 1H). $^{13}$C NMR (100 MHz, DMSO-d$_6$) δ ppm 40.97, 45.13, 99.48, 113.51, 125.73, 130.72, 137.04, 154.81. LRMS (ESI) m/z 255.9/257.9 [(M+H)]$^+$, calc'd for C$_8$H$_{10}$BrN$_5$: 256.11.

Part B. N1-(3-bromoimidazo[1,2-b]pyridazin-6-yl)-N2-isopropylethane-1,2-diamine

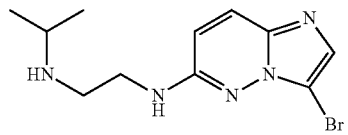 [SMILES: CC(C)NCCNc1ccc2ncc(Br)n2n1]

Glacial acetic acid [64-19-7] (1.6 mL, 28.0 mmol) was added to a stirred suspension of N1-(3-bromoimidazo[1,2-b]pyridazin-6-yl)ethane-1,2-diamine (7.0 g, 27.2 mmol), acetone [67-64-1] (2.4 mL, 32.6 mmol), sodium cyanoborohydride [25895-80-7] (1.8 g, 27.2 mmol) and powdered, activated 4 Angstrom molecular sieve (4 g). The flask was N$_2$ blanketed, closed with a septum, and the mixture allowed to stir at ambient temperature for 3d, then filtered. The filtrate was evaporated, and the residue partitioned between 10% (w/v) aqueous NaHCO$_3$ and ethyl acetate. The extract was dried (CaSO$_4$), and evaporated to afford a clear orange oil. This oil was triturated in heptane to precipitate N1-(3-bromoimidazo[1,2-b]pyridazin-6-yl)-N2-isopropylethane-1,2-diamine as 2.3 g of yellow powder, mp. 87-88° C. $^1$H NMR (400 MHz, DMSO-d$_6$) δ ppm 0.99 (d, J=6.32 Hz, 5H) 1.60 (br. s., 1H) 2.71-2.81 (m, 3H) 3.34 (q, J=6.32 Hz, 2H) 6.73 (d, J=9.85 Hz, 1H) 7.07 (t, J=5.31 Hz, 1H) 7.47 (s, 1H) 7.68 (d, J=9.60 Hz, 1H). $^{13}$C NMR (100 MHz, DMSO-d$_6$) δ ppm 22.92, 41.48, 45.29, 47.81, 98.98, 112.99, 125.26, 130.24, 136.53, 154.24. LRMS (ESI) m/z 297.9/299.9 [(M+H)]$^+$, calc'd for C$_{11}$H$_{16}$BrN$_5$: 289.19.

Part C. [2-(3-Bromo-imidazo[1,2-b]pyridazin-6-ylamino)-ethyl]-isopropyl-carbamic acid tert-butyl ester To a rapidly stirred, ambient temperature, N$_2$ blanketed, solution of N1-(3-bromoimidazo[1,2-b]pyridazin-6-yl)-N2-isopropylethane-1,2-diamine (633.3 mg, 2.1 mmol) and Hunig's base [7087-68-5] (0.5 mL, 2.9 mmol) in ethyl acetate (30 mL) was added solid di-tert-butyl dicarbonate [24424-99-5] (556.6 mg, 2.6 mmol). Once complete, the reaction was washed with brine, dried (MgSO$_4$), and evaporated to provide 894.5 mg of yellow solid. This solid was recrystallized from ethyl acetate heptane to afford [2-(3-bromo-imidazo[1,2-b]pyridazin-6-ylamino)-ethyl]-isopropyl-carbamic acid tert-butyl ester as 559.5 mg of white crystalline powder, mp. 154-155° C. $^1$H NMR (400 MHz, DMSO-d$_6$) δ ppm 1.16 (d, J=6.82 Hz, 6H) 1.40 (s, 9H) 2.49-2.52 (m, 1H) 3.26-3.35 (m, 2H) 3.35-3.42 (m, 2H) 6.68 (d, J=9.85 Hz, 1H) 7.32 (s, 1H) 7.49 (s, 1H) 7.71 (d, J=9.60 Hz, 1H). $^{13}$C NMR (100 MHz, DMSO-d$_6$) δ ppm 20.55, 28.08, 78.46, 98.93, 112.85, 125.52, 130.41, 136.57, 154.10. LRMS (ESI) m/z 297.9/299.9 [(M+H)]$^+$, calc'd for C$_{16}$H$_{24}$BrN$_5$O$_2$: 398.31.

5.6.73. Synthesis of {2-[3-(4-Carbamoyl-phenyl)-imidazo[1,2-b]pyridazin-6-ylamino]-ethyl}-phenyl-carbamic acid ethyl ester

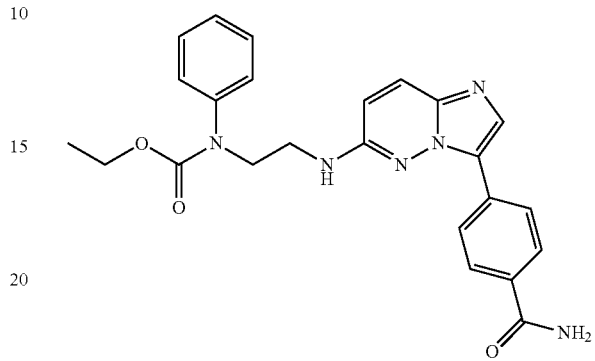

Part A.
2,2,2-Trifluoro-N-(2-phenylamino-ethyl)-acetamide

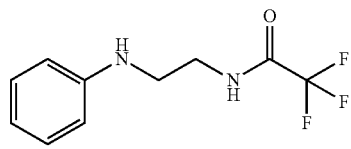 [SMILES: O=C(NCCNc1ccccc1)C(F)(F)F]

Ethyl trifluoroacetate [383-63-1] (5.5 mL, 46.1 mmol) was added to a stirred, 0° C., solution of N1-phenylethane-1,2-diamine [1664-40-0] (5.0 mL, 38.4 mmol) in THF (125 mL) and was allowed to stir and warm to ambient temperature under N$_2$ blanket over 17 h then was partitioned between brine and ethyl acetate. The extract was dried (MgSO$_4$) and evaporated to provide 10.2 g of clear dark yellow liquid. LRMS (ESI) m/z 232.9 [(M+H)]$^+$, calc'd for C$_{10}$H$_{11}$F$_3$N$_2$O: 232.21.

Part B. Phenyl-[2-(2,2,2-trifluoro-acetylamino)-ethyl]-carbamic acid ethyl ester

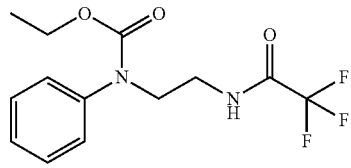 [SMILES: CCOC(=O)N(CCNC(=O)C(F)(F)F)c1ccccc1]

Ethyl chloroformate [541-41-3] (1.4 mL, 14.7 mmol) was added to an ambient temperature solution of 2,2,2-trifluoro-N-(2-phenylamino-ethyl)-acetamide (3.4 g, 14.6 mmol) and N-methyl morpholine [109-02-4] (2.0 mL, 17.7 mmol) in ethyl acetate (145 mL) and stirred under N$_2$ blanket for 17 h. The reaction suspension was then washed with dilute aqueous hydrochloric acid, brine, dried (MgSO$_4$), evaporated and carried on to the next synthetic step without further isolation.

Part C. [2-(3-Bromo-imidazo[1,2-b]pyridazin-6-ylamino)-ethyl]-phenyl-carbamic acid ethyl ester

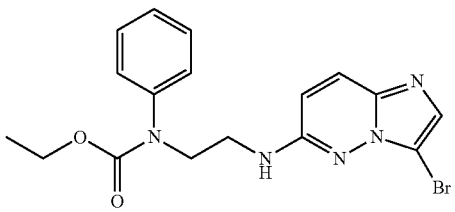 [SMILES: CCOC(=O)N(CCNc1ccc2ncc(Br)n2n1)c1ccccc1]

Crude phenyl-[2-(2,2,2-trifluoro-acetylamino)-ethyl]-carbamic acid ethyl ester (2.2 g, 7.3 mmol) was combine with 3-bromo-6-fluoro-imidazo[1,2-b]pyridazine (892.5 mg, 4.1 mmol) and potassium carbonate [584-08-7] (2.9 g, 20.6 mmol) in a 20% (v/v) solution of water in 1,2-dimethoxyethane (25 mL) and heated to 85° C. for 5 d. The reaction mixture was then partitioned between water and ethyl acetate and the extract flash chromatographed (silica gel eluted with 100% ethyl acetate) to yield 863.1 mg of white crystalline powder, mp. 160-161° C. $^1$H NMR (400 MHz, DMSO-d$_6$) δ ppm 1.08 (t, J=7.06 Hz, 2H) 2.51 (dt, J=3.58, 1.85 Hz, 1H) 3.35 (s, 1H) 3.46 (q, J=6.39 Hz, 2H) 3.90 (t, J=6.50 Hz, 2H) 4.04 (q, J=7.06 Hz, 2H) 6.65 (d, J=9.70 Hz, 1H) 7.19-7.25 (m, 1H) 7.31-7.39 (m, 4H) 7.48 (s, 1H) 7.69 (d, J=9.70 Hz, 1H). $^{13}$C NMR (100 MHz, DMSO-d$_6$) δ ppm 14.16, 38.85, 47.84, 60.82, 98.79, 112.62, 125.31, 125.99, 126.79, 128.63, 130.18, 136.35, 141.81, 153.79, 154.64. LRMS (ESI) m/z 403.9/405.9 [(M+H)]$^+$, calc'd for C$_{17}$H$_{18}$BrN$_6$O$_2$: 404.27.

Part D. {2-[3-(4-Carbamoyl-phenyl)-imidazo[1,2-b]pyridazin-6-ylamino]-ethyl}-phenyl-carbamic acid ethyl ester To a mixture of [2-(3-bromo-imidazo[1,2-b]pyridazin-6-ylamino)-ethyl]-phenyl-carbamic acid ethyl ester (354.7 mg, 0.9 mmol), (4-carbamoylphenyl)boronic acid [123088-59-5] (174.2 mg, 1.1 mmol), potassium phosphate tribasic monohydrate [27176-10-9] (368.8 mg, 1.6 mmol), and [1,1'-bis(diphenylphosphino)ferrocene]dichloropalladium(II), complex with dichloromethane [95464-05-4] (74.4 mg, 0.1 mmol) contained in a 25 mL round bottomed flask was added a solution of 30% (v/v) water in 1,2-dimethoxyethane (13 mL) and a magnetic stir bar. The reaction pot was fitted to a reflux condenser, lowered into an ambient temperature oil bath, and the system taken through 10 evacuation/N$_2$ blanket cycles while being rapidly stirred. The rapidly stirred, N$_2$ blanketed, reaction was heated to an oil bath temperature of 85° C. for 17 h then cooled and partitioned between brine and ethyl acetate. The phase separated extract was dried (MgSO$_4$), evaporated, flash chromatographed (silica gel eluted with 10% (v/v) methanol/ethyl acetate) and further purified by preparative RP-HPLC to provide {2-[3-(4-carbamoyl-phenyl)-imidazo[1,2-b]pyridazin-6-ylamino]-ethyl}-phenyl-carbamic acid ethyl ester as a white powder, mp. 227-228° C. $^1$H NMR (400 MHz, DMSO-d$_6$) δ ppm 1.03 (t, J=7.07 Hz, 2H) 2.51 (dt, J=3.73, 1.80 Hz, 2H) 3.31 (s, 1H) 3.48 (q, J=6.23 Hz, 2H) 3.91-4.04 (m, 3H) 6.69 (d, J=9.85 Hz, 1H) 7.18-7.35 (m, 5H) 7.76 (d, J=9.85 Hz, 1H) 7.91-8.01 (m, 3H) 8.21 (d, J=8.59 Hz, 2H). $^{13}$C NMR (100 MHz, DMSO-d$_6$) δ ppm 14.25, 48.18, 60.95, 112.37, 124.91, 125.75, 126.00, 126.35, 127.18, 127.79, 128.77, 130.81, 131.93, 132.15, 137.57, 141.78, 153.40, 154.85, 167.49. LRMS (ESI) m/z 445.1 [(M+H)]$^+$, calc'd for C$_{24}$H$_{24}$N$_6$O$_3$: 444.50.

5.6.74. Synthesis of 4-(6-Butylamino-imidazo[1,2-b]pyridazin-3-yl)-N-(2,2-dimethyl-[1,3]dioxolan-4-ylmethyl)-benzamide

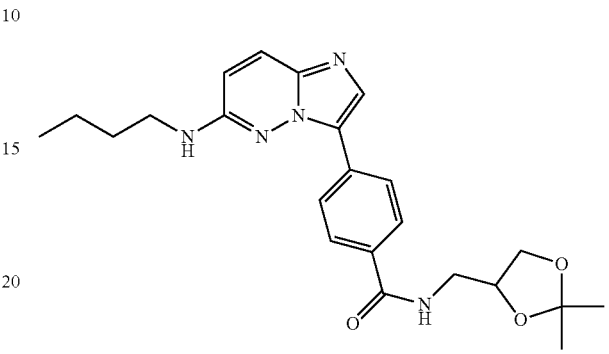

Part A. 4-(6-(butylamino)imidazo[1,2-b]pyridazin-3-yl)benzoic acid

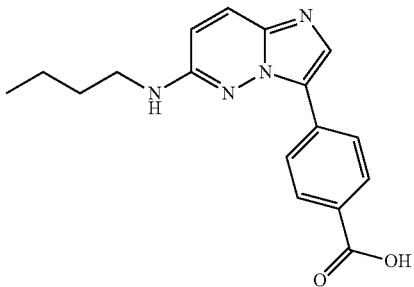 [SMILES: CCCCNc1ccc2ncc(-c3ccc(C(=O)O)cc3)n2n1]

The aryl bromide and the boronic ester were coupled using the same Suzuki reaction conditions as example 5.6.19 to obtain the carboxylic acid product.

Part B. 4-(6-Butylamino-imidazo[1,2-b]pyridazin-3-yl)-N-(2,2-dimethyl-[1,3]dioxolan-4-ylmethyl)-benzamide The regular amide coupling of the carboxylic acid with (2,2-dimethyl-1,3-dioxolan-4-yl)methanamine afforded 71% product. $^1$H NMR (400 MHz, METHANOL-d$_4$) δ ppm 1.02 (t, J=7.33 Hz, 3H) 1.36 (s, 3H) 1.45 (s, 3H) 1.49-1.57 (m, 2H) 1.67-1.76 (m, 2H) 3.40 (t, J=7.20 Hz, 2H) 3.58 (d, J=5.31 Hz, 2H) 3.80 (dd, J=8.46, 6.19 Hz, 1H) 4.12 (dd, J=8.34, 6.32 Hz, 1H) 4.36 (t, J=5.81 Hz, 1H) 6.73 (d, J=9.60 Hz, 1H) 7.63 (d, J=9.60 Hz, 1H) 7.87 (s, 1H) 7.90-7.97 (m, 2H) 8.29-8.36 (m, 2H); LRMS (ESI) m/e 424.0 [(M+H)$^+$, calcd for C$_{23}$H$_{29}$N$_5$O$_3$ 423.0].

5.6.75. Synthesis of 4-(6-Butylamino-imidazo[1,2-b]pyridazin-3-yl)-N-(2,3-dihydroxy-propyl)-benzamide

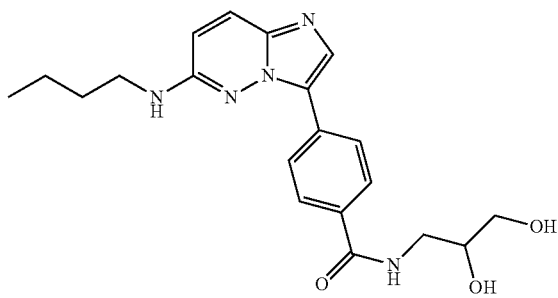 [SMILES: CCCCNc1ccc2ncc(-c3ccc(C(=O)NCC(O)CO)cc3)n2n1]

To 150 mg (0.355 mmol) of 4-(6-butylamino-imidazo[1,2-b]pyridazin-3-yl)-N-(2,2-dimethyl-[1,3]dioxolan-4-ylmethyl)-benzamide was added 15 ml of AcOH and 5 mL of water and heated to 60° C. for 1.5 hr. It was concentrated and the crude was purified on the acetic PREP HPLC to yield 107 mg (79%) of the titled compound. $^1$H NMR (400 MHz, METHANOL-$d_4$) δ ppm 1.00 (t, J=7.39 Hz, 3H) 1.42-1.55 (m, 2H) 1.66-1.76 (m, 2H) 3.40 (t, J=7.17 Hz, 2H) 3.43-3.52 (m, 1H) 3.56-3.65 (m, 3H) 3.84-3.93 (m, 1H) 7.24 (d, J=9.92 Hz, 1H) 7.96 (d, J=9.92 Hz, 1H) 8.00-8.05 (m, 2H) 8.23-8.28 (m, 2H) 8.30 (s, 1H); LRMS (ESI) m/e 384.0 [(M+H)$^+$, calcd for $C_{20}H_{25}N_5O_3$ 383.0]

5.6.76. Synthesis of 7-(6-Butylamino-imidazo[1,2-b]pyridazin-3-yl)-quinazolin-4-ol

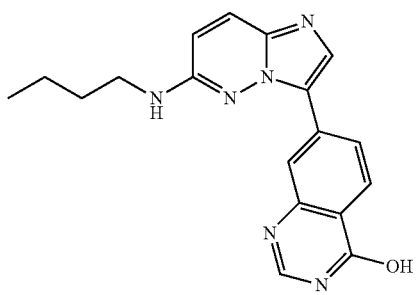 [SMILES: CCCCNc1ccc2ncc(-c3ccc4c(O)ncnc4c3)n2n1]

Part A. 7-(4,4,5,5-tetramethyl-1,3,2-dioxaborolan-2-yl)quinazolin-4-ol

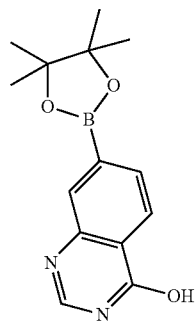 [SMILES: CC1(C)OB(c2ccc3c(O)ncnc3c2)OC1(C)C]

To 87.2 mg (0.356 mmol) of the 4-bromo-2-nitrobenzamide dissolved in 5 mL of formaldehyde was added iron powder (50 mg, 0.89 mmol). The resulting mixture is stirred for 2 hrs at 80° C. It was diluted with 20 mL EtOAc, and 10 mL of 2:1 DCM/IPA solution. The resulting mixture was then filtered through a pad of sand, and then concentrated. To the residue obtained was added 99 mg (0.391 mmol) of bis(pinacolato)diboron, followed by KOAc (105 mg, 1.07 mmol), PdCl$_2$(dppf).DCM (29 mg, 0.04 mmol) and 18 mL of dioxane. The resulting mixture was heated at 80° C. overnight. After cooling, it was diluted with EtOAc, washed with brine, and dried over MgSO$_4$. It was concentrated and purified on the ISCO (silica gel) and eluted with 1-10% MeOH/DCM, to obtain 78 mg (81%) of the boronic ester.

Part B. 7-(6-Butylamino-imidazo[1,2-b]pyridazin-3-yl)-quinazolin-4-ol

To (60 mg, 0.223 mmol) of the aryl bromide, in a microwavable vial was added (73 mg, 0.268 mmol) of the boronic ester, K$_3$PO$_4$ (142 mg, 0.669 mmol), PdCl$_2$(PPh$_3$)$_3$ (16 mg, 0.022 mmol), 3 mL of DME and 1 mL of water. The resulting mixture was microwaved for 30 minutes at 140° C. Dilute with 15 mL of EtOAC, and wash with about 10 mL of brine. The organic layer was dried over MgSO$_4$, and concentrated. The crude mixture was redissolved in 3 ml solution of 2:1 MeOH/H$_2$O. It was filtered and purified on the PREP HPLC to give 41 mg (55%) of the desired product. [The procedure is used for all the Suzuki coupling reactions unless stated otherwise. Boronic acids work just like the boronic esters.] $^1$H NMR (400 MHz, METHANOL-$d_4$) δ ppm 0.99 (t, J=7.39 Hz, 3H) 1.45-1.56 (m, 2H) 1.68-1.77 (m, 2H) 3.46 (t, J=7.06 Hz, 2H) 7.28 (d, J=9.92 Hz, 1H) 7.99 (d, J=9.70 Hz, 1H) 8.22-8.28 (m, 2H) 8.37 (d, J=8.38 Hz, 1H) 8.45 (s, 1H) 8.63 (d, J=1.54 Hz, 1H); LRMS (ESI) m/e 335.0 [(M+H)$^+$, calcd for $C_{18}H_{18}N_6O$ 334.0].

5.6.77. Synthesis of iso-propyl methyl(2-((3-(4-(pyrrolidin-2-yl)phenyl)imidazo[1,2-b]pyridazin-6-yl)amino)ethyl)carbamate

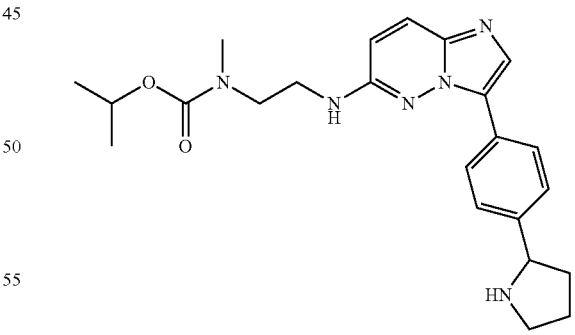

The titled compound was obtained using a process similar to that described in example 5.6.68. $^1$H NMR (400 MHz, METHANOL-$d_4$) δ ppm 8.56 (s, 1H), 8.28 (br. s., 2H), 7.83 (s, 1H), 7.68 (d, J=9.35 Hz, 1H), 7.60 (d, J=8.34 Hz, 2H), 6.73 (d, J=9.85 Hz, 1H), 4.66 (dd, J=9.60, 6.82 Hz, 1H), 3.66 (br. s., 1H), 3.59 (br. s., 3H), 3.41-3.55 (m, 2H), 2.94 (s, 3H), 2.48-2.56 (m, 1H), 2.19-2.34 (m, 3H), 1.00-1.23 (d, J=5.05 Hz, 6H); LRMS (ESI) m/e 423.1 [(M+H)$^+$, calcd for $C_{23}H_{31}N_6O_2$. 423.5].

5.6.78. Synthesis of tert-butyl(2-((3-(2-methoxyphenyl)imidazo[1,2-b]pyridazin-6yl)amino)ethyl)(methyl)carbamate

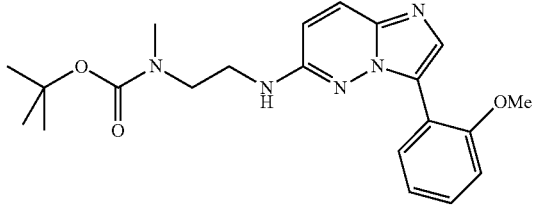 [SMILES: COc1ccccc1-c1cnc2ccc(NCCN(C)C(=O)OC(C)(C)C)nn12]

The titled compound was obtained using a process similar to that described in example 5.6.68. ¹H NMR (400 MHz, METHANOL-d₄) δ ppm 8.04 (s, 1H), 7.97 (br. s., 1H), 7.90 (br. s., 1H), 7.52-7.57 (m, 1H), 7.13-7.24 (m, 3H), 3.90 (s, 3H), 3.42-3.49 (m, 4H), 2.74 (s, 3H), 1.30-1.38 (br. s., 9H); LRMS (ESI) m/e 398.1 [(M+H)⁺, calcd for C₂₁H₂₈N₅O₃ 398.5].

5.6.79. Synthesis of isopropyl methyl(2-((3-(thiazol-4-yl)imidazo[1,2-b]pyridazin-6-yl)amino)ethyl)carbamate

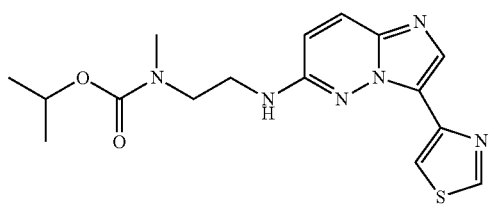 [SMILES: CC(C)OC(=O)N(C)CCNc1ccc2ncc(-c3cscn3)n2n1]

The titled compound was obtained using a process similar to that described in example 5.6.68. ¹H NMR (400 MHz, METHANOL-d₄) δ ppm 9.19 (s, 1H), 8.65-8.85 (bs, 1H), 8.31 (s, 1H), 7.97 (d, J=9.85 Hz, 1H), 7.18 (d, J=9.35 Hz, 1H), 4.78 (m, 1H), 3.64-3.75 (m, 4H), 2.98 (s, 3H), 1.06-1.25 (m, 6H); LRMS (ESI) m/e 361.1 [(M+H)⁺, calcd for C₁₆H₂₀N₆O₂S 361.4].

5.6.80. Synthesis of 4-(6-((2-(2-cyano-N-methylacetamido)ethyl)amino)imidazo[1,2-b]pyridazin-3-yl)benzamide

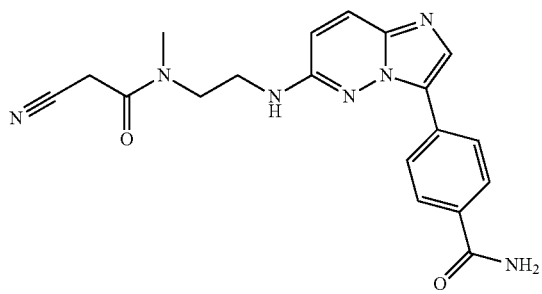 [SMILES: CN(CCNc1ccc2ncc(-c3ccc(C(N)=O)cc3)n2n1)C(=O)CC#N]

Part A. N-(2-((3-bromoimidazo[1,2-b]pyridazin-6-yl)amino)ethyl)-2-cyano-N-methylacetamide

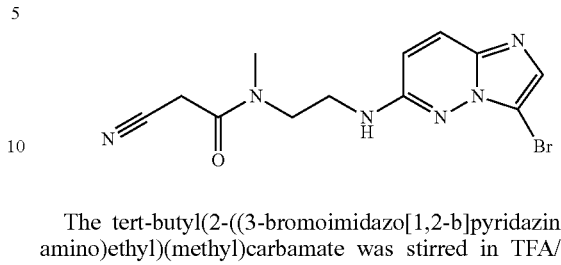

The tert-butyl(2-((3-bromoimidazo[1,2-b]pyridazin-6-yl)amino)ethyl)(methyl)carbamate was stirred in TFA/DCM solution (2:1) for 0.5 hr and then concentrated. The resulting amine-TFA salt was amidated under the conditions described in example 5.6.61, part C with 2-cyanoacetic acid to obtain the amide in 63% yield.

Part B. 4-(6-((2-(2-cyano-N-methylacetamido)ethyl)amino)imidazo[1,2-b]pyridazin-3-yl)benzamide The reaction of the amide with (4-carbamoylphenyl)boronic acid under Suzuki coupling conditions as described in example 5.6.19 afforded the desired product in 28% yield. ¹H NMR (400 MHz, METHANOL-d₄) δ ppm 2.87 (s, 1H) 2.95 (s, 2H) 3.56-3.67 (m, 4H) 3.73 (s, 2H) 7.16 (d, J=9.92 Hz, 1H) 7.94 (d, J=9.70 Hz, 1H) 8.00-8.06 (m, 2H) 8.17 (d, J=8.38 Hz, 2H) 8.21-8.28 (m, 1H); LRMS (ESI) m/e 378.0 [(M+H)⁺, calcd for C₁₉H₁₉N₇O₂ 377.0].

5.6.81. Synthesis of 2-((3-(3-methoxypyridin-4-yl)imidazo[1,2-b]pyridazin-6-yl)amino)ethyl tert-butyl (methyl)carbamate

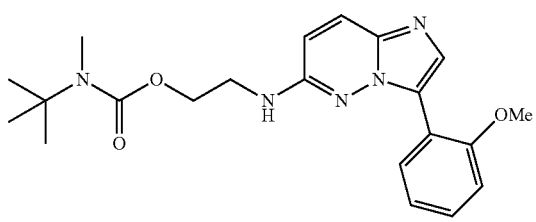 [SMILES: COc1ccccc1-c1cnc2ccc(NCCOC(=O)N(C)C(C)(C)C)nn12]

Part A.
N-(tert-butyl)-N-methyl-1H-imidazole-1-carboxamide

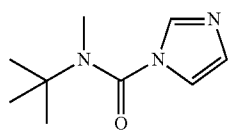

To a suspension of N,N'-carbonyldiimidazole (CDI, 1.76 g, 11 mmol) in THF (18 mL) was added t-butylmethylamine (1.2 mL, 10 mmol). The reaction was refluxed for overnight, then cooled, concentrated, taken up with DCM and water, and extracted. The organic layer (DCM) was dried with anhydrous sodium sulfate, filtered and concentrated to give N-(tert-butyl)-N-methyl-1H-imidazole-1-carboxamide as sticky oil (0.27 g, 15% yield). LRMS (ESI) m/e 182.1 [(M+H)⁺, calcd for C₉H₁₆N₃O 182.2].

Part B. 1-(tert-butyl(methyl)carbamoyl)-3-methyl-1H-imidazol-3-ium

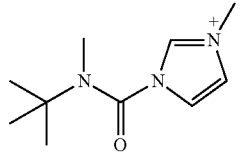

To a solution of N-(tert-butyl)-N-methyl-1H-imidazole-1-carboxamide (0.27 g, 1.5 mmol) in acetonitrile (3 mL) was added methyl iodide (0.4 mL, 6.0 mmol). The reaction was concentrated in vacuo after stirring at rt for 24 h to give 1-(tert-butyl(methyl)carbamoyl)-3-methyl-1H-imidazol-3-ium (0.28 g, 100%).

Part C. 2-((3-bromoimidazo[1,2-b]pyridazin-6-yl)amino)ethyl tert-butyl(methyl)carbamate

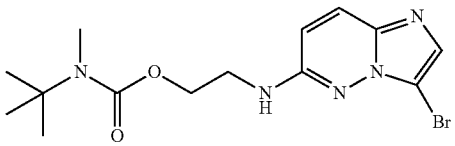 [SMILES: CN(C(=O)OCCNc1ccc2ncc(Br)n2n1)C(C)(C)C]

To a solution of 2-((3-bromoimidazo[1,2-b]pyridazin-6-yl)amino)ethanol (0.35 g, 1.5 mmol) and 1-(tert-butyl(methyl)carbamoyl)-3-methyl-1H-imidazol-3-ium (0.30 g, 1.5 mmol) in THF/DMF (6.0 mL/3.0 mL) was added NaH (0.15 g, 60% in mineral oil, 2.5 mmol). The reaction was stirred for 24 h and then quenched with water, extracted with ether, concentrated and purified by ISCO column chromatography give 2-((3-bromoimidazo[1,2-b]pyridazin-6-yl)amino)ethyl tert-butyl(methyl)carbamate as product (0.17 g, 31% yield). LRMS (ESI) m/e 372.0 [(M+H)$^+$, calcd for $C_{14}H_{21}BrN_5O_2$ 371.2].

Part D. 2-((3-(3-methoxypyridin-4-yl)imidazo[1,2-b]pyridazin-6-yl)amino)ethyl tert-butyl(methyl)carbamate The titled compound was obtained using Suzuki coupling as described in example 5.6.68. $^1$H NMR (400 MHz, METHANOL-d$_4$) δ ppm 8.70 (d, J=5.31 Hz, 1H), 8.43 (s, 1H), 8.13 (s, 1H), 7.73 (s, 1H), 7.71 (s, 1H), 6.84 (s, 1H), 6.82 (s, 1H), 4.31 (t, J=5.68 Hz, 2H), 4.10 (s, 3H), 3.70 (t, J=5.68 Hz, 2H), 2.89 (s, 3H), 1.35 (s, 9H); LRMS (ESI) m/e 399.3 [(M+H)$^+$, calcd for $C_{20}H_{27}N_6O_3$ 399.5].

5.6.82. Synthesis of N-(2-isopropoxyethyl)-3-(3-methoxypyridin-4-yl)imidazo[1,2-b]pyridazin-6-amine

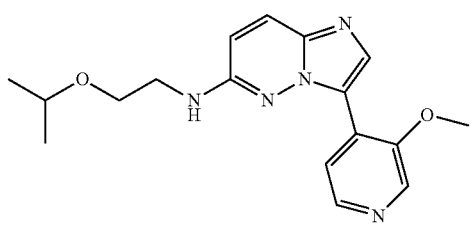 [SMILES: COc1cnccc1-c1cnc2ccc(NCCOC(C)C)nn12]

The titled compound was obtained as described in example 5.6.68. $^1$H NMR (400 MHz, METHANOL-d$_4$) δ ppm 8.66 (d, J=5.29 Hz, 1H), 8.36 (br. s., 1H), 8.21 (d, J=4.41 Hz, 1H), 8.06 (br. s., 1H), 7.63 (d, J=9.70 Hz, 1H), 6.79 (d, J=9.70 Hz, 1H), 4.57 (br. s., 1H), 4.03 (s, 3H), 3.58-3.67 (m, 3H), 3.47-3.52 (m, 2H), 1.11 (d, J=6.17 Hz, 6H); LRMS (ESI) m/e 328.1 [(M+H)$^+$, calcd for $C_{17}H_{22}N_5O_2$ 328.4].

5.6.83. Synthesis of [2-(3-Cyclopropyl-imidazo[1,2-b]pyridazin-6-ylamino)-ethyl]-isopropyl-carbamic acid isopropyl ester

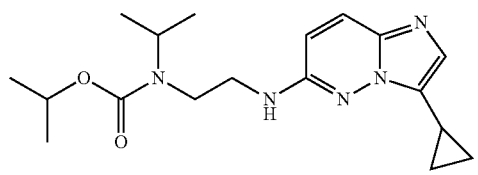 [SMILES: CC(C)OC(=O)N(CCNc1ccc2ncc(C3CC3)n2n1)C(C)C]

Part A. [2-(3-Bromo-imidazo[1,2-b]pyridazin-6-ylamino)-ethyl]-isopropyl-carbamic acid isopropyl ester

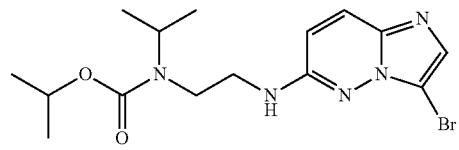 [SMILES: CC(C)OC(=O)N(CCNc1ccc2ncc(Br)n2n1)C(C)C]

To a rapidly stirred, ambient temperature, N$_2$ blanketed, solution of N1-(3-bromoimidazo[1,2-b]pyridazin-6-yl)-N2-isopropylethane-1,2-diamine (945.0 mg, 3.2 mmol) and Hunig's base [7087-68-5] (0.7 mL, 3.8 mmol) in ethyl acetate (32 mL) was added a 1.0M solution of isopropyl chloroformate in toluene (3.2 mL). Once complete, the reaction was washed with brine, dried (MgSO$_4$), and evaporated to provide 1.2 g of tan solid. This solid was recrystallized from ethyl acetate heptane to afford [2-(3-bromo-imidazo[1,2-b]pyridazin-6-ylamino)-ethyl]-isopropyl-carbamic acid isopropyl ester as 750 mg of white crystalline powder, mp. 146-147° C. $^1$H NMR (400 MHz, DMSO-d$_6$) δ ppm 1.17 (d, J=6.82 Hz, 12H) 3.31-3.35 (m, 2H) 3.38-3.44 (m, 2H) 4.80 (dt, J=12.06, 5.97 Hz, 1H) 6.67 (d, J=9.85 Hz, 1H) 7.34 (t, J=5.68 Hz, 1H) 7.49 (s, 1H) 7.71 (d, J=9.60 Hz, 1H). $^{13}$C NMR (100 MHz, DMSO-d$_6$) δ ppm 20.44, 21.95, 47.01, 67.46, 98.94, 112.84, 125.54, 130.42, 136.57, 154.10. LRMS (ESI) m/z 297.9/299.9 [(M+H)]$^+$, calc'd for $C_{16}H_{22}BrN_6O_2$: 384.28.

Part B. [2-(3-Cyclopropyl-imidazo[1,2-b]pyridazin-6-ylamino)-ethyl]-isopropyl-carbamic acid isopropyl ester A solution of 10% (v/v) water in THF (25 mL) was added to a mixture of [2-(3-bromo-imidazo[1,2-b]pyridazin-6-ylamino)-ethyl]-isopropyl-carbamic acid isopropyl ester (515.1 mg, 1.34 mmol), potassium cyclopropyltrifluoroborate [1065010-87-1] (396.8 mg, 2.7 mmol), cesium carbonate [534-17-8] (1.3 g, 4.0 mmol), and [1,1'-bis(diphenylphosphino)ferrocene]dichloropalladium(II), complex with dichloromethane [95464-05-4] (110.4 mg, 0.1 mmol) contained in a 50 mL round bottomed flask. The reaction pot was fitted to a reflux condenser and the system taken through 10 evacuation/N2 blanket cycles while being rapidly stirred. The rapidly stirred, N₂ blanketed, reaction was heated reflux for 4d then cooled and filtered. The filtrate was partitioned between brine and ethyl acetate and the phase separated organic extract dried (MgSO₄) and evaporated to give a black oil which was purified by preparatory RP-HPLC to provide 41.6 mg of [2-(3-cyclopropyl-imidazo[1,2-b]pyridazin-6-ylamino)-ethyl]-isopropyl-carbamic acid isopropyl ester as a white solid. ¹H NMR (400 MHz, METHANOL-d₄) δ ppm 0.77-0.84 (m, 2H) 0.98-1.06 (m, 2H) 1.20-1.32 (m, 14H) 2.08-2.19 (m, 1H) 3.43-3.50 (m, 2H) 3.50-3.59 (m, 2H) 6.61 (d, J=9.70 Hz, 1H) 7.08 (s, 1H) 7.52 (d, J=9.70 Hz, 1H). LRMS (ESI) m/z 346.2 [(M+H)]⁺, calc'd for C₁₈H₂₇N₆O₂: 345.45.

5.6.84. Synthesis of (S)-tert-butyl 2-(((3-(4-carbamoylphenyl)imidazo[1,2-b]pyridazin-6-yl)amino)methyl)pyrrolidine-1-carboxylate

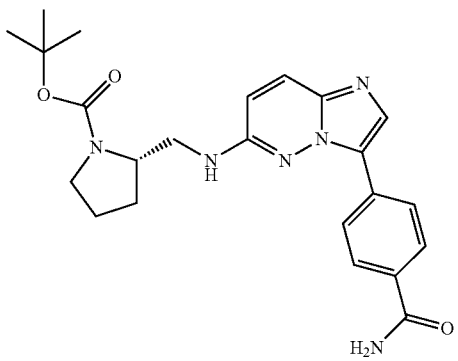 [SMILES: CC(C)(C)OC(=O)N1CCC[C@H]1CNc1ccc2ncc(-c3ccc(C(N)=O)cc3)n2n1]

The titled compound was obtained using the approach described in example 5.6.68. ¹H NMR (400 MHz, METHANOL-d₄) δ ppm 8.24-8.34 (m, 2H), 7.97-8.01 (m, 2H), 7.87 (s, 1H), 7.66 (d, J=8.84 Hz, 1H), 6.77 (br. s., 1H), 4.17 (br. s., 1H), 3.68 (br. s., 1H), 3.44-3.55 (m, 1H), 3.35-3.44 (m, 3H), 1.91-2.05 (m, 3H), 1.87 (br. s., 1H), 1.38-1.48 (m, 5H), 1.34 (br. s., 4H); LRMS (ESI) m/e 437.2 [(M+H)⁺, calcd for C₂₃H₂₉N₆O₃ 437.5].

5.6.85. Synthesis of (S)-tert-butyl 2-(((3-(4-(aminomethyl)phenyl)imidazo[1,2-b]pyridazin-6-yl)amino)methyl)pyrrolidine-1-carboxylate

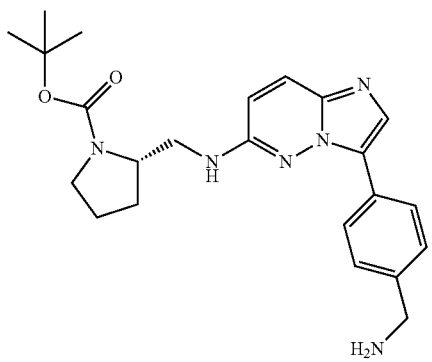 [SMILES: CC(C)(C)OC(=O)N1CCC[C@H]1CNc1ccc2ncc(-c3ccc(CN)cc3)n2n1]

The titled compound was obtained using the approach described in example 5.6.68. ¹H NMR (400 MHz, METHANOL-d₄) δ ppm 8.27 (br. s., 2H), 7.82 (br. s., 1H), 7.66 (d, J=9.35 Hz, 1H), 7.58 (d, J=8.34 Hz, 2H), 6.77 (d, J=9.09 Hz, 1H), 4.18 (s, 3H), 3.36-3.50 (m, 4H), 1.85-2.04 (m, 4H), 1.33-1.48 (m, 9H); LRMS (ESI) m/e 437.2 [(M+H)⁺, calcd for C₂₃H₂₉N₆O₃ 437.5].

5.6.86. Synthesis of (R)-tert-butyl 2-(((3-(4-(aminomethyl)phenyl)imidazo[1,2-b]pyridazin-6-yl)amino)methyl)pyrrolidine-1-carboxylate

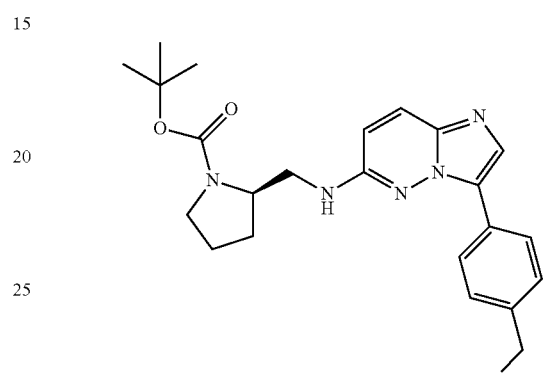

The titled compound was obtained using the approach described in example 5.6.68. ¹H NMR (400 MHz, METHANOL-d₄) δ ppm 8.27 (br. s., 2H), 7.82 (br. s., 1H), 7.66 (d, J=9.35 Hz, 1H), 7.58 (d, J=8.34 Hz, 2H), 6.77 (d, J=9.09 Hz, 1H), 4.18 (s, 3H), 3.36-3.50 (m, 4H), 1.85-2.04 (m, 4H), 1.33-1.48 (m, 9H); LRMS (ESI) m/e 437.2 [(M+H)⁺, calcd for C₂₃H₂₉N₆O₃ 437.5].

5.6.87. Synthesis of N-(2-isopropoxyethyl)-3-(isothiazol-5-yl)imidazo[1,2-b]pyridazin-6-amine

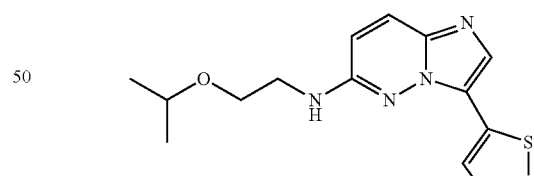

The titled compound was obtained using the approach described in example 5.6.68. ¹H NMR (400 MHz, METHANOL-d₄) δ ppm 8.60 (d, J=2.02 Hz, 1H), 8.45 (s, 1H), 8.01 (d, J=1.77 Hz, 1H), 7.95 (d, J=9.85 Hz, 1H), 7.25 (d, J=9.85 Hz, 1H), 3.80-3.85 (m, 2H), 3.69-3.77 (m, 3H), 1.21 (d, J=6.32 Hz, 6H); LRMS (ESI) m/e 304.1 [(M+H)⁺, calcd for C₁₄H₁₈N₅OS 304.4].

5.6.88. Synthesis of tert-butyl 2-(2-((3-(4-(aminomethyl)phenyl)imidazo[1,2-b]pyridazin-6-yl)amino)ethyl)pyrrolidine-1-carboxylate

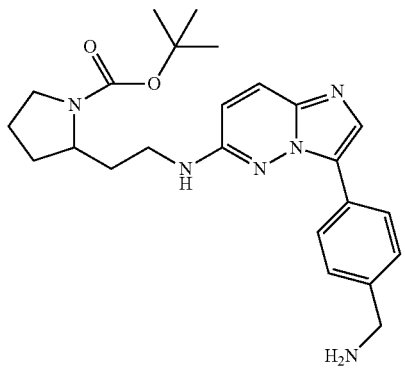 [SMILES: CC(C)(C)OC(=O)N1CCCC1CCNc1ccc2ncc(-c3ccc(CN)cc3)n2n1]

The titled compound was obtained using the approach described in example 5.6.68. $^1$H NMR (400 MHz, METHANOL-d$_4$) δ ppm 8.53 (s, 1H), 8.27 (d, J=8.34 Hz, 2H), 7.81 (s, 1H), 7.64 (d, J=9.60 Hz, 1H), 7.57 (d, J=8.34 Hz, 2H), 6.73 (d, J=9.60 Hz, 1H), 4.18 (s, 2H), 3.92-3.98 (m, 1H), 3.52 (br. s., 1H), 3.35-3.46 (m, 3H), 1.67-2.22 (m, 6H), 1.48 (br. s., 4H), 1.28 (br. s., 5H); LRMS (ESI) m/e 437.3 [(M+H)$^+$, calcd for C$_{24}$H$_{33}$N$_6$O$_2$ 437.5].

5.6.89. Synthesis of 3-(4-(aminomethyl)phenyl)-N-(2-(cyclopentyloxy)ethyl)imidazo[1,2-b]pyridazin-6-amine

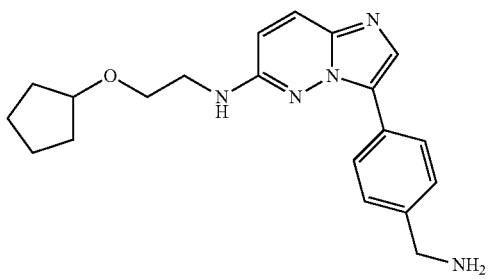 [SMILES: NCc1ccc(-c2cnc3ccc(NCCOC4CCCC4)nn23)cc1]

Part A. 3-bromo-N-(2-(cyclopentyloxy)ethyl)imidazo[1,2-b]pyridazin-6-amine

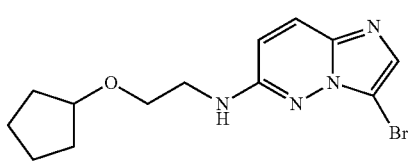 [SMILES: Brc1cnc2ccc(NCCOC3CCCC3)nn12]

The 2-(cyclopentyloxy)ethanamine was reacted with 3-bromo-6-fluoroimidazo[1,2-b]pyridazine, using the amine displacement conditions described in example 5.6.42, part A to afford 69% product.

Part B. tert-butyl 4-(6-((2-(cyclopentyloxy)ethyl)amino)imidazo[1,2-b]pyridazin-3-yl)benzylcarbamate

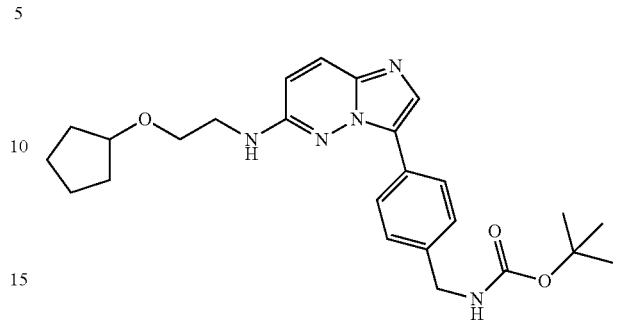

The 3-bromo-N-(2-(cyclopentyloxy)ethyl)imidazo[1,2-b]pyridazin-6-amine was coupled with (4-(((tert-butoxycarbonyl)amino)methyl)phenyl)boronic acid under the Suzuki coupling conditions as described in example 5.6.76, Part B to obtain 70% product.

Part C. 3-(4-(aminomethyl)phenyl)-N-(2-(cyclopentyloxy)ethyl)imidazo[1,2-b]pyridazin-6-amine The tert-butoxycarbonyl protection was removed by using 10 equivalents of AcCl in MeOH at 0° C. over 4 hr to obtain 100% yield of the desired compound. $^1$H NMR (400 MHz, METHANOL-d$_4$) δ ppm 1.55 (d, J=3.54 Hz, 2H) 1.63-1.81 (m, 6H) 3.57 (t, J=5.31 Hz, 2H) 3.67 (q, J=5.05 Hz, 2H) 3.93-4.05 (m, 1H) 4.21-4.31 (m, 2H) 7.29-7.41 (m, 1H) 7.70 (d, J=8.08 Hz, 2H) 7.96-8.05 (m, 1H) 8.18-8.25 (m, 2H) 8.25-8.31 (m, 1H); $^{13}$C NMR (101 MHz, METHANOL-d$_4$) δ ppm 24.59 (s, 1C) 33.34 (s, 1C) 43.09 (s, 1C) 44.12 (s, 1C) 67.41 (s, 1C) 83.26 (s, 1C) 120.08 (s, 1C) 121.33 (s, 1C) 121.60 (s, 1C) 128.35 (s, 1C) 129.81 (s, 1C) 130.45 (s, 1C) 130.65 (s, 1C) 134.28 (s, 1C) 135.94 (s, 1C) 146.70-146.90 (m, 1C) 157.40 (s, 1C); LRMS (ESI) m/e 352.0 [(M+H)$^+$, calcd for C$_{20}$H$_{25}$N$_5$O 351.0].

5.6.90. Synthesis of (S)-isopropyl 2-(((3-vinylimidazo[1,2-b]pyridazin-6-yl)amino)methyl)pyrrolidine-1-carboxylate

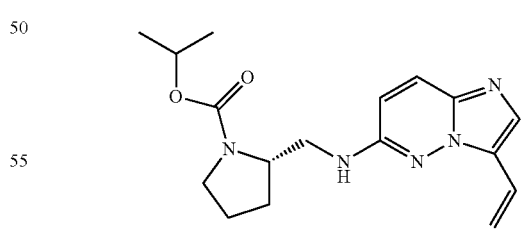

The titled compound was obtained using the approach described in example 5.6.68. $^1$H NMR (400 MHz, METHANOL-d$_4$) d ppm 7.52-7.59 (m, 2H), 6.95-7.00 (m, 1H), 6.68 (d, J=9.60 Hz, 1H), 6.20 (d, J=1.52 Hz, 1H), 6.16 (d, J=1.52 Hz, 1H), 5.37 (d, J=1.52 Hz, 1H), 5.34 (d, J=1.77 Hz, 1H), 4.88 (quin, J=6.25 Hz, 1H), 4.22 (Rs, 1H), 3.40-3.64 (m, 4H), 1.87-2.05 (m, 4H), 1.18-1.25 (m, 6H); LRMS (ESI) m/e 330.3 [(M+H)$^+$, calcd for C$_{17}$H$_{24}$N$_5$O$_2$ 330.4].

5.6.91. Synthesis of (S)-isopropyl 2-(((3-(prop-1-en-2-yl)imidazo[1,2-b]pyridazin-6-yl)amino)methyl)pyrrolidine-1-carboxylate

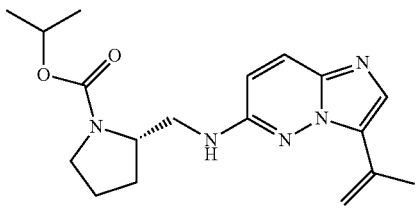 [SMILES: C=C(C)c1cnc2ccc(NC[C@@H]3CCCN3C(=O)OC(C)C)nn12]

The titled compound was obtained using the approach described in example 5.6.68. $^1$H NMR (400 MHz, METHANOL-d$_4$) δ ppm 7.60 (d, J=9.85 Hz, 1H), 7.47 (s, 1H), 6.70 (d, J=9.60 Hz, 1H), 6.43 (s, 1H), 5.27 (s, 1H), 4.86 (dt, J=12.44, 6.28 Hz, 1H), 4.21 (br. s., 1H), 3.54-3.61 (m, 1H), 3.35-3.50 (m, 3H), 2.23 (s, 3H), 1.86-2.05 (m, 4H), 1.21 (dd, J=12.13, 6.06 Hz, 6H); LRMS (ESI) m/e 344.2 [(M+H)$^+$, calcd for C$_{18}$H$_{26}$N$_5$O$_2$ 344.4].

5.6.92. Synthesis of (S)-isopropyl 2-(((3-cyclopropylimidazo[1,2-b]pyridazin-6-yl)amino)methyl)pyrrolidine-1-carboxylate

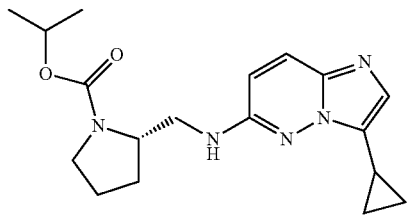 [SMILES: CC(C)OC(=O)N1CCC[C@H]1CNc1ccc2ncc(C3CC3)n2n1]

The titled compound was obtained using the approach described in example 5.6.68. $^1$H NMR (400 MHz, METHANOL-d$_4$) δ ppm 7.85 (m, J=9.85 Hz, 1H), 7.52 (s, 1H), 7.17-7.21 (m, 1H), 4.84-4.90 (m, 1H), 4.25 (d, J=6.57 Hz, 1H), 3.63-3.69 (m, 1H), 3.42-3.57 (m, 3H), 2.24-2.31 (m, 1H), 1.90-2.08 (m, 4H), 1.16-1.25 (m, 8H), 0.90-0.94 (m, 2H); LRMS (ESI) m/e 344.2 [(M+H)$^+$, calcd for C$_{18}$H$_{26}$N$_5$O$_2$ 344.4].

5.6.93. Synthesis of N-(2-(cyclopentyloxy)ethyl)-3-(2-methoxypyridin-3-yl)imidazo[1,2-b]pyridazin-6-amine

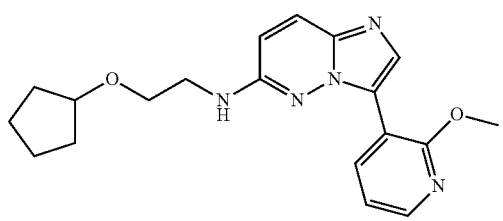 [SMILES: COc1ncccc1-c1cnc2ccc(NCCOC3CCCC3)nn12]

The titled compound was obtained using the approach described in example 5.6.68. $^1$H NMR (400 MHz, METHANOL-d$_4$) δ ppm 8.76 (dd, J=7.58, 1.77 Hz, 1H), 8.13 (dd, J=4.80, 1.77 Hz, 1H), 7.89 (s, 1H), 7.64 (d, J=9.60 Hz, 1H), 7.08 (dd, J=7.45, 4.93 Hz, 1H), 6.76 (d, J=9.60 Hz, 1H), 4.05 (s, 3H), 3.97 (dd, J=5.18, 3.41 Hz, 1H), 3.64 (t, J=5.94 Hz, 2H), 3.51 (t, J=5.94 Hz, 2H), 1.62-1.76 (m, 6H), 1.50-1.58 (m, 2H); LRMS (ESI) m/e 354.2 [(M+H)$^+$, calcd for C$_{19}$H$_{24}$N$_5$O$_2$ 354.4].

5.6.94. Synthesis of (S)-tert-butyl 3-(((3-(3-methoxypyridin-4-yl)imidazo[1,2-b]pyridazin-6-yl)amino)methyl)pyrrolidine-1-carboxylate

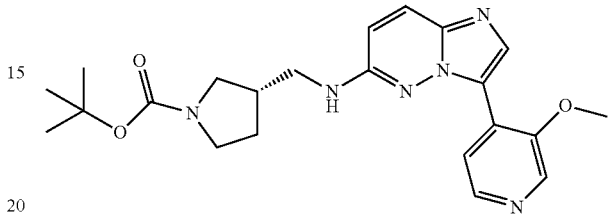

The titled compound was obtained using the approach described in example 5.6.68. $^1$H NMR (400 MHz, METHANOL-d$_4$) δ ppm 8.64 (d, J=5.05 Hz, 1H), 8.43 (s, 1H), 8.29 (d, J=5.05 Hz, 1H), 8.10 (s, 1H), 7.69 (d, J=9.60 Hz, 1H), 6.80 (d, J=9.85 Hz, 1H), 4.08 (s, 3H), 3.2-3.56 (m, 5H), 3.36 (br. s., 1H), 2.69 (m, 1H), 2.08 (m, 1H), 1.78 (m, 1H), 1.44 (s, 9H); LRMS (ESI) m/e 425.3 [(M+H)$^+$, calcd for C$_{22}$H$_{29}$N$_6$O$_3$ 425.5].

5.6.95. Synthesis of (S)-tert-butyl 2-(((3-bromoimidazo[1,2-b]pyridazin-6-yl)amino)methyl)pyrrolidine-1-carboxylate

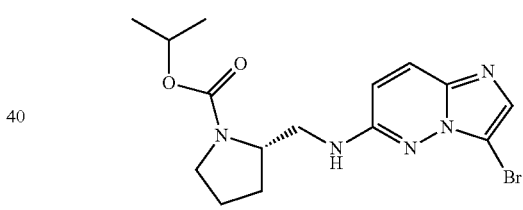

The titled compound was obtained using the approach described in example 5.6.68. $^1$H NMR (400 MHz, METHANOL-d$_4$) δ ppm 7.57 (d, J=9.60 Hz, 1H), 7.41 (s, 1H), 6.73 (d, J=9.60 Hz, 1H), 3.55-3.61 (m, 1H), 3.39-3.52 (m, 3H), 3.37 (s, 1H), 2.08 (br. s., 1H), 1.87-2.03 (m, 3H), 1.43 (s, 9H); LRMS (ESI) m/e 398.1 [(M+H)$^+$, calcd for C$_{16}$H$_{22}$BrN$_6$O$_2$ 397.3].

5.6.96. Synthesis of (S)-isopropyl 2-(((3-cyanoimidazo[1,2-b]pyridazin-6-yl)amino)methyl)pyrrolidine-1-carboxylate

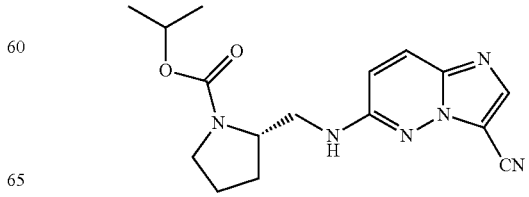

A solution of (S)-iso-propyl 2-(((3-bromoimidazo[1,2-b]pyridazin-6-yl)amino)methyl)pyrrolidine-1-carboxylate (300 mg, 0.79 mmol), NaCN (46 mg, 0.94 mmol), CuI (15 mg, 0.08 mmol), KI (27 mg, 0.16 mmol) and N1,N2-dimethylethane-1,2-diamine (0.085 mL, 0.79 mmol) in toluene (0.8 mL) was stirred at 110° C. for 12 h. The reaction was cooled, concentrated, taken up with EtOAc and water, extracted and dried organic layer with MgSO₄. The organic layer was concentrated and purified by ISCO (0-5% MeOH/DCM), then following PREP HPLC (neutral) to give (S)-isopropyl 2-(((3-cyanoimidazo[1,2-b]pyridazin-6-yl)amino)methyl)pyrrolidine-1-carboxylate (63 mg, 25% yield). ¹H NMR (400 MHz, METHANOL-d₄) δ ppm 8.00 (s, 1H), 7.72 (d, J=9.85 Hz, 1H), 6.91 (d, J=9.85 Hz, 1H), 4.20 (m, 1H), 3.38-3.61 (m, 4H), 1.97-2.05 (m, 4H), 1.16-1.25 (m, 6H); LRMS (ESI) m/e 329.2 [(M+H)⁺, calcd for C₁₆H₂₁N₆O₂ 329.4].

5.6.97. Synthesis of (3-Cyclopent-1-enyl-imidazo[1,2-b]pyridazin-6-yl)-[2-(2-ethoxy-phenyl)-ethyl]-amine

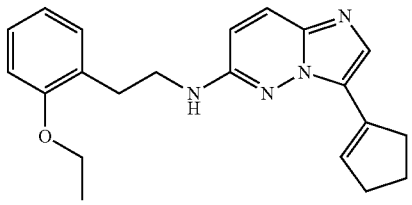 [SMILES: CCOc1ccccc1CCNc1ccc2ncc(C3=CCCC3)n2n1]

Part A. (3-Bromo-imidazo[1,2-b]pyridazin-6-yl)-[2-(2-ethoxy-phenyl)-ethyl]-amine

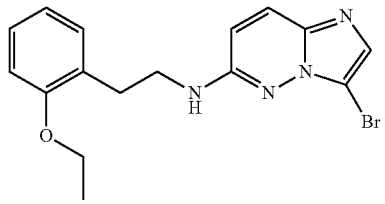 [SMILES: CCOc1ccccc1CCNc1ccc2ncc(Br)n2n1]

A mixture of 3-bromo-6-fluoro-imidazo[1,2-b]pyridazine (648 mg, 3 mmol), 2-ethoxy-phenethylamine (1 g, 6 mmol) and triethylamine (1 ml) in isopropyl alcohol (2 ml) was heated in a microwave at 140° C. for 20 min. The reaction mixture was concentrated and the residue was subjected to ISCO (40 g column), to gave the titled compound (980 mg). ¹H NMR (400 MHz, CHLOROFORM-d) δ ppm 1.47 (t, J=6.95 Hz, 3H) 3.04 (t, J=6.69 Hz, 2H) 3.64-3.72 (m, 2H) 4.06-4.17 (m, 2H) 4.97 (br. s., 1H) 6.40 (d, J=9.60 Hz, 1H) 6.87-7.02 (m, 2H) 7.17-7.32 (m, 2H) 7.47 (s, 1H) 7.54 (d, J=9.60 Hz, 1H). LRMS (ESI) m/z 361 and 363.1 [(M+H)]⁺, calc'd for C₁₆H₁₇BrN₄O: 361.24.

Part B. (3-Cyclopent-1-enyl-imidazo[1,2-b]pyridazin-6-yl)-[2-(2-ethoxy-phenyl)-ethyl]-amine A mixture of (3-bromo-imidazo[1,2-b]pyridazin-6-yl)-[2-(2-ethoxy-phenyl)-ethyl]-amine (90 mg, 0.25 mmol), 2-cyclopent-1-enyl-4,4,5,5-tetramethyl-[1,3,2]dioxaborolane (97 mg, 0.5 mmol), K₂CO₃ (104 mg, 0.75 mmol) and dichlorobis(triphenylphosphine)palladium(II) (8.8 mg, 0.013 mmol) in MeCN/water (2.8 ml/0.7 ml) was heated in a microwave at 150° C. for 15 min. The water layer was removed and the organic layer was concentrated. The residue was subjected to ISCO. The product was further purified by preparative to give the titled compound (60 mg).
¹H NMR (400 MHz, CHLOROFORM-d) δ ppm 1.46 (t, J=6.95 Hz, 3H) 1.99-2.07 (m, 2H) 2.64-2.70 (m, 2H) 2.82-2.88 (m, 2H) 3.06 (t, J=6.62 Hz, 2H) 3.66-3.72 (m, 2H) 4.11 (q, J=7.06 Hz, 2H) 4.77-4.84 (m, 1H) 6.37 (d, J=9.70 Hz, 1H) 6.88-6.95 (m, 2H) 7.02 (t, J=1.98 Hz, 1H) 7.18-7.27 (m, 2H) 7.46 (s, 1H) 7.62 (d, J=9.48 Hz, 1H). LRMS (ESI) m/z 349.2 [(M+H)]⁺, calc'd for C₂₁H₂₄N₄O: 348.45.

5.6.98. Synthesis of (S)-tert-butyl-2-(((3-(2-oxopyrrolidin-1-yl)imidazo[1,2-b]pyridazin-6-yl)amino)methyl)pyrrolidine-1-carboxylate

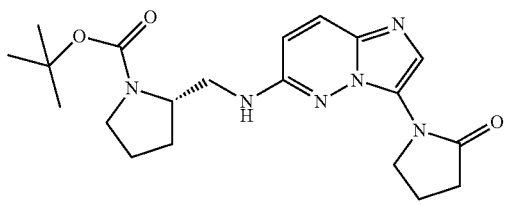 [SMILES: CC(C)(C)OC(=O)N1CCC[C@H]1CNc1ccc2ncc(N3CCCC3=O)n2n1]

Part A. 4-bromo-N-(6-chloroimidazo[1,2-b]pyridazin-3-yl)butanamide

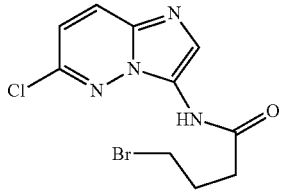 [SMILES: O=C(CCCBr)Nc1cnc2ccc(Cl)nn12]

To 1.0 g (5.930 mmol) of 6-chloroimidazo[1,2-b]pyridazin-3-amine dissolved in 15 mL of THF was added 4-bromobutanoyl chloride (1.21 g, 6.52 mmol) and pyridine (0.96 mL, 11.86 mmol). This mixture was stirred for 1 hr at rt, and then diluted with 30 mL EtOAc and quenched with aq. NaHCO₃. The organic layer was separated and washed with brine, dried over MgSO₄, and concentrated. The solid obtained (1.39 g, 74% yield) was pure enough to be used for the next step without further purification.

Part B. 1-(6-chloroimidazo[1,2-b]pyridazin-3-yl)pyrrolidin-2-one

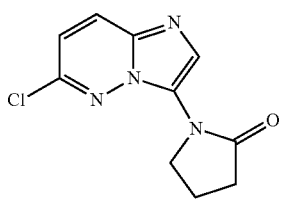 [SMILES: O=C1CCCN1c1cnc2ccc(Cl)nn12]

To 1.0 g of 4-bromo-N-(6-chloroimidazo[1,2-b]pyridazin-3-yl)butanamide (3.15 mmol) dissolved in 39 mL DMF was added NaH (189 mg, 4.72 mmol), and stirred at rt for 0.5 hr. Dilute with 50 mL EtOAc and separate the organic layer. Wash twice with water, once with brine and dry over MgSO$_4$. Concentrate to obtain the product 0.49 g (66%). No purification was needed.

Part C. (S)-tert-butyl 2-(((3-(2-oxopyrrolidin-1-yl)imidazo[1,2-b]pyridazin-6-yl)amino)methyl)pyrrolidine-1-carboxylate The 1-(6-chloroimidazo[1,2-b]pyridazin-3-yl)pyrrolidin-2-one was reacted with (S)-tert-butyl 2-(aminomethyl)pyrrolidine-1-carboxylate using the amine displacement conditions described in example 5.6.42, Part A to afford the desired product in 73% yield. $^1$H NMR (400 MHz, CHLOROFORM-d) δ ppm 1.38-1.46 (m, 10H) 1.71 (br. s., 1H) 1.80-1.91 (m, 2H) 1.95-2.08 (m, 1H) 2.22 (quin, J=7.55 Hz, 2H) 2.50-2.58 (m, 2H) 3.22-3.41 (m, 4H) 3.90 (q, J=6.69 Hz, 2H) 4.16 (br. s., 1H) 6.40 (d, J=9.70 Hz, 1H) 7.44 (s, 1H) 7.54 (d, J=9.70 Hz, 1H); LRMS (ESI) m/401.0 [(M+H)$^+$, calcd for C$_{20}$H$_{28}$N$_6$O$_3$ 400.0].

5.6.99. Synthesis of 1-{2-[3-(4-Aminomethyl-phenyl)-imidazo[1,2-b]pyridazin-6-ylamino]-ethyl}-3-tert-butyl-imidazolidin-2-one

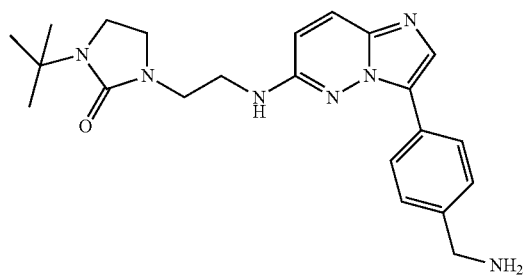 [SMILES: CC(C)(C)N1CCN(CCNc2ccc3ncc(-c4ccc(CN)cc4)n3n2)C1=O]

Part A. 1-[2-(3-Bromo-imidazo[1,2-b]pyridazin-6-ylamino)-ethyl]-3-tert-butyl-imidazolidin-2-one

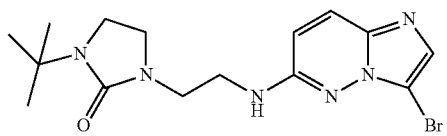 [SMILES: CC(C)(C)N1CCN(CCNc2ccc3ncc(Br)n3n2)C1=O]

A mixture of 1-tert-butyl-imidazolidin-2-one (1.42 g, 10 mmol) and NaH (600 mg, 60% oil dispersion, 15 mmol) in THF (50 ml) was stirred at rt for 2 h. then cooled to 0° C. A solution of bromoacetonitrile (1.4 ml, 20 mmol) in THF (30 ml) was added slowly to the reaction mixture. The resulting mixture was stirred at rt for overnight. The mixture was treated with small amount of water and then the mixture was passed through a silica pad. The filtrate was concentrated and the residue was subjected to a short column to give the crude product which was further purified by another short column to give the product.

To a solution of above product (1.6 g, 8.8 mmol) in THF (20 ml) at 0° C. was added a solution of BH$_3$THF in THF (1 M, 100 ml). The resulting mixture was stirred at 0° C. for 30 min. then at rt for 4 h. The mixture was then cooled to 0° C. again and treated with cold HCl (6 N, 20 ml) to strong acidic pH. The organic solvent was removed under reduced pressure. The residue was treated with NaOH (4 N, ~30 ml) to pH>10, then extracted with EtOAc (5×75 ml). The combined extracts were dried (Na$_2$SO$_4$) and concentrated to give the desired product.

A mixture of above product (350 mg, 1.89 mmol), 3-bromo-6-fluoro-imidazo[1,2-b]pyridazine (216 mg, 1 mmol), and triethylamine (0.5 ml) in isopropyl alcohol (1.5 ml) was heated in a microwave at 140° C. for 20 min. The reaction mixture was concentrated and the residue was subjected to ISCO (40 g column), to gave the titled compound (180 mg). LRMS (ESI) m/z 381 and 383.2 [(M+H)]$^+$, calc'd for C$_{15}$H$_{21}$BrN$_6$O: 381.28.

Part B. 1-{2-[3-(4-Aminomethyl-phenyl)-imidazo[1,2-b]pyridazin-6-ylamino]-ethyl}-3-tert-butyl-imidazolidin-2-one A mixture of 1-[2-(3-bromo-imidazo[1,2-b]pyridazin-6-ylamino)-ethyl]-3-tert-butyl-imidazolidin-2-one (75 mg, 0.2 mmol), (4-aminomethylphenyl)boronic acid hydrochloride (49 mg, 0.26 mmol), K$_2$CO$_3$ (83 mg, 0.6 mmol) and dichlorobis(triphenylphosphine)palladium(II) (7 mg, 0.01 mmol) in MeCN/water (2.8 ml/0.7 ml) was heated in a microwave at 150° C. for 15 min. The reaction mixture was diluted with MeCN and filtered. The filtrate was subjected to preparative HPLC to give the titled compound (64.8 mg). $^1$H NMR (400 MHz, METHANOL-d$_4$) δ ppm 1.26 (s, 9H) 3.24-3.31 (m, 4H) 3.40 (t, J=5.95 Hz, 2H) 3.52 (t, J=5.95 Hz, 2H) 4.17 (s, 2H) 6.70 (d, J=9.70 Hz, 1H) 7.54-7.63 (m, 3H) 7.77 (s, 1H) 8.19-8.23 (m, 2H) 8.56 (s, 1H). LRMS (ESI) m/z 408.4 [(M+H)]$^+$, calc'd for C$_{22}$H$_{29}$N$_7$O: 407.52.

5.6.100. Synthesis of (S)-tert-butyl 2-(((3-(4-(aminomethyl)phenyl)imidazo[1,2-b]pyridazin-6-yl)amino)methyl)piperidine-1-carboxylate

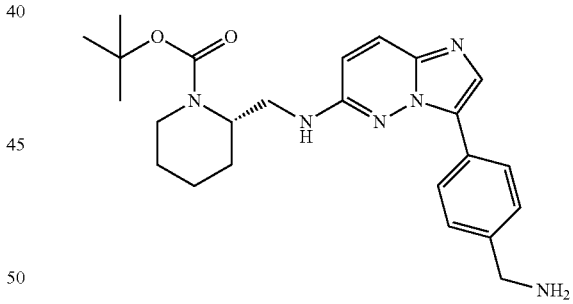

Part A. (S)-tert-butyl 2-(((3-bromoimidazo[1,2-b]pyridazin-6-yl)amino)methyl)piperidine-1-carboxylate

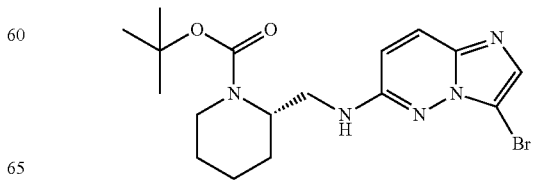

The reaction of 3-bromo-6-fluoroimidazo[1,2-b]pyridazine and (S)-tert-butyl 2-(aminomethyl)piperidine-1-carboxylate under the amine displacement conditions described in example 5.6.42, Part A, gave the aryl amine in 38% yield.

Part B. (S)-tert-butyl 2-(((3-(4-(aminomethyl)phenyl)imidazo[1,2-b]pyridazin-6-yl)amino)methyl)-piperidine-1-carboxylate The (S)-tert-butyl 2-(((3-bromoimidazo[1,2-b]pyridazin-6-yl)amino)methyl)piperidine-1-carboxylate was subjected to the Suzuki coupling reaction described in example 5.6.19, Part B with the respective boronic acids to afford expected products (S)-tert-butyl 2-(((3-(4-(aminomethyl)phenyl)imidazo[1,2-b]pyridazin-6-yl)amino)methyl)piperidine-1-carboxylate. $^1$H NMR (400 MHz, METHANOL-d$_4$) δ ppm 1.14 (br. s., 9H) 1.59-1.73 (m, 5H) 1.78 (br. s., 1H) 3.00 (t, J=12.63 Hz, 1H) 3.50 (dd, J=14.15, 4.55 Hz, 1H) 3.67-3.80 (m, 1H) 4.00 (d, J=12.38 Hz, 1H) 4.19 (s, 2H) 4.87 (br. s., 1H) 6.72 (d, J=9.60 Hz, 1H) 7.57 (m, J=8.34 Hz, 2H) 7.67 (d, J=9.85 Hz, 1H) 7.82 (s, 1H) 8.27 (m, J=8.34 Hz, 2H); LRMS (ESI) m/437.0 [(M+H)$^+$, calcd for C$_{24}$H$_{32}$N$_6$O$_2$ 436.0]

5.6.101. Synthesis of 3-(4-(aminomethyl)phenyl)-N-((2-methyltetrahydrofuran-2-yl)methyl)imidazo[1,2-b]pyridazin-6-amine

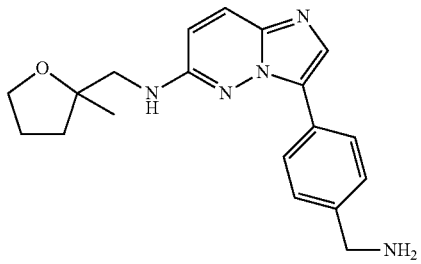 [SMILES: CC1(CNc2ccc3ncc(-c4ccc(CN)cc4)n3n2)CCCO1]

The titled compound was obtained using the approach described in example 5.6.68. $^1$H NMR (400 MHz, METHANOL-d$_4$) δ ppm 8.55 (s, 1H), 8.25 (d, J=7.83 Hz, 2H), 7.80 (s, 1H), 7.66 (d, J=9.60 Hz, 1H), 7.57 (d, J=8.08 Hz, 2H), 6.83 (d, J=9.60 Hz, 1H), 4.17 (s, 2H), 3.91 (t, J=6.19 Hz, 2H), 3.56 (d, J=13.64 Hz, 1H), 3.46 (d, J=13.64 Hz, 1H), 1.97-2.06 (m, 3H), 1.70-1.80 (m, 1H), 1.31 (s, 3H); LRMS (ESI) m/e 338.2 [(M+H)$^+$, calcd for C$_{19}$H$_{24}$N$_5$O 338.4].

5.6.102. Synthesis of 4-(3-Bromo-imidazo[1,2-b]pyridazin-6-yl)-piperazine-1-carboxylic acid isopropyl ester

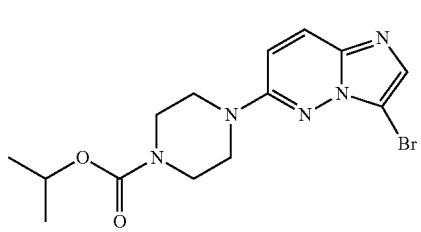

Part A. 4-(3-Bromo-imidazo[1,2-b]pyridazin-6-yl)-piperazine-1-carboxylic acid tert-butyl ester

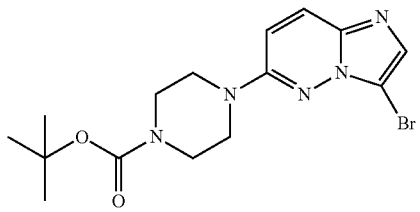 [SMILES: CC(C)(C)OC(=O)N1CCN(c2ccc3ncc(Br)n3n2)CC1]

3-Bromo-6-chloro-imidazo[1,2-b]pyridazine [13526-66-4] (1.1 g, 4.5 mmol) and piperazine [110-85-0] (3.6 g, 41.8 mmol) were ground together in a mortar to an intimate mixture and transferred to a 15 mL round bottomed flask containing a magnetic stir bar. The flask was fitted to a reflux condenser, N$_2$ blanketed, and the reaction pot immersed in an ambient temperature oil bath. While the neat solid mixture stirred, the bath was heated to 120° C. over 0.5 h and held at nominal temperature for a total of 17 h. The bath was removed and the molten reaction allowed to cool and to solidify. The solid mass was dissolved in methanol, transferred to a separatory funnel, and partitioned between brine (pH adjusted to 10 with 3N aqueous sodium hydroxide) and ethyl acetate. The phase separated extract was dried (MgSO$_4$) and evaporated to afford 0.9 g of 3-bromo-6-piperazin-1-yl-imidazo[1,2-b]pyridazine as a light yellow solid which was used without further purification. LRMS (ESI) m/z 282.1/284.1 [(M+H)]$^+$, calc'd for C$_{10}$H$_{12}$BrN$_5$: 282.14.

A solution of 3-bromo-6-piperazin-1-yl-imidazo[1,2-b]pyridazine (4.3 g, 15.3 mmol), di-t-butyl dicarbonate [24424-99-5] (3.7 g, 16.9 mmol), and Hunig's base [7087-68-5] (3.0 mL, 17.2 mmol) in ethyl acetate (160 mL) was stirred at ambient temperature for 17 h then washed with brine, dried (CaSO$_4$), and evaporated to yield 5.5 g of yellow solid which was recrystallized form ethyl acetate/heptane to provide 2.9 g of 4-(3-bromo-imidazo[1,2-b]pyridazin-6-yl)-piperazine-1-carboxylic acid tert-butyl ester as a white powder, 178-180° C. $^1$H NMR (400 MHz, DMSO-d$_6$) δ ppm 1.43 (s, 9H) 3.27-3.31 (m, 3H) 3.45-3.56 (m, 8H) 7.24 (d, J=9.92 Hz, 1H) 7.61 (s, 1H) 7.90 (d, J=9.92 Hz, 1H). $^{13}$C NMR (100 MHz, DMSO-d$_6$) δ ppm 27.88, 45.00, 78.96, 99.17, 110.57, 125.97, 131.45, 136.41, 153.72, 154.90. LRMS (ESI) m/z 382.1/384.1 [(M+H)]$^+$, calc'd for C$_{15}$H$_{20}$BrN$_5$O$_2$: 382.26.

Part B.
3-Bromo-6-piperazin-1-yl-imidazo[1,2-b]pyridazine dihydrochloride

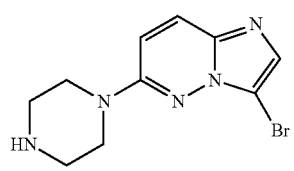

Concentrated hydrochloric acid (6.4 mL) was added to a solution of 4-(3-bromo-imidazo[1,2-b]pyridazin-6-yl)-piperazine-1-carboxylic acid tert-butyl ester 2.9 g, 7.6 mmol) in methanol (150 mL), allowed to stir at ambient temperature overnight, then evaporated to dryness. The resultant yellow solid was dissolved in methanol and the stirred solution diluted with diethyl ether to precipitate 3-bromo-6-piperazin-1-yl-imidazo[1,2-b]pyridazine dihydrochloride as 2.6 g of white powder, mp. 275-276° C. (dec.). $^1$H NMR (400 MHz, DMSO-d$_6$) δ ppm 3.24 (br. s., 4H) 3.82-3.92 (m, 4H) 7.57 (d, J=10.11 Hz, 1H) 8.05 (s, 1H) 8.12 (d, J=10.10 Hz, 1H) 9.70 (br. s., 1H). $^{13}$C NMR (100 MHz, DMSO-d$_6$) δ ppm 41.86, 42.37, 101.30, 114.15, 124.22, 127.20, 134.76, 155.43. LRMS (ESI) m/z 282.1/284.1 [(M+H)]$^+$, calc'd for C$_{10}$H$_{12}$BrN$_5$: 282.14.

Part C. 4-(3-Bromo-imidazo[1,2-b]pyridazin-6-yl)-piperazine-1-carboxylic acid isopropyl ester To a rapidly stirred, ambient temperature, N$_2$ blanketed, solution of 3-bromo-6-piperazin-1-yl-imidazo[1,2-b]pyridazine (0.9 g, 3.1 mmol) and Hunig's base [7087-68-5] (0.8 mL, 4.6 mmol) in ethyl acetate (60 mL) was added a 1.0M solution of isopropyl chloroformate in toluene (3.3 mL). Once complete, the reaction was washed with brine, dried (MgSO$_4$), preloaded onto silica gel, chromatographed (Silica gel, eluted with 100% ethyl acetate) and crystallized from heptane to afford 717.7 mg of white crystalline powder, mp. 123-124° C. $^1$H NMR (400 MHz, DMSO-d$_6$) δ ppm 1.22 (d, J=6.32 Hz, 6H) 3.44-3.54 (m, 4H) 3.67-3.79 (m, 4H) 4.82 (spt, J=6.23 Hz, 1H) 6.77 (d, J=7.83 Hz, 1H) 7.97 (s, 1H) 8.69 (d, J=7.83 Hz, 1H). $^{13}$C NMR (100 MHz, DMSO-d$_6$) δ ppm 21.94, 42.80, 43.87, 68.17, 77.32, 97.66, 136.47, 143.87, 144.40, 154.29, 155.64. LRMS (ESI) m/z 368.0/370.0 [(M+H)]$^+$, calc'd for C$_{14}$H$_{18}$BrN$_5$O$_2$: 368.24.

5.6.103. Synthesis of 4-[3-(3-Methoxy-pyridin-4-yl)-imidazo[1,2-b]pyridazin-6-yl]-piperazine-1-carboxylic acid isopropyl ester

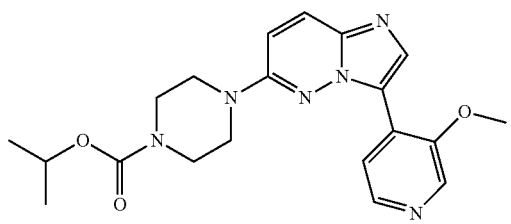 [SMILES: COc1cnccc1-c1cnc2ccc(N3CCN(C(=O)OC(C)C)CC3)nn12]

This compound was prepared using the approach described in example 5.6.111 from 4-(3-bromo-imidazo[1,2-b]pyridazin-6-yl)-piperazine-1-carboxylic acid isopropyl ester (281.1 mg, 0.8 mmol) and 3-methoxypyridine-4-boronic acid hydrate [1072952-50-1] (217.4 mg, 1.2 mmol) to provide 209.4 mg of 4-[3-(3-methoxy-pyridin-4-yl)-imidazo[1,2-b]pyridazin-6-yl]-piperazine-1-carboxylic acid isopropyl ester di-hydrochloride as white powder, mp. 217-218° C. (dec.). $^1$H NMR (400 MHz, DMSO-d$_6$) δ ppm 1.23 (d, J=6.32 Hz, 5H) 2.51 (dt, J=3.73, 1.80 Hz, 3H) 3.54-3.60 (m, 4H) 3.61-3.67 (m, 4H) 4.18 (s, 3H) 4.83 (quin, J=6.25 Hz, 1H) 7.66 (d, J=10.11 Hz, 1H) 8.21 (d, J=9.85 Hz, 1H) 8.64-8.67 (m, 2H) 8.77 (s, 1H) 9.08 (d, J=5.81 Hz, 1H). $^{13}$C NMR (100 MHz, DMSO-d$_6$) δ ppm 21.96, 42.58, 45.26, 57.69, 68.22, 115.12, 119.36, 121.73, 124.86, 126.61, 135.30, 136.82, 152.56, 154.26, 155.31. LRMS (ESI) m/z 397.2 [(M+H)]$^+$, calc'd for C$_{20}$H$_{24}$N$_6$O$_3$: 396.45.

5.6.104. Synthesis of (S)-tert-butyl 2-(((3-ethylimidazo[1,2-b]pyridazin-6-yl)amino)methyl)pyrrolidine-1-carboxylate

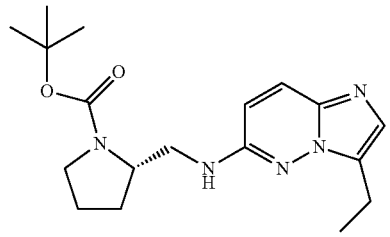 [SMILES: CCc1cnc2ccc(NC[C@@H]3CCCN3C(=O)OC(C)(C)C)nn12]

To a solution of PdCl$_2$dppf (25 mg, 0.03 mmol) and (S)-tert-butyl 2-(((3-bromoimidazo[1,2-b]pyridazin-6-yl)amino)methyl)pyrrolidine-1-carboxylate (100 mg, 0.2 mmol) in dioxane (2 mL) was added diethylzinc (0.24 ml, 1 M in hexane), DiBAL-H (0.008 mL, 1M in toluene) at room temperature. The reaction mixture was heated to 100° C. and stirred for 2 h. Filtered off celite, and concentrated the filtrate, purified by Prep HPLC (neutral) to give (S)-tert-butyl 2-(((3-ethylimidazo[1,2-b]pyridazin-6-yl)amino)methyl)pyrrolidine-1-carboxylate as oil. $^1$H NMR (400 MHz, METHANOL-d$_4$) δ ppm 7.55 (d, J=9.60 Hz, 1H), 7.22 (s, 1H), 6.66 (d, J=9.60 Hz, 1H), 4.18 (br. s., 1H), 3.55 (br. s., 1H), 3.37-3.49 (m, 3H), 2.91 (q, J=7.49 Hz, 2H), 1.87-2.07 (m, 4H), 1.44 (br. s., 9H), 1.36 (t, J=7.45 Hz, 3H); LRMS (ESI) m/e 346.3 [(M+H)]$^+$, calcd for C$_{18}$H$_{28}$N$_6$O$_2$ 346.4.

5.6.105. Synthesis of (S)-2-(Imidazo[1,2-b]pyridazin-6-ylaminomethyl)-pyrrolidine-1-carboxylic acid tert-butyl ester

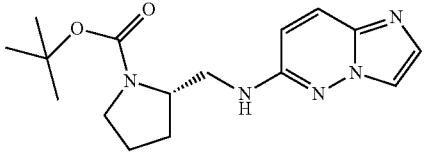 [SMILES: CC(C)(C)OC(=O)N1CCC[C@H]1CNc1ccc2nccn2n1]

1.6 M n-butyl lithium in hexanes (5.8 mL, 9.3 mmol) was rapidly syringed into a stirred, colorless, N$_2$ blanketed solution of (S)-2-[(3-bromo-imidazo[1,2-b]pyridazin-6-ylamino)-methyl]-pyrrolidine-1-carboxylic acid tert-butyl ester (1.8 g, 4.6 mmol) in anhydrous THF (100 mL) held at −73° C. The reaction solution immediately turned brown in color and was allowed to stir for 5 minutes. The generated aryl lithium was quenched by the careful addition of saturated aqueous NH$_4$Cl (2 mL). The reaction solution was partitioned between brine and ethyl acetate, the extract dried (CaSO$_4$), and the crude product flash chromatographed (silica gel, eluted with 10% (v/v methanol/ethyl acetate) and crystallized from ethyl acetate/heptane to provide S)-2-(imidazo[1,2-b]pyridazin-6-ylaminomethyl)-pyrrolidine-1-carboxylic acid tert-butyl ester as 1.5 g of off white powder, mp. 161-162° C. $^1$H NMR (400 MHz, DMSO-d$_6$) δ ppm 1.40 (s, 9H) 1.72-1.95 (m, 4H) 3.10-3.22 (m, 1H) 3.28 (br. s., 2H) 3.41-3.53 (m, 1H)

3.92-4.05 (m, 1H) 6.65 (d, J=9.60 Hz, 1H) 6.96 (br. s., 1H) 7.36 (d, J=0.76 Hz, 1H) 7.66 (d, J=9.60 Hz, 2H). $^{13}$C NMR (100 MHz, DMSO-d$_6$) δ ppm 23.15, 28.13, 43.14, 45.96, 46.36, 55.57, 56.15, 78.30, 112.50, 116.01, 125.26, 130.32, 135.78, 153.75. LRMS (ESI) m/z 318.3 [(M+H)]$^+$, calc'd for $C_{16}H_{23}N_6O_2$: 317.36.

5.6.106. Synthesis of [3-(2,3-Dihydro-benzofuran-7-yl)-imidazo[1,2-b]pyridazin-6-yl]-(4,4,4-trifluoro-butyl)-amine

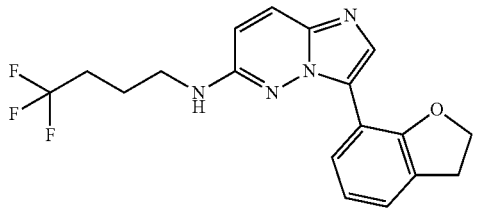 [SMILES: FC(F)(F)CCCNc1ccc2ncc(-c3cccc4c3OCC4)n2n1]

Part A. (3-Bromo-imidazo[1,2-b]pyridazin-6-yl)-(4,4,4-trifluoro-butyl)-amine

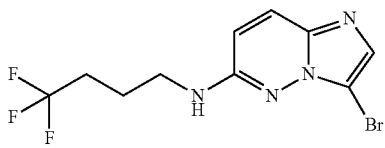 [SMILES: FC(F)(F)CCCNc1ccc2ncc(Br)n2n1]

A stirred solution of 3-bromo-6-fluoro-imidazo[1,2-b]pyridazine (1.7 g, 7.6 mmol), 4,4,4-trifluoro-butylamine hydrochloride [84153-82-2] (1.3 g, 7.6 mmol), and Hunig's base [7087-68-5] (4.0 mL, 23.0 mmol) in 2-propanol (40 mL) was heated to 65° C., under N$_2$ blanket for 3d, cooled, and partitioned between brine (pH adjusted to 10 with 3N aqueous sodium hydroxide) and ethyl acetate. The phase separated extract was dried (MgSO$_4$) and evaporated to provide 2.3 g of yellow solid. LRMS (ESI) m/z 323.1/325.1 [(M+H)]$^+$, calc'd for $C_{10}H_{10}BrF_3N_4$: 323.12.

Part B. [3-(2,3-Dihydro-benzofuran-7-yl)-imidazo[1,2-b]pyridazin-6-yl]-(4,4,4-trifluoro-butyl)-amine To a mixture of (3-bromo-imidazo[1,2-b]pyridazin-6-yl)-(4,4,4-trifluoro-butyl)-amine (442.4 mg, 1.4 mmol), 7-(4,4,5,5-tetramethyl-[1,3,2]dioxaborolan-2-yl)-2,3-dihydro-benzofuran [934586-50-2] (404.4 mg, 1.6 mmol), potassium phosphate tribasic monohydrate [27176-10-9] (632.1 mg, 2.7 mmol), and [1,1'-bis(diphenylphosphino)ferrocene]dichloropalladium(II), complex with dichloromethane [95464-05-4] (116.7 mg, 0.1 mmol) contained in a 50 mL round bottomed flask was added a solution of 30% (v/v) water in 1,2-dimethoxyethane (25 mL) and a magnetic stir bar. The reaction pot was fitted to a reflux condenser, lowered into an ambient temperature oil bath, and the system taken through 10 evacuation/N$_2$ blanket cycles while being rapidly stirred. The rapidly stirred, N$_2$ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried (MgSO$_4$) and evaporated to afford brown solid which was purified by preparative RP-HPLC. Isolated product was dissolved in methanol, diluted with concentrated hydrochloric acid, evaporated to dryness, redissolved in methanol and precipitated by the addition of diethyl ether. Filtration of the precipitate yielded 162.0 mg of [3-(2,3-dihydro-benzofuran-7-yl)-imidazo[1,2-b]pyridazin-6-yl]-(4,4,4-trifluoro-butyl)-amine monohydrochloride salt as a white powder, mp. 299-300° C. $^1$H NMR (400 MHz, DMSO-d$_6$) δ ppm 1.88 (quin, J=7.52 Hz, 2H) 2.32-2.46 (m, 2H) 3.31 (t, J=8.84 Hz, 2H) 3.34-3.41 (m, 2H) 4.69 (t, J=8.72 Hz, 2H) 7.00 (t, J=7.71 Hz, 1H) 7.28 (d, J=9.85 Hz, 1H) 7.36 (dd, J=7.33, 1.01 Hz, 1H) 8.06 (d, J=9.85 Hz, 1H) 8.09 (br. s., 1H) 8.22 (d, J=8.08 Hz, 1H) 8.26 (s, 1H). $^{19}$F NMR (376 MHz, DMSO-d$_6$) δ ppm −64.62. $^{13}$C NMR (100 MHz, DMSO-d$_6$) δ ppm 20.40, 20.43, 29.04, 30.01, 30.29, 30.57, 30.84, 71.69, 108.63, 110.72, 118.75, 120.16, 121.07, 121.12, 123.71, 125.72, 125.99, 126.24, 128.07, 128.99, 132.10, 155.03, 156.77. LRMS (ESI) m/z 363.2 [(M+H)]$^+$, calc'd for $C_{18}H_{17}F_3N_4O$: 362.36.

5.6.107. Synthesis of (S)-2-[(3-Iodo-imidazo[1,2-b]pyridazin-6-ylamino)-methyl]-pyrrolidine-1-carboxylic acid tert-butyl ester

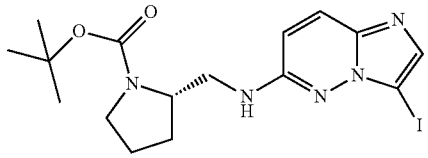 [SMILES: CC(C)(C)OC(=O)N1CCC[C@H]1CNc1ccc2ncc(I)n2n1]

N-iodosuccinimide [516-12-1] (1.1 g, 4.7 mmol) was added to an ambient temperature solution of (S)-3-(imidazo[1,2-b]pyridazin-6-ylaminomethyl)-pyrrolidine-1-carboxylic acid tert-butyl ester (1.4 g, 4.3 mmol) in DMF (43 mL) and allowed to stir under N$_2$ blanket overnight then poured into a stirred aqueous solution of 5% (w/v) sodium meta bisulfite precipitate product and the two phase mixture extracted with ethyl acetate. The extract was dried (CaSO$_4$), evaporated, and recrystallized from chilled ethyl acetate to yield 0.6 g of (S)-2-[(3-iodo-imidazo[1,2-b]pyridazin-6-ylamino)-methyl]-pyrrolidine-1-carboxylic acid tert-butyl ester as a white powder, mp. 138-139° C. $^1$H NMR (400 MHz, DMSO-d$_6$) δ ppm 1.37 (br. s., 8H) 1.79 (dd, J=9.98, 5.18 Hz, 1H) 1.84-1.92 (m, 2H) 1.97 (br. s., 1H) 3.23-3.40 (m, 4H) 3.42-3.53 (m, 1H) 4.01 (br. s., 1H) 6.69 (d, J=9.60 Hz, 1H) 7.09 (t, J=5.94 Hz, 1H) 7.47 (s, 1H) 7.64 (d, J=9.60 Hz, 1H). $^{13}$C NMR (100 MHz, DMSO-d$_6$) δ ppm 22.35, 23.20, 28.11, 28.54, 43.21, 45.99, 46.35, 56.25, 70.08, 78.32, 112.67, 125.09, 136.22, 137.90, 154.42.

5.6.108. Synthesis of 4-(3-Pyridin-4-yl-imidazo[1,2-b]pyridazin-6-yl)-piperazine-1-carboxylic acid isopropyl ester

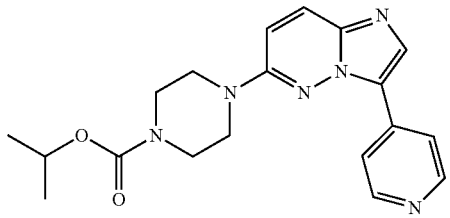 [SMILES: CC(C)OC(=O)N1CCN(c2ccc3ncc(-c4ccncc4)n3n2)CC1]

This compound was prepared using the approach described in example 5.6.111 from 4-(3-bromo-imidazo[1,2-b]pyridazin-6-yl)-piperazine-1-carboxylic acid isopropyl ester (101.1 mg, 0.3 mmol) and pyridine-4-boronic acid [1692-15-5] (39.9 mg, 0.3 mmol) to provide 51.3 mg of 4-(3-pyridin-4-yl-imidazo[1,2-b]pyridazin-6-yl)-piperazine-1-carboxylic acid isopropyl ester di-hydrochloride as yellow powder, mp. 195-196° C. (dec.). $^1$H NMR (400 MHz, DMSO-$d_6$) δ ppm 1.23 (d, J=6.32 Hz, 6H) 2.50 (br. s., 2H) 3.52-3.62 (m, 4H) 3.62-3.70 (m, 3H) 4.79-4.88 (m, 1H) 7.58 (d, J=10.11 Hz, 1H) 8.16 (d, J=10.10 Hz, 1H) 8.73-8.84 (m, 3H) 8.90 (d, J=6.06 Hz, 2H). $^{13}$C NMR (100 MHz, DMSO-$d_6$) δ ppm 21.97, 30.40, 42.61, 45.32, 68.22, 114.29, 120.46, 122.56, 125.88, 135.61, 139.37, 141.63, 143.40, 154.26, 155.42. LRMS (ESI) m/z 367.3 [(M+H)]$^+$, calc'd for $C_{19}H_{22}N_6O_2$: 366.43.

5.6.109. Synthesis of (S)-tert-butyl 2-(((3-(hydroxymethyl)imidazo[1,2-b]pyridazin-6-yl)amino)methyl)pyrrolidine-1-carboxylate

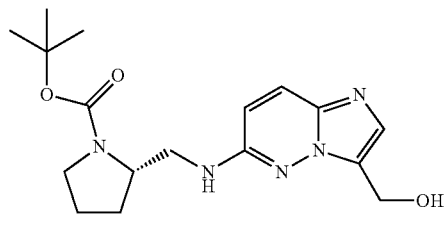 [SMILES: CC(C)(C)OC(=O)N1CCC[C@H]1CNc1ccc2ncc(CO)n2n1]

Part A.
(6-chloroimidazo[1,2-b]pyridazin-3-yl)methanol

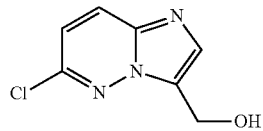 [SMILES: OCc1cnc2ccc(Cl)nn12]

To a solution of 6-chloroimidazo[1,2-b]pyridazine-3-carbaldehyde (0.55 g, 3 mmol) in methanol (20 mL) was added sodium borohydride (0.15 g, 4 mmol) in a small portions at rt. After stirring at rt for 30 min, the reaction was quenched with water, and extracted with DCM to give crude product (0.55 g, 100% yield). 40 mg of crude product was purified by Prep HPLC to give (6-chloroimidazo[1,2-b]pyridazin-3-yl)methanol as a white solid. $^1$H NMR (400 MHz, CHLOROFORM-d) δ ppm 7.95 (d, J=9.35 Hz, 1H), 7.79 (s, 1H), 7.11 (d, J=9.35 Hz, 1H), 5.07 (s, 2H); LRMS (ESI) m/e 184.0 [(M+H)$^+$, calcd for $C_7H_7ClN_3O$ 184.6].

Part B. (S)-tert-butyl 2-(((3-(hydroxymethyl)imidazo[1,2-b]pyridazin-6-yl)amino)methyl)pyrrolidine-1-carboxylate The titled compound was prepared using the approach described in example 5.6.68. $^1$H NMR (400 MHz, METHANOL-$d_4$) δ ppm 7.58 (d, J=9.60 Hz, 1H), 7.40 (s, 1H), 6.70 (d, J=9.60 Hz, 1H), 4.85-4.94 (m, 2H), 4.54 (br. s., 1H), 4.14-4.20 (m, 1H), 3.35-3.74 (m, 5H), 1.99-2.08 (m, 1H), 1.87-1.99 (m, 3H), 1.47 (br. s., 9H); LRMS (ESI) m/e 348.3 [(M+H)$^+$, calcd for $C_{17}H_{26}N_5O_3$ 348.4].

5.6.110. Synthesis of (R)-3-{2-[3-(4-Aminomethyl-phenyl)-imidazo[1,2-b]pyridazin-6-ylamino]-ethyl}-4-isopropyl-oxazolidin-2-one

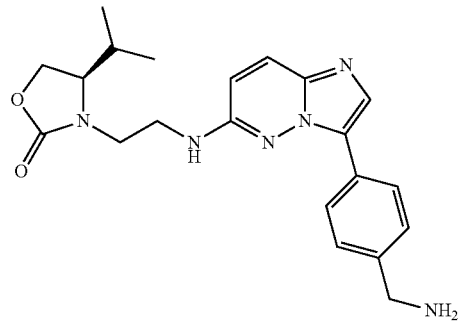 [SMILES: CC(C)[C@@H]1COC(=O)N1CCNc1ccc2ncc(-c3ccc(CN)cc3)n2n1]

Part A. (R)-3-[2-(3-Bromo-imidazo[1,2-b]pyridazin-6-ylamino)-ethyl]-4-isopropyl-oxazolidin-2-one

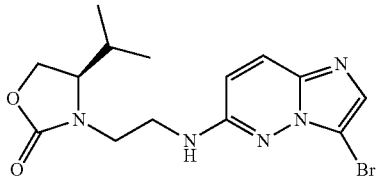 [SMILES: CC(C)[C@@H]1COC(=O)N1CCNc1ccc2ncc(Br)n2n1]

A mixture of (R)-4-isopropyl-oxazolidin-2-one (1.3 g, 10 mmol) and NaH (480 mg, 60% oil dispersion, 12 mmol) in THF (50 ml) was stirred at rt for 2 h. then cooled to 0° C. A solution of bromoacetonitrile (1.4 ml, 20 mmol) in THF (30 ml) was added slowly to the reaction mixture. The resulting mixture was stirred at rt for overnight. The mixture was treated with small amount of water and then the mixture was passed through a silica pad. The filtrate was concentrated and the residue was subjected to a short column to give the crude product. The process was repeated and both crude product were combined and further purified by another short column to give the product (3.3 g).

To a solution of above product (3.3 g, 19 mmol) in THF (40 ml) at 0° C. was added a solution of $BH_3$THF in THF (1 M, 200 ml). The resulting mixture was stirred at 0° C. for 30 min. then at rt for 4 h. The mixture was then cooled to 0° C. again and treated with cold HCl (6 N, 20 ml) to strong acidic pH. The organic solvent was removed under reduced pressure. The residue was treated with NaOH (4 N, ~40 ml) to pH>10, then extracted with EtOAc (5×80 ml) and DCM (5×80 ml). The combined extracts from both solvent were dried ($Na_2SO_4$) and concentrated. EtOAc concentrate afford 1.9 g desired product (not clean) and 650 mg of cleaner product was obtained from the DCM concentrate.

A mixture of above product (1.9 g, 11 mmol), 3-bromo-6-fluoro-imidazo[1,2-b]pyridazine (650 mg, 3 mmol), and triethylamine (1.5 ml) in isopropyl alcohol (8 ml) was heated in a microwave at 140° C. for 20 min. twice. The reaction mixture was concentrated and the residue was subjected to ISCO (40 g column), to gave the titled compound (345 mg). LRMS (ESI) m/z 368 and 370.2 [(M+H)]⁺, calc'd for $C_{14}H_{18}BrN_5O_2$: 368.24.

Part B. (R)-3-{2-[3-(4-Aminomethyl-phenyl)-imidazo[1,2-b]pyridazin-6-ylamino]-ethyl}-4-isopropyl-oxazolidin-2-one A mixture of (R)-3-[2-(3-bromo-imidazo[1,2-b]pyridazin-6-ylamino)-ethyl]-4-isopropyl-oxazolidin-2-one (95 mg, 0.26 mmol), (4-aminomethylphenyl)boronic acid hydrochloride (63.7 mg, 0.34 mmol), $K_2CO_3$ (108 mg, 0.78 mmol) and dichlorobis(triphenylphosphine)palladium(II) (9.1 mg, 0.013 mmol) in MeCN/water (3.2 ml/0.8 ml) was heated in a microwave at 150° C. for 15 min. The reaction mixture was diluted with MeCN and filtered. The filtrate was subjected to preparative HPLC to give the titled compound as HCOOH salt (86.3 mg). $^1$H NMR (400 MHz, METHANOL-$d_4$) ppm 0.84 (dd, J=6.95, 0.88 Hz, 6H) 2.09 (td, J=6.95, 3.54 Hz, 1H) 3.26-3.31 (m, 1H) 3.59-3.71 (m, 2H) 3.85 (dt, J=13.96, 6.79 Hz, 1H) 3.95 (ddd, J=8.65, 5.24, 3.54 Hz, 1H) 4.11-4.19 (m, 4H) 6.74 (d, J=9.60 Hz, 1H) 7.58 (d, J=8.34 Hz, 2H) 7.68 (d, J=9.85 Hz, 1H) 7.81 (s, 1H) 8.21-8.26 (m, 2H) 8.52 (s, 1H). LRMS (ESI) m/z 395.3 [(M+H)]⁺, calc'd for $C_{21}H_{26}N_6O_2$: 394.48.

5.6.111. Synthesis of 4-(3-Phenyl-imidazo[1,2-b]pyridazin-6-yl)-piperazine-1-carboxylic acid isopropyl ester

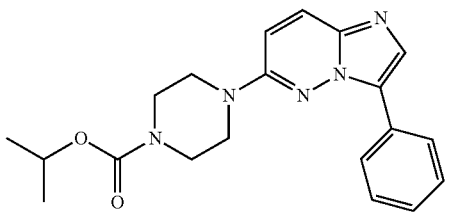 [SMILES: CC(C)OC(=O)N1CCN(c2ccc3ncc(-c4ccccc4)n3n2)CC1]

To a mixture of 4-(3-bromo-imidazo[1,2-b]pyridazin-6-yl)-piperazine-1-carboxylic acid isopropyl ester (330.0 mg, 0.9 mmol), phenyl boronic acid [98-80-8] (131.4 mg, 1.1 mmol), potassium phosphate tribasic monohydrate [27176-10-9] (416.4 mg, 1.8 mmol), and [1,1'-bis(diphenylphosphino)ferrocene]dichloropalladium(II), complex with dichloromethane [95464-05-4] (77.1 mg, 0.1 mmol) contained in a 50 mL round bottomed flask was added a solution of 30% (v/v) water in 1,2-dimethoxyethane (25 mL) and a magnetic stir bar. The reaction pot was fitted to a reflux condenser, lowered into an ambient temperature oil bath, and the system taken through 10 evacuation/$N_2$ blanket cycles while being rapidly stirred. The rapidly stirred, $N_2$ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried ($MgSO_4$) and evaporated to afford an orange oil which was purified by preparative RP-HPLC. Isolated product was dissolved in methanol, diluted with concentrated hydrochloric acid, evaporated to dryness, redissolved in methanol and precipitated by the addition of diethyl ether. Filtration of the precipitate yielded 154.6 mg of 4-(3-phenyl-imidazo[1,2-b]pyridazin-6-yl)-piperazine-1-carboxylic acid isopropyl ester monohydrochloride salt as a white crystalline powder, mp. 232-233° C. (dec). $^1$H NMR (400 MHz, DMSO-$d_6$) δ ppm 1.22 (d, J=6.32 Hz, 6H) 3.50-3.60 (m, 4H) 3.60-3.70 (m, 4H) 4.77-4.87 (m, 1H) 7.50 (d, J=7.58 Hz, 1H) 7.55-7.71 (m, 2H) 7.77 (d, J=10.11 Hz, 1H) 8.05-8.17 (m, 2H) 8.25 (d, J=10.11 Hz, 1H) 8.54 (s, 1H). $^{13}$C NMR (100 MHz, DMSO-$d_6$) δ ppm 21.95, 42.49, 44.98, 68.23, 116.22, 120.94, 122.22, 126.28, 127.18, 128.09, 128.83, 129.05, 132.74, 154.26, 155.80. LRMS (ESI) m/z 366.2 [(M+H)]⁺, calc'd for $C_{20}H_{23}N_5O_2$: 395.44.

5.6.112. Synthesis of 4-[3-(3-Methoxy-pyridin-4-yl)-imidazo[1,2-b]pyridazin-6-yl]-piperazine-1-carboxylic acid tert-butyl ester

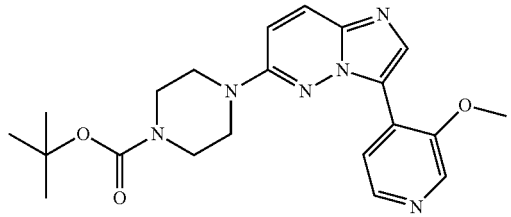 [SMILES: COc1cnccc1-c1cnc2ccc(N3CCN(C(=O)OC(C)(C)C)CC3)nn12]

To a mixture of 4-(3-bromo-imidazo[1,2-b]pyridazin-6-yl)-piperazine-1-carboxylic acid tert-butyl ester (524.4 mg, 1.4 mmol), 3-methoxypyridine-4-boronic acid hydrate [1072952-50-1] (253.1 mg, 1.7 mmol), potassium phosphate tribasic monohydrate [27176-10-9] (632.2 mg, 2.8 mmol), and [1,1'-bis(diphenylphosphino)ferrocene]dichloropalladium(II), complex with dichloromethane [95464-05-4] (117.6 mg, 0.1 mmol) contained in a 50 mL round bottomed flask was added a solution of 30% (v/v) water in 1,2-dimethoxyethane (25 mL) and a magnetic stir bar. The reaction pot was fitted to a reflux condenser, lowered into an ambient temperature oil bath, and the system taken through 10 evacuation/$N_2$ blanket cycles while being rapidly stirred. The rapidly stirred, $N_2$ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried ($CaSO_4$) and evaporated to afford a brown oil which was purified by preparative RP-HPLC to obtain a white powder, mp. 205-206° C. (dec.). $^1$H NMR (400 MHz, DMSO-$d_6$) δ ppm 1.43 (s, 9H) 3.46-3.55 (m, 8H) 4.02 (s, 3H) 7.30 (d, J=10.10 Hz, 1H) 8.00 (d, J=9.85 Hz, 1H) 8.13 (s, 1H) 8.35 (d, J=5.05 Hz, 1H) 8.41 (d, J=5.05 Hz, 1H) 8.51 (s, 1H). $^{13}$C NMR (100 MHz, DMSO-$d_6$) δ ppm 28.04, 45.53, 56.33, 79.10, 111.13, 120.39, 120.75, 124.25, 126.24, 134.48, 135.69, 137.20, 142.26, 151.08, 153.85, 154.60. LRMS (ESI) m/z 411.3 [(M+H)]⁺, calc'd for $C_{21}H_{26}N_6O_3$: 410.48.

5.6.113. Synthesis of 1-(4-(3-Bromoimidazo[1,2-b]pyridazin-6-yl)piperazin-1-yl)-3,3-dimethylbutan-1-one

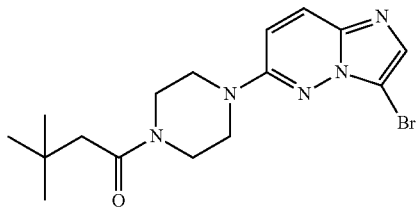

To a rapidly stirred, ambient temperature, N₂ blanketed, suspension of 3-bromo-6-piperazin-1-yl-imidazo[1,2-b]pyridazine (dihydrochloride (400.5 mg, 1.1 mmol) and 3,3-dimethylbutanoyl chloride [7065-46-5] (0.2 mL, 1.4 mmol) in ethyl acetate (50 mL) was added Hunig's base [7087-68-5] (0.8 mL, 4.6 mmol) and the reaction allowed to stir over night. Once complete, the reaction was washed with brine, dried (MgSO₄), and crystallized from chilled ethyl acetate/heptane to afford 392.5 mg of white crystalline powder, mp. 170-171° C. $^1$H NMR (400 MHz, DMSO-d₆) δ ppm 1.02 (s, 9H) 2.30 (s, 2H) 3.57 (d, J=7.06 Hz, 4H) 3.63-3.72 (m, 4H) 7.26 (d, J=9.92 Hz, 1H) 7.63 (s, 1H) 7.91 (d, J=9.92 Hz, 1H). $^{13}$C NMR (100 MHz, DMSO-d₆) δ ppm 29.57, 30.81, 40.12, 43.50, 45.26, 45.34, 99.17, 110.56, 125.96, 131.44, 136.42, 154.89, 169.49. LRMS (ESI) m/z 380.1/382.1 [(M+H)]⁺, calc'd for $C_{16}H_{22}BrN_5O$: 380.28.

5.6.114. Synthesis of 1-(4-(3-(3-Methoxypyridin-4-yl)imidazo[1,2-b]pyridazin-6-yl)piperazin-1-yl)-3,3-dimethylbutan-1-one

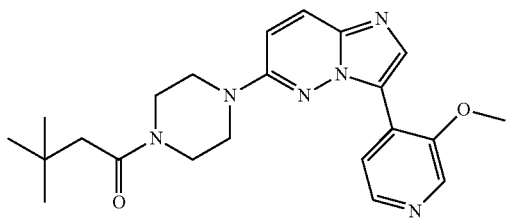

To a mixture of 1-(4-(3-bromoimidazo[1,2-b]pyridazin-6-yl)piperazin-1-yl)-3,3-dimethylbutan-1-one (168.9 mg, 0.4 mmol), 3-methoxypyridine-4-boronic acid hydrate [1072952-50-1] (82.3 mg, 0.5 mmol), potassium phosphate tribasic monohydrate [27176-10-9] (210.4 mg, 0.9 mmol), and [1,1'-bis(diphenylphosphino)ferrocene]dichloropalladium(II), complex with dichloromethane [95464-05-4] (33.8 mg, 0.1 mmol) contained in a 25 mL round bottomed flask was added a solution of 30% (v/v) water in 1,2-dimethoxyethane (13 mL) and a magnetic stir bar. The reaction pot was fitted to a reflux condenser, lowered into an ambient temperature oil bath, and the system taken through 10 evacuation/N₂ blanket cycles while being rapidly stirred. The rapidly stirred, N₂ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried (MgSO₄) and evaporated to afford a brown oil which was purified by preparative RP-HPLC. Isolated product was dissolved in methanol, diluted with concentrated hydrochloric acid, evaporated to dryness, redissolved in methanol and precipitated by the addition of diethyl ether. Filtration of the precipitate yielded 59.7 mg of 1-(4-(3-(3-methoxypyridin-4-yl)imidazo[1,2-b]pyridazin-6-yl)piperazin-1-yl)-3,3-dimethylbutan-1-one di-hydrochloride salt as a light yellow powder, mp. 211-212° C. (dec). $^1$H NMR (400 MHz, DMSO-d₆) δ ppm 1.00-1.04 (m, 9H) 2.26-2.35 (m, 2H) 3.57-3.66 (m, 4H) 3.70 (br. s., 4H) 4.14-4.21 (m, 3H) 7.68 (d, J=9.85 Hz, 1H) 8.20 (dd, J=10.10, 2.02 Hz, 1H) 8.65 (d, J=2.53 Hz, 2H) 8.75-8.80 (m, 1H) 9.04-9.10 (m, 1H). $^{13}$C NMR (100 MHz, DMSO-d₆) δ ppm 29.70, 30.94, 43.69, 45.00, 45.43, 45.70, 57.70, 109.35, 115.22, 119.35, 121.79, 124.70, 126.64, 130.45, 134.42, 135.21, 136.68, 152.58, 155.32, 169.63. LRMS (ESI) m/z 409.2 [(M+H)]⁺, calc'd for $C_{22}H_{28}N_6O_2$: 408.50.

5.6.115. Synthesis of 4-[3-(2-Methoxy-phenyl)-imidazo[1,2-b]pyridazin-6-yl]-piperazine-1-carboxylic acid isopropyl ester

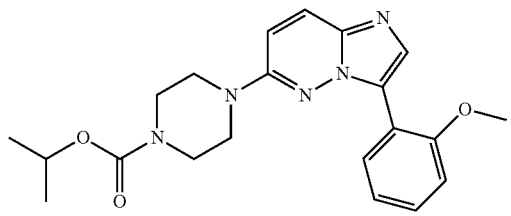 [SMILES: COc1ccccc1-c1cnc2ccc(N3CCN(C(=O)OC(C)C)CC3)nn12]

Prepared similarly to example 5.6.111 from 4-(3-bromo-imidazo[1,2-b]pyridazin-6-yl)-piperazine-1-carboxylic acid isopropyl ester (310.0 mg, 0.8 mmol) and 2-methoxyphenylboronic acid [5720-06-9] (153.6 mg, 1.0 mmol) to provide 172.7 mg of 4-[3-(2-methoxy-phenyl)-imidazo[1,2-b]pyridazin-6-yl]-piperazine-1-carboxylic acid isopropyl ester monohydrochloride as white powder, mp. 243-244° C. (dec.). $^1$H NMR (400 MHz, DMSO-d₆) δ ppm 1.09-1.24 (m, 7H) 3.54-3.61 (m, 5H) 3.82-3.87 (m, 4H) 4.76-4.84 (m, 1H) 7.15 (t, J=7.33 Hz, 1H) 7.24 (d, J=8.08 Hz, 1H) 7.49-7.56 (m, 1H) 7.78 (d, J=10.11 Hz, 1H) 7.90 (d, J=7.58 Hz, 1H) 8.22-8.31 (m, 2H). $^{13}$C NMR (100 MHz, DMSO-d₆) δ ppm 21.92, 42.46, 44.82, 55.70, 68.21, 111.70, 114.19, 116.39, 120.27, 121.81, 122.20, 125.03, 130.44, 131.14, 131.75, 154.24, 155.62, 156.93. LRMS (ESI) m/z 396.2 [(M+H)]⁺, calc'd for $C_{21}H_{25}N_5O_3$: 395.47.

5.6.116. Synthesis of (S)-tert-butyl 2-(((3-(prop-1-en-1-yl)imidazo[1,2-b]pyridazin-6-yl)amino)methyl)piperidine-1-carboxylate

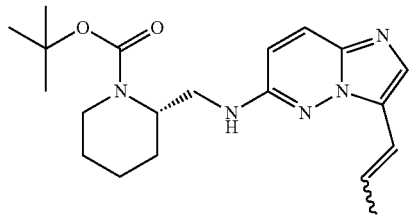

The Suzuki coupling following the procedure described in example 5.6.19 afforded a mixture of E and Z isomers. $^1$H NMR (400 MHz, CHLOROFORM-d) δ ppm 1.35 (br. s., 6H) 1.42 (br. s., 3H) 1.61-1.74 (m, 3H) 1.78 (br. s., 3H) 1.98-2.08 (m, 3H) 2.40 (br. s., 1H) 3.11 (t, J=12.76 Hz, 1H) 3.27-3.40 (m, 1H) 4.13 (d, J=13.89 Hz, 1H) 4.50 (br. s., 1H) 5.87-6.00 (m, 1H) 6.75-6.94 (m, 2H) 7.59-7.72 (m, 2H); LRMS (ESI) m/372.0 [(M+H)]⁺, calcd for $C_{20}H_{29}N_5O_2$ 371.0]

5.6.117. Synthesis of (S)-tert-butyl 2-(((3-propylimidazo[1,2-b]pyridazin-6-yl)amino)methyl)piperidine-1-carboxylate

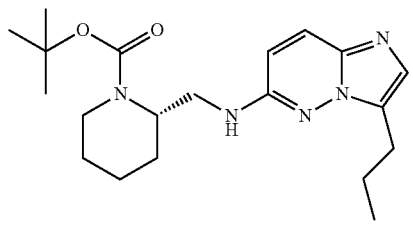 [SMILES: CCCc1cnc2ccc(NC[C@@H]3CCCCN3C(=O)OC(C)(C)C)nn12]

The reduction of the double bond was carried out by vigorous stirring of 0.135 mmol in 25 mL of MeOH with 0.2 equivalent of Palladium on carbon (10% Pd/C) over hydrogen under atmospheric pressure for 8 hr. It was then filtered, concentrated and purified on the PREP HPLC to obtain the desired product in 58% yield. $^1$H NMR (400 MHz, CHLOROFORM-d) δ ppm 1.04 (m, 3H) 1.28-1.49 (m, 9H) 1.63 (d, J=12.38 Hz, 1H) 1.67-1.91 (m, 7H) 2.82-2.95 (m, 4H) 3.35 (br. s., 1H) 4.01 (d, J=11.87 Hz, 1H) 4.62 (d, J=7.33 Hz, 1H) 6.40 (dd, J=9.60, 2.27 Hz, 1H) 7.28 (d, J=2.78 Hz, 1H) 7.70 (dd, J=9.47, 2.15 Hz, 1H); LRMS (ESI) m/374.0 [(M+H)$^+$, calcd for $C_{20}H_{31}N_5O_2$ 373.0].

5.6.118. Synthesis of (S)-2-[3-(2-Methoxy-phenyl)-imidazo[1,2-b]pyridazin-6-yl]-hexahydro-pyrrolo[1,2-c]imidazol-3-one

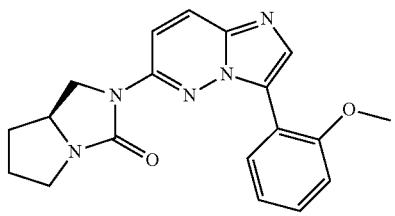 [SMILES: COc1ccccc1-c1cnc2ccc(N3C[C@@H]4CCCN4C3=O)nn12]

Part A. (S)-3-bromo-N-(pyrolidin-2-ylmethyl)imidazo[1,2-b]pyridazin-6-amine

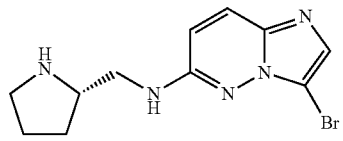 [SMILES: Brc1cnc2ccc(NC[C@@H]3CCCN3)nn12]

To a solution of (S)-tert-butyl 2-(((3-bromoimidazo[1,2-b]pyridazin-6-yl)amino)methyl)pyrrolidine-1-carboxylate (13.4 g, 33.8 mmol) in MeOH (100 mL) was cooled to 0° C. and added acetyl chloride (24 mL, 338 mL) dropwise. The reaction was warmed to rt and stirred for overnight, and concentrated to give (S)-3-bromo-N-(pyrrolidin-2-ylmethyl)imidazo[1,2-b]pyridazin-6-amine as HCl salt (11 g, 100% yield). LRMS (ESI) m/e 298.0 [(M+H)$^+$, calcd for $C_{11}H_{15}BrN_5$ 298.2].

Part B. (S)-2-[(3-Bromo-imidazo[1,2-b]pyridazin-6-ylamino)-methyl]-pyrrolidine-1-carboxylic acid vinyl ester

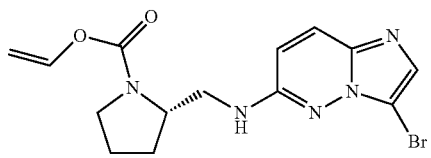 [SMILES: C=COC(=O)N1CCC[C@H]1CNc1ccc2ncc(Br)n2n1]

To a solution of (S)-2-[(3-bromo-imidazo[1,2-b]pyridazin-6-ylamino)-methyl]-pyrrolidine-1-carboxylic acid tert-butyl ester (450 mg, 1.14 mmol) in DCM (10 ml) was added TFA (4 ml). The resulting mixture was stand for 0.5 h. The mixture was concentrated and the residue was dried under vacuum for overnight.

The product from above was dissolved in DCM (10 ml) and DIEA (993 ul, 5.7 mmol) was added. The mixture was cooled to 0° C. and vinyl chloroformate (145 ul, 1.17 mmol) was added dropwise. The resulting mixture was stirred at 0° C. for 2 h, then at rt for overnight. The mixture was concentrated and the residue was subjected to ISCO (40 g column) to give the titled compound (251 mg). LRMS (ESI) m/z 366.1 and 368.1 [(M+H)]$^+$, calc'd for $C_{14}H_{16}BrN_5O_2$: 366.22.

Part C. (S)-2-[3-(2-Methoxy-phenyl)-imidazo[1,2-b]pyridazin-6-yl]-hexahydro-pyrrolo[1,2-c]imidazol-3-one A mixture of (S)-2-[(3-bromo-imidazo[1,2-b]pyridazin-6-ylamino)-methyl]-pyrrolidine-1-carboxylic acid vinyl ester (125 mg, 0.34 mmol), (2-methoxyphenyl)boronic acid (67.2 mg, 0.44 mmol), $K_2CO_3$ (141 mg, 1.02 mmol) and dichlorobis(triphenylphosphine)palladium(II) (12 mg, 0.017 mmol) in MeCN/water (3.2 ml/0.8 ml) was heated in a microwave at 150° C. for 15 min. The reaction was repeated at 140° C. After removal of the water the reaction mixtures was combined and diluted with MeCN and filtered. The filtrate was subjected to preparative HPLC to give the titled compound (S)-2-[3-(2-Methoxy-phenyl)-imidazo[1,2-b]pyridazin-6-yl]-hexahydro-pyrrolo[1,2-c]imidazol-3-one (76.5 mg). $^1$H NMR (400 MHz, CHLOROFORM-d) δ ppm 1.39-1.51 (m, 1H) 1.89-2.02 (m, 1H) 2.05-2.18 (m, 2H) 3.18-3.26 (m, 1H) 3.72-3.96 (m, 6H) 4.09-4.16 (m, 1H) 7.04-7.13 (m, 2H) 7.35-7.42 (m, 1H) 7.90-7.96 (m, 1H) 8.03-8.10 (m, 2H) 8.40 (dd, J=9.85, 2.78 Hz, 1H). LRMS (ESI) m/z 350.2 [(M+H)]$^+$, calc'd for $C_{19}H_{19}N_5O_2$: 349.4.

5.6.119. Synthesis of 3-(4-(aminomethyl)phenyl)-N-((1-(2,2,2-trifluoroethyl)pyrrolidin-2-yl)methyl)imidazo[1,2-b]pyridazin-6-amine

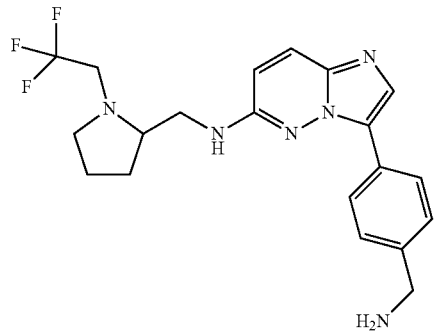 [SMILES: NCc1ccc(-c2cnc3ccc(NCC4CCCN4CC(F)(F)F)nn23)cc1]

The titled compound was obtained using the approach described in example 5.6.68. $^1$H NMR (400 MHz, METHANOL-$d_4$) δ ppm 8.47 (s, 1H), 8.15-8.19 (m, 2H), 7.73 (s, 1H), 7.59 (m, J=9.70 Hz, 1H), 7.49 (d, J=8.60 Hz, 2H), 6.70-6.73 (m, 1H), 4.09 (s, 2H), 3.55 (dd, J=13.45, 3.97 Hz, 1H), 3.35-3.44 (m, 1H), 3.14-3.24 (m, 2H), 2.96-3.10 (m, 2H), 2.46-2.53 (m, 1H), 1.91-2.00 (m, 1H), 1.74-1.85 (m, 2H), 1.62-1.70 (m, 1H); LRMS (ESI) m/e 405.2 [(M+H)$^+$, calcd for $C_{20}H_{24}F_3N_6$ 405.4].

5.6.120. Synthesis of 4-(3-Phenyl-imidazo[1,2-b]pyridazin-6-yl)-piperazine-1-carboxylic acid tert-butyl ester

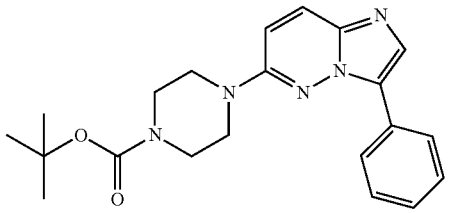 [SMILES: CC(C)(C)OC(=O)N1CCN(c2ccc3ncc(-c4ccccc4)n3n2)CC1]

Part A. 4-Imidazo[1,2-b]pyridazin-6-yl-piperazine-1-carboxylic acid tert-butyl ester

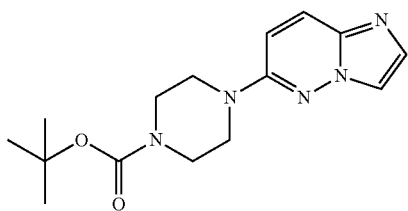 [SMILES: CC(C)(C)OC(=O)N1CCN(c2ccc3nccn3n2)CC1]

An intimate mixture of 6-chloro-imidazo[1,2-b]pyridazine [6775-88-6] (4.1 g, 26.5 mmol and piperazine [110-85-0] (11.4 g, 132.8 mmol) was heated to 120° C. and stirred as a melt under N₂ blanket for 2 h. The cooled reaction was partitioned between water and ethyl acetate, the extract dried (MgSO₄), and evaporated to yield 5.6 g of 6-piperazin-1-yl-imidazo[1,2-b]pyridazine which, without purification, was suspended in ethyl acetate (250 mL). To this stirred mixture was added Hunig's base [7087-68-5] (9.6 mL, 55.1 mmol) and di-tert-butyl pyrocarbonate [24424-99-5] (7.2 g, 33.2 mmol). The N₂ blanketed mixture was stirred overnight at ambient temperature then partitioned between brine and ethyl acetate. The phase separated extract was dried (CaSO₄), evaporated, and crystallized from ethyl acetate/heptane to provide a white crystalline powder, mp. 122-123° C. $^1$H NMR (400 MHz, DMSO-d₆) δ ppm 1.43 (s, 9H) 3.46 (s, 8H) 7.16 (d, J=10.11 Hz, 1H) 7.50 (s, 1H) 7.81-7.94 (m, 2H). $^{13}$C NMR (100 MHz, DMSO-d₆) δ ppm 28.03, 42.66, 45.42, 79.07, 110.58, 116.43, 125.91, 131.62, 135.77, 153.88, 154.71. LRMS (ESI) m/z 304.2 [(M+H)]⁺, calc'd for C₁₅H₂₁N₅O₂: 303.37.

Part B. 4-(3-Iodo-imidazo[1,2-b]pyridazin-6-yl)-piperazine-1-carboxylic acid tert-butyl ester

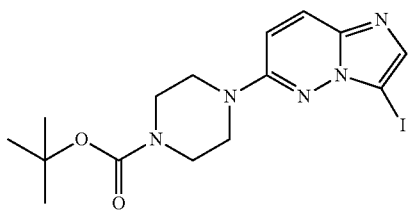 [SMILES: CC(C)(C)OC(=O)N1CCN(c2ccc3ncc(I)n3n2)CC1]

A solution of 4-imidazo[1,2-b]pyridazin-6-yl-piperazine-1-carboxylic acid tert-butyl ester (3.6 g, 11.8 mmol) and N-iodosuccinimide [516-12-1] (3.1 g, 13.1 mmol) in DMF (120 mL) was stirred under N₂ blanket at ambient temperature for 2 h then partitioned between 5% (w/v) aqueous sodium metabisulfite and ethyl acetate. The organic phase was washed with brine, dried (CaSO₄), evaporated, and crystallized from ethyl acetate/heptane to provide a white crystalline powder, mp. 203-204° C. (dec.). $^1$H NMR (400 MHz, DMSO-d₆) δ ppm 1.43 (s, 9H) 3.45-3.51 (m, 4H) 3.51-3.58 (m, 4H) 7.19 (d, J=9.92 Hz, 1H) 7.61 (s, 1H) 7.85 (d, J=9.92 Hz, 1H). $^{13}$C NMR (100 MHz, DMSO-d₆) δ ppm 27.89, 45.06, 70.52, 78.95, 110.55, 125.66, 137.28, 137.71, 153.73, 154.88. LRMS (ESI) m/z 430.0 (M+H)]⁺, calc'd for C₁₅H₂₀IN₅O₂: 429.26.

Part C. 4-(3-Phenyl-imidazo[1,2-b]pyridazin-6-yl)-piperazine-1-carboxylic acid tert-butyl ester 4-(3-Phenyl-imidazo[1,2-b]pyridazin-6-yl)-piperazine-1-carboxylic acid tert-butyl ester was prepared using the approach described in example 5.6.112 from 4-(3-iodo-imidazo[1,2-b]pyridazin-6-yl)-piperazine-1-carboxylic acid tert-butyl ester (513.4 mg, 1.2 mmol) and phenyl boronic acid [98-80-6] (178.3 mg, 1.5 mmol) to obtain 220.2 mg of white powder, mp. 101-103° C. (dec.). $^1$H NMR (400 MHz, DMSO-d₆) δ ppm 1.44 (s, 9H) 3.52 (br. s., 8H) 7.22 (d, J=9.85 Hz, 1H) 7.31-7.37 (m, 1H) 7.46-7.54 (m, 2H) 7.95 (d, J=10.11 Hz, 1H) 8.00 (s, 1H) 8.11-8.18 (m, 2H). $^{13}$C NMR (100 MHz, DMSO-d₆) δ ppm 28.03, 42.73, 45.56, 79.08, 110.13, 125.75, 126.24, 126.93, 127.14, 128.61, 129.03, 131.07, 137.15, 153.85, 154.63. LRMS (ESI) m/z 411.3 [(M+H)]⁺, calc'd for C₂₁H₂₅N₅O₂: 379.47.

5.6.121. Synthesis of 4-[3-(3-Methoxy-pyridin-4-yl)-imidazo[1,2-b]pyridazin-6-yl]-[1,4]diazepane-1-carboxylic acid tert-butyl ester

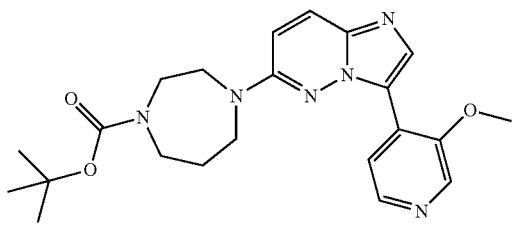 [SMILES: COc1cnccc1-c1cnc2ccc(N3CCCN(C(=O)OC(C)(C)C)CC3)nn12]

Part A. tert-Butyl 4-(3-bromoimidazo[1,2-b]pyridazin-6-yl)-1,4-diazepane-1-carboxylate

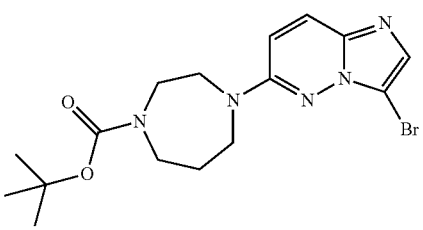 [SMILES: CC(C)(C)OC(=O)N1CCCN(c2ccc3ncc(Br)n3n2)CC1]

A stirred solution of 3-bromo-6-fluoroimidazo[1,2-b]pyridazine (1.6 g, 7.6 mmol), tert-butyl 1,4-diazepane-1-carboxylate [112275-50-0] (4.4 mL, 22.6 mmol), and Hunig's base [7087-68-5] (5.3 mL, 30.4 mmol) in 2-propanol (25 mL) was heated to 65° C. for 3d then partitioned between brine and ethyl acetate. The extract was dried (CaSO$_4$) and evaporated to provide 5.9 g of clear orange liquid which was flash chromatographed (silica gel eluted with 10% (v/v) methanol/ethyl acetate) and crystallized from ethyl acetate/heptane to afford 2.0 g of white powder, mp. 101-102° C. $^1$H NMR (400 MHz, DMSO-d$_6$) δ ppm (rotomers present) 1.03 (s, 5H) 1.17 (s, 4H) 1.73 (br. s., 1H) 1.85 (br. s., 1H) 2.43-2.47 (m, 1H) 3.20-3.29 (m, 3H) 3.49 (d, J=5.51 Hz, 1H) 3.55-3.66 (m, 3H) 3.70-3.79 (m, 2H) 7.05 (d, J=9.92 Hz, 1H) 7.49 (d, J=7.28 Hz, 1H) 7.78 (d, J=9.70 Hz, 1H). $^{13}$C NMR (100 MHz, DMSO-d$_6$) δ ppm (rotomers present) 24.50, 24.83, 27.45, 27.61, 44.10, 44.78, 44.83, 45.33, 47.58, 47.74, 48.01, 48.09, 78.11, 78.27, 98.80, 109.23, 109.61, 125.65, 125.77, 130.81, 130.89, 136.07, 153.01, 153.18, 153.90, 154.19. LRMS (ESI) m/z 396.1/398.1 [(M+H)]$^+$, calc'd for C$_{16}$H$_{22}$BrN$_5$O$_2$: 396.29.

Part B. 4-[3-(3-Methoxy-pyridin-4-yl)-imidazo[1,2-b]pyridazin-6-yl]-[1,4]diazepane-1-carboxylic acid tert-butyl ester To a mixture of tert-butyl 4-(3-bromoimidazo[1,2-b]pyridazin-6-yl)-1,4-diazepane-1-carboxylate (329.9 mg, 0.8 mmol), (3-methoxy pyridin-4-yl)boronic acid monohydrate [1072952-50-1] (153.6 mg, 1.0 mmol), potassium phosphate tribasic monohydrate [27176-10-9] (384.1 mg, 1.7 mmol), and [1,1'-bis(diphenylphosphino)ferrocene]dichloropalladium(II), complex with dichloromethane [95464-05-4] (69.2 mg, 0.1 mmol) contained in a 50 mL round bottomed flask was added a solution of 30% (v/v) water in 1,2-dimethoxyethane (25 mL) and a magnetic stir bar. The reaction pot was fitted to a reflux condenser, lowered into an ambient temperature oil bath, and the system taken through 10 evacuation/N$_2$ blanket cycles while being rapidly stirred. The rapidly stirred, N$_2$ blanketed, reaction was heated to an oil bath temperature of 85° C. for 6 h then cooled and partitioned between brine (pH adjusted to 10 with 3N aqueous sodium hydroxide) and ethyl acetate. The phase separated extract was dried (MgSO$_4$) and evaporated to afford a brown solid which was purified by preparative RP-HPLC to provide 4-[3-(3-methoxy-pyridin-4-yl)-imidazo[1,2-b]pyridazin-6-yl]-[1,4]diazepane-1-carboxylic acid tert-butyl ester as 79.5 mg of off white powder, mp. 115-116° C. $^1$H NMR (400 MHz, DMSO-d$_6$) δ ppm (rotomers present) 1.01 (s, 4H) 1.20 (s, 4H) 1.91 (s, 2H) 2.51 (dt, J=3.60, 1.86 Hz, 2H) 3.27-3.35 (m, 4H) 3.57 (br. s., 1H) 3.64 (s, 1H) 3.70 (br. s., 2H) 3.81 (d, J=16.67 Hz, 2H) 4.02 (s, 3H) 7.19 (d, J=9.85 Hz, 1H) 7.93 (s, 1H) 8.11 (d, J=8.59 Hz, 1H) 8.32 (d, J=5.05 Hz, 1H) 8.49-8.54 (m, 2H). $^{13}$C NMR (100 MHz, DMSO-d$_6$) δ ppm (rotomers present) 13.89, 22.03, 24.66, 24.75, 27.49, 27.74, 31.20, 44.27, 44.96, 45.60, 47.99, 48.26, 48.39, 56.31, 78.25, 78.41, 109.66, 109.87, 119.88, 120.03, 120.27, 124.50, 126.00, 126.08, 134.46, 135.39, 135.52, 136.92, 141.96, 150.98, 152.56, 152.65, 154.01, 154.34. LRMS (ESI) m/z 425.2 [(M+H)]$^+$, calc'd for C$_{22}$H$_{28}$N$_6$O$_3$: 424.51.

5.6.122. Synthesis of [1-(3-Bromo-imidazo[1,2-b]pyridazin-6-yl)-pyrrolidin-3-yl]-methyl-carbamic acid tert-butyl ester

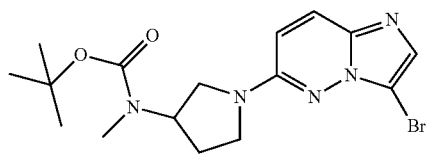 [SMILES: CN(C(=O)OC(C)(C)C)C1CCN(c2ccc3ncc(Br)n3n2)C1]

A mixture of methyl-pyrrolidin-3-yl-carbamic acid tert-butyl ester (1.2 g, 6 mmol), 3-bromo-6-fluoro-imidazo[1,2-b]pyridazine (648 mg, 3 mmol), and triethylamine (1.67 ml, 12 mmol) in isopropyl alcohol (3 ml) was heated in a microwave at 140° C. for 20 min. The reaction mixture was allowed to stand for overnight and the white solid was collected by filtration and washed with MeOH to give the titled compound (750 mg). The filtrate was concentrated and the residue was subjected to ISCO (40 g column), to give further titled compound (360 mg). $^1$H NMR (400 MHz, CHLOROFORM-d) δ ppm 1.45-1.52 (m, 9H) 2.03-2.27 (m, 2H) 2.83 (s, 3H) 3.39-3.54 (m, 2H) 3.69-3.77 (m, 2H) 6.58 (d, J=9.92 Hz, 1H) 7.49 (s, 1H) 7.65 (d, J=9.70 Hz, 1H). LRMS (ESI) m/z 396.1 and 398 [(M+H)]$^+$, calc'd for C$_{16}$H$_{22}$BrN$_6$O$_2$: 396.29.

5.6.123. Synthesis of (S)-5-(((3-bromoimidazo[1,2-b]pyridazin-6-yl)amino)methyl)pyrrolidin-2-one

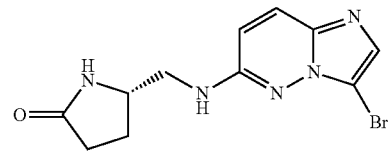 [SMILES: O=C1CC[C@@H](CNc2ccc3ncc(Br)n3n2)N1]

Part A. (S)-2-((5-oxopyrrolidin-2-yl)methyl)isoindoline-1,3-dione

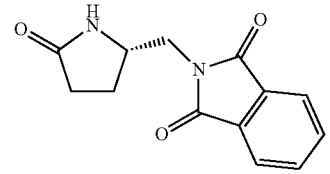 [SMILES: O=C1CC[C@@H](CN2C(=O)c3ccccc3C2=O)N1]

To (S)-5-(hydroxymethyl)pyrrolidin-2-one (2.00 g, 17.39 mmol) dissolve in 25 mL THF was added phthalimide (2.81 g, 19.13 mmol), triphenylphosphine (5.01 g, 19.13 mmol) and diisopropylazodi-carboxylate (3.33 g, 19.13 mmol). This mixture was stirred for about 16 hr, and then diluted with 200 mL of hexanes and 2 mL of DCM, and then cool at −30° C. The product precipitated and was filtered and dried (4.11 g, 96%, white solid).

Part B. (S)-5-(aminomethyl)pyrrolidin-2-one

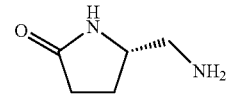

To 244 mg (1 mmol) of the (S)-2-((5-oxopyrrolidin-2-yl)methyl)isoindoline-1,3-dione dissolved in 25 mL of EtOH was added hydrazine (500 mg, 10 mmol), and this mixture was refluxed for 4 hr. It was cooled to rt and the titled compound crystallized out, and it was filtered and dried (114 mg, 100% yield).

Part C. (S)-5-(((3-bromoimidazo[1,2-b]pyridazin-6-yl)amino)methyl)pyrrolidin-2-one The (S)-5-(aminomethyl)pyrrolidin-2-one was reacted with 3-bromo-6-fluoroimidazo[1,2-b]pyridazine under the amine displacement conditions described in example 5.6.42, Part A, to obtain the titled in 62% yield. $^1$H NMR (400 MHz, METHANOL-$d_4$) δ ppm 1.90-2.04 (m, 1H) 2.24-2.50 (m, 3H) 3.46-3.56 (m, 2H) 4.09 (quin, J=5.84 Hz, 1H) 6.74 (d, J=9.70 Hz, 1H) 7.43 (s, 1H) 7.60 (d, J=9.70 Hz, 1H); LRMS (ESI) m/310.0 doublet [(M+H)$^+$, calcd for $C_{11}H_{12}BrN_5O$ 309.0].

5.6.124. Synthesis of (S)-5-(((3-Bromoimidazo[1,2-b]pyridazin-6-yl)amino)methyl)-1-isopentylpyrrolidin-2-one

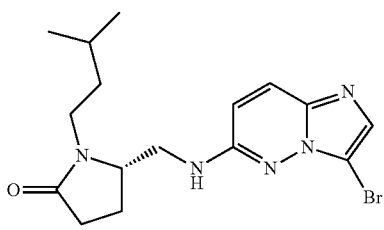 [SMILES: CC(C)CCN1C(=O)CC[C@H]1CNc1ccc2ncc(Br)n2n1]

Part A. (S)-2-(1-isopentyl-5-oxopyrrolidin-2-yl)methyl)isoindoline-1,3-dione

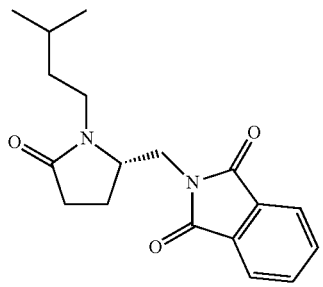 [SMILES: CC(C)CCN1C(=O)CC[C@H]1CN1C(=O)c2ccccc2C1=O]

To 244 mg (1.000 mmol) of (S)-2-((5-oxopyrrolidin-2-yl)methyl)isoindoline-1,3-dione dissolved in 4 mL of DMSO was added (227 mg, 1.500 mmol) of 1-bromo-3-methylbutane, and 60% NaH (42 mg, 1.050 mmol). After 1 hr stirring at 70° C., the reaction mixture was cooled to rt, and diluted with EtOAc and quenched with water. The organic layer was separated, washed with brine and dried over MgSO$_4$. It was concentrated and purified on silica gel eluting with 15-100% EtOAc/hexanes to obtain 48% of the desired product.

Part B.
(S)-5-(aminomethyl)-1-isopentylpyrrolidin-2-one

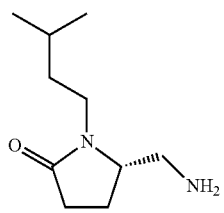

The (S)-2-((1-isopentyl-5-oxopyrrolidin-2-yl)methyl)isoindoline-1,3-dione was subjected to the phthalimide deprotection procedure described in example 5.6.123, Part B, to obtain 100% yield of the desired product.

Part C. (S)-5-(((3-bromoimidazo[1,2-b]pyridazin-6-yl)amino)methyl)-1-isopentylpyrrolidin-2-one The 3-bromo-6-fluoroimidazo[1,2-b]pyridazine was reacted with (S)-5-(aminomethyl)-1-isopentylpyrrolidin-2-one under the amine displacement conditions described in example 5.6.42, Part A to afford 60% titled compound. $^1$H NMR (400 MHz, CHLOROFORM-d) δ ppm 0.95 (d, J=6.32 Hz, 6H) 1.39-1.66 (m, 3H) 1.95-2.08 (m, 1H) 2.13-2.26 (m, 1H) 2.31-2.53 (m, 2H) 3.02 (ddd, J=13.89, 9.22, 4.93 Hz, 1H) 3.48 (dt, J=14.15, 5.18 Hz, 1H) 3.79 (ddd, J=13.77, 9.35, 6.95 Hz, 1H) 3.91 (ddd, J=14.08, 7.01, 2.91 Hz, 1H) 4.00-4.11 (m, 1H) 5.42 (t, J=5.31 Hz, 1H) 6.67 (d, J=9.60 Hz, 1H) 7.52 (s, 1H) 7.66 (d, J=9.85 Hz, 1H); LRMS (ESI) m/380.0 doublet [(M+H)$^+$, calcd for $C_{16}H_{22}BrN_5O$ 379.0].

5.6.125. Synthesis of 2,2-Dimethyl-1-[4-(3-phenyl-imidazo[1,2-b]pyridazin-6-yl)-piperazin-1-yl]-propan-1-one

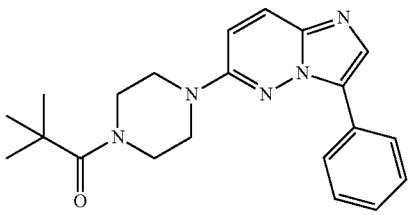 [SMILES: CC(C)(C)C(=O)N1CCN(c2ccc3ncc(-c4ccccc4)n3n2)CC1]

Part A. 1-[4-(3-Bromo-imidazo[1,2-b]pyridazin-6-yl)-piperazin-1-yl]-2,2-dimethyl-propan-1-one

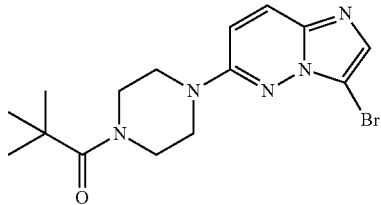 [SMILES: CC(C)(C)C(=O)N1CCN(c2ccc3ncc(Br)n3n2)CC1]

Hunig's base [7087-99-5] (1.8 mL, 10.3 mmol) was added to an ambient temperature stirred suspension of 3-bromo-6-piperazin-1-yl-imidazo[1,2-b]pyridazine dihydrochloride (907.1 mg, 2.6 mmol) in ethyl acetate (50 mL). After 30 minutes, pivaloyl chloride [3282-30-2] (0.3 mL, 2.5 mmol) was added and the suspension stirred under N$_2$ blanket for 17 h then washed with brine, dried (MgSO$_4$), and diluted with heptane. Chilling the stirred solution crystallized out a white powder which was isolated by filtration, 618.5 mg. LRMS (ESI) m/z 366.0/368.0 [(M+H)]$^+$, calc'd for $C_{16}H_{20}BrN_6O$: 366.26.

Part B. 2,2-Dimethyl-1-[4-(3-phenyl-imidazo[1,2-b]pyridazin-6-yl)-piperazin-1-yl]-propan-1-one To a mixture of 1-[4-(3-bromo-imidazo[1,2-b]pyridazin-6-yl)-piperazin-1-yl]-2,2-dimethyl-propan-1-one (526.7 mg, 1.4 mmol), phenyl boronic acid [98-80-8] (211.3 mg, 1.7 mmol), potassium phosphate tribasic monohydrate [27176-10-9] (664.4 mg, 2.9 mmol), and [1,1'-bis(diphenylphosphino) ferrocene]dichloropalladium(II), complex with dichloromethane [95464-05-4] (123.2 mg, 0.2 mmol) contained in a 50 mL round bottomed flask was added a solution of 30% (v/v) water in 1,2-dimethoxyethane (25 mL) and a magnetic stir bar. The reaction pot was fitted to a reflux condenser, lowered into an ambient temperature oil bath, and the system taken through 10 evacuation/$N_2$ blanket cycles while being rapidly stirred. The rapidly stirred, $N_2$ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried ($MgSO_4$) and evaporated to afford a clear orange oil which was purified by preparative RP-HPLC. Isolated product was dissolved in methanol, diluted with concentrated hydrochloric acid, evaporated to dryness, redissolved in methanol and precipitated by the addition of diethyl ether. Filtration of the precipitate yielded 85.8 mg of 2,2-dimethyl-1-[4-(3-phenyl-imidazo[1,2-b]pyridazin-6-yl)-piperazin-1-yl]-propan-1-one monohydrochloride salt as a light yellow powder, mp. 277-278° C. (dec). $^1$H NMR (400 MHz, DMSO-$d_6$) δ ppm 1.24 (s, 9H) 3.59-3.67 (m, 4H) 3.71-3.79 (m, 4H) 7.55-7.64 (m, 2H) 8.06-8.15 (m, 2H) 8.57 (br. s., 1H). $^{13}$C NMR (100 MHz, DMSO-$d_6$) δ ppm 28.00, 38.08, 43.85, 45.30, 116.00, 121.14, 122.29, 126.29, 127.20, 128.85, 129.04, 155.84, 175.34. LRMS (ESI) m/z 364.2 [(M+H)]$^+$, calc'd for $C_{21}H_{26}N_6O$: 363.47.

5.6.126. Synthesis of (S)-5-(((3-(4-(aminomethyl) phenyl)imidazo[1,2-b]pyridazin-6-yl)amino)methyl)-1-isopentylpyrrolidin-2-one

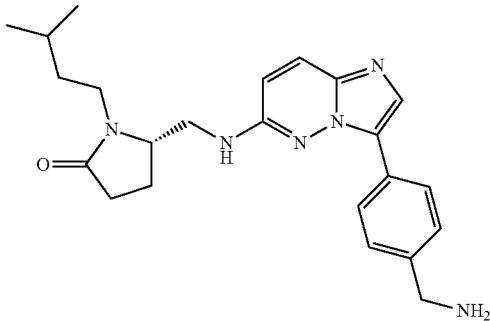 [SMILES: CC(C)CCN1C(=O)CC[C@H]1CNc1ccc2ncc(-c3ccc(CN)cc3)n2n1]

The Suzuki coupling following the procedure described in example 5.6.19 afforded the titled compound in 71% yield. $^1$H NMR (400 MHz, METHANOL-$d_4$) δ ppm 0.78-0.90 (m, 6H) 1.31-1.50 (m, 3H) 1.93-2.06 (m, 1H) 2.12-2.36 (m, 2H) 2.39-2.52 (m, 1H) 3.09 (ddd, J=13.83, 8.15, 5.56 Hz, 1H) 3.56-3.75 (m, 3H) 3.99-4.08 (m, 1H) 4.19 (s, 2H) 6.78 (d, J=9.85 Hz, 1H) 7.58 (m, J=8.34 Hz, 2H) 7.70 (d, J=9.85 Hz, 1H) 7.80 (s, 1H) 8.20 (m, J=8.34 Hz, 2H); LRMS (ESI) m/407.0 [(M+H)$^+$, calcd for $C_{23}H_{30}N_6O$ 406.0].

5.6.127. Synthesis of 4-(3-Bromoimidazo[1,2-b]pyridazin-6-yl)-N-(tert-butyl)piperazine-1-carboxamide

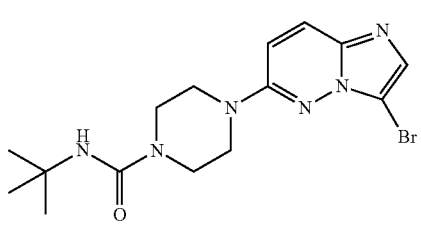 [SMILES: CC(C)(C)NC(=O)N1CCN(c2ccc3ncc(Br)n3n2)CC1]

To a rapidly stirred, 0° C., $N_2$ blanketed, suspension of 3-bromo-6-piperazin-1-yl-imidazo[1,2-b]pyridazine dihydrochloride (934.9 mg, 2.6 mmol) and Hunig's base [7087-68-5] (1.8 mL, 10.6 mmol) in dichloromethane (26 mL) was added 2-isocyanato-2-methylpropane [1609-86-5] (340 μL, 2.9 mmol). The suspension was permitted to stir and warm to ambient temperature over 17 h and was then partitioned between brine and ethyl acetate. The organic phase was reduced in volume to precipitate product as 442.1 mg of yellow solid. A 129.3 mg aliquot was purified by preparative RP-HPLC to yield 61.8 mg of 4-(3-bromoimidazo[1,2-b]pyridazin-6-yl)-N-(tert-butyl)piperazine-1-carboxamide as a white powder, mp. 199-200° C. $^1$H NMR (400 MHz, DMSO-$d_6$) δ ppm 1.28 (s, 8H) 2.51 (s, 1H) 3.30 (s, 1H) 3.39-3.46 (m, 4H) 3.48-3.54 (m, 4H) 7.26 (d, J=10.11 Hz, 1H) 7.61 (s, 1H) 7.88 (d, J=10.11 Hz, 1H). $^{13}$C NMR (100 MHz, DMSO-$d_6$) δ ppm 29.15, 43.05, 45.27, 49.94, 99.27, 110.77, 126.00, 131.50, 136.54, 155.16, 156.93. LRMS (ESI) m/z 381.1/383.1 [(M+H)]$^+$, calc'd for $C_{15}H_{21}BrN_6O$: 381.28.

5.6.128. Synthesis of (S)-2-(((3-bromoimidazo[1,2-b]pyridazin-6-yl)amino)methyl)-N-(tert-butyl)pyrrolidine-1-carboxamide

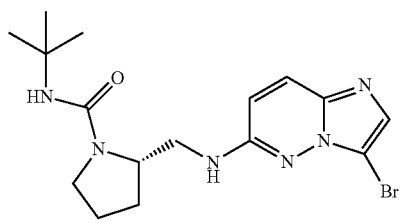 [SMILES: CC(C)(C)NC(=O)N1CCC[C@H]1CNc1ccc2ncc(Br)n2n1]

To a solution of (S)-3-bromo-N-(pyrrolidin-2-ylmethyl) imidazo[1,2-b]pyridazin-6-amine (400 mg, 1.2 mmol) and triethylamine (0.5 mL, 3.5 mmol) in DCM (10 mL) was added t-butyl isocyanate (0.2 mL, 1.75 mmol) dropwise. After stirring at it for 2 h, the reaction mixture was concentrated and purified by ISCO column chromatography (10% MeOH/DCM) to give (S)-2-(((3-bromoimidazo[1,2-b]pyridazin-6-yl)amino)methyl)-N-(tert-butyl)pyrrolidine-1-carboxamide (360 mg, 76% yield). $^1$H NMR (400 MHz, METHANOL-$d_4$) δ ppm 7.58 (d, J=9.60 Hz, 1H), 7.42 (s, 1H), 6.72 (d, J=9.85 Hz, 1H), 5.07 (s, 1H), 4.26 (dd, J=6.57, 1.77 Hz, 1H), 3.35-3.48 (m, 4H), 2.09-2.20 (m, 1H), 1.90-2.05 (m, 3H), 1.26 (s, 9H); LRMS (ESI) m/e 395.2 [(M+H)$^+$, calcd for $C_{16}H_{24}BrN_6O$ 396.3].

5.6.129. Synthesis of (S)-1-(2-(((3-bromoimidazo[1,2-b]pyridazin-6-yl)(methyl)amino)methyl)pyrrolidin-1-yl)-3-methylbutan-1-one

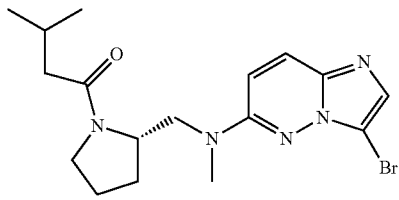 [SMILES: CC(C)CC(=O)N1CCC[C@H]1CN(C)c1ccc2ncc(Br)n2n1]

To a solution of (S)-1-(2-(((3-bromoimidazo[1,2-b]pyridazin-6-yl)amino)methyl)pyrrolidin-1-yl)-3-methylbutan-1-one (380 mg, 1.0 mmol) in THF (10 mL) was added sodium hydride (120 mg, 3.0 mmol) at rt. After stirring for 15 min, methyl iodide was added dropwise. The reaction was stirred at it for overnight and worked up with ammonium chloride solution, extracted with ethyl acetate, concentrated and purified by ISCO column chromatography (10% MeOH/DCM) to give non-pure product. It was further purified by Prep HPLC (neutral) to give (S)-1-(2-(((3-bromoimidazo[1,2-b]pyridazin-6-yl)(methyl)amino)methyl)pyrrolidin-1-yl)-3-methylbutan-1-one as oil. $^1$H NMR (400 MHz, METHANOL-d$_4$) δ ppm 7.65-7.75 (m, 1H), 7.44-7.52 (m, 1H), 7.04-7.22 (m, 1H), 4.45-4.61 (m, 1H), 3.45-3.92 (m, 4H), 3.19-3.23 (m, 3H), 1.90-2.32 (m, 7H), 0.78-0.92 (m, 6H); LRMS (ESI) m/e 394.1 [(M+H)$^+$, calcd for C$_{17}$H$_{25}$BrN$_5$O 395.3].

5.6.130. Synthesis of (S)-3-methyl-1-(2-((methyl(3-(pyridin-4-yl)imidazo[1,2-b]pyridazin-6-yl)amino)methyl)pyrrolidin-1-yl)butan-1-one (with minor rotamers)

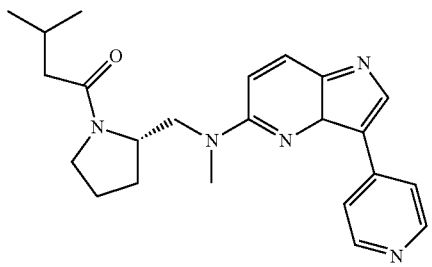 [SMILES: CC(C)CC(=O)N1CCC[C@H]1CN(C)C1=NC2C(c3ccncc3)=CN=C2C=C1]

This compound was prepared using the approach described in example 5.6.68. $^1$H NMR (400 MHz, METHANOL-d$_4$) δ ppm 8.50-8.73 (m, 2H), 8.16-8.31 (m, 2H), 7.93-8.16 (m, 1H), 7.65-7.93 (m, 1H), 7.38 (d, J=10.11 Hz, 1H), 4.49 (q, J=5.81 Hz, 1H), 3.96 (dd, J=14.78, 5.94 Hz, 1H), 3.37-3.66 (m, 3H), 3.25 (m, 3H), 2.07-2.20 (m, 3H), 1.88-2.06 (m, 4H), 0.72-0.96 (m, 6H); LRMS (ESI) m/e 393.2 [(M+H)$^+$, calcd for C$_{22}$H$_{29}$N$_6$O 393.5].

5.6.131. Synthesis of N-(tert-Butyl)-4-(3-phenylimidazo[1,2-b]pyridazin-6-yl)piperazine-1-carboxamide

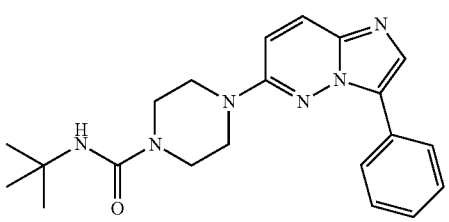 [SMILES: CC(C)(C)NC(=O)N1CCN(c2ccc3ncc(-c4ccccc4)n3n2)CC1]

To a mixture of 4-(3-bromoimidazo[1,2-b]pyridazin-6-yl)-N-(tert-butyl)piperazine-1-carboxamide (301.0 mg, 0.8 mmol), phenyl boronic acid [98-80-8] (117.8 mg, 1.0 mmol), potassium phosphate tribasic monohydrate [27176-10-9] (366.4 mg, 1.6 mmol), and [1,1'-bis(diphenylphosphino)ferrocene]dichloropalladium(II), complex with dichloromethane [95464-05-4] (68.7 mg, 0.1 mmol) contained in a 50 mL round bottomed flask was added a solution of 30% (v/v) water in 1,2-dimethoxyethane (25 mL) and a magnetic stir bar. The reaction pot was fitted to a reflux condenser, lowered into an ambient temperature oil bath, and the system taken through 10 evacuation/N$_2$ blanket cycles while being rapidly stirred. The rapidly stirred, N$_2$ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried (MgSO$_4$) and evaporated to afford a brown oil which was purified by preparative RP-HPLC. Isolated product was dissolved in methanol, diluted with concentrated hydrochloric acid, evaporated to dryness, redissolved in methanol and precipitated by the addition of diethyl ether. Filtration of the precipitate yielded 39.3 mg of N-(tert-butyl)-4-(3-phenylimidazo[1,2-b]pyridazin-6-yl)piperazine-1-carboxamide monohydrochloride salt as a white powder, mp. 210-211° C. (dec). $^1$H NMR (400 MHz, DMSO-d$_6$) δ ppm 1.28 (s, 8H) 2.51 (br. s., 2H) 3.47 (br. s., 4H) 3.57-3.63 (m, 4H) 7.49 (s, 1H) 7.55-7.60 (m, 2H) 7.76 (d, J=10.11 Hz, 1H) 8.11 (d, J=7.58 Hz, 2H) 8.21 (d, J=10.10 Hz, 1H) 8.48 (s, 1H). $^{13}$C NMR (100 MHz, DMSO-d$_6$) δ ppm 29.15, 42.92, 45.19, 49.98, 116.08, 121.27, 122.26, 126.43, 127.18, 128.08, 128.78, 129.02, 132.90, 155.89, 156.83. LRMS (ESI) m/z 379.2 [(M+H)]$^+$, calc'd for C$_{21}$H$_{26}$N$_6$O: 378.48.

5.6.132. Synthesis of tert-Butyl(1-(3-(pyridin-4-yl)imidazo[1,2-b]pyridazin-6-yl)piperidin-3-yl)carbamate

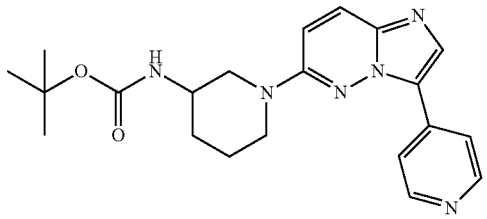 [SMILES: CC(C)(C)OC(=O)NC1CCCN(c2ccc3ncc(-c4ccncc4)n3n2)C1]

This compound was prepared using the approach described in example 5.6.42. $^1$H NMR (400 MHz, CHLOROFORM-d) δ ppm 1.48 (s, 9H) 1.57-1.64 (m, 1H) 1.78 (ddt, J=13.34, 8.88, 4.44, 4.44 Hz, 1H) 1.91 (ddd, J=13.56, 6.62, 3.20 Hz, 1H) 1.96-2.06 (m, 1H) 3.27 (dd, J=12.90, 7.61 Hz, 1H) 3.43 (t, J=9.15 Hz, 1H) 3.70-3.79 (m, 1H) 3.99 (d, J=12.79 Hz, 1H) 4.70 (br. s., 1H) 6.98 (d, J=9.92 Hz, 1H) 7.80 (d, J=9.92 Hz, 1H) 8.03-8.08 (m, 3H) 8.66-8.73 (m, 2H); LRMS (ESI) m/395.0 [(M+H)$^+$, calcd for C$_{21}$H$_{26}$N$_6$O$_2$ 394.0].

5.6.133. Synthesis of (3aR,6aS)-tert-butyl 5-(3-bromoimidazo[1,2-b]pyridazin-6-yl)hexahydropyrrolo[3,4-c]pyrrole-2(1H)-carboxylate

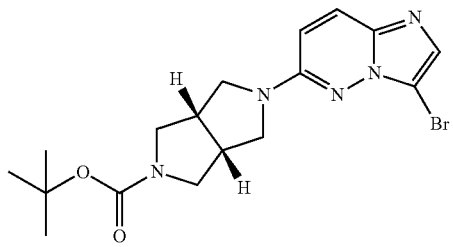 [SMILES: CC(C)(C)OC(=O)N1C[C@@H]2CN(c3ccc4ncc(Br)n4n3)C[C@@H]2C1]

This compound was prepared using the approach described in example 5.6.42, Part A. $^1$H NMR (400 MHz, CHLOROFORM-d) δ ppm 1.49 (s, 9H) 1.57 (s, 2H) 3.06 (br. s., 2H) 3.39 (br. s., 2H) 3.50 (d, J=9.35 Hz, 2H) 3.69 (br. s., 2H)

3.76-3.89 (m, 2H) 6.60 (d, J=9.85 Hz, 1H) 7.53 (s, 1H) 7.68 (d, J=9.85 Hz, 1H); LRMS (ESI) m/408.0 [(M+H)⁺ doublet, calcd for C₁₇H₂₂BrN₆O₂ 407.0].

5.6.134. Synthesis of 3-bromo-6-(3-phenylpyrrolidin-1-yl)imidazo[1,2-b]pyridazine

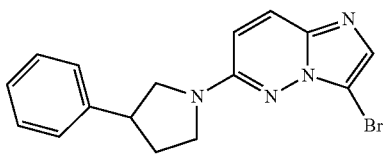 [SMILES: Brc1cnc2ccc(N3CCC(c4ccccc4)C3)nn12]

This compound was prepared using the approach described in example 5.6.42, Part A. ¹H NMR (400 MHz, CHLOROFORM-d) δ ppm 2.15-2.29 (m, 1H) 2.44-2.55 (m, 1H) 3.51-3.73 (m, 3H) 3.80-3.89 (m, 1H) 4.01-4.11 (m, 1H) 6.65 (d, J=9.60 Hz, 1H) 7.29-7.42 (m, 5H) 7.52 (s, 1H) 7.68 (d, J=9.60 Hz, 1H); LRMS (ESI) m/343.0 [(M+H)⁺ doublet, calcd for C₁₆H₁₅BrN₄ 342.0].

5.6.135. Synthesis of tert-butyl 2-(1-(3-bromoimidazo[1,2-b]pyridazin-6-yl)pyrrolidin-2-yl)acetate

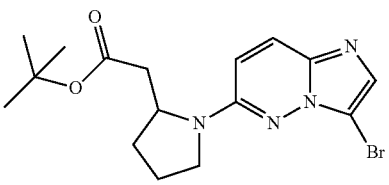 [SMILES: CC(C)(C)OC(=O)CC1CCCN1c1ccc2ncc(Br)n2n1]

This compound was prepared using the approach described in example 5.6.42, Part A.
¹H NMR (400 MHz, CHLOROFORM-d) δ ppm 1.46-1.51 (m, 10H) 1.96-2.24 (m, 4H) 2.31 (dd, J=14.99, 9.92 Hz, 1H) 2.97 (dd, J=14.77, 3.09 Hz, 1H) 3.42-3.53 (m, 1H) 3.59-3.70 (m, 1H) 4.48 (ddt, J=10.01, 7.25, 2.73, 2.73 Hz, 1H) 6.66 (d, J=9.70 Hz, 1H) 7.51 (s, 1H) 7.67 (d, J=9.70 Hz, 1H); LRMS (ESI) m/381.0 [(M+H)⁺ doublet, calcd for C₁₆H₂₁BrN₄O₂ 380.0].

5.6.136. Synthesis of S-Isopropyl 4-(3-bromoimidazo[1,2-b]pyridazin-6-yl)piperazine-1-carbothioate

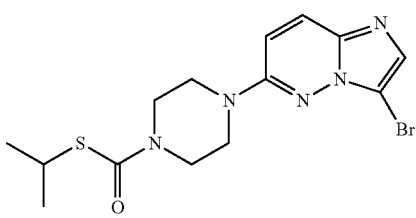 [SMILES: CC(C)SC(=O)N1CCN(c2ccc3ncc(Br)n3n2)CC1]

Hunig's base [7087-68-5] (0.4 mL, 2.4 mmol), then S-isopropyl carbonochloridothioate [13889-93-5] (0.2 mL, 1.6 mmol) were added to a stirred, ambient temperature solution of 3-bromo-6-piperazin-1-yl-imidazo[1,2-b]pyridazine (450.0 mg, 1.6 mmol) in ethyl acetate (30 mL). Then rapidly formed suspension was stirred overnight, under N₂ blanket, then washed with brine, dried (MgSO₄), evaporated, and crystallized from ethyl acetate/heptane to afford 482.9 mg of white powder, mp. 186-187° C. ¹H NMR (400 MHz, DMSO-d₆) δ ppm 1.30 (d, J=6.82 Hz, 6H) 2.51 (dt, J=3.60, 1.86 Hz, 1H) 3.49-3.59 (m, 1H) 3.59-3.71 (m, 7H) 7.58 (d, J=9.85 Hz, 1H) 8.09-8.13 (m, 2H). ¹³C NMR (100 MHz, DMSO-d₆) δ ppm 23.22, 35.48, 44.71, 101.63, 110.84, 113.71, 114.69, 116.58, 119.46, 123.56, 126.04, 134.22, 155.61, 157.77, 158.15, 158.53, 158.90, 166.18. LRMS (ESI) m/z 384.0/386.0 [(M+H)]⁺, calc'd for C₁₄H₁₅BrN₆OS: 384.30.

5.6.137. Synthesis of 3-Bromo-6-(4-(pyrazin-2-yl)piperazin-1-yl)imidazo[1,2-b]pyridazine

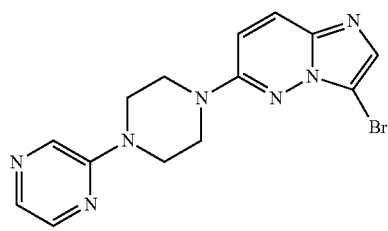 [SMILES: Brc1cnc2ccc(N3CCN(c4cnccn4)CC3)nn12]

This compound was prepared using the approach described in example 5.6.42, Part A. ¹H NMR (400 MHz, CHLOROFORM-d) δ ppm 3.70-3.87 (m, 8H) 6.90 (d, J=10.11 Hz, 1H) 7.58 (s, 1H) 7.75 (d, J=9.85 Hz, 1H) 7.94 (d, J=2.53 Hz, 1H) 8.13 (dd, J=2.53, 1.52 Hz, 1H) 8.23 (d, J=1.52 Hz, 1H); LRMS (ESI) m/360.0 [(M+H)⁺ doublet, calcd for C₁₄H₁₄BrN₇ 359.0].

5.6.138. Synthesis of tert-butyl(2-(1-(3-bromoimidazo[1,2-b]pyridazin-6-yl)piperidin-4-yl)ethyl)carbamate

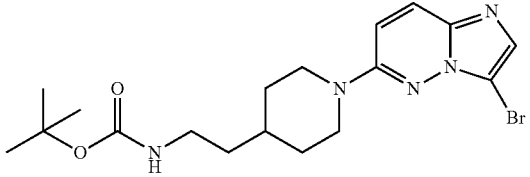 [SMILES: CC(C)(C)OC(=O)NCCC1CCN(c2ccc3ncc(Br)n3n2)CC1]

This compound was prepared using the approach described in example 5.6.42, Part A. ¹H NMR (400 MHz, CHLOROFORM-d) δ ppm 1.19-1.40 (m, 2H) 1.41-1.53 (m, 11H) 1.60 (dtd, J=10.71, 7.15, 7.15, 3.79 Hz, 1H) 1.85 (d, J=12.38 Hz, 2H) 2.88-3.01 (m, 2H) 3.21 (q, J=6.57 Hz, 2H) 4.21 (d, J=13.14 Hz, 2H) 6.84 (d, J=9.85 Hz, 1H) 7.52 (s, 1H) 7.64 (d, J=9.85 Hz, 1H); LRMS (ESI) m/424.0 [(M+H)⁺ doublet, calcd for C₁₈H₂₆BrN₅O₂ 423.0].

5.6.139. Synthesis of Methyl-[1-(3-pyridin-4-yl-imidazo[1,2-b]pyridazin-6-yl)-pyrrolidin-3-yl]-carbamic acid tert-butyl ester

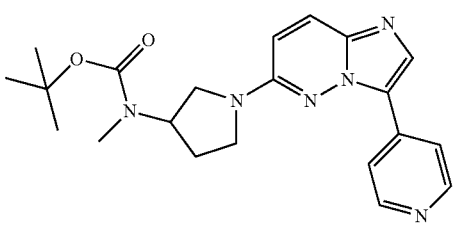 [SMILES: CN(C(=O)OC(C)(C)C)C1CCN(c2ccc3ncc(-c4ccncc4)n3n2)C1]

A mixture of [1-(3-bromo-imidazo[1,2-b]pyridazin-6-yl)-pyrrolidin-3-yl]-methyl-carbamic acid tert-butyl ester (100 mg, 0.25 mmol), 4-pyridinylboronic acid (40 mg, 0.33 mmol), $K_2CO_3$ (104 mg, 0.75 mmol) and dichlorobis(triphenylphosphine)palladium(II) (8.8 mg, 0.013 mmol) in MeCN/water (3.2 ml/0.8 ml) was heated in a microwave at 150° C. for 15 min. The water layer was removed and the organic layer was diluted with MeCN and filtered. The filtrate was subjected to preparative HPLC to give the titled compound (25.3 mg). $^1$H NMR (400 MHz, METHANOL-$d_4$) δ ppm 1.50-1.55 (m, 9H) 2.22-2.32 (m, 2H) 2.89 (s, 3H) 3.46-3.57 (m, 2H) 3.72-3.80 (m, 2H) 4.91 (t, J=7.61 Hz, 1H) 6.95 (d, J=9.92 Hz, 1H) 7.77 (d, J=9.70 Hz, 1H) 8.11 (s, 1H) 8.23-8.27 (m, 2H) 8.53-8.58 (m, 2H). LRMS (ESI) m/z 395.2 [(M+H)]$^+$, calc'd for $C_{21}H_{26}N_6O_2$: 394.48.

5.6.140. Synthesis of S-Isopropyl 4-(3-phenylimidazo[1,2-b]pyridazin-6-yl)piperazine-1-carbothioate

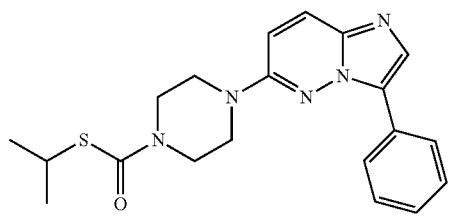

To a mixture of S-isopropyl 4-(3-bromoimidazo[1,2-b]pyridazin-6-yl)piperazine-1-carbothioate (360.9 mg, 0.9 mmol), phenyl boronic acid [98-80-8] (137.5 mg, 1.1 mmol), potassium phosphate tribasic monohydrate [27176-10-9] (438.1 mg, 1.9 mmol), and [1,1'-bis(diphenylphosphino)ferrocene]dichloropalladium(II), complex with dichloromethane [95464-05-4] (78.4 mg, 0.1 mmol) contained in a 50 mL round bottomed flask was added a solution of 30% (v/v) water in 1,2-dimethoxyethane (25 mL) and a magnetic stir bar. The reaction pot was fitted to a reflux condenser, lowered into an ambient temperature oil bath, and the system taken through 10 evacuation/$N_2$ blanket cycles while being rapidly stirred. The rapidly stirred, $N_2$ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried ($MgSO_4$) and evaporated to afford a dark brown oil which was purified by preparative RP-HPLC. Isolated product was dissolved in methanol, diluted with concentrated hydrochloric acid, evaporated to dryness, redissolved in methanol and precipitated by the addition of diethyl ether. Filtration of the precipitate yielded 226.9 mg of S-isopropyl 4-(3-phenylimidazo[1,2-b]pyridazin-6-yl)piperazine-1-carbothioate monohydrochloride salt as a white powder, mp. 276-277° C. (dec). $^1$H NMR (400 MHz, DMSO-$d_6$) δ ppm 1.30 (d, J=6.82 Hz, 6H) 2.49-2.52 (m, 2H) 3.52 (dt, J=13.64, 6.82 Hz, 1H) 3.60-3.71 (m, 7H) 7.46-7.51 (m, 1H) 7.55-7.60 (m, 2H) 7.77 (d, J=10.11 Hz, 1H) 8.09-8.13 (m, 2H) 8.25 (d, J=10.10 Hz, 1H) 8.54 (s, 1H). $^{13}$C NMR (100 MHz, DMSO-$d_6$) δ ppm 23.27, 35.50, 44.94, 116.00, 121.27, 122.33, 126.38, 127.14, 128.02, 128.82, 128.97, 132.91. LRMS (ESI) m/z 384.0/386.0 [(M+H)]$^+$, calc'd for $C_{20}H_{23}N_5OS$: 381.50.

5.6.141. Synthesis of N-Isopropyl-4-(3-phenylimidazo[1,2-b]pyridazin-6-yl)piperazine-1-carboxamide

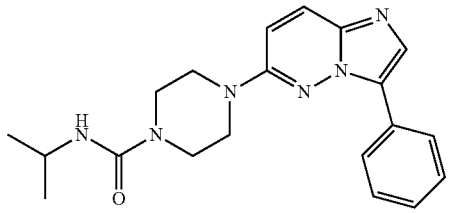 [SMILES: CC(C)NC(=O)N1CCN(c2ccc3ncc(-c4ccccc4)n3n2)CC1]

Part A. 4-(3-Bromoimidazo[1,2-b]pyridazin-6-yl)-N-isopropylpiperazine-1-carboxamide

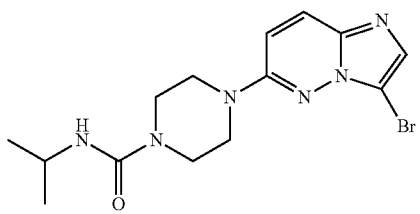 [SMILES: CC(C)NC(=O)N1CCN(c2ccc3ncc(Br)n3n2)CC1]

2-Isocyanatopropane [1795-48-8] (120 µL, 1.2 mmol) was added, via syringe, to a stirred, ambient temperature, clear, colorless solution of 3-bromo-6-piperazin-1-yl-imidazo[1,2-b]pyridazine (334.6 mg, 1.2 mmol) in dichloromethane (20 mL). The solution was allowed to proceed for 17 h then evaporated to dryness to afford 481.5 mg of light yellow solid foam. LRMS (ESI) m/z 367.0/369.0 [(M+H)]$^+$, calc'd for $C_{14}H_{19}BrN_6O$: 367.25.

Part B. N-Isopropyl-4-(3-phenylimidazo[1,2-b]pyridazin-6-yl)piperazine-1-carboxamide To a mixture of 4-(3-bromoimidazo[1,2-b]pyridazin-6-yl)-N-isopropylpiperazine-1-carboxamide (481.5 mg, 1.3 mmol), phenyl boronic acid [98-80-8] (191.8 mg, 1.6 mmol), potassium phosphate tribasic monohydrate [27176-10-9] (608.4 mg, 2.6 mmol), and [1,1'-bis(diphenylphosphino)ferrocene]dichloropalladium(II), complex with dichloromethane [95464-05-4] (111.4 mg, 0.1 mmol) contained in a 50 mL round bottomed flask was added a solution of 30% (v/v) water in 1,2-dimethoxyethane (25 mL) and a magnetic stir bar. The reaction pot was fitted to a reflux condenser, lowered into an ambient temperature oil bath, and the system taken through 10 evacuation/$N_2$ blanket cycles while being rapidly stirred. The rapidly stirred, $N_2$ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried ($MgSO_4$) and evaporated to afford a brown oil which was purified by preparative RP-HPLC. Isolated product was dissolved in methanol, diluted with concentrated hydrochloric acid, evaporated to dryness, redissolved in methanol and precipitated by the addition of diethyl ether. Filtration of the precipitate yielded 219.4 mg of N-isopropyl-4-(3-phenylimidazo[1,2-b]pyridazin-6-yl)piperazine-1-carboxamide monohydrochloride salt as a white powder, mp. 217-218° C. (dec.). $^1$H NMR (400 MHz, DMSO-d$_6$) δ ppm 1.08 (d, J=6.57 Hz, 6H) 2.51 (d, J=1.52 Hz, 2H) 3.50 (d, J=5.05 Hz, 4H) 3.56-3.63 (m, 4H) 3.73-3.82 (m, 1H) 7.49 (d, J=7.33 Hz, 1H) 7.54-7.60 (m, 2H) 7.80 (d, J=10.10 Hz, 1H) 8.08-8.13 (m, 2H) 8.22 (d, J=10.11 Hz, 1H) 8.53 (s, 1H). $^{13}$C NMR (100 MHz, DMSO-d$_6$) δ ppm 22.88, 41.82, 42.69, 45.13, 116.22, 120.96, 122.08, 126.38, 127.20, 128.03, 128.76, 129.02, 132.77, 155.89, 156.69. LRMS (ESI) m/z 365.1 [(M+H)]$^+$, calc'd for C$_{20}$H$_{24}$N$_6$O: 364.45. mw=364.45.

5.6.142. Synthesis of (S)-tert-butyl 2-(((3-aminoimidazo[1,2-b]pyridazin-6-yl)amino)methyl)pyrrolidine-1-carboxylate and (S)-tert-butyl 2-(((3-acetamidoimidazo[1,2-b]pyridazin-6-yl)amino)methyl)pyrrolidine-1-carboxylate

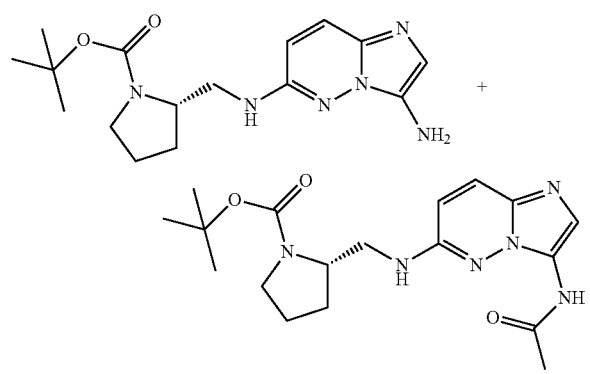

Part A.
N-(6-chloroimidazo[1,2-b]pyridazin-3-yl)acetamide

To a solution 6-chloroimidazo[1,2-b]pyridazin-3-amine and triethylamine (0.8 mL, 6.0 mmol) in DCM (25 mL) was added acetyl chloride dropwise and stirred at rt for overnight. The mixture was concentrated and purified by ISCO column chromatography (10% MeOH/DCM) to give not very pure N-(6-chloroimidazo[1,2-b]pyridazin-3-yl)acetamide (500 mg, 95% yield). 60 mg of non-pure material was further purified by Prep HPLC (neutral) to give pure N-(6-chloroimidazo[1,2-b]pyridazin-3-yl)acetamide. $^1$H NMR (400 MHz, METHANOL-d$_4$) δ ppm 8.01 (d, J=9.35 Hz, 1H), 7.94 (s, 1H), 7.26 (d, J=9.35 Hz, 1H), 2.29 (s, 3H); LRMS (ESI) m/e 210.9 [(M+H)$^+$, calcd for C$_8$H$_8$ClN$_4$O 211.6].

Part B. (S)-tert-butyl 2-(((3-aminoimidazo[1,2-b]pyridazin-6-yl)amino)methyl)pyrrolidine-1-carboxylate and (S)-tert-butyl 2-(((3-acetamidoimidazo[1,2-b]pyridazin-6-yl)amino)methyl)pyrrolidine-1-carboxylate The title compounds were prepared using the approach described in example 5.6.68.

(S)-tert-butyl 2-(((3-aminoimidazo[1,2-b]pyridazin-6-yl)amino)methyl)pyrrolidine-1-carboxylate: $^1$H NMR (400 MHz, METHANOL-d$_4$) δ ppm 7.43-7.46 (m, 1H), 6.80-6.87 (m, 1H), 6.48-6.51 (m, 1H), 4.19 (br. s., 1H), 3.40-3.79 (m, 4H), 1.96-2.04 (m, 4H), 1.41-1.50 (m, 9H); LRMS (ESI) m/e 333.1 [(M+H)$^+$, calcd. for C$_{16}$H$_{25}$N$_6$O$_2$ 333.4].

(S)-tert-butyl 2-(((3-acetamidoimidazo[1,2-b]pyridazin-6-yl)amino)methyl)pyrrolidine-1-carboxylate: $^1$H NMR (400 MHz, METHANOL-d$_4$) δ ppm 7.51-7.67 (m, 2H), 6.61-6.91 (m, 1H), 2.89-4.30 (m, 6H), 1.80-2.37 (m, 7H), 1.45-1.49 (m, 9H); LRMS (ESI) m/e 375.2 [(M+H)$^+$, calcd for C$_{18}$H$_{27}$N$_6$O$_3$ 375.5].

5.6.143. Synthesis of 4-[3-(2-Methoxy-pyridin-4-yl)-imidazo[1,2-b]pyridazin-6-yl]-piperazine-1-carboxylic acid isopropyl ester

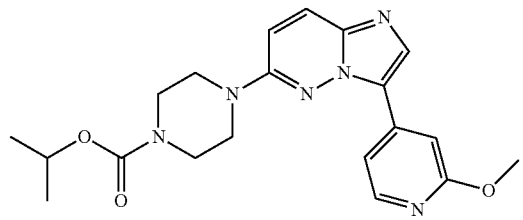 [SMILES: COc1cc(-c2cnc3ccc(N4CCN(C(=O)OC(C)C)CC4)nn23)ccn1]

This compound was prepared using the approach described in example 5.6.111 from 4-(3-bromo-imidazo[1,2-b]pyridazin-6-yl)-piperazine-1-carboxylic acid isopropyl ester (452.7 mg, 1.2 mmol) and 2-methoxypyridine-4-boronic acid [762262-09-9] (225.6 mg, 1.5 mmol) to provide 229.7 mg 4-[3-(2-Methoxy-pyridin-4-yl)-imidazo[1,2-b]pyridazin-6-yl]-piperazine-1-carboxylic acid isopropyl ester di-hydrochloride as white powder, mp. 215-216° C. (dec.). $^1$H NMR (400 MHz, DMSO-d$_6$) δ ppm 1.22 (d, J=6.06 Hz, 6H) 2.51 (s, 2H) 3.53-3.60 (m, 4H) 3.62-3.72 (m, 4H) 3.94 (s, 2H) 4.82 (spt, J=6.19 Hz, 1H) 7.65 (s, 1H) 7.75-7.83 (m, 2H) 8.25 (d, J=10.11 Hz, 1H) 8.33 (d, J=5.56 Hz, 1H) 8.81 (s, 1H). $^{13}$C NMR (100 MHz, DMSO-d$_6$) δ ppm 21.95, 42.48, 45.02, 53.67, 68.26, 106.68, 114.00, 116.54, 122.59, 124.17, 125.11, 134.06, 137.16, 147.16, 154.28, 155.83, 163.92. LRMS (ESI) m/z 397.1 [(M+H)]$^+$, calc'd for C$_{20}$H$_{24}$N$_6$O$_3$: 396.45.

5.6.144. Synthesis of (S)-1-(3,3-dimethylbutyl)-5-(((3-(2-methoxypyridin-3-yl)imidazo[1,2-b]pyridazin-6-yl)amino)methyl)pyrrolidin-2-one

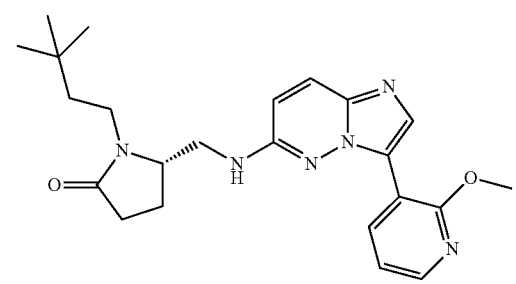 [SMILES: COc1ncccc1-c1cnc2ccc(NC[C@@H]3CCC(=O)N3CCC(C)(C)C)nn12]

This compound was prepared using the approach described in example 5.6.126. ¹H NMR (400 MHz, CHLOROFORM-d) δ ppm 0.91 (s, 9H) 1.35 (td, J=12.25, 5.56 Hz, 1H) 1.48 (td, J=12.38, 4.55 Hz, 1H) 1.90-2.05 (m, 1H) 2.11-2.25 (m, 1H) 2.30-2.53 (m, 2H) 2.88-3.01 (m, 1H) 3.49 (dt, J=14.21, 4.01 Hz, 1H) 3.67-3.81 (m, 2H) 3.95-4.04 (m, 1H) 4.07 (s, 3H) 5.10 (br. s., 1H) 6.66 (d, J=9.60 Hz, 1H) 7.04 (dd, J=7.45, 4.93 Hz, 1H) 7.84 (d, J=9.60 Hz, 1H) 8.06 (s, 1H) 8.19 (dd, J=5.05, 1.77 Hz, 1H) 8.61 (dd, J=7.58, 1.77 Hz, 1H); LRMS (ESI) m/423.0 [(M+H)⁺, calcd for $C_{23}H_{30}N_6O_2$ 422.0].

5.6.145. Synthesis of 4-[3-(2-Isopropoxy-phenyl)-imidazo[1,2-b]pyridazin-6-yl]-piperazine-1-carboxylic acid isopropyl ester

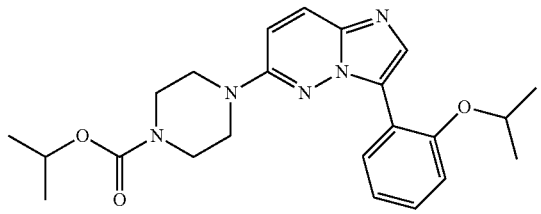 [SMILES: CC(C)OC(=O)N1CCN(c2ccc3ncc(-c4ccccc4OC(C)C)n3n2)CC1]

This compound was prepared using the approach described in example 5.6.111 from 4-(3-bromo-imidazo[1,2-b]pyridazin-6-yl)-piperazine-1-carboxylic acid isopropyl ester (370.2 mg, 1.0 mmol) and 2-isopropoxyphenylboronic acid [138008-97-6] (217.4 mg, 1.2 mmol) to provide 250.7 mg of 4-[3-(2-isopropoxy-phenyl)-imidazo[1,2-b]pyridazin-6-yl]-piperazine-1-carboxylic acid isopropyl ester monohydrochloride as white powder, mp. 216-217° C. (dec.). ¹H NMR (400 MHz, DMSO-d₆) δ ppm 1.22 (dd, J=18.95, 6.06 Hz, 11H) 2.51 (dt, J=3.54, 1.77 Hz, 3H) 3.47-3.53 (m, 4H) 3.54-3.60 (m, 4H) 4.69-4.83 (m, 2H) 7.08-7.13 (m, 1H) 7.22 (d, J=8.34 Hz, 1H) 7.47 (td, J=7.89, 1.64 Hz, 1H) 7.78 (d, J=10.11 Hz, 1H) 7.95 (dd, J=7.71, 1.64 Hz, 1H) 8.25 (t, J=5.05 Hz, 2H). ¹³C NMR (100 MHz, DMSO-d₆) δ ppm 21.70, 21.92, 42.50, 44.87, 68.20, 70.05, 113.38, 115.03, 116.05, 119.86, 121.98, 122.68, 124.87, 130.37, 130.78, 131.87, 154.25, 154.99, 155.54. LRMS (ESI) m/z 424.1 [(M+H)]⁺, calc'd for $C_{23}H_{29}N_5O_3$: 423.52.

5.6.146. Synthesis of Isopropyl 4-(3-bromoimidazo[1,2-b]pyridazin-6-yl)-3-methylpiperazine-1-carboxylate

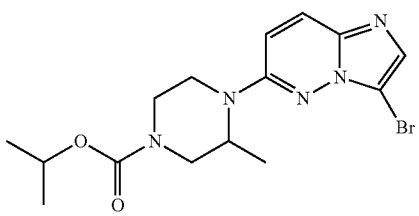 [SMILES: CC(C)OC(=O)N1CCN(c2ccc3ncc(Br)n3n2)C(C)C1]

Part A. tert-Butyl 4-(3-bromoimidazo[1,2-b]pyridazin-6-yl)-3-methylpiperazine-1-carboxylate

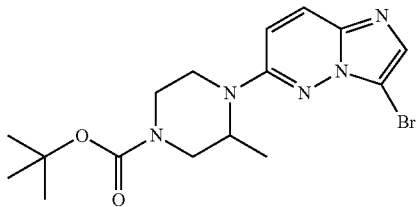 [SMILES: CC1CN(C(=O)OC(C)(C)C)CCN1c1ccc2ncc(Br)n2n1]

A stirred suspension of tert-butyl 3-methyl piperazine-1-carboxylate [120737-59-9] (987.7 mg, 4.9 mmol), 3-bromo-6-fluoro-imidazo[1,2-b]pyridazine (361.7 mg, 4.9 mmol), and Hunig's base [7087-68-5] (0.9 mL, 5.2 mmol) in 2-propanol (40 mL) was heated to 65° C., under N₂ blanket, for 21 d. The cooled reaction suspension was partitioned between brine and ethyl acetate and the extract dried (MgSO₄) and evaporated to obtain 1.2 g of clear brown oil. LRMS (ESI) m/z 215.9/217.9 [(M+H)]⁺, calc'd for $C_{16}H_{22}BrN_6O_2$: 396.29.

Part B. 3-Bromo-6-(2-methylpiperazin-1-yl)imidazo[1,2-b]pyridazine dihydrochloride

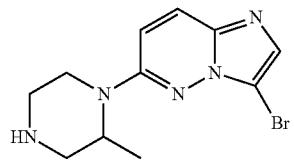 [SMILES: CC1CNCCN1c1ccc2ncc(Br)n2n1]

Concentrated hydrochloric acid (3.0 mL) was added to a solution of tert-butyl 4-(3-bromoimidazo[1,2-b]pyridazin-6-yl)-3-methylpiperazine-1-carboxylate (1.2 g, 3.1 mmol) in methanol (60 mL) and allowed to stir at ambient temperature under N₂ blanket for 3d. The solution was then evaporated to dryness to provide 1.1 g of light brown solid. LRMS (ESI) m/z 295.9/297.9 [(M+H)]⁺, calc'd for $C_{11}H_{14}BrN_5$. 296.17.

Part C. Isopropyl 4-(3-bromoimidazo[1,2-b]pyridazin-6-yl)-3-methylpiperazine-1-carboxylate Hunig's base [7087-68-5] (2.1 mL, 12.1 mmol) was added to an ambient temperature, stirred suspension of 3-bromo-6-(2-methylpiperazin-1-yl)imidazo[1,2-b]pyridazine dihydrochloride (1.1 g, 3.0 mmol) in ethyl acetate (150 mL). The suspension was stirred for 1.5 h then a 1.0M solution of isopropyl chloroformate in toluene (3.0 mL) was slowly added and the reaction allowed to proceed for 17 h then washed with brine. The ethyl acetate phase was dried (MgSO₄) and evaporated. Product was purified by preparative RP-HPLC to provide 52.1 mg of racemic isopropyl 4-(3-bromoimidazo[1,2-b]pyridazin-6-yl)-3-methylpiperazine-1-carboxylate as a light yellow solid, mp. 52-54° C. ¹H NMR (400 MHz, DMSO-d₆) δ ppm 1.11 (d, J=6.57 Hz, 3H) 1.15-1.25 (m, 6H) 2.51 (dt, J=3.73, 1.80 Hz, 2H) 3.15 (dd, J=12.88, 2.78 Hz, 2H) 3.86 (d, J=13.39 Hz, 1H) 3.98 (d, J=13.39 Hz, 2H) 4.47 (br. s., 1H) 4.78-4.87 (m, 1H) 7.23 (d, J=10.10 Hz, 1H) 7.64 (s, 1H) 7.91 (d, J=10.11 Hz, 1H). ¹³C NMR (100 MHz, DMSO-d₆) δ ppm 13.53, 21.90, 42.71, 48.04, 68.05, 99.42, 110.59, 126.00, 131.15, 136.33, 154.41, 154.71. LRMS (ESI) m/z 382.0/384.0 [(M+H)]+, calc'd for $C_{16}H_{20}BrN_6O_2$: 382.26.

5.6.147. Synthesis of Isopropyl 4-(3-bromoimidazo[1,2-b]pyridazin-6-yl)-2-methylpiperazine-1-carboxylate

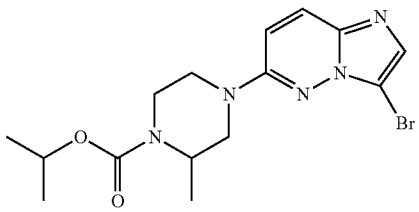 [SMILES: CC(C)OC(=O)N1CCN(c2ccc3ncc(Br)n3n2)CC1C]

Part A. 4-tert-Butyl 1-isopropyl 2-methyl Piperazine-1,4-dicarboxylate

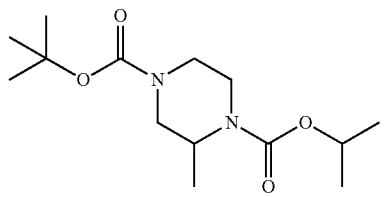 [SMILES: CC(C)OC(=O)N1CCN(C(=O)OC(C)(C)C)CC1C]

To stirred, 0° C., solution of tert-butyl 3-methylpiperazine-1-carboxylate [120737-59-9] (3.0 g, 148.4 mmol) and Hunig's base [7087-65-5] (31.0 mL, 178.0 mmol) in ethyl acetate (300 mL) was added a 1.0 M solution of isopropyl chloroformate in toluene (150 mL). The reaction was allowed to stir and warm to ambient temperature overnight under $N_2$ blanket. The reaction mixture was then washed with brine, dried (CaSO$_4$), and evaporated to afford 4.2 g of clear yellow oil. LRMS (ESI) m/z 193.1 [(M+H)]+, calc'd for $C_{14}H_{26}N_2O_4$: 286.37.

Part B. Isopropyl 2-methylpiperazine-1-carboxylate hydrochloride

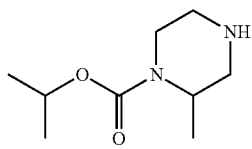

Concentrated hydrochloric acid (6.0 mL) was added to a solution of 4-tert-butyl 1-isopropyl 2-methylpiperazine-1,4-dicarboxylate (4.2 g, 14.6 mmol) in methanol (250 mL) and allowed to stir at ambient temperature under $N_2$ blanket for 3d. The solution was then evaporated to dryness and the resultant viscous yellow oil triturated in acetone to precipitate a fine white powder which was isolated by filtration, under $N_2$ blanket, to afford 2.0 g. LRMS (ESI) m/z 187.0 [(M+H)]+, calc'd for $C_9H_{18}N_2O_2$: 186.26.

Part C. Isopropyl 4-(3-bromoimidazo[1,2-b]pyridazin-6-yl)-2-methylpiperazine-1-carboxylate A stirred suspension of isopropyl 2-methylpiperazine-1-carboxylate hydrochloride (1.8 g, 8.0 mmol), 3-bromo-6-fluoro-imidazo[1,2-b]pyridazine (1.5 g, 6.6 mmol), and Hunig's base [7087-68-5] (5.5 mL, 31.6 mmol) in 2-propanol (40 mL) was heated to reflux, under $N_2$ blanket, for 2 d. The cooled reaction suspension was partitioned between brine and ethyl acetate and the extract dried (MgSO$_4$) and evaporated to obtain 3.0 g of light brown solid. An aliquot of 217 mg of this sample was purified by preparative RP-HPLC to provide 76.4 mg of racemic isopropyl 4-(3-bromoimidazo[1,2-b]pyridazin-6-yl)-2-methylpiperazine-1-carboxylate as a light yellow powder, mp. 144-145° C. $^1$H NMR (400 MHz, DMSO-d$_6$) δ ppm 1.13-1.24 (m, 10H) 2.49-2.52 (m, 2H) 3.19-3.32 (m, 2H) 3.87 (d, J=13.39 Hz, 1H) 4.02 (d, J=13.39 Hz, 1H) 4.78-4.86 (m, 1H) 7.22 (d, J=10.10 Hz, 1H) 7.60 (s, 1H) 7.89 (d, J=10.11 Hz, 1H). $^{13}$C NMR (100 MHz, DMSO-d$_6$) δ ppm 15.57, 21.93, 37.98, 44.82, 46.94, 48.94, 68.01, 99.25, 110.49, 126.08, 131.50, 136.47, 154.20, 155.35. LRMS (ESI) m/z 382.0/384.0 [(M+H)]+, calc'd for $C_{15}H_{20}BrN_5O_2$: 382.26.

5.6.148. Synthesis of 4-[3-(2-Hydroxy-pyridin-3-yl)-imidazo[1,2-b]pyridazin-6-yl]-piperazine-1-carboxylic acid isopropyl ester

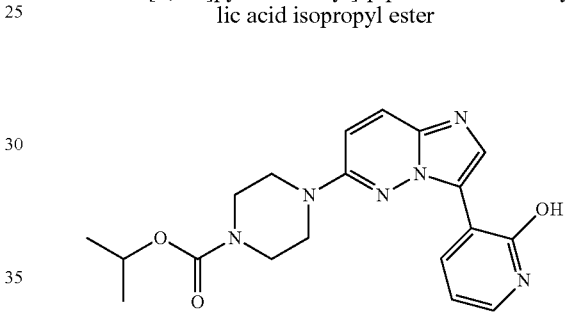

Prepared from 4-[3-(2-methoxy-pyridin-3-yl)-imidazo[1,2-b]pyridazin-6-yl]-piperazine-1-carboxylic acid isopropyl ester by hydrochloric acid hydrolysis in methanol to provide 4-[3-(2-methoxy-pyridin-3-yl)-imidazo[1,2-b]pyridazin-6-yl]-piperazine-1-carboxylic acid isopropyl ester di-hydrochloride as a white powder, mp. 275-276° C. $^1$H NMR (400 MHz, DMSO-d$_6$) δ ppm 1.15 (d, J=6.06 Hz, 5H) 3.51 (br. s., 7H) 4.37 (s, 4H) 4.67-4.79 (m, 1H) 6.51 (t, J=6.82 Hz, 1H) 7.45-7.57 (m, 2H) 7.97 (d, J=10.10 Hz, 1H) 8.41 (s, 1H) 8.65 (dd, J=7.33, 1.77 Hz, 1H). $^{13}$C NMR (100 MHz, DMSO-d$_6$) δ ppm 21.58, 42.23, 44.60, 69.30, 106.47, 115.89, 116.31, 121.12, 122.00, 122.89, 131.50, 135.26, 139.85, 155.11, 155.49, 159.85. LRMS (ESI) m/z 383.1 [(M+H)]+, calc'd for $C_{19}H_{22}N_6O_3$: 382.43.

5.6.149. Synthesis of (S)-Tert-butyl 2-(((3-(difluoromethyl)imidazo[1,2-b]pyridazin-6-yl)amino)methyl)pyrrolidine-1-carboxylate

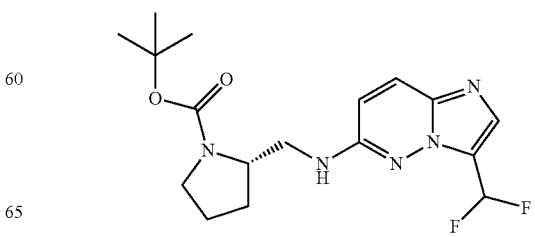

Part A.
6-chloro-3-(difluoromethyl)imidazo[1,2-b]pyridazine

To a solution of 6-chloroimidazo[1,2-b]pyridazine-3-carbaldehyde (0.36 g, 2 mmol) in DCM (1 mL) was added a solution of Deoxo-Fluor (0.67 mL, 3.6 mmol) in DCM (2 mL) and EtOH (0.023 mL, 0.5 mmol) at rt. After stirring at it for overnight, the solution was poured into saturated $NaHCO_3$ and extracted with DCM (2×20 mL), dried over $Na_2SO_4$, filtered and evaporated in vacuo. The crude was purified by ISCO column chromatography (50% EtOAC/hexane) to give 6-chloro-3-(difluoromethyl)imidazo[1,2-b]pyridazine as white solid (180 mg, 50% yield). $^1$H NMR (400 MHz, METHANOL-$d_4$) δ ppm 8.15 (d, J=9.60 Hz, 1H), 8.03-8.06 (m, 1H), 7.18-7.49 (m, 2H); LRMS (ESI) m/e 203.9 [(M+H)$^+$, calcd for $C_7H_5ClF_2N_3$ 204.6].

Part B. (S)-tert-butyl 2-(((3-(difluoromethyl)imidazo[1,2-b]pyridazin-6-yl)amino)methyl)pyrrolidine-1-carboxylate This compound was prepared using the approach described in example 5.6.68. $^1$H NMR (400 MHz, METHANOL-$d_4$) δ ppm 7.62-7.67 (m, 2H), 7.10-7.40 (m, 1H), 6.81 (d, J=9.60 Hz, 1H), 4.15 (bs, 1H), 3.37-3.41 (m, 4H), 1.87-2.06 (m, 4H), 1.44 (br. s., 9H); LRMS (ESI) m/e 368.0 [(M+H)$^+$, calcd for $C_{17}H_{24}F_2N_6O_2$ 368.4].

5.6.150. Synthesis of (S)—N-(tert-butyl)-2-(((3-cyanoimidazo[1,2-b]pyridazin-6-yl)amino)methyl)pyrrolidine-1-carboxamide

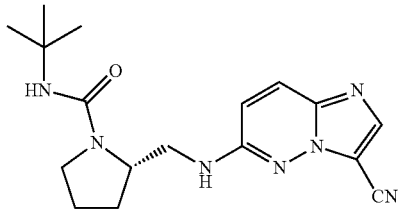 [SMILES: CC(C)(C)NC(=O)N1CCC[C@H]1CNc1ccc2ncc(C#N)n2n1]

This compound was prepared using the approach described in example 5.6.68. $^1$H NMR (400 MHz, METHANOL-$d_4$) δ ppm 8.02 (s, 1H), 7.73 (d, J=9.85 Hz, 1H), 6.91 (d, J=9.85 Hz, 1H), 5.15 (s, 1H), 4.25 (m, 1H), 3.35-3.50 (m, 3H), 3.30 (m, 1H), 1.92-2.17 (m, 4H), 1.30 (s, 9H); LRMS (ESI) m/e 342.3 [(M+H)$^+$, calcd for $C_{17}H_{24}N_7O$ 342.4].

5.6.151. Synthesis of 4-[3-(2-Methoxy-pyridin-3-yl)-imidazo[1,2-b]pyridazin-6-yl]-piperazine-1-carboxylic acid isopropyl ester

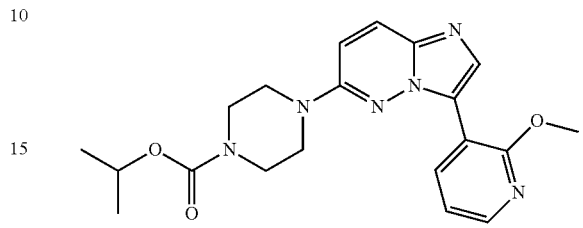

This compound was prepared using the approach described in example 5.6.111 from 4-(3-bromo-imidazo[1,2-b]pyridazin-6-yl)-piperazine-1-carboxylic acid isopropyl ester (309.2 mg, 0.8 mmol) and 2-methoxypyridine-3-boronic acid [163105-90-6] (154.8 mg, 1.0 mmol) to provide 94.0 mg of 4-[3-(2-methoxy-pyridin-3-yl)-imidazo[1,2-b]pyridazin-6-yl]-piperazine-1-carboxylic acid isopropyl ester di-hydrochloride as yellow powder, mp. 179-181° C. (dec.). $^1$H NMR (400 MHz, DMSO-$d_6$) δ ppm 1.20-1.24 (m, 6H) 2.51 (dt, J=3.54, 1.77 Hz, 2H) 3.50-3.61 (m, 7H) 3.62-3.68 (m, 1H) 3.98 (s, 2H) 4.78-4.86 (m, 1H) 7.24 (dd, J=7.58, 5.05 Hz, 1H) 7.69 (d, J=10.10 Hz, 1H) 8.18-8.25 (m, 1H) 8.28-8.35 (m, 2H) 8.56 (dd, J=7.58, 1.77 Hz, 1H). $^{13}$C NMR (100 MHz, DMSO-$d_6$) δ ppm 21.93, 42.50, 45.01, 53.64, 68.20, 109.84, 115.44, 116.90, 122.75, 122.83, 125.22, 133.07, 138.18, 146.97, 154.26, 155.45, 159.81. LRMS (ESI) m/z 397.0 [(M+H)]$^+$, calc'd for $C_{20}H_{24}N_6O_3$: 396.45.

5.6.152. Synthesis of tert-butyl 4-(3-bromoimidazo[1,2-b]pyridazin-6-yl)hexahydropyrrolo[3,2-b]pyrrole-1(2H)-carboxylate

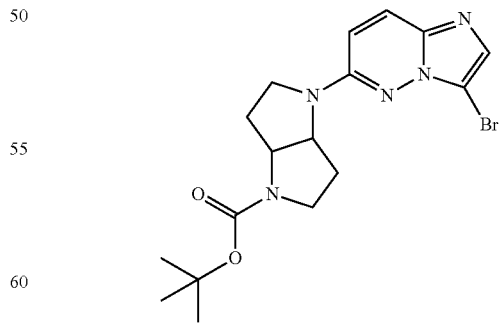

This compound was prepared using the approach described in example 5.6.68. $^1$H NMR (400 MHz, METHANOL-$d_4$) δ ppm 7.73 (d, J=9.85 Hz, 1H), 7.44-7.50 (m, 1H), 6.96-6.99 (m, 1H), 4.49-4.66 (m, 2H), 3.52-3.85 (m, 3H), 3.21-3.39 (m, 2H), 2.14-2.32 (m, 3H), 1.46-1.57 (m, 9H); LRMS (ESI) m/e 409.9 [(M+H)⁺, calcd for $C_{17}H_{23}BrN_6O$ 409.3].

5.6.153. Synthesis of (S)-tert-butyl 2-(((3-(methyl-carbamoyl)imidazo[1,2-b]pyridazin-6-yl)amino) methyl)pyrrolidine-1-carboxylate

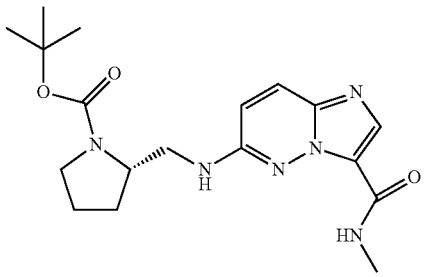 [SMILES: CNC(=O)c1cnc2ccc(NC[C@@H]3CCCN3C(=O)OC(C)(C)C)nn12]

Part A.
6-chloroimidazo[1,2-b]pyridazine-3-carboxylic acid

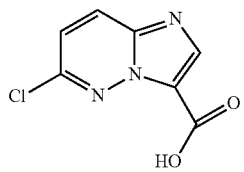 [SMILES: O=C(O)c1cnc2ccc(Cl)nn12]

To a solution of 6-chloroimidazo[1,2-b]pyridazine-3-carbaldehyde (1.82 g, 10 mmol), in t-BuOH (90 mL) and 2-methyl-2-butene in THF (30 mL, 2.0 M) was added a solution of sodium chlorite (80%, 9.0 g, 100 mmol) and $NaH_2PO_4$ (1 g, 8 mmol) in water (45 mL). The mixture was stirred at rt for overnight, concentrated, diluted with water, acidified to PH=4, precipitated white solid, filtered to give 6-chloroimidazo[1,2-b]pyridazine-3-carboxylic acid as white solid (1.2 g, 67% yield)). ¹H NMR (400 MHz, DMSO-d₆) δ ppm 8.29 (d, J=9.60 Hz, 1H), 8.22 (s, 1H), 7.50 (d, J=9.60 Hz, 1H); LRMS (ESI) m/e 198.1 [(M+H)⁺, calcd for $C_7H_6ClN_3O_2$ 198.6].

Part B. 6-chloro-N-methylimidazo[1,2-b]pyridazine-3-carboxamide

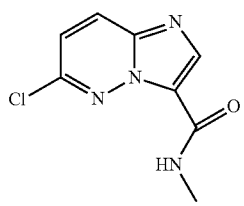

Regular amide coupling reaction afforded the titled compound. ¹H NMR (400 MHz, METHANOL-d₄) δ ppm 8.37 (d, J=1.77 Hz, 1H), 8.24 (dd, J=9.60, 2.02 Hz, 1H), 7.56 (dd, J=9.47, 2.15 Hz, 1H), 3.08 (d, J=2.02 Hz, 3H); LRMS (ESI) m/e 211.0 [(M+H)⁺, calcd for $C_8H_8ClN_4O$ 211.6].

Part C. (S)-tert-butyl 2-(((3-(methylcarbamoyl)imidazo[1,2-b]pyridazin-6-yl)amino)methyl)pyrrolidine-1-carboxylate This compound was prepared using the approach described in example 5.6.68. ¹H NMR (400 MHz, CHLOROFORM-d) δ ppm 8.66 (br. s., 1H), 8.19 (s, 1H), 7.82 (d, J=9.60 Hz, 1H), 7.28 (s, 1H), 7.22 (br. s., 1H), 6.72 (d, J=9.60 Hz, 1H), 4.29 (br. s., 1H), 3.32-3.51 (m, 5H), 3.07-3.11 (m, 3H), 2.11-2.21 (m, 1H), 1.91-2.02 (m, 2H), 1.77-1.85 (m, 1H), 1.46-1.52 (m, 9H); LRMS (ESI) m/e 375.2 [(M+H)⁺, calcd for $C_{18}H_{27}N_6O_3$ 375.4].

5.6.154. Synthesis of Isopropyl 5-(3-(2-methoxyphenyl)imidazo[1,2-b]pyridazin-6-yl)-2,5-diazabicyclo [2.2.1]heptane-2-carboxylate

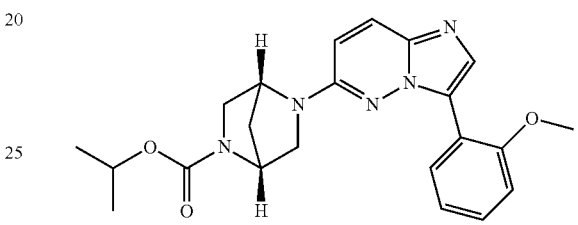

Part A. (1S,4S)-2-tert-Butyl 5-isopropyl 2,5-diazabicyclo[2.2.1]heptane-2,5-dicarboxylate

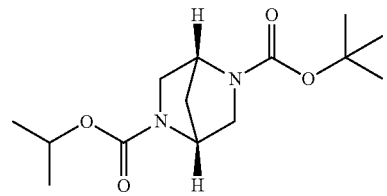 [SMILES: CC(C)OC(=O)N1C[C@H]2C[C@@H]1CN2C(=O)OC(C)(C)C]

To a stirred, ambient temperature, solution (1S,4S)-tert-butyl 2,5-diazabicyclo[2.2.1]heptane-2-carboxylate [113451-59-5] (1.0 g, 5.0 mmol) and Hunig's base [7087-68-5] (1.4 mL, 8.0 mmol) in ethyl acetate (120 mL) was slowly added a 1.0M solution of isopropyl chloroformate in toluene (5.1 mL) over the course of 10 minutes. The reaction was allowed to stir over night then was washed with brine, dried (MgSO₄), and evaporated to obtain 1.3 g of yellow oil. LRMS (ESI) m/z 285.1 [(M+H)]⁺, calc'd for $C_{14}H_{24}N_2O_4$: 284.35.

Part B. (1S,4S)-Isopropyl 2,5-diazabicyclo[2.2.1]heptane-2-carboxylate

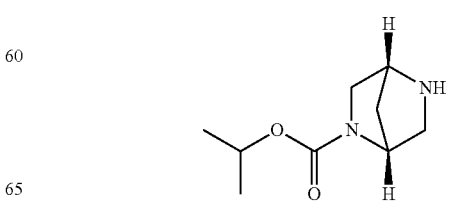

(1S,4S)-2-tert-Butyl 5-isopropyl 2,5-diazabicyclo[2.2.1]heptane-2,5-dicarboxylate (1.3 g, 4.6 mmol) was dissolved in methanol (200 mL). Concentrated hydrochloric acid (6 mL, 72 mmol) was added and the solution stirred at 50° C. for 2 h, then evaporated to dryness to provide (1S,4S)-isopropyl 2,5-diazabicyclo[2.2.1]heptane-2-carboxylate hydrochloride as 0.9 g of white solid. LRMS (ESI) m/z 185.1 [(M+H)]+, calc'd for $C_9H_{16}N_2O_2$: 184.24.

Part C. Isopropyl 5-(3-bromoimidazo[1,2-b]pyridazin-6-yl)-2,5-diazabicyclo[2.2.1]heptane-2-carboxylate

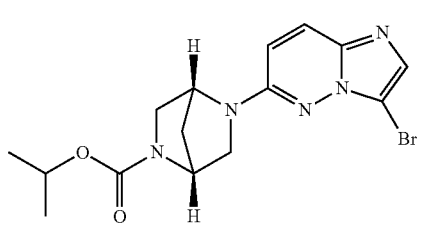 [SMILES: CC(C)OC(=O)N1C[C@H]2C[C@@H]1CN2c1ccc2ncc(Br)n2n1]

A solution of (1S,4S)-isopropyl 2,5-diazabicyclo[2.2.1]heptane-2-carboxylate hydrochloride (0.9 g, 4.2 mmol), 3-bromo-6-fluoroimidazo[1,2-b]pyridazine (1.0 g, 4.6 mmol), and Hunig's base [7087-68-5] (3.0 mL, 17.2 mmol) in 2-propanol (21 mL) was stirred at reflux under $N_2$ blanket for 3d then partitioned between brine and ethyl acetate. The extract was dried ($MgSO_4$) and evaporated to obtain 1.6 g of yellow solid. LRMS (ESI) m/z 380.0/382.0 [(M+H)]+, calc'd for $C_{16}H_{18}BrN_6O_2$: 380.24.

Part D. Isopropyl 5-(3-(2-methoxyphenyl)imidazo[1,2-b]pyridazin-6-yl)-2,5-diazabicyclo[2.2.1]heptane-2-carboxylate To a mixture of isopropyl 5-(3-bromoimidazo[1,2-b]pyridazin-6-yl)-2,5-diazabicyclo[2.2.1]heptane-2-carboxylate (429.1 mg, 1.1 mmol), 2-methoxyphenylboronic acid [5720-06-9] (206.7 mg, 1.4 mmol), potassium phosphate tribasic monohydrate [27176-10-9] (520.7 mg, 2.3 mmol), and [1,1'-bis(diphenylphosphino)-ferrocene]dichloropalladium(II), complex with dichloromethane [95464-05-4] (93.4 mg, 0.1 mmol) contained in a 50 mL round bottomed flask was added a solution of 30% (v/v) water in 1,2-dimethoxyethane (25 mL) and a magnetic stir bar. The reaction pot was fitted to a reflux condenser, lowered into an ambient temperature oil bath, and the system taken through 10 evacuation/$N_2$ blanket cycles while being rapidly stirred. The rapidly stirred, $N_2$ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried ($MgSO_4$), evaporated and flash chromatographed (silica get eluted with 10% (v/v) methanol/ethyl acetate to afford a brown oil which was further purified by preparative RP-HPLC. Isolated product was dissolved in methanol, diluted with concentrated hydrochloric acid, evaporated to dryness, redissolved in methanol and precipitated by the addition of diethyl ether. Filtration of the precipitate yields 207.1 mg of the product monohydrochloride salt as a yellow powder, mp. 173-174° C. 1H NMR (400 MHz, DMSO-$d_6$) δ ppm 1.06-1.31 (m, 7H) 1.91-2.06 (m, 2H) 3.30 (br. s., 1H) 3.40 (br. s., 2H) 3.58 (d, J=9.60 Hz, 1H) 3.84 (5, 3 H) 4.54 (d, J=9.60 Hz, 1H) 4.67-4.79 (m, 1H) 4.84 (br. s., 1H) 7.13 (br. s., 1H) 7.24 (d, J=8.08 Hz, 1H) 7.51 (t, J=7.20 Hz, 2H) 7.95 (br. s., 1H) 8.20 (d, J=10.11 Hz, 1H) 8.27 (s, 1H). 13C NMR (100 MHz, DMSO-$d_6$) δ ppm 13.88, 21.94, 22.00, 28.29, 31.19, 36.44, 36.92, 52.49, 55.67, 56.08, 56.44, 56.95, 57.43, 67.74, 111.65, 114.33, 116.61, 120.16, 121.59, 121.87, 124.72, 130.33, 131.05, 131.70, 153.57, 153.74, 156.91. LRMS (ESI) m/z 408.3 [(M+H)]+, calc'd for $C_{22}H_{25}N_5O_3$: 407.47

5.6.155. Synthesis of [4-(3-Pyridin-2-yl-imidazo[1,2-b]pyridazin-6-yl)-piperazin-1-yl]-pyrrolidin-1-yl-methanone

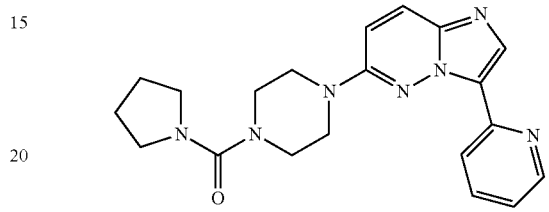

Part A. [4-(3-Bromo-pyrazolo[1,5-a]pyrimidin-5-yl)-piperazin-1-yl]-pyrrolidin-1-yl-methanone

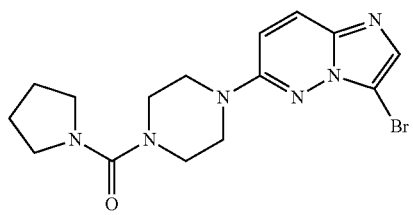 [SMILES: O=C(N1CCCC1)N1CCN(c2ccc3ncc(Br)n3n2)CC1]

To a magnetically stirred, ambient temperature, $N_2$ blanketed, solution of 3-bromo-6-piperazin-1-yl-imidazo[1,2-b]pyridazine dihydrochloride (3.1 g, 8.8 mmol) and Hunig's base [7087-68-5] (6.2 mL, 35.6 mmol) in ethyl acetate (200 mL) was added pyrrolidine-1-carbonyl chloride [1192-63-8] (1.2 mL, 10.9 mmol). The reaction was allowed to proceed over night to result in a well stirred suspension. Once complete, the reaction was washed with brine, dried ($MgSO_4$), and diluted with heptane to afford precipitate a fine light yellow powder, 2.6 g in two crops. LRMS (ESI) m/z 379.0/381.0 [(M+H)]+, calc'd for $C_{15}H_{19}BrN_6O$: 379.26.

Part B. [4-(3-Pyridin-2-yl-imidazo[1,2-b]pyridazin-6-yl)-piperazin-1-yl]-pyrrolidin-1-yl-methanone To a mixture of [4-(3-bromo-pyrazolo[1,5-a]pyrimidin-5-yl)-piperazin-1-yl]-pyrrolidin-1-yl-methanone (381.0 mg, 01.0 mmol), 2-(4,4,5,5-tetramethyl-1,3,2-dioxaborolan-2-yl)pyridine [874186-98-8] (512.7 mg, 2.5 mmol), copper chloride [7758-89-6] (99.4 mg, 1.0 mmol), cesium carbonate [534-17-8] (651.8 mg, 2.0 mmol) and [1,1'-bis(diphenylphosphino)ferrocene]dichloropalladium(II), complex with dichloromethane [95464-05-4] (82.1 mg, 0.1 mmol) contained in a 25 mL round bottomed flask was added anhydrous DMF and a magnetic stir bar. The reaction pot was fitted to a reflux condenser, lowered into an ambient temperature oil bath, and the system taken through 10 evacuation/$N_2$ blanket cycles while being rapidly stirred. The rapidly stirred, $N_2$ blanketed, reaction was heated to an oil bath temperature of 100° C. for 17 h then cooled and partitioned between brine and ethyl acetate. The phase separated extract was dried (MgSO₄) and evaporated to afford a brown oil which was purified by preparative RP-HPLC. Isolated product was dissolved in methanol, diluted with concentrated hydrochloric acid, evaporated to dryness, redissolved in methanol and precipitated by the addition of diethyl ether. Filtration of the precipitate yielded 83.2 mg of [4-(3-pyridin-2-yl-imidazo[1,2-b]pyridazin-6-yl)-piperazin-1-yl]-pyrrolidin-1-yl-methanone dihydrochloride salt as a light yellow powder, mp. 202-203° C. ¹H NMR (400 MHz, DMSO-d₆) δ ppm 1.73-1.84 (m, 4H) 3.33 (t, J=6.44 Hz, 4H) 3.36-3.43 (m, 4H) 3.62-3.72 (m, 4H) 7.45-7.52 (m, 1H) 7.66 (d, J=10.11 Hz, 1H) 8.08 (td, J=7.83, 1.77 Hz, 1H) 8.18 (d, J=10.10 Hz, 1H) 8.54 (s, 1H) 8.60 (d, J=8.08 Hz, 1H) 8.72 (d, J=4.55 Hz, 1H). ¹³C NMR (100 MHz, DMSO-d₆) δ ppm 25.04, 45.05, 45.27, 47.84, 114.83, 121.12, 123.43, 123.55, 126.59, 127.01, 134.87, 138.20, 145.21, 149.07, 155.74, 161.49. LRMS (ESI) m/z 378.2 [(M+H)]⁺, calc'd for C₂₀H₂₃N₇O: 377.45.

5.6.156. Synthesis of {(S)-1-[3-(2-Methoxy-pyridin-3-yl)-imidazo[1,2-b]pyridazin-6-yl]-pyrrolidin-3-yl}-methyl-carbamic acid isopropyl ester

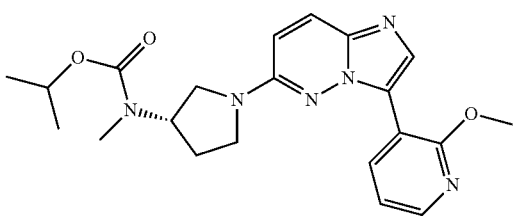 [SMILES: COc1ncccc1-c1cnc2ccc(N3CC[C@H](N(C)C(=O)OC(C)C)C3)nn12]

Part A. [(S)-1-(3-Bromo-imidazo[1,2-b]pyridazin-6-yl)-pyrrolidin-3-yl]-methyl-carbamic acid tert-butyl ester

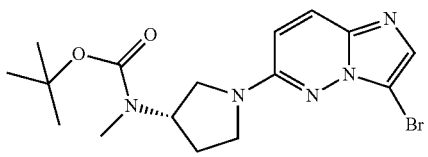

A mixture of (S)-pyrrolidin-3-yl-carbamic acid tert-butyl ester (2.8 g, 15 mmol), 3-bromo-6-fluoro-imidazo[1,2-b]pyridazine (2.16 g, 10 mmol), and triethylamine (5.58 ml, 40 mmol) in isopropyl alcohol (10 ml) was heated in a microwave at 140° C. for 30 min. The reaction mixture was concentrated and the residue was passed through a short column to afford the desired product (3.8 g). To a solution of above product (3.8 g) in DMF (40 ml) at 0° C. was added MeI (1.13 ml). The mixture was stirred at 0° C. for 5 min., NaH (800 mg, 60% oil dispersion, 20 mmol) was added portionwise. The reaction mixture was stirred at 0° C. for 5 min. and at rt for 30 min., then it was treated with water and diluted with EtOAc (250 ml). The mixture was washed with water (100 ml) and brine (100 ml). The aqueous layer was back extracted with EtOAc (2×50 ml). The combined EtOAc was dried (Na₂SO₄) and concentrated. The residue was subjected to ISCO (120 g column) to afford the titled compound (3.1 g). ¹H NMR (400 MHz, CHLOROFORM-d) δ ppm 1.43 (s, 9H) 2.04-2.22 (m, 2H) 2.78 (s, 3H) 3.37 (dd, J=10.80, 7.28 Hz, 1H) 3.46 (dt, J=10.36, 8.05 Hz, 1H) 3.65-3.72 (m, 2H) 4.87 (br. s., 1H) 6.53 (d, J=9.70 Hz, 1H) 7.44 (s, 1H) 7.64 (d, J=9.70 Hz 1H). LRMS (ESI) m/z 396 and 398.1 [(M+H)]⁺, calc'd for C₁₆H₂₂BrN₆O₂: 396.29.

Part B. [(S)-1-(3-Bromo-imidazo[1,2-b]pyridazin-6-yl)-pyrrolidin-3-yl]-methyl-carbamic acid isopropyl ester To a solution of [(S)-1-(3-bromo-imidazo[1,2-b]pyridazin-6-yl)-pyrrolidin-3-yl]-methyl-carbamic acid tert-butyl ester (1.35 g, 3.4 mmol) in MeOH (80 ml) at 0° C. was added AcCl (2.5 ml, 35 mmol). The resulting mixture was stirred at rt for overnight. The mixture was concentrated to afford a white solid as the product (1.25 g).

The above product (610 mg, 1.65 mmol) and DIEA (1.44 ml, 8.25 mmol)) was suspended in THF (15 ml). To the suspension was added a solution of isopropyl chloroformate in toluene (1M, 2 ml, 2 mmol). The resulting mixture was stirred at it for 5 h. The mixture was concentrated and the residue was subjected to ISCO (12 g column) to give the titled compound (350 mg). ¹H NMR (400 MHz, CHLOROFORM-d) δ ppm 1.27 (d, J=6.32 Hz, 6H) 2.09-2.28 (m, 2H) 2.87 (s, 3H) 3.39-3.56 (m, 2H) 3.68-3.79 (m, 2H) 4.96 (m, 2H) 6.57 (d, J=9.85 Hz, 1H) 7.49 (s, 1H) 7.64 (d, J=9.85 Hz, 1H). LRMS (ESI) m/z 382.1 and 384.1 [(M+H)]⁺, calc'd for C₁₅H₂₀BrN₅O₂: 382.26.

Part C. {(S)-1-[3-(2-Methoxy-pyridin-3-yl)-imidazo[1,2-b]pyridazin-6-yl]-pyrrolidin-3-yl}-methyl-carbamic acid isopropyl ester A mixture of [(S)-1-(3-bromo-imidazo[1,2-b]pyridazin-6-yl)-pyrrolidin-3-yl]-methyl-carbamic acid isopropyl ester (88 mg, 0.23 mmol), 2-methoxypyridine-3-boronic acid (46 mg, 0.3 mmol), K₂CO₃ (95 mg, 0.69 mmol) and dichlorobis(triphenylphosphine)palladium(II) (8.4 mg, 0.012 mmol) in MeCN/water (3.2 ml/0.8 ml) was heated in a microwave at 150° C. for 15 min. The water layer was removed and the organic layer was diluted with MeCN and filtered. The filtrate was subjected to preparative HPLC to give the titled compound (82.5 mg). ¹H NMR (400 MHz, CHLOROFORM-d) δ ppm 1.29 (d, J=6.06 Hz, 6H) 2.13-2.32 (m, 2H) 2.89 (s, 3H) 3.43 (dd, J=10.48, 6.95 Hz, 1H) 3.48-3.56 (m, 1H) 3.69-3.76 (m, 2H) 4.09 (s, 3H) 4.99 (dt, J=12.38, 6.19 Hz, 2H) 6.62 (d, J=9.85 Hz, 1H) 7.04 (dd, J=7.45, 4.93 Hz, 1H) 7.79 (d, J=9.85 Hz, 1H) 8.13-8.19 (m, 2H) 8.86 (dd, J=7.71, 1.64 Hz, 1H). LRMS (ESI) m/z 411.2 [(M+H)]⁺, calc'd for C₂₁H₂₆N₆O₃: 410.48.

5.6.157. Synthesis of Cyclopentanecarboxylic acid {(S)-1-[3-(2-hydroxy-pyridin-3-yl)-imidazo[1,2-b]pyridazin-6-yl]-pyrrolidin-3-yl}-methyl-amide

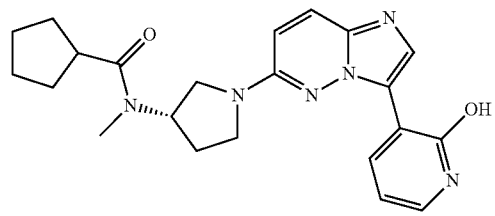 [SMILES: CN(C(=O)C1CCCC1)[C@H]1CCN(c2ccc3ncc(-c4cccnc4O)n3n2)C1]

Part A. {(S)-1-[3-(2-Methoxy-pyridin-3-yl)-imidazo[1,2-b]pyridazin-6-yl]-pyrrolidin-3-yl}-methyl-carbamic acid tert-butyl ester

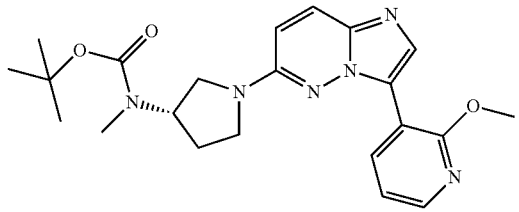 [SMILES: COc1ncccc1-c1cnc2ccc(N3CC[C@H](N(C)C(=O)OC(C)(C)C)C3)nn12]

A mixture of [(S)-1-(3-bromo-imidazo[1,2-b]pyridazin-6-yl)-pyrrolidin-3-yl]-methyl-carbamic acid tert butyl ester (83 mg, 0.21 mmol), 2-methoxypyridine-3-boronic acid (43 mg, 0.28 mmol), $K_2CO_3$ (87 mg, 0.63 mmol) and dichlorobis(triphenylphosphine)palladium(II) (7.4 mg, 0.011 mmol) in MeCN/water (3.2 ml/0.8 ml) was heated in a microwave at 150° C. for 15 min. The water layer was removed and the organic layer was diluted with MeCN and filtered. The filtrate was subjected to preparative HPLC to give the titled compound (69.3 mg). $^1$H NMR (400 MHz, CHLOROFORM-d) δ ppm 1.50 (s, 9H) 2.11-2.29 (m, 2H) 2.84 (s, 3H) 3.40 (dd, J=10.48, 6.95 Hz, 1H) 3.46-3.53 (m, 1H) 3.67-3.74 (m, 2H) 4.08 (s, 3H) 4.94 (br. s., 1H) 6.61 (d, J=9.60 Hz, 1H) 7.03 (dd, J=7.58, 4.80 Hz, 1H) 7.77 (d, J=9.85 Hz, 1H) 8.12-8.18 (m, 2H) 8.86 (dd, J=7.58, 1.77 Hz, 1H). LRMS (ESI) m/z 425.3 [(M+H)]$^+$, calc'd for $C_{22}H_{28}N_6O_3$: 424.51.

Part B. Cyclopentanecarboxylic acid {(S)-1-[3-(2-hydroxy-pyridin-3-yl)-imidazo[1,2-b]pyridazin-6-yl]-pyrrolidin-3-yl}-methyl-amide To a solution of {(S)-1-[3-(2-methoxy-pyridin-3-yl)-imidazo[1,2-b]pyridazin-6-yl]-pyrrolidin-3-yl}-methyl-carbamic acid tert-butyl ester (540 mg, 1.27 mmol) in MeOH (40 ml) at 0° C. was added AcCl (1.2 ml), 16.8 mmol). The resulting mixture was stirred at rt for overnight. The mixture was concentrated to afford the product.

To a mixture of above product (80 mg, 0.2 mmol) and TEA (112 ul, 0.8 mmol) in DCM (2 ml) was added cyclopentanecarbonyl chloride at rt. The resulting mixture was stirred at rt for overnight. The mixture was concentrated and the residue was subjected to preparative HPLC to afford the titled compound (49.9 mg). $^1$H NMR (400 MHz, CHLOROFORM-d) δ ppm 1.57-1.67 (m, 2H) 1.74-1.93 (m, 6H) 2.12-2.22 (m, 1H) 2.27-2.35 (m, 1H) 2.95 (t, J=7.28 Hz, 2H) 3.04 (s, 2H) 3.42 (dd, J=10.14, 6.62 Hz, 1H) 3.52-3.62 (m, 1H) 3.78 (t, J=9.04 Hz, 2H) 5.50 (t, J=7.28 Hz, 1H) 6.47-6.51 (m, 1H) 6.63 (d, J=9.70 Hz, 1H) 7.40 (d, J=5.95 Hz, 1H) 7.83 (d, J=9.48 Hz, 1H) 8.77 (s, 1H) 9.12 (d, J=6.62 Hz, 1H). LRMS (ESI) m/z 407.2 [(M+H)]$^+$, calc'd for $C_{22}H_{26}N_6O_2$: 406.49.

5.6.158. Synthesis of (S)—N-(1-(3-(2-methoxyphenyl)imidazo[1,2-b]pyridazin-6-yl)pyrrolidin-3-yl)-N-methylpyrrolidine-1-carboxamide

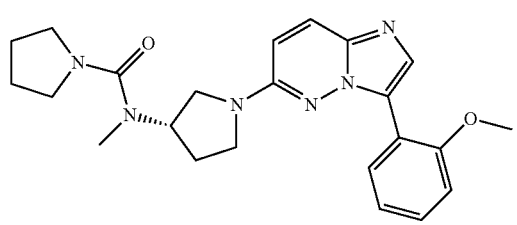 [SMILES: COc1ccccc1-c1cnc2ccc(N3CC[C@H](N(C)C(=O)N4CCCC4)C3)nn12]

This compound was prepared using the approach described in example 5.6.42. $^1$H NMR (400 MHz, CHLOROFORM-d) δ ppm 1.78-1.92 (m, 4H) 2.13 (dq, J=12.63, 8.76 Hz, 1H) 2.21-2.32 (m, 1H) 2.81 (s, 3H) 3.31-3.50 (m, 6H) 3.67-3.82 (m, 2H) 3.89 (s, 3H) 4.64 (quin, J=7.83 Hz, 1H) 6.59 (d, J=9.60 Hz, 1H) 7.04 (d, J=8.34 Hz, 1H) 7.09 (td, J=7.58, 1.01 Hz, 1H) 7.33 (ddd, J=8.21, 7.45, 1.77 Hz, 1H) 7.74 (d, J=9.60 Hz, 1H) 7.99 (s, 1H) 8.30 (dd, J=7.71, 1.64 Hz, 1H); LRMS (ESI) m/421.0 [(M+H)$^+$, calcd for $C_{23}H_{28}N_6O_2$ 420.0].

5.6.159. Synthesis of (S)—N-(1-(3-(2-methoxypyridin-3-yl)imidazo[1,2-b]pyridazin-6-yl)pyrrolidin-3-yl)-N-methylpyrrolidine-1-carboxamide

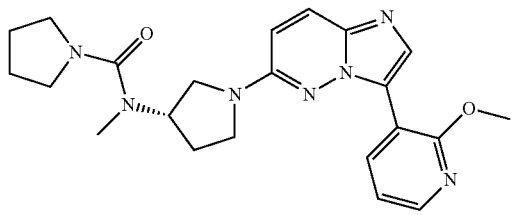 [SMILES: COc1ncccc1-c1cnc2ccc(N3CC[C@H](N(C)C(=O)N4CCCC4)C3)nn12]

This compound was prepared using the approach described in example 5.6.42. $^1$H NMR (400 MHz, CHLOROFORM-d) δ ppm 1.82-1.93 (m, 4H) 2.12-2.25 (m, 1H) 2.27-2.38 (m, 1H) 2.85 (s, 3H) 3.35-3.46 (m, 5H) 3.47-3.56 (m, 1H) 3.70-3.78 (m, 1H) 3.83 (dd, J=10.36, 8.08 Hz, 1H) 4.09 (s, 3H) 4.61-4.74 (m, 1H) 6.70 (d, J=9.85 Hz, 1H) 7.05 (dd, J=7.58, 5.05 Hz, 1H) 7.92 (d, J=9.85 Hz, 1H) 8.12-8.20 (m, 2H) 8.85 (dd, J=7.58, 1.77 Hz, 1H); LRMS (ESI) m/422.0 [(M+H)$^+$, calcd for $C_{22}H_{27}N_7O_2$ 421.0].

5.6.160. Synthesis of (S)-isopropyl(1-(3-(5-fluoro-2-methoxyphenyl)imidazo[1,2-b]pyridazin-6-yl)pyrrolidin-3-yl)(methyl)carbamate

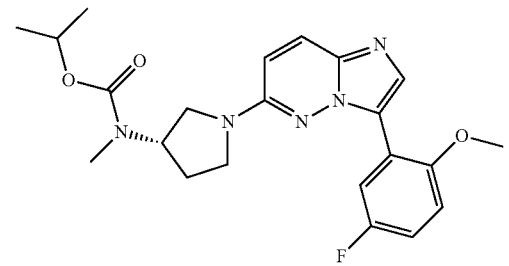 [SMILES: COc1ccc(F)cc1-c1cnc2ccc(N3CC[C@H](N(C)C(=O)OC(C)C)C3)nn12]

Part A. [(S)-1-(3-Bromo-imidazo[1,2-b]pyridazin-6-yl)-pyrrolidin-3-yl]-methyl-amine

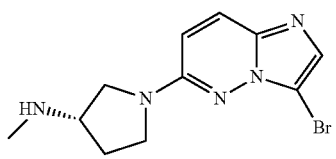 [SMILES: CN[C@H]1CCN(c2ccc3ncc(Br)n3n2)C1]

[(S)-1-(3-Bromo-imidazo[1,2-b]pyridazin-6-yl)-pyrrolidin-3-yl]-carbamic acid tert-butyl ester (1.2 g, 3.1 mmol) taken up in 15 mL DMF and cooled to 0° C. in an ice bath. Iodomethane (342 uL, 5.42 mmol) added and stirred 5 minutes. Then sodium hydride 60% in oil (251 mg, 6.2 mmol) was slowly added. Reaction stirred 5 minutes at 0° C. then removed from ice bath and stirred 30 minutes at room temperature. Reaction was quenched with ice then extracted with ethyl acetate 2×. Ethyl acetate fractions combined dried over magnesium sulfate filtered reduce in vacuo. This was then taken up in 26 mL DCM and 4 mL TFA added. Stirred 1 hour until complete by LC/MS. Reaction washed with 1N NaOH, DCM layer removed dried over magnesium sulfate filtered, reduced in vacuo to get 951 mg crude product carried on as is to part B. LRMS (ESI) m/z 296/298 [(M+H)]$^+$, calc'd for $C_{11}H_{14}BrN_5$: 296.17.

Part B. [(S)-1-(3-Bromo-imidazo[1,2-b]pyridazin-6-yl)-pyrrolidin-3-yl]-methyl-carbamic acid isopropyl ester

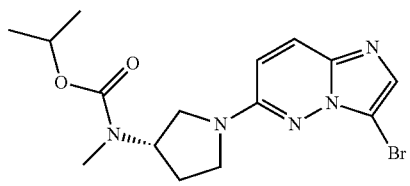 [SMILES: CC(C)OC(=O)N(C)[C@H]1CCN(c2ccc3ncc(Br)n3n2)C1]

[(S)-1-(3-Bromo-imidazo[1,2-b]pyridazin-6-yl)-pyrrolidin-3-yl]-methyl-amine (951 mg, 3.2 mmol) was taken up in DCM, and ethyl chloroformate (459 uL, 4.8 mmol) and triethylamine (895 uL, 6.4 mmol) were added. The reaction was stirred at room temperature under nitrogen for 1 hour. The reaction mixture was then washed with water then 1N HCl. The DCM layer was dried over magnesium sulfate, filtered and reduced in vacuo to give crude product (1.1 g) that was used as is in part C. LRMS (ESI) m/z 382/384 [(M+H)]$^+$, calc'd for $C_{15}H_{20}BrN_5O_2$: 382.26.

Part C. (S)-isopropyl(1-(3-(5-fluoro-2-methoxyphenyl)imidazo[1,2-b]pyridazin-6-yl)pyrrolidin-3-yl)(methyl)carbamate

[(S)-1-(3-Bromo-imidazo[1,2-b]pyridazin-6-yl)-pyrrolidin-3-yl]-methyl-carbamic acid isopropyl ester (120 mg, 0.3 mmol), 5-fluoro-2-methoxy phenyl boronic acid (107 mg, 0.6 mmol), potassium carbonate (65 mg, 0.45 mmol), and Pd(dppf)Cl$_2$ dichloromethane (26 mg, 0.03 mmol) were taken up in 2 mL acetonitrile and 1 mL water and microwaved in a sealed tube at 140° C. for 15 minutes. Reaction was then filtered through celite with acetonitrile reduced in vacuo, then purified on shimadzu neutral phase prep and product fractions lyophilized to get 52 mg (S)-isopropyl(1-(3-(5-fluoro-2-methoxyphenyl)imidazo[1,2-b]pyridazin-6-yl)pyrrolidin-3-yl)(methyl)carbamate. $^1$H NMR (400 MHz, DMSO-d$_6$) δ 8.33-8.38 (m, 1H), 7.99 (s, 1H), 7.91 (d, J=9.85 Hz, 1H), 7.13-7.18 (m, 2H), 6.92 (d, J=9.85 Hz, 1H), 4.76-4.86 (m, 2H), 3.87 (s, 3H), 3.63-3.70 (m, 2H), 3.36-3.50 (m, 2H), 2.80 (s, 3H), 2.10-2.22 (m, 2H), 1.21 (d, J=6.32 Hz, 6H). (ESI) m/z 428 [(M+H)]$^+$, calc'd for $C_{22}H_{26}FN_5O_3$: 427.4.

5.6.161. Synthesis of (S)-isopropyl(1-(3-(2-methoxy-5-methylpyridin-3-yl)imidazo[1,2-b]pyridazin-6-yl)pyrrolidin-3-yl)(methyl)carbamate

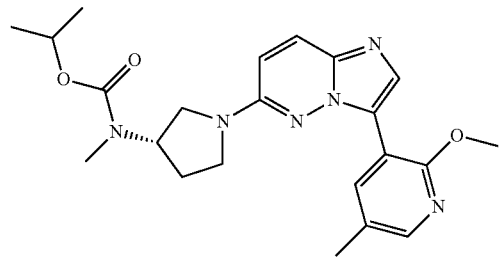 [SMILES: COc1ncc(C)cc1-c1cnc2ccc(N3CC[C@H](N(C)C(=O)OC(C)C)C3)nn12]

[(S)-1-(3-Bromo-imidazo[1,2-b]pyridazin-6-yl)-pyrrolidin-3-yl]-methyl-carbamic acid isopropyl ester (120 mg, 0.3 mmol), 2-methoxy-5-methylpyridine-3-boronic acid (105 mg, 0.6 mmol), potassium carbonate (65 mg, 0.45 mmol), and Pd(dppf)Cl$_2$ dichloromethane (26 mg, 0.03 mmol) were taken up in 2 mL acetonitrile and 1 mL water and microwaved in a sealed tube at 140° C. for 15 minutes. Reaction was then filtered through celite with acetonitrile reduced in vacuo, the purified on shimadzu neutral phase prep and product fractions lyophilized to afford 65 mg (S)-isopropyl(1-(3-(2-methoxy-5-methylpyridin-3-yl)imidazo[1,2-b]pyridazin-6-yl)pyrrolidin-3-yl)(methyl)carbamate. $^1$H NMR (400 MHz, DMSO-d$_6$) δ 8.75 (d, J=2.02 Hz, 1H), 7.99 (s, 1H), 7.94-7.97 (m, 1H), 7.91 (d, J=9.60 Hz, 1H), 6.92 (d, J=9.85 Hz, 1H), 4.75-4.85 (m, 2H), 3.95 (s, 3H), 3.64-3.70 (m, 2H), 3.38-3.51 (m, 2H), 2.81 (s, 3H), 2.29 (s, 3H), 2.11-2.23 (m, 2H), 1.21 (d, J=6.32 Hz, 6H). (ESI) m/z 425 [(M+H)]$^+$, calc'd for $C_{22}H_{28}N_6O_3$: 424.5.

5.6.162. Synthesis of {(S)-1-[3-(1,6-Dimethyl-2-oxo-1,2-dihydro-pyridin-3-yl)-imidazo[1,2-b]pyridazin-6-yl]-pyrrolidin-3-yl}-methyl-carbamic acid isopropyl ester

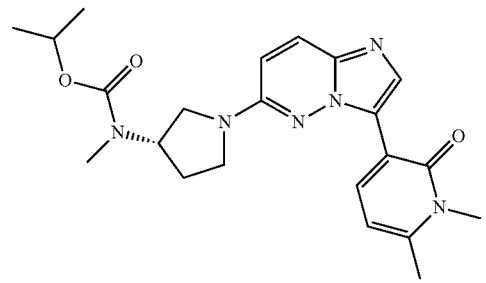 [SMILES: Cc1ccc(-c2cnc3ccc(N4CC[C@H](N(C)C(=O)OC(C)C)C4)nn23)c(=O)n1C]

Part A. 3-Bromo-1,6-dimethyl-1H-pyridin-2-one

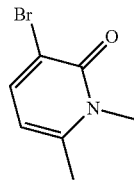

3-Bromo-6-methylpyridine-2-ol (2 g, 10.6 mmol) was taken up in THF and stirred. Sodium hydride (60% in oil 510 mg, 12.7 mmol) was added portion wise then stirred 30 minutes. Lithium bromide (1.85 g, 21.2 mmol) was added and stirred for 1 hour. Then iodomethane (1.32 mL, 21.2 mmol) was added and the reaction mixture was stirred overnight. The reaction mixture was diluted with DCM and washed with 1N NaOH. The DCM layer was dried over magnesium sulfate, filtered and dried in vacuo to afford 1.19 g product carried on to next step as is. LRMS (ESI) m/z 202/204 [(M+H)]+, calc'd for $C_7H_8BrNO$: 202.05.

Part B. 1,6-dimethyl-1H-pyridine-2-one-3-boronic acid

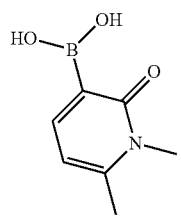

3-Bromo-1,6-dimethyl-1H-pyridin-2-one (1.19 g, 5.9 mmol) taken up in 10 mL DMF under nitrogen. Bis(pinacalato)diborane (2.24 g, 8.8 mmol), potassium acetate (1.73 g, 17.7 mmol), and PD(dppf)Cl₂ dichloromethane (481 mg, 0.59 mmol) were added, and the reaction mixture was heated to 85° C. and stirred overnight. The reaction mixture was cooled to room temperature and filtered through celite with acetonitrile. This was reduced in vacuo and taken up in 1N NaOH and washed with DCM. The aqueous layer was then made acidic with 1N HCl and extracted with DCM. The DCM layer was dried over magnesium sulfate filtered and reduced in vacuo to yield 929 mg>90% for use in Part C. LRMS (ESI) m/z 167 [(M+H)]+, calc'd for $C_7H_{10}BNO_3$: 166.97.

Part C. {(S)-1-[3-(1,6-Dimethyl-2-oxo-1,2-dihydro-pyridin-3-yl)-imidazo[1,2-b]pyridazin-6-yl]-pyrrolidin-3-yl}-methyl-carbamic acid isopropyl ester

[(S)-1-(3-Bromo-imidazo[1,2-b]pyridazin-6-yl)-pyrrolidin-3-yl]-methyl-carbamic acid isopropyl ester (120 mg, 0.3 mmol), 1,6-dimethyl-1H-pyridine-2-one-3-boronic acid (105 mg, 0.6 mmol), potassium carbonate (65 mg, 0.45 mmol), and Pd(dppf)Cl₂ dichloromethane (26 mg, 0.3 mmol) were taken up in 2 mL acetonitrile and 1 mL water and microwaved in a sealed tube at 140° C. for 15 minutes. The reaction mixture was then filtered through celite with acetonitrile, reduced in vacuo, and purified on Shimadzu neutral phase prep and the product fractions were lyophilized to get 43 mg {(S)-1-[3-(1,6-Dimethyl-2-oxo-1,2-dihydro-pyridin-3-yl)-imidazo[1,2-b]pyridazin-6-yl]-pyrrolidin-3-yl}-methyl-carbamic acid isopropyl ester. ¹H NMR (400 MHz, DMSO-d₆) δ 8.91 (d, J=7.58 Hz, 1H), 8.45 (s, 1H), 7.88 (d, J=9.60 Hz, 1H), 6.87 (d, J=9.85 Hz, 1H), 6.36 (d, J=8.08 Hz, 1H), 4.77-4.88 (m, 2H), 3.67 (dd, J=7.58, 10.61 Hz, 2H), 3.39-3.51 (m, 2H), 3.31 (s, 2H), 2.82 (s, 3H), 2.42 (s, 3H), 2.10-2.22 (m, 2H), 1.22 (dd, J=1.89, 6.19 Hz, 6H). (ESI) m/z 425 [(M+H)]+, calc'd for $C_{22}H_{28}N_6O_3$: 424.51.

5.6.163. Synthesis of (S)-isopropyl(1-(3-(2-methoxy-6-methylpyridin-3-yl)imidazo[1,2-b]pyridazin-6-yl)pyrrolidin-3-yl)(methyl)carbamate

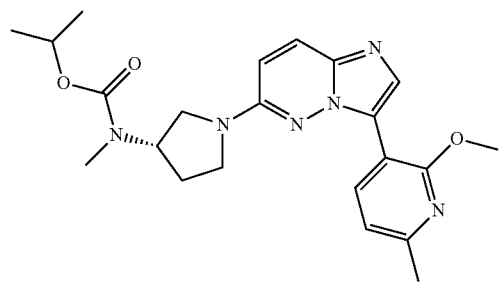 [SMILES: COc1nc(C)ccc1-c1cnc2ccc(N3CC[C@H](N(C)C(=O)OC(C)C)C3)nn12]

To 80 mg (0.217 mmol) of (S)-isopropyl(1-(3-bromoimidazo[1,2-b]pyridazin-6-yl)pyrrolidin-3-yl)(methyl)carbamate in a microwave vial was added, 54 mg (0.326 mmol) of (2-methoxy-6-methylpyridin-3-yl)boronic acid, 92 mg (0.435 mmol) of K₃PO₄, 18 mg (0.022 mmol) PdCl₂(dppf)₂, 3 mL of DME and then 1 mL water. The resulting mixture was microwaved at 140° C. for 0.5 hr. It was diluted with EtOAc, washed with brine, and the organic layer was dried over MgSO₄. It was concentrated and purified on the neutral PREP HPLC to obtain 50.6 mg of the desired product. ¹H NMR (400 MHz, CHLOROFORM-d) δ ppm 1.30 (d, J=6.32 Hz, 6H) 2.13-2.31 (m, 2H) 2.53 (s, 3H) 2.89 (s, 3H) 3.43 (dd, J=10.61, 7.07 Hz, 1H) 3.49-3.56 (m, 1H) 3.70-3.76 (m, 2H) 4.06 (s, 3H) 4.99 (m, 2H) 6.61 (d, J=9.85 Hz, 1H) 6.89 (d, J=7.83 Hz, 1H) 7.79 (d, J=9.85 Hz, 1H) 8.12 (s, 1H) 8.69 (d, J=7.83 Hz, 1H). LRMS (ESI) m/e 425 [(M+H)+, calcd for $C_{22}H_{28}N_6O_3$ 424].

5.6.164. Synthesis of (S)-2-amino-1-(4-(3-(2-methoxypyridin-3-yl)imidazo[1,2-b]pyridazin-6-yl)piperazin-1-yl)-4-methylpentan-1-one

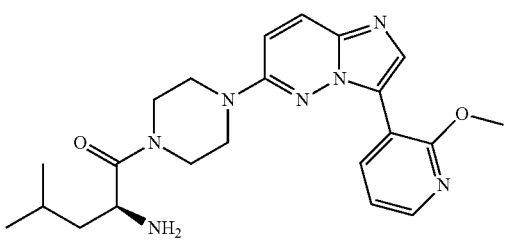 [SMILES: COc1ncccc1-c1cnc2ccc(N3CCN(C(=O)[C@@H](N)CC(C)C)CC3)nn12]

Part A. (S)-tert-Butyl(4-methyl-1-oxo-1-(piperazin-1-yl)pentan-2-yl)carbamate

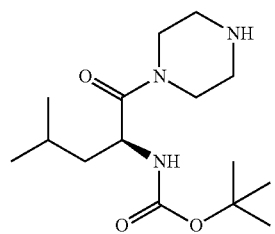 [SMILES: CC(C)C[C@H](NC(=O)OC(C)(C)C)C(=O)N1CCNCC1]

To 1.00 g (4.33 mmol) of (S)-2-((tert-butoxycarbonyl)amino)-4-methylpentanoic acid was added 750 mg (8.66 mmol) of piperazine, 20 mL of DCM, 1.34 g (6.5 mmol) of DCC and 17.9 mL (12.99 mmol) of TEA. This was allowed to stir overnight at room temperature. The next morning, it was diluted with more DCM, and filtered. The filtrate was concentrated and purified in the ISCO using a 40 gram column and eluting with 0-10% MeOH/DCM to obtain the desired product in 79% yield.

Part B. (S)-tert-Butyl(1-(4-(imidazo[1,2-b]pyridazin-6-yl)piperazin-1-yl)-4-methyl-1-oxopentan-2-yl)carbamate

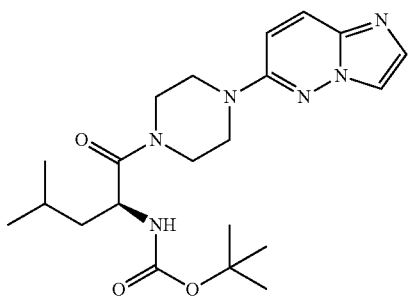 [SMILES: CC(C)C[C@H](NC(=O)OC(C)(C)C)C(=O)N1CCN(c2ccc3nccn3n2)CC1]

To 305 mg (2.23 mmol) of 6-fluoroimidazo[1,2-b]pyridazine, was added 1.00 g (3.34 mmol) of (S)-tert-butyl(4-methyl-1-oxo-1-(piperazin-1-yl)pentan-2-yl)carbamate, 10 mL of isopropyl alcohol, and 0.93 mL (6.68 mmol) of TEA. This was microwaved at 150° C. for 0.5 hr. It was diluted with EtOAc, washed with brine, and the organic layer was dried over $MgSO_4$, and then concentrated. It was purified on the ISCO with a 40 gram column eluting with 0-10% MeOH/DCM to obtain the desired product in 78% yield.

Part C. (S)-tert-Butyl(1-(4-(3-bromoimidazo[1,2-b]pyridazin-6-yl)piperazin-1-yl)-4-methyl-1-oxopentan-2yl)carbamate

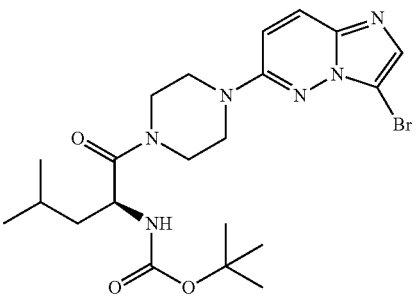 [SMILES: CC(C)C[C@H](NC(=O)OC(C)(C)C)C(=O)N1CCN(c2ccc3ncc(Br)n3n2)CC1]

To 104 mg (0.25 mmol) of (S)-tert-butyl(1-(4-(imidazo[1,2-b]pyridazin-6-yl)piperazin-1-yl)-4-methyl-1-oxopentan-2-yl)carbamate dissolved in 5 mL of AcOH was added bromine (48 mg, 0.3 mmol) and the resulting mixture was stirred at room temperature. After 0.25 hr, the reaction was done, and concentrated by rotavap and then by high vacuum pump to obtain 139 mg (100% yield) of mono-acetic acid salt of the desired product.

Part D. (S)-2-Amino-1-[4-(3-bromo-pyrazolo[1,5-a]pyrimidin-5-yl)-piperazin-1-yl]-4-methylpentan-1-one

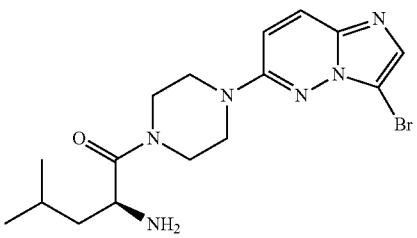 [SMILES: CC(C)C[C@H](N)C(=O)N1CCN(c2ccc3ncc(Br)n3n2)CC1]

To 139 mg (0.25 mmol) the mono-acetic acid salt of (S)-tert-butyl(1-(4-(3-bromoimidazo[1,2-b]pyridazin-6-yl)piperazin-1-yl)-4-methyl-1-oxopentan-2-yl)carbamate in 5 ml DCM was added 2 mL of TFA, and the resulting mixture stirred at room temperature for 1 hr. This was concentrated to obtain 100% desired product (as di-TFA salt).

Part E. (S)-2-amino-1-(4-(3-(2-methoxypyridin-3-yl)imidazo[1,2-b]pyridazin-6-yl)piperazin-1-yl)-4-methylpentan-1-one To 124 mg (0.20 mmol) of (S)-2-amino-1-(4-(3-bromoimidazo[1,2-b]pyridazin-6-yl)piperazin-1-yl)-4-methylpentan-1-one (di-TFA acid salt) in a microwaveable vial was added 51 mg (0.33 mmol) of the (2-methoxypyridin-3-yl)boronic acid, 110 mg (0.80 mmol) of $K_2CO_3$, 31 mg of $PdCl_2(dppf)_2$ 3 mL of MeCN and 1.5 mL of water. This was microwaved for 0.5 hr at 140° C. It was then diluted with EtOAc, washed with brine, and the organic layer was dried over $MgSO_4$ and concentrated. It was purified on by neutral PREP HPLC to obtain 51.6 mg (61%) of the desired product. $^1$H NMR (400 MHz, METHANOL-$d_4$) δ ppm 0.98-1.10 (m, 6H) 1.60-1.84 (m, 3H) 3.48-3.60 (m, 2H) 3.62-3.81 (m, 5H) 3.94-4.02 (m, 1H) 4.05 (s, 3H) 4.48 (dd, J=9.47, 4.17 Hz, 1H) 7.13 (dd, J=7.45, 4.93 Hz, 1H) 7.27 (d, J=9.85 Hz, 1H) 7.88 (d, J=9.85 Hz, 1H) 8.01 (s, 1H) 8.17 (dd, J=5.05, 1.77 Hz, 1H) 8.51 (s, 2H) 8.66 (dd, J=7.58, 1.77 Hz, 1H).

5.6.165. Synthesis of Methyl 1-(3-(2-methoxypyridin-3-yl)imidazo[1,2-b]pyridazin-6-yl)-1H-pyrazole-4-carboxylate

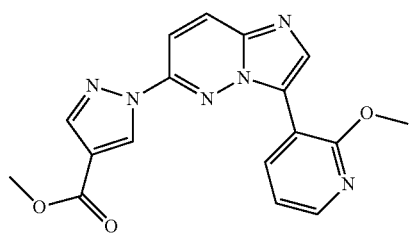

163

Part A. 3-Bromo-6-hydrazinylimidazo[1,2-b]pyridazine

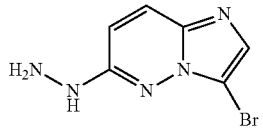 [SMILES: NNc1ccc2ncc(Br)n2n1]

A suspension of 3-bromo-6-fluoroimidazo[1,2-b]pyridazine (2.16 g, 10 mmol) in hydrazine monohydrate (10 mL) was heated at 70° C. for 30 minutes. The mixture was cooled to room temperature, and the titled compound (1.78 g) was collected by filtration. $^1$H NMR (400 MHz, DMSO-$d_6$) δ ppm 4.27 (br. s., 2H) 6.78 (d, J=9.60 Hz, 1H) 7.51 (s, 1H) 7.73 (dd, J=9.60, 1.52 Hz, 1H) 8.20 (br. s., 1H).

Part B. Methyl 1-(3-bromoimidazo[1,2-b]pyridazin-6-yl)-1H-pyrazole-4-carboxylate

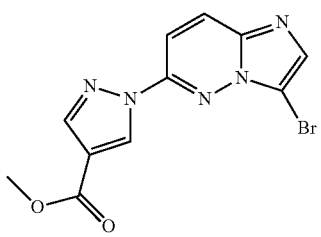 [SMILES: COC(=O)c1cnn(-c2ccc3ncc(Br)n3n2)c1]

A mixture of 3-bromo-6-hydrazinylimidazo[1,2-b]pyridazine (866 mg, 3.8 mmol) and methyl 2-formyl-3-oxopropanoate (500 mg, 3.8 mmol) in EtOH (20 mL) was heated at 70° C. overnight. The mixture was concentrated and treated with MeOH. The titled compound (410 mg) was collected by filtration. $^1$H NMR (400 MHz, CHLOROFORM-d) δ ppm 3.94 (s, 3H) 7.84 (s, 1H) 8.01 (d, J=9.60 Hz, 1H) 8.11 (d, J=9.60 Hz, 1H) 8.19 (s, 1H) 9.09 (s, 1H).

Part C. Methyl 1-(3-(2-methoxypyridin-3-yl)imidazo[1,2-b]pyridazin-6-yl)-1H-pyrazole-4-carboxylate The captioned compound was obtained using typical Suzuki coupling conditions with methyl 1-(3-bromoimidazo[1,2-b]pyridazin-6-yl)-1H-pyrazole-4-carboxylate and an appropriate boronic acid. $^1$H NMR (400 MHz, CHLOROFORM-d) δ ppm 3.92 (s, 3H) 4.08 (s, 3H) 7.15 (dd, J=7.58, 5.05 Hz, 1H) 7.98 (d, J=9.60 Hz, 1H) 8.14-8.21 (m, 2H) 8.26-8.33 (m, 2H) 8.46 (dd, J=7.58, 2.02 Hz, 1H) 8.83 (s, 1H). LRMS (ESI) m/z 351.0 [(M+H)]$^+$, calc'd for $C_{22}H_{29}N_7O_2$: 350.33.

5.6.166. Synthesis of Macrocycle

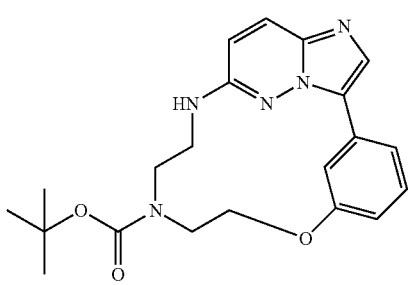 [SMILES: CC(C)(C)OC(=O)N1CCNc2ccc3ncc(n3n2)-c2cccc(c2)OCC1]

164

Part A. 2-(3-Bromo-phenoxy)-ethanol

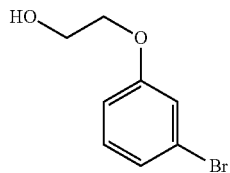 [SMILES: OCCOc1cccc(Br)c1]

2-Bromoethanol [540-51-2] (5.8 mL, 78.9 mmol) was added to a stirred ambient temperature suspension of 3-bromophenol [591-20-8] (9.0 g, 52.3 mmol) and potassium carbonate [584-08-7] (36.2 g, 262.1 mmol) in acetone (260 mL) contained in a 500 mL round bottomed flask. The reaction flask was fitted with a reflux condenser and heated to reflux overnight, cooled, filtered and evaporated to obtain 11.7 g of clear light brown oil. Flash chromatography (silica gel, eluted with 50% (v/v) ethyl acetate/heptane) provided 4.5 g of 2-(3-bromo-phenoxy)-ethanol as a clear yellow oil. LRMS (ESI) m/z 217.0/219.0 [(M+H)]$^+$, calc'd for $C_8H_9O_2Br$: 217.06.

Part B. N1-(2-(3-bromophenoxy)ethyl)ethane-1,2-diamine

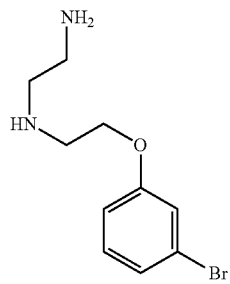

To a magnetically stirred, ambient temperature solution of 2-(3-bromo-phenoxy)-ethanol (3.6 g, 16.7 mmol) and N-methylmorpholine [109-02-4] (2.2 mL, 20.0 mmol) in ethyl acetate (200 mL) was added methanesulfonyl chloride [124-63-0] (1.3 mL, 16.8 mmol). The reaction was stirred over night then washed with brine and the phase separated ethyl acetate extract dried (MgSO$_4$) and added to a stirred ambient temperature solution of ethylenediamine [107-15-3] (33.3 mL, 497.0 mmol) in ethyl acetate (300 mL) from a pressure equalizing addition funnel over the course of 15 minutes. The addition funnel was replaced with a condenser and the reaction refluxed for 4 h then cooled and washed with brine. The ethyl acetate phase was dried (CaSO$_4$) and evaporated to obtain N$^1$-(2-(3-bromophenoxy)ethyl)ethane-1,2-diamine as 4.7 g of clear yellow liquid. LRMS (ESI) m/z 259.1/261.1 [(M+H)]$^+$, calc'd for $C_{10}H_{15}BrN_2O$: 259.15.

Part C. N-{2-[2-(3-Bromo-phenoxy)-ethylamino]-ethyl}-2,2,2-trifluoro-acetamide

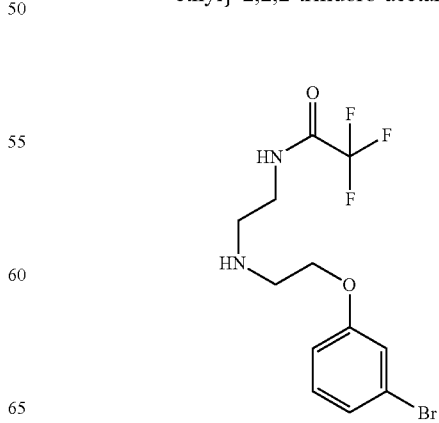

To a stirred, 0° C., solution of N¹-(2-(3-bromophenoxy) ethyl)ethane-1,2-diamine (4.7 g, 17.9 mmol) in anhydrous tetrahydrofuran (180 mL) was added ethyl trifluoroacetate [383-63-1] (2.1 mL, 17.9 mmol). The resultant solution was allowed to stir under N₂ blanket for 15 minutes then evaporated to dryness to obtain N-{2-[2-(3-Bromo-phenoxy)-ethylamino]-ethyl}-2,2,2-trifluoro-acetamide as 6.3 g of yellow solid. LRMS (ESI) m/z 355.1/357.1 [(M+H)]⁺, calc'd for $C_{12}H_{14}BrF_3N_2O_2$: 355.16.

Part D. [2-(3-Bromo-phenoxy)-ethyl]-[2-(2,2,2-trifluoro-acetylamino)-ethyl]-carbamic acid tert-butyl ester

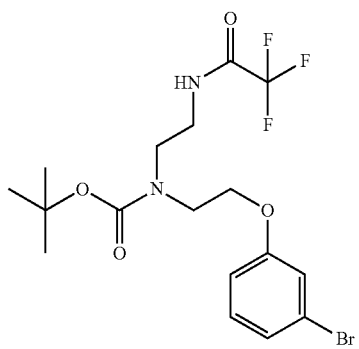 [SMILES: CC(C)(C)OC(=O)N(CCNC(=O)C(F)(F)F)CCOc1cccc(Br)c1]

Di-t-butyl pyrocarbonate [24424-99-5] (4.7 g, 21.44 mmol) was added to an ambient temperature solution of N-{2-[2-(3-Bromo-phenoxy)-ethylamino]-ethyl}-2,2,2-trifluoro-acetamide (6.3 g, 17.6 mmol) and Hunig's base [7087-68-5] (3.1 mL, 17.8 mmol) in ethyl acetate (150 mL) and allowed to stir under N₂ blanket for 1 h then washed with brine, dried (CaSO₄), evaporated, and flash chromatographed (silica gel, eluted with 30% (v/v) ethyl acetate/heptane) to provide 5.5 g of [2-(3-bromo-phenoxy)-ethyl]-[2-(2,2,2-trifluoro-acetylamino)-ethyl]-carbamic acid tert-butyl ester as a clear colorless oil. LRMS (ESI) m/z 399.1/401.1 [(M-tert-bu+H)]⁺, calc'd for $C_{17}H_{22}BrF_3N_2O_4$: 455.28.

Part E. (2-Amino-ethyl)-[2-(3-bromo-phenoxy)-ethyl]-carbamic acid tert-butyl ester

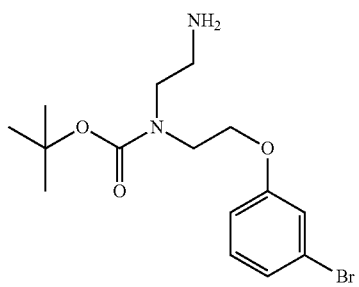 [SMILES: CC(C)(C)OC(=O)N(CCN)CCOc1cccc(Br)c1]

Potassium carbonate [584-08-7] (35.8 g, 259.2 mmol) was added to a solution of [2-(3-bromo-phenoxy)-ethyl]-[2-(2,2,2-trifluoro-acetylamino)-ethyl]-carbamic acid tert-butyl ester (4.7 g, 10.3 mmol) in 10% (v/v) aqueous methanol (200 mL) and stirred at 50° C. for 5 h. The reaction mixture was filtered, the filtrate evaporated to dryness, dissolved in ethyl acetate, washed with brine, dried (CaSO₄) and evaporated to yield 3.8 g of (2-amino-ethyl)-[2-(3-bromo-phenoxy)-ethyl]-carbamic acid tert-butyl ester as a clear yellow oil. LRMS (ESI) m/z 359.1/361.1 [(M+H)]⁺, calc'd for $C_{15}H_{23}BrN_2O_3$: 359.27.

Part F. [2-(3-Bromo-imidazo[1,2-b]pyridazin-6-ylamino)-ethyl]-[2-(3-bromo-phenoxy)-ethyl]-carbamic acid tert-butyl ester

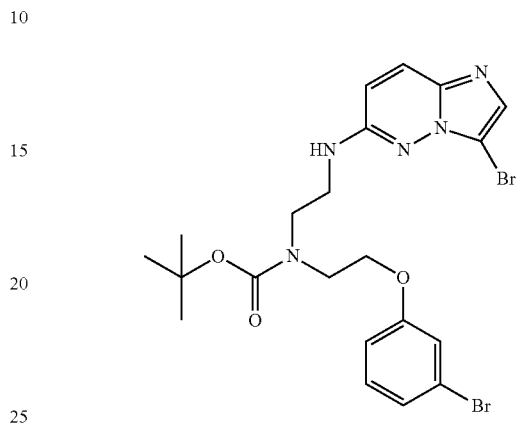

A stirred mixture of 3-bromo-6-fluoro-imidazo[1,2-b]pyridazine (1.9 g, 9.0 mmol), (2-amino-ethyl)-[2-(3-bromophenoxy)-ethyl]-carbamic acid tert-butyl ester (3.8 g, 10.6 mmol), and Hunig's base [7087-68-5] (3.1 mL, 17.8 mmol) in 2-propanol (45 mL) was heated to 65° C., under N₂ blanket, for 17 h. The cooled reaction solution was partitioned between brine and ethyl acetate. The extract was dried (CaSO₄) and evaporated to afford 5.1 g of brown oil. This oil was flash chromatographed (silica gel, eluted with 100% ethyl acetate), then the product crystallized (ethyl acetate/heptane) to afford [2-(3-bromo-imidazo[1,2-b]pyridazin-6-ylamino)-ethyl]-[2-(3-bromo-phenoxy)-ethyl]-carbamic acid tert-butyl ester as 2.7 g of fine white crystalline powder, mp. 134-135° C. ¹H NMR (400 MHz, DMSO-d₆) ppm 1.27 (br. s., 5H) 1.33 (br. s., 4H) 2.51 (s, 1H) 3.41-3.52 (m, 3H) 3.55 (br. s., 1H) 3.63 (br. s., 2H) 4.14 (br. s., 2H) 6.69 (d, J=9.35 Hz, 1H) 6.94 (dd, J=8.21, 2.15 Hz, 1H) 7.08-7.29 (m, 4H) 7.48 (s, 1H) 7.70 (d, J=9.60 Hz, 1H). ¹³C NMR (100 MHz, DMSO-d₆) δ ppm 27.85, 45.46, 45.77, 46.28, 66.04, 78.72, 99.00, 112.79, 113.89, 117.34, 122.05, 123.50, 125.47, 130.35, 131.10, 136.55, 153.98, 154.76, 159.27. LRMS (ESI) m/z 554.1/556.1/558.1 [(M+H)]⁺, calc'd for $C_{21}H_{25}Br_2N_5O_3$: 555.27.

Part G. Macrocycle

To a mixture of [2-(3-bromo-imidazo[1,2-b]pyridazin-6-ylamino)-ethyl]-[2-(3-bromo-phenoxy)-ethyl]-carbamic acid tert-butyl ester (818.1 mg, 1.47 mmol), bis(pinacolato) diboron [73183-34-3] (1.9 g, 7.4 mmol), potassium phosphate tribasic monohydrate [27176-10-9] (1.7 g, 7.3 mmol), and [1,1'-bis(diphenylphosphino)-ferrocene]dichloropalladium(II), complex with dichloromethane [95464-05-4] (241.2 mg, 0.3 mmol) contained in a 250 mL round bottomed flask was added a solution of 30% (v/v) water in 1,2-dimethoxyethane (125 mL) and a magnetic stir bar. The reaction pot was fitted to a reflux condenser, lowered into an ambient temperature oil bath, and the system taken through 10 evacuation/N₂ blanket cycles while being rapidly stirred. The rapidly stirred, N₂ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried ($CaSO_4$) and evaporated to afford a brown oil which was purified by preparative RP-HPLC. Chromatography fractions were combined, extracted with ethyl acetate, dried ($CaSO_4$), and diluted with heptane to precipitate macrocycle product as 39.4 mg of white powder, mp. 244-245° C. (dec.) $^1$H NMR (400 MHz, DMSO-$d_6$) δ ppm 1.45 (s, 8H) 3.37 (br. s., 2H) 3.49-3.67 (m, 4H) 4.22-4.35 (m, 2H) 6.68 (dd, J=9.60, 6.82 Hz, 1H) 6.79-6.85 (m, 1H) 7.30-7.48 (m, 3H) 7.78 (d, J=9.60 Hz, 1H) 7.92 (d, J=3.03 Hz, 1H) 8.45-8.61 (m, 1H). $^{13}$C NMR (100 MHz, DMSO-$d_6$) δ ppm 27.96, 27.99, 38.49, 61.97, 79.22, 79.26, 108.11, 108.21, 111.93, 115.57, 117.89, 118.03, 126.01, 126.32, 129.84, 130.08, 130.51, 137.29, 152.90, 154.53, 156.75. LRMS (ESI) m/z 396.0 [(M+H)]$^+$, calc'd for $C_{21}H_{26}N_6O_3$: 395.47. HRMS (MS/MS) m/z 396.2021 [(M+H)]$^+$, calc'd for $C_{21}H_{26}N_6O_3$: 396.2036.

5.6.167. P81 Filter Plate Assay

Compounds were serially diluted into a Labcyte LDV plate (Labcyte, cat#LP-0200) using a Mutiprobe (PerkinElmer) and Biomek FX (Beckman Coulter) so that the highest compound concentration was at 96 μM. Compounds were then pinged (75 nL per well) into a Greiner 384-well reaction plate (Greiner, #781076) using an ECHO 550 Liquid Handler (Labcyte). A total of 12 μl reaction buffer (IMAP buffer containing Tween and DTT, from Molecular Devices) was then added to each well of columns 1 and 13 for the negative controls and 12 μl of 2×AAK1 (0.2 nM full-length human protein, NCBI accession no. NP_055726.2) was added to the remaining wells. Enzyme was then pre-incubated with compound for 10 minutes at RT. Reactions were initiated upon Minitrak (PerkinElmer) addition of 12 μl substrate mix containing 2×Mu2 (0.2 μM, full length human protein), 2× cold ATP (2 μM), and 1.3 μCi of hot $^{33}$P-ATP. Reactions proceeded for one hour at RT. Meanwhile, Millipore 384-well P81 filter plates (Millipore, catalog #MZPHNOW10) were placed on a plate washer (Zoom ZW, from Titertek) and pre-wet with 50 μl 1% phosphoric acid. Kinase reactions were then stopped upon addition of 24 μl of 2% phosphoric acid to each well and the Minitrak was then used to transfer 40 μl from each well into the pre-wet Millipore 384-well P81 filter plates. Reaction mixtures were incubated for 10 minutes at RT in the P81 plates, followed by washing five times with 100 μl/well of 1% phosphoric acid using the Zoom filter washer. The bottom of each filter plate was sealed followed by addition of 20 μl Microscint 40 to each well, sealing the top of the plates with Flashplate cover, and then waiting one hour until reading on the TopCount (PerkinElmer).

5.6.168. HEK281 Cell-Based Assay

HEK293F cells were cultured in media containing DMEM (Gibco, cat. #11965), 10% FBS (SAFC Biosciences, cat. #12103C), 1×GPS (glutamine, penicillin and streptomycin). On day one, cells were plated on a 10 cm dish so that they are ~80% confluent at time of transfection. Roughly 12 million cells were in a 10 cm dish at time of transfection. On day two, each dish was transfected with 48 ug DNA and 144 ul Lipofectamine 2000 (Invitrogen, cat.#11668-019). The DNA was comprised of a mixture (per 10 cm dish) containing 3 ug AAK1/HA/pIRES (full length human, NCBI accession no. NP_055726.2), 45 μg Flag/AP2MI/pcDNA (full length human), and 1.5 ml OPTI-MEM. The Lipofectamine 2000 is made up of a mixture (per 10 cm dish) containing 144 μl Lipofectamine 2000 and 1.5 ml OPTI-MEM. Each mixture was transferred to individual 15 ml tubes and incubated at RT for 5 minutes, and then the two mixes were combined and incubated at RT for 20 minutes. Growth media was then aspirated from each 10 cm plate and replaced with 10 ml of DMEM+10% FBS (no GPS). Finally, 3 ml DNA/Lipofectamine mix was added to each 10 cm dish and mix gently followed by incubate of plate overnight at 37° C. and 5% $CO_2$.

On day three, compounds were diluted in 100% DMSO at 1000× final concentration, followed by 3-fold serial dilutions for a total of 5 concentrations tested. Four compounds were tested per 10 cm dish. One ul of each compound dilution was then pipetted into a deep-well, 96-well plate, followed by addition of 500 μl DMEM+0.5% FBS into each well for a 2× final concentration of each compound. Cells were resuspended in a 10 cm dish by simple pipetting (HEK293 cells come off the plate that easy at this point) and then transferred to a 50 ml conical tube and pelleted by centrifugation at 1000 rpm for 5 min. Cell pellets were then resuspended in 2.75 ml DMEM+0.5% FBS per 10 cm dish and 100 μl of cell suspension transferred into each well of 96-well TC plate. Finally, 100 μl of 2× compound diluted in DMEM+0.5% FBS was then added into wells containing cell suspension for a 1× final concentration. Plates were then incubated at 37° C. and 5% $CO_2$ for 3 hours followed by transferring of cell suspensions from each well into 12-tube PCR strips. The PCR strips were spun in a tip rack at 1000 rpm for 5 minutes to pellet cells and media was then removed by pipetting without disturbing the cell pellet.

To prepare for Western Blot analysis, cell pellets were resuspend in 40 ul 1×LDS-PAGE sample buffer (Invitrogen, cat.#NP0008)+2× Halt phophatase and protease inhibitor cocktail (Thermo Scientific, cat.#1861284), followed by sonicating each with microtip sonicator set at 5 for 8-10 seconds. Five ul of 10× NuPage Sample Reducing Agent (with 50 mM DTT) was to each sample followed by heat denaturing at 70 C for 10 min on PCR machine. A total of 10 μl per sample was loaded into each lane of a 4-20% Tris-Glycine Criterion 26-well gel (Biorad, cat.#345-0034) for the phospho-mu2 blot and 10 μl per lane in a 4-12% Bis-Tris (+MES buffer) NuPAGE 26-well gel (Invitrogen, cat.#WG1403BX10) for the mu2 blot. For controls, 2 ng of phospho-mu2 or 20 ng mu2/Flag proteins were loaded in the last well of each gel. After SDS-PAGE, samples on each gel were transferred to PVDF membrane using an iBlot and membranes were blocked for one hour in TBST+5% milk, followed by wash 3× for 5-10 min with TBST. Criterion gels were probed with rabbit anti-phospho-mu2 (1:5000; a rabbit polyclonal antibody produced by New England Peptide and affinity purified at Lexicon) in TBST+5% BSA, whereas, NuPAGE gels were probed with mouse anti-Flag (1:500; Sigma, cat.#F1804) in TBST+5% milk, and these primary antibodies were incubated overnight at 4° C. on a rocker.

On day four, Western blots were washed 3× for 5-10 minutes with TBST, probe with anti-rabbit-HRP (1:2000; Bio-Rad, cat.#170-6515) or anti-mouse-HRP (1:2000; Biorad, cat.#170-6516) in TBST+5% milk for 1 hour at RT, washed 3× for 10 minutes with TBST, and developed with ECL reagent (GE Healthcare, cat.#RPN2132) on a Versadoc. Finally, the camera was set up to take a picture every 30 seconds for 10 minutes and the best image saved for each blot with no saturated signal (when the signal is saturated, the bands will be highlighted red). A volume analysis on each band was performed to obtain density values. Percent inhibition was calculated for each sample by first normalizing to total Mu2 expression levels and then comparing to 0% and 100% controls. $IC_{50}$ values were then calculated using Excel fitting software.

5.6.169. In Vitro Data

In vitro data obtained for various compounds of the invention are provided below in Table 1, wherein "MW" means molecular weight, "P81 Assay" refers to the P81 filter plate assay described above, "CBA" refers to the HEK281 cell-based assay described above, "—" means that results for the given assay were not obtained, "*" means less than or equal to 1.0 μM, "" means a value of less than or equal to 0.1 μM, and "*" means less than or equal to 0.01 μM.

TABLE 1

| Compound | MW | CBA IC$_{50}$ | P81 IC$_{50}$ |
| --- | --- | --- | --- |
| (2S)-ethyl 2-(((3-(4-(pyrrolidin-2-yl)phenyl)imidazo[1,2-b]pyridazin-6-yl)amino)methyl)pyrrolidine-1-carboxylate | 434.5 | ** | — |
| (2S)-methyl 2-(((3-(4-(pyrrolidin-2-yl)phenyl)imidazo[1,2-b]pyridazin-6-yl)amino)methyl)pyrrolidine-1-carboxylate | 420.5 | ** | — |
| (2S)-tetrahydrofuran-3-yl 2-(((3-(pyridin-4-yl)imidazo[1,2-b]pyridazin-6-yl)amino)methyl)pyrrolidine-1-carboxylate | 408.5 | — | *** |
| (2S)-tetrahydrofuran-3-yl 2-(((3-bromoimidazo[1,2-b]pyridazin-6-yl)amino)methyl)pyrrolidine-1-carboxylate | 410.3 | — | *** |
| (4-(3-(2-methoxyphenyl)imidazo[1,2-b]pyridazin-6-yl)piperazin-1-yl)(pyrrolidin-1-yl)methanone | 406.5 | ** | *** |
| (4-(3-(2-methoxyphenyl)imidazo[1,2-b]pyridazin-6-yl)piperazin-1-yl)(piperidin-1-yl)methanone | 420.5 | ** | *** |
| (4-(3-(2-methoxypyridin-3-yl)imidazo[1,2-b]pyridazin-6-yl)piperazin-1-yl)(pyrrolidin-1-yl)methanone | 407.5 | ** | *** |
| (4-(3-(2-methoxypyridin-3-yl)imidazo[1,2-b]pyridazin-6-yl)piperazin-1-yl)(piperidin-1-yl)methanone | 421.5 | ** | *** |
| (4-(3-(3-methoxypyridin-4-yl)imidazo[1,2-b]pyridazin-6-yl)piperazin-1-yl)(pyrrolidin-1-yl)methanone | 407.5 | ** | *** |
| (4-(3-(pyridin-2-yl)imidazo[1,2-b]pyridazin-6-yl)piperazin-1-yl)(pyrrolidin-1-yl)methanone | 377.4 | ** | *** |
| (4-(3-phenylimidazo[1,2-b]pyridazin-6-yl)piperazin-1-yl)(piperidin-1-yl)methanone | 390.5 | ** | *** |
| (4-(3-phenylimidazo[1,2-b]pyridazin-6-yl)piperazin-1-yl)(pyrrolidin-1-yl)methanone | 376.5 | * | *** |
| (4-(6-((2-(cyclopentyloxy)ethyl)amino)imidazo[1,2-b]pyridazin-3-yl)phenyl)methanol | 352.4 | — | *** |
| (4-aminopiperidin-1-yl)(4-(6-(butylamino)imidazo[1,2-b]pyridazin-3-yl)phenyl)methanone | 392.5 | * | — |
| (R)-isopropyl methyl(2-((3-(4-(pyrrolidin-2-yl)phenyl)imidazo[1,2-b]pyridazin-6-yl)amino)ethyl)carbamate | 422.5 | ** | — |
| (R)—N-butyl-3-(4-(pyrrolidin-2-yl)phenyl)imidazo[1,2-b]pyridazin-6-amine | 335.4 | * | — |
| (S)-1-(2-(((3-(2,4-dimethylthiazol-5-yl)imidazo[1,2-b]pyridazin-6-yl)amino)methyl)pyrrolidin-1-yl)-3-methylbutan-1-one | 412.6 | *** | *** |
| (S)-1-(2-(((3-(2-chlorophenyl)imidazo[1,2-b]pyridazin-6-yl)amino)methyl)pyrrolidin-1-yl)-3-methylbutan-1-one | 411.9 | — | — |
| (S)-1-(2-(((3-(2-fluoropyridin-4-yl)imidazo[1,2-b]pyridazin-6-yl)amino)methyl)pyrrolidin-1-yl)-3-methylbutan-1-one | 396.5 | — | *** |
| (S)-1-(2-(((3-(2-methoxyphenyl)imidazo[1,2-b]pyridazin-6-yl)amino)methyl)pyrrolidin-1-yl)-3-methylbutan-1-one | 407.5 | *** | — |
| (S)-1-(2-(((3-(2-methoxyphenyl)imidazo[1,2-b]pyridazin-6-yl)amino)methyl)pyrrolidin-1-yl)ethanone | 365.4 | ** | — |
| (S)-1-(2-(((3-(3-chlorophenyl)imidazo[1,2-b]pyridazin-6-yl)amino)methyl)pyrrolidin-1-yl)-3-methylbutan-1-one | 411.9 | *** | *** |
| (S)-1-(2-(((3-(3-fluorophenyl)imidazo[1,2-b]pyridazin-6-yl)amino)methyl)pyrrolidin-1-yl)-3-methylbutan-1-one | 395.5 | *** | *** |
| (S)-1-(2-(((3-(3-methoxyphenyl)imidazo[1,2-b]pyridazin-6-yl)amino)methyl)pyrrolidin-1-yl)-3-methylbutan-1-one | 407.5 | ** | *** |
| (S)-1-(2-(((3-(3-methoxypyridin-4-yl)imidazo[1,2-b]pyridazin-6-yl)amino)methyl)pyrrolidin-1-yl)ethanone | 366.4 | ** | — |
| (S)-1-(2-(((3-(3-methoxypyridin-4-yl)imidazo[1,2-b]pyridazin-6-yl)amino)methyl)pyrrolidin-1-yl)-3-methylbutan-1-one | 408.5 | *** | — |
| (S)-1-(2-(((3-(4-(aminomethyl)phenyl)imidazo[1,2-b]pyridazin-6-yl)amino)methyl)pyrrolidin-1-yl)-3-methylbutan-1-one | 406.5 | *** | — |
| (S)-1-(2-(((3-(4-(aminomethyl)phenyl)imidazo[1,2-b]pyridazin-6-yl)amino)methyl)pyrrolidin-1-yl)-2,2-dimethylpropan-1-one | 406.5 | ** | *** |
| (S)-1-(2-(((3-(4-(aminomethyl)phenyl)imidazo[1,2-b]pyridazin-6-yl)amino)methyl)pyrrolidin-1-yl)butan-1-one | 392.5 | *** | *** |
| (S)-1-(2-(((3-(4-(aminomethyl)phenyl)imidazo[1,2-b]pyridazin-6-yl)amino)methyl)pyrrolidin-1-yl)-3,3-dimethylbutan-1-one | 420.6 | ** | *** |
| (S)-1-(2-(((3-(4-fluorophenyl)imidazo[1,2-b]pyridazin-6-yl)amino)methyl)pyrrolidin-1-yl)-3-methylbutan-1-one | 395.5 | ** | *** |
| (S)-1-(2-(((3-(4-methoxyphenyl)imidazo[1,2-b]pyridazin-6-yl)amino)methyl)pyrrolidin-1-yl)-3-methylbutan-1-one | 407.5 | * | *** |
| (S)-1-(2-(((3-(cyclopent-1-en-1-yl)imidazo[1,2-b]pyridazin-6-yl)amino)methyl)pyrrolidin-1-yl)-3-methylbutan-1-one | 367.5 | — | *** |
| (S)-1-(2-(((3-(pyridin-4-yl)imidazo[1,2-b]pyridazin-6-yl)amino)methyl)pyrrolidin-1-yl)butan-1-one | 364.4 | — | *** |
| (S)-1-(2-(((3-bromoimidazo[1,2-b]pyridazin-6-yl)amino)methyl)pyrrolidin-1-yl)-3-methylbutan-1-one | 380.3 | ** | — |

TABLE 1-continued

| Compound | MW | CBA IC$_{50}$ | P81 IC$_{50}$ |
|---|---|---|---|
| (S)-1-(3,3-dimethylbutyl)-5-(((3-(2-methoxyphenyl)imidazo[1,2-b]pyridazin-6-yl)amino)methyl)pyrrolidin-2-one | 421.5 | * | *** |
| (S)-1-(3,3-dimethylbutyl)-5-(((3-(2-methoxypyridin-3-yl)imidazo[1,2-b]pyridazin-6-yl)amino)methyl)pyrrolidin-2-one | 422.5 | *** | *** |
| (S)-1-(3,3-dimethylbutyl)-5-(((3-(pyridin-4-yl)imidazo[1,2-b]pyridazin-6-yl)amino)methyl)pyrrolidin-2-one | 392.5 | — | *** |
| (S)-1-(3,3-dimethylbutyl)-5-(((3-phenylimidazo[1,2-b]pyridazin-6-yl)amino)methyl)pyrrolidin-2-one | 391.5 | * | *** |
| (S)-1-methylcyclopentyl 2-(((3-bromoimidazo[1,2-b]pyridazin-6-yl)amino)methyl)pyrrolidine-1-carboxylate | 422.3 | * | *** |
| (S)-2-(((3-bromoimidazo[1,2-b]pyridazin-6-yl)amino)methyl)-N-(tert-butyl)pyrrolidine-1-carboxamide | 395.3 | ** | *** |
| (S)-2,2,2-trifluoroethyl (1-(3-(2-methoxypyridin-3-yl)imidazo[1,2-b]pyridazin-6-yl)pyrrolidin-3-yl)(methyl)carbamate | 450.4 | ** | *** |
| (S)-2-amino-N-(4-(6-(butylamino)imidazo[1,2-b]pyridazin-3-yl)benzyl)-4-methylpentanamide | 408.5 | ** | — |
| (S)-2-cyclopropyl-N-(1-(3-(2-hydroxypyridin-3-yl)imidazo[1,2-b]pyridazin-6-yl)pyrrolidin-3-yl)-N-methylacetamide | 392.5 | — | *** |
| (S)-2-methoxyethyl (1-(3-(2-methoxypyridin-3-yl)imidazo[1,2-b]pyridazin-6-yl)pyrrolidin-3-yl)(methyl)carbamate | 426.5 | — | ** |
| (S)-3-(4-(aminomethyl)phenyl)-N-((tetrahydrofuran-2-yl)methyl)imidazo[1,2-b]pyridazin-6-amine | 323.4 | ** | — |
| (S)-3-(6-(((1-(3-methylbutanoyl)pyrrolidin-2-yl)methyl)amino)imidazo[1,2-b]pyridazin-3-yl)benzonitrile | 402.5 | ** | *** |
| (S)-3,3,3-trifluoro-1-(2-(((3-phenylimidazo[1,2-b]pyridazin-6-yl)amino)methyl)pyrrolidin-1-yl)propan-1-one | 403.4 | *** | *** |
| (S)-3,3,3-trifluoro-N-(1-(3-(2-hydroxypyridin-3-yl)imidazo[1,2-b]pyridazin-6-yl)pyrrolidin-3-yl)-N-methylpropanamide | 420.4 | — | *** |
| (S)-3,3-dimethyl-1-(2-(((3-(pyridin-4-yl)imidazo[1,2-b]pyridazin-6-yl)amino)methyl)pyrrolidin-1-yl)butan-1-one | 392.5 | ** | *** |
| (S)-3-methyl-1-(2-(((3-(2-methylpyridin-4-yl)imidazo[1,2-b]pyridazin-6-yl)amino)methyl)pyrrolidin-1-yl)butan-1-one | 392.5 | ** | *** |
| (S)-3-methyl-1-(2-(((3-(m-tolyl)imidazo[1,2-b]pyridazin-6-yl)amino)methyl)pyrrolidin-1-yl)butan-1-one | 391.5 | * | *** |
| (S)-3-methyl-1-(2-(((3-(pyridin-4-yl)imidazo[1,2-b]pyridazin-6-yl)amino)methyl)pyrrolidin-1-yl)butan-1-one | 378.5 | ** | — |
| (S)-3-methyl-1-(2-(((3-phenylimidazo[1,2-b]pyridazin-6-yl)amino)methyl)pyrrolidin-1-yl)butan-1-one | 377.5 | ** | *** |
| (S)-4-(6-(((1-(3-methylbutanoyl)pyrrolidin-2-yl)methyl)amino)imidazo[1,2-b]pyridazin-3-yl)benzonitrile | 402.5 | *** | *** |
| (S)-5-(((3-(4-(aminomethyl)phenyl)imidazo[1,2-b]pyridazin-6-yl)amino)methyl)-1-isopentylpyrrolidin-2-one | 406.5 | ** | *** |
| (S)-5-(((3-(4-(aminomethyl)phenyl)imidazo[1,2-b]pyridazin-6-yl)amino)methyl)-1-(3,3-dimethylbutyl)pyrrolidin-2-one | 420.6 | ** | *** |
| (S)-5-(((3-bromoimidazo[1,2-b]pyridazin-6-yl)amino)methyl)-1-(3,3-dimethylbutyl)pyrrolidin-2-one | 394.3 | ** | *** |
| (S)-cyclobutyl 2-(((3-(2-methoxyphenyl)imidazo[1,2-b]pyridazin-6-yl)amino)methyl)pyrrolidine-1-carboxylate | 421.5 | ** | *** |
| (S)-cyclobutyl 2-(((3-(pyridin-4-yl)imidazo[1,2-b]pyridazin-6-yl)amino)methyl)pyrrolidine-1-carboxylate | 392.5 | *** | *** |
| (S)-cyclobutyl 2-(((3-bromoimidazo[1,2-b]pyridazin-6-yl)amino)methyl)pyrrolidine-1-carboxylate | 394.3 | ** | *** |
| (S)-cyclopentyl 2-(((3-(4-(aminomethyl)phenyl)imidazo[1,2-b]pyridazin-6-yl)amino)methyl)pyrrolidine-1-carboxylate | 434.5 | *** | *** |
| (S)-cyclopentyl 2-(((3-(pyridin-4-yl)imidazo[1,2-b]pyridazin-6-yl)amino)methyl)pyrrolidine-1-carboxylate | 406.5 | *** | *** |
| (S)-cyclopentyl 2-(((3-bromoimidazo[1,2-b]pyridazin-6-yl)amino)methyl)pyrrolidine-1-carboxylate | 408.3 | *** | *** |
| (S)-cyclopentyl 2-(((3-cyanoimidazo[1,2-b]pyridazin-6-yl)amino)methyl)pyrrolidine-1-carboxylate | 354.4 | — | *** |
| (S)-cyclopentyl 2-(((3-phenylimidazo[1,2-b]pyridazin-6-yl)amino)methyl)pyrrolidine-1-carboxylate | 405.5 | ** | *** |
| (S)-cyclopropylmethyl 2-(((3-(pyridin-4-yl)imidazo[1,2-b]pyridazin-6-yl)amino)methyl)pyrrolidine-1-carboxylate | 392.5 | — | *** |
| (S)-cyclopropylmethyl 2-(((3-bromoimidazo[1,2-b]pyridazin-6-yl)amino)methyl)pyrrolidine-1-carboxylate | 394.3 | — | *** |
| (S)-ethyl (1-(3-(2-methoxypyridin-3-yl)imidazo[1,2-b]pyridazin-6-yl)pyrrolidin-3-yl)(methyl)carbamate | 396.4 | ** | *** |
| (S)-ethyl 2-(((3-(2-methoxyphenyl)imidazo[1,2-b]pyridazin-6-yl)amino)methyl)pyrrolidine-1-carboxylate | 395.5 | ** | — |
| (S)-ethyl 2-(((3-(3-methoxypyridin-4-yl)imidazo[1,2-b]pyridazin-6-yl)amino)methyl)pyrrolidine-1-carboxylate | 396.4 | ** | — |
| (S)-ethyl 2-(((3-(4-(aminomethyl)phenyl)imidazo[1,2-b]pyridazin-6-yl)amino)methyl)pyrrolidine-1-carboxylate | 394.5 | *** | — |
| (S)-ethyl 2-(((3-(pyridin-4-yl)imidazo[1,2-b]pyridazin-6-yl)amino)methyl)pyrrolidine-1-carboxylate | 366.4 | ** | — |

TABLE 1-continued

| Compound | MW | CBA IC$_{50}$ | P81 IC$_{50}$ |
|---|---|---|---|
| (S)-ethyl 2-(((3-bromoimidazo[1,2-b]pyridazin-6-yl)amino)methyl)pyrrolidine-1-carboxylate | 368.2 | ** | — |
| (S)-isopropyl (1-(3-(2-(difluoromethoxy)pyridin-3-yl)imidazo[1,2-b]pyridazin-6-yl)pyrrolidin-3-yl)(methyl)carbamate | 446.5 | — | *** |
| (S)-isopropyl (1-(3-(2-methoxy-6-methylpyridin-3-yl)imidazo[1,2-b]pyridazin-6-yl)pyrrolidin-3-yl)(methyl)carbamate | 424.5 | *** | *** |
| (S)-isopropyl (1-(3-(2-methoxypyridin-3-yl)imidazo[1,2-b]pyridazin-6-yl)pyrrolidin-3-yl)(methyl)carbamate | 410.5 | *** | *** |
| (S)-isopropyl (1-(3-(3,6-dimethoxypyridazin-4-yl)imidazo[1,2-b]pyridazin-6-yl)pyrrolidin-3-yl)(methyl)carbamate | 441.5 | ** | *** |
| (S)-isopropyl (1-(3-bromoimidazo[1,2-b]pyridazin-6-yl)pyrrolidin-3-yl)(methyl)carbamate | 382.3 | — | *** |
| (S)-isopropyl 2-(((3-(2-methoxyphenyl)imidazo[1,2-b]pyridazin-6-yl)amino)methyl)pyrrolidine-1-carboxylate | 409.5 | *** | — |
| (S)-isopropyl 2-(((3-(3-methoxypyridin-4-yl)imidazo[1,2-b]pyridazin-6-yl)amino)methyl)pyrrolidine-1-carboxylate | 410.5 | *** | — |
| (S)-isopropyl 2-(((3-(4-(aminomethyl)phenyl)imidazo[1,2-b]pyridazin-6-yl)amino)methyl)pyrrolidine-1-carboxylate | 408.5 | *** | — |
| (S)-isopropyl 2-(((3-(prop-1-en-2-yl)imidazo[1,2-b]pyridazin-6-yl)amino)methyl)pyrrolidine-1-carboxylate | 343.4 | ** | — |
| (S)-isopropyl 2-(((3-bromoimidazo[1,2-b]pyridazin-6-yl)amino)methyl)pyrrolidine-1-carboxylate | 382.3 | * | — |
| (S)-isopropyl 2-(((3-cyanoimidazo[1,2-b]pyridazin-6-yl)amino)methyl)pyrrolidine-1-carboxylate | 328.4 | * | *** |
| (S)-isopropyl 2-(((3-cyclopropylimidazo[1,2-b]pyridazin-6-yl)amino)methyl)pyrrolidine-1-carboxylate | 343.4 | * | — |
| (S)-isopropyl 2-(((3-vinylimidazo[1,2-b]pyridazin-6-yl)amino)methyl)pyrrolidine-1-carboxylate | 329.4 | *** | — |
| (S)-isopropyl methyl(1-(3-(pyridin-3-yl)imidazo[1,2-b]pyridazin-6-yl)pyrrolidin-3-yl)carbamate | 380.4 | ** | *** |
| (S)-isopropyl methyl(1-(3-(pyridin-4-yl)imidazo[1,2-b]pyridazin-6-yl)pyrrolidin-3-yl)carbamate | 380.4 | — | ** |
| (S)-isopropyl methyl(2-((3-(4-(pyrrolidin-2-yl)phenyl)imidazo[1,2-b]pyridazin-6-yl)amino)ethyl)carbamate | 422.5 | ** | — |
| (S)-methyl 2-(((3-(2-methoxyphenyl)imidazo[1,2-b]pyridazin-6-yl)amino)methyl)pyrrolidine-1-carboxylate | 381.4 | ** | — |
| (S)-methyl 2-(((3-(3-methoxypyridin-4-yl)imidazo[1,2-b]pyridazin-6-yl)amino)methyl)pyrrolidine-1-carboxylate | 382.4 | ** | — |
| (S)-methyl 2-(((3-(4-(aminomethyl)phenyl)imidazo[1,2-b]pyridazin-6-yl)amino)methyl)pyrrolidine-1-carboxylate | 380.4 | ** | — |
| (S)-methyl 2-(((3-bromoimidazo[1,2-b]pyridazin-6-yl)amino)methyl)pyrrolidine-1-carboxylate | 354.2 | * | — |
| (S)-N-(1-(3-(2-hydroxypyridin-3-yl)imidazo[1,2-b]pyridazin-6-yl)pyrrolidin-3-yl)-N-methylcyclopentanecarboxamide | 406.5 | — | ** |
| (S)-N-(1-(3-(2-hydroxypyridin-3-yl)imidazo[1,2-b]pyridazin-6-yl)pyrrolidin-3-yl)-2-methoxy-N-methylacetamide | 382.4 | — | * |
| (S)-N-(1-(3-(2-hydroxypyridin-3-yl)imidazo[1,2-b]pyridazin-6-yl)pyrrolidin-3-yl)-N,3-dimethylbutanamide | 394.5 | — | ** |
| (S)-N-(1-(3-(2-hydroxypyridin-3-yl)imidazo[1,2-b]pyridazin-6-yl)pyrrolidin-3-yl)-N,3,3-trimethylbutanamide | 408.5 | * | ** |
| (S)-N-(1-(3-(2-hydroxypyridin-3-yl)imidazo[1,2-b]pyridazin-6-yl)pyrrolidin-3-yl)-N-methylbutyramide | 380.4 | — | ** |
| (S)-N-(1-(3-(2-methoxyphenyl)imidazo[1,2-b]pyridazin-6-yl)pyrrolidin-3-yl)-N-methylpyrrolidine-1-carboxamide | 420.5 | ** | *** |
| (S)-N-(1-(3-(2-methoxypyridin-3-yl)imidazo[1,2-b]pyridazin-6-yl)pyrrolidin-3-yl)-N-methylpyrrolidine-1-carboxamide | 421.5 | ** | *** |
| (S)-N-(1-(3-(2-methoxypyridin-3-yl)imidazo[1,2-b]pyridazin-6-yl)pyrrolidin-3-yl)-N-methylbutyramide | 394.5 | — | ** |
| (S)-N-(1-(3-bromoimidazo[1,2-b]pyridazin-6-yl)pyrrolidin-3-yl)-N-methylbutyramide | 366.3 | — | * |
| (S)-N-(1-(3-bromoimidazo[1,2-b]pyridazin-6-yl)pyrrolidin-3-yl)-N-methylpyrrolidine-1-carboxamide | 393.3 | — | ** |
| (S)-N-(tert-butyl)-2-(((3-(2-methoxyphenyl)imidazo[1,2-b]pyridazin-6-yl)amino)methyl)pyrrolidine-1-carboxamide | 422.5 | ** | *** |
| (S)-N-(tert-butyl)-2-(((3-(pyridin-4-yl)imidazo[1,2-b]pyridazin-6-yl)amino)methyl)pyrrolidine-1-carboxamide | 393.5 | ** | *** |
| (S)-N-(tert-butyl)-2-(((3-phenylimidazo[1,2-b]pyridazin-6-yl)amino)methyl)pyrrolidine-1-carboxamide | 392.5 | ** | *** |
| (S)-N-butyl-3-(4-(pyrrolidin-2-yl)phenyl)imidazo[1,2-b]pyridazin-6-amine | 335.4 | ** | — |
| (S)-N-cyclopentyl-2-(((3-(2-methoxyphenyl)imidazo[1,2-b]pyridazin-6-yl)amino)methyl)pyrrolidine-1-carboxamide | 434.5 | * | *** |
| (S)-neopentyl 2-(((3-(4-(aminomethyl)phenyl)imidazo[1,2-b]pyridazin-6-yl)amino)methyl)pyrrolidine-1-carboxylate | 436.5 | *** | *** |
| (S)-neopentyl 2-(((3-(pyridin-4-yl)imidazo[1,2-b]pyridazin-6-yl)amino)methyl)pyrrolidine-1-carboxylate | 408.5 | ** | *** |

TABLE 1-continued

| Compound | MW | CBA IC$_{50}$ | P81 IC$_{50}$ |
|---|---|---|---|
| (S)-neopentyl 2-(((3-bromoimidazo[1,2-b]pyridazin-6-yl)amino)methyl)pyrrolidine-1-carboxylate | 410.3 | ** | — |
| (S)-N-methyl-N-(1-(3-(pyridin-2-yl)imidazo[1,2-b]pyridazin-6-yl)pyrrolidin-3-yl)pyrrolidine-1-carboxamide | 391.5 | — | ** |
| (S)-N-methyl-N-(1-(3-(pyridin-3-yl)imidazo[1,2-b]pyridazin-6-yl)pyrrolidin-3-yl)butyramide | 364.4 | — | * |
| (S)-N-methyl-N-(1-(3-(pyridin-4-yl)imidazo[1,2-b]pyridazin-6-yl)pyrrolidin-3-yl)pyrrolidine-1-carboxamide | 391.5 | — | ** |
| (S)-N-methyl-N-(1-(3-(pyridin-4-yl)imidazo[1,2-b]pyridazin-6-yl)pyrrolidin-3-yl)butyramide | 364.4 | — | ** |
| (S)-N-neopentyl-2-(((3-phenylimidazo[1,2-b]pyridazin-6-yl)amino)methyl)pyrrolidine-1-carboxamide | 406.5 | ** | *** |
| (S)-propyl 2-(((3-bromoimidazo[1,2-b]pyridazin-6-yl)amino)methyl)pyrrolidine-1-carboxylate | 382.3 | — | *** |
| (S)-tert-butyl (1-(3-(2-methoxyphenyl)imidazo[1,2-b]pyridazin-6-yl)pyrrolidin-3-yl)(methyl)carbamate | 423.5 | ** | *** |
| (S)-tert-butyl (1-(3-(2-methoxypyridin-3-yl)imidazo[1,2-b]pyridazin-6-yl)pyrrolidin-3-yl)(methyl)carbamate | 424.5 | ** | *** |
| (S)-tert-butyl (1-(3-bromoimidazo[1,2-b]pyridazin-6-yl)pyrrolidin-3-yl)(methyl)carbamate | 396.3 | * | *** |
| (S)-tert-butyl 2-(((3-(2-methoxyphenyl)imidazo[1,2-b]pyridazin-6-yl)amino)methyl)pyrrolidine-1-carboxylate | 423.5 | *** | — |
| (S)-tert-butyl 2-(((3-(3-methoxypyridin-4-yl)imidazo[1,2-b]pyridazin-6-yl)amino)methyl)piperidine-1-carboxylate | 438.5 | ** | — |
| (S)-tert-butyl 2-(((3-(4-(aminomethyl)phenyl)imidazo[1,2-b]pyridazin-6-yl)amino)methyl)pyrrolidine-1-carboxylate | 422.5 | *** | *** |
| (S)-tert-butyl 2-(((3-(4-(aminomethyl)phenyl)imidazo[1,2-b]pyridazin-6-yl)amino)methyl)piperidine-1-carboxylate | 436.5 | *** | — |
| (S)-tert-butyl 2-(((3-(4-carbamoylphenyl)imidazo[1,2-b]pyridazin-6-yl)amino)methyl)pyrrolidine-1-carboxylate | 436.5 | *** | *** |
| (S)-tert-butyl 2-(((3-(difluoromethyl)imidazo[1,2-b]pyridazin-6-yl)amino)methyl)pyrrolidine-1-carboxylate | 367.4 | * | *** |
| (S)-tert-butyl 2-(((3-(methylcarbamoyl)imidazo[1,2-b]pyridazin-6-yl)amino)methyl)pyrrolidine-1-carboxylate | 374.4 | ** | *** |
| (S)-tert-butyl 2-(((3-(pyridin-4-yl)imidazo[1,2-b]pyridazin-6-yl)amino)methyl)piperidine-1-carboxylate | 408.5 | ** | — |
| (S)-tert-butyl 2-(((3-(trifluoromethyl)imidazo[1,2-b]pyridazin-6-yl)amino)methyl)pyrrolidine-1-carboxylate | 385.4 | ** | — |
| (S)-tert-butyl 2-(((3-bromoimidazo[1,2-b]pyridazin-6-yl)amino)methyl)pyrrolidine-1-carboxylate | 396.3 | ** | — |
| (S)-tert-butyl 2-(((3-bromoimidazo[1,2-b]pyridazin-6-yl)amino)methyl)azetidine-1-carboxylate | 382.3 | ** | *** |
| (S)-tert-butyl 2-(((3-chloroimidazo[1,2-b]pyridazin-6-yl)amino)methyl)pyrrolidine-1-carboxylate | 351.8 | ** | — |
| (S)-tert-butyl 2-(((3-ethylimidazo[1,2-b]pyridazin-6-yl)amino)methyl)pyrrolidine-1-carboxylate | 345.4 | ** | — |
| (S)-tert-butyl 2-(((3-iodoimidazo[1,2-b]pyridazin-6-yl)amino)methyl)pyrrolidine-1-carboxylate | 443.3 | *** | — |
| (S)-tert-butyl 2-(((3-methylimidazo[1,2-b]pyridazin-6-yl)amino)methyl)pyrrolidine-1-carboxylate | 331.4 | ** | *** |
| (S)-tert-butyl 2-(((3-phenylimidazo[1,2-b]pyridazin-6-yl)amino)methyl)pyrrolidine-1-carboxylate | 393.5 | *** | *** |
| (S)-tert-butyl 2-(2-((3-(4-(aminomethyl)phenyl)imidazo[1,2-b]pyridazin-6-yl)amino)ethyl)pyrrolidine-1-carboxylate | 436.5 | ** | — |
| (S)-tert-butyl 3-(((3-(3-methoxypyridin-4-yl)imidazo[1,2-b]pyridazin-6-yl)amino)methyl)pyrrolidine-1-carboxylate | 424.5 | * | — |
| (S)-tert-butyl 3-(((3-(4-(aminomethyl)phenyl)imidazo[1,2-b]pyridazin-6-yl)amino)methyl)pyrrolidine-1-carboxylate | 422.5 | ** | — |
| (S)-tert-butyl 3-(((3-bromoimidazo[1,2-b]pyridazin-6-yl)amino)methyl)pyrrolidine-1-carboxylate | 396.3 | * | — |
| (S)-tert-butyl methyl(1-(3-(pyridin-3-yl)imidazo[1,2-b]pyridazin-6-yl)pyrrolidin-3-yl)carbamate | 394.5 | — | *** |
| (S)-tert-butyl methyl(1-(3-(pyridin-4-yl)imidazo[1,2-b]pyridazin-6-yl)pyrrolidin-3-yl)carbamate | 394.5 | * | *** |
| (S)-vinyl 2-(((3-(2-methoxyphenyl)imidazo[1,2-b]pyridazin-6-yl)amino)methyl)pyrrolidine-1-carboxylate | 393.4 | ** | *** |
| 1-(2-((3-(4-(aminomethyl)phenyl)imidazo[1,2-b]pyridazin-6-yl)amino)ethyl)-3-(tert-butyl)imidazolidin-2-one | 407.5 | ** | — |
| 1-(4-(3-(3-methoxypyridin-4-yl)imidazo[1,2-b]pyridazin-6-yl)piperazin-1-yl)-3,3-dimethylbutan-1-one | 408.5 | ** | — |
| 1-(5-(6-((2-(methyl(phenyl)amino)ethyl)amino)imidazo[1,2-b]pyridazin-3-yl)thiophen-2-yl)ethanone | 391.5 | ** | — |
| 1-(5-(6-((3-(methylamino)propyl)amino)imidazo[1,2-b]pyridazin-3-yl)thiophen-2-yl)ethanone | 329.4 | * | — |
| 1-(5-(6-((3-methoxypropyl)amino)imidazo[1,2-b]pyridazin-3-yl)thiophen-2-yl)ethanone | 330.4 | * | — |
| 1-(5-(6-(butyl(methyl)amino)imidazo[1,2-b]pyridazin-3-yl)thiophen-2-yl)ethanone | 328.4 | ** | — |

TABLE 1-continued

| Compound | MW | CBA IC$_{50}$ | P81 IC$_{50}$ |
|---|---|---|---|
| 1-(5-(6-(isobutylamino)imidazo[1,2-b]pyridazin-3-yl)thiophen-2-yl)ethanone | 314.4 | * | — |
| 1-(5-(6-(propylamino)imidazo[1,2-b]pyridazin-3-yl)thiophen-2-yl)ethanone | 300.4 | * | — |
| 1-(tert-butyl)-3-(2-((3-(3-methoxypyridin-4-yl)imidazo[1,2-b]pyridazin-6-yl)amino)ethyl)imidazolidin-2-one | 409.5 | ** | — |
| 2,2-dimethyl-1-(4-(3-phenylimidazo[1,2-b]pyridazin-6-yl)piperazin-1-yl)propan-1-one | 363.5 | — | ** |
| 2-fluoroethyl isopropyl(2-((3-(3-methoxypyridin-4-yl)imidazo[1,2-b]pyridazin-6-yl)amino)ethyl)carbamate | 416.4 | * | — |
| 3-(2,4-dimethylthiazol-5-yl)-N-(2-isobutoxyethyl)imidazo[1,2-b]pyridazin-6-amine | 345.5 | * | — |
| 3-(2-aminopyridin-4-yl)-N-(3-(tert-butoxy)propyl)imidazo[1,2-b]pyridazin-6-amine | 340.4 | * | — |
| 3-(2-aminopyridin-4-yl)-N-butylimidazo[1,2-b]pyridazin-6-amine | 282.3 | * | — |
| 3-(2-methoxypyridin-3-yl)-N-((tetrahydrofuran-3-yl)methyl)imidazo[1,2-b]pyridazin-6-amine | 325.4 | * | — |
| 3-(3-methoxypyridin-4-yl)-N-(4,4,4-trifluorobutyl)imidazo[1,2-b]pyridazin-6-amine | 351.3 | *** | — |
| 3-(4-(((2-methoxyethyl)amino)methyl)phenyl)-N-pentylimidazo[1,2-b]pyridazin-6-amine | 367.5 | * | — |
| 3-(4-((2-(dimethylamino)ethoxy)methyl)phenyl)-N-(3,3-dimethylbutyl)imidazo[1,2-b]pyridazin-6-amine | 395.5 | ** | — |
| 3-(4-((2-aminoethoxy)methyl)phenyl)-N-(3,3-dimethylbutyl)imidazo[1,2-b]pyridazin-6-amine | 367.5 | ** | — |
| 3-(4-(1H-tetrazol-5-yl)phenyl)-N-butylimidazo[1,2-b]pyridazin-6-amine | 334.4 | * | — |
| 3-(4-(2-aminoethoxy)phenyl)-N-butylimidazo[1,2-b]pyridazin-6-amine | 325.4 | ** | — |
| 3-(4-(3-aminopropoxy)phenyl)-N-(3,3-dimethylbutyl)imidazo[1,2-b]pyridazin-6-amine | 367.5 | ** | — |
| 3-(4-(3-aminopropoxy)phenyl)-N-(3-phenylpropyl)imidazo[1,2-b]pyridazin-6-amine | 401.5 | ** | — |
| 3-(4-(aminomethyl)-3-fluorophenyl)-N-butylimidazo[1,2-b]pyridazin-6-amine | 313.4 | * | — |
| 3-(4-(aminomethyl)phenyl)-N-((1-(2,2,2-trifluoroethyl)pyrrolidin-2-yl)methyl)imidazo[1,2-b]pyridazin-6-amine | 404.4 | ** | *** |
| 3-(4-(aminomethyl)phenyl)-N-((tetrahydrofuran-3-yl)methyl)imidazo[1,2-b]pyridazin-6-amine | 323.4 | * | — |
| 3-(4-(aminomethyl)phenyl)-N-(1-oxaspiro[4.4]nonan-3-yl)imidazo[1,2-b]pyridazin-6-amine | 363.5 | ** | — |
| 3-(4-(aminomethyl)phenyl)-N-(2-(cyclopentyloxy)ethyl)imidazo[1,2-b]pyridazin-6-amine | 351.4 | ** | — |
| 3-(4-(aminomethyl)phenyl)-N-(2-(neopentyloxy)ethyl)imidazo[1,2-b]pyridazin-6-amine | 353.5 | ** | — |
| 3-(4-(aminomethyl)phenyl)-N-(2-(tert-butoxy)ethyl)imidazo[1,2-b]pyridazin-6-amine | 339.4 | ** | — |
| 3-(4-(aminomethyl)phenyl)-N-(2-(trifluoromethoxy)phenethyl)imidazo[1,2-b]pyridazin-6-amine | 427.4 | *** | — |
| 3-(4-(aminomethyl)phenyl)-N-(2-cyclohexylethyl)imidazo[1,2-b]pyridazin-6-amine | 349.5 | ** | — |
| 3-(4-(aminomethyl)phenyl)-N-(2-cyclopropylethyl)imidazo[1,2-b]pyridazin-6-amine | 307.4 | * | — |
| 3-(4-(aminomethyl)phenyl)-N-(2-ethoxyphenethyl)imidazo[1,2-b]pyridazin-6-amine | 387.5 | ** | — |
| 3-(4-(aminomethyl)phenyl)-N-(2-fluorophenethyl)imidazo[1,2-b]pyridazin-6-amine | 361.4 | ** | — |
| 3-(4-(aminomethyl)phenyl)-N-(2-isobutoxyethyl)imidazo[1,2-b]pyridazin-6-amine | 339.4 | ** | — |
| 3-(4-(aminomethyl)phenyl)-N-(2-isopropoxyethyl)imidazo[1,2-b]pyridazin-6-amine | 325.4 | ** | — |
| 3-(4-(aminomethyl)phenyl)-N-(2-methoxyphenethyl)imidazo[1,2-b]pyridazin-6-amine | 373.5 | *** | — |
| 3-(4-(aminomethyl)phenyl)-N-(2-methylbutyl)imidazo[1,2-b]pyridazin-6-amine | 309.4 | * | — |
| 3-(4-(aminomethyl)phenyl)-N-(2-phenoxyethyl)imidazo[1,2-b]pyridazin-6-amine | 359.4 | * | — |
| 3-(4-(aminomethyl)phenyl)-N-(3-(2-fluorophenyl)propyl)imidazo[1,2-b]pyridazin-6-amine | 375.4 | ** | — |
| 3-(4-(aminomethyl)phenyl)-N-(3-(3-fluorophenyl)propyl)imidazo[1,2-b]pyridazin-6-amine | 375.4 | ** | — |
| 3-(4-(aminomethyl)phenyl)-N-(3-(4-fluorophenyl)propyl)imidazo[1,2-b]pyridazin-6-amine | 375.4 | ** | — |
| 3-(4-(aminomethyl)phenyl)-N-(3-(cyclopentyloxy)propyl)imidazo[1,2-b]pyridazin-6-amine | 365.5 | ** | — |

TABLE 1-continued

| Compound | MW | CBA IC$_{50}$ | P81 IC$_{50}$ |
|---|---|---|---|
| 3-(4-(aminomethyl)phenyl)-N-(3-(tert-butoxy)propyl)imidazo[1,2-b]pyridazin-6-amine | 353.5 | ** | — |
| 3-(4-(aminomethyl)phenyl)-N-(3-(trifluoromethyl)phenethyl)imidazo[1,2-b]pyridazin-6-amine | 411.4 | ** | — |
| 3-(4-(aminomethyl)phenyl)-N-(3,3-dimethylbutyl)imidazo[1,2-b]pyridazin-6-amine | 323.4 | ** | — |
| 3-(4-(aminomethyl)phenyl)-N-(3-fluorophenethyl)imidazo[1,2-b]pyridazin-6-amine | 361.4 | ** | — |
| 3-(4-(aminomethyl)phenyl)-N-(3-fluoropropyl)imidazo[1,2-b]pyridazin-6-amine | 299.3 | * | — |
| 3-(4-(aminomethyl)phenyl)-N-(3-methoxyphenethyl)imidazo[1,2-b]pyridazin-6-amine | 373.5 | ** | — |
| 3-(4-(aminomethyl)phenyl)-N-(3-phenylpropyl)imidazo[1,2-b]pyridazin-6-amine | 357.5 | ** | — |
| 3-(4-(aminomethyl)phenyl)-N-(4-fluorobutyl)imidazo[1,2-b]pyridazin-6-amine | 313.4 | ** | — |
| 3-(4-(aminomethyl)phenyl)-N-(4-fluorophenethyl)imidazo[1,2-b]pyridazin-6-amine | 361.4 | * | — |
| 3-(4-(aminomethyl)phenyl)-N-(4-methoxyphenethyl)imidazo[1,2-b]pyridazin-6-amine | 373.5 | ** | — |
| 3-(4-(aminomethyl)phenyl)-N-(4-phenylbutyl)imidazo[1,2-b]pyridazin-6-amine | 371.5 | ** | — |
| 3-(4-(aminomethyl)phenyl)-N-(5-fluoropentyl)imidazo[1,2-b]pyridazin-6-amine | 327.4 | * | — |
| 3-(4-(aminomethyl)phenyl)-N-(cyclobutylmethyl)imidazo[1,2-b]pyridazin-6-amine | 307.4 | * | — |
| 3-(4-(aminomethyl)phenyl)-N-(cyclohexylmethyl)imidazo[1,2-b]pyridazin-6-amine | 335.4 | * | — |
| 3-(4-(aminomethyl)phenyl)-N-(cyclopentylmethyl)imidazo[1,2-b]pyridazin-6-amine | 321.4 | * | — |
| 3-(4-(aminomethyl)phenyl)-N-(cyclopropylmethyl)imidazo[1,2-b]pyridazin-6-amine | 293.4 | * | — |
| 3-(4-(aminomethyl)phenyl)-N-butyl-7-methylimidazo[1,2-b]pyridazin-6-amine | 309.4 | ** | — |
| 3-(4-(aminomethyl)phenyl)-N-butylimidazo[1,2-b]pyridazin-6-amine | 295.4 | * | — |
| 3-(4-(aminomethyl)phenyl)-N-butyl-N-methylimidazo[1,2-b]pyridazin-6-amine | 309.4 | * | — |
| 3-(4-(aminomethyl)phenyl)-N-cyclohexylimidazo[1,2-b]pyridazin-6-amine | 321.4 | * | — |
| 3-(4-(aminomethyl)phenyl)-N-isobutylimidazo[1,2-b]pyridazin-6-amine | 295.4 | * | — |
| 3-(4-(aminomethyl)phenyl)-N-isopentylimidazo[1,2-b]pyridazin-6-amine | 309.4 | * | — |
| 3-(4-(aminomethyl)phenyl)-N-neopentylimidazo[1,2-b]pyridazin-6-amine | 309.4 | ** | — |
| 3-(4-(aminomethyl)phenyl)-N-pentylimidazo[1,2-b]pyridazin-6-amine | 309.4 | * | — |
| 3-(4-(aminomethyl)phenyl)-N-phenethylimidazo[1,2-b]pyridazin-6-amine | 343.4 | * | — |
| 3-(4-(aminomethyl)phenyl)-N-propylimidazo[1,2-b]pyridazin-6-amine | 281.4 | * | — |
| 3-(6-((2-(cyclopentyloxy)ethyl)amino)imidazo[1,2-b]pyridazin-3-yl)phenol | 338.4 | * | *** |
| 3-(benzo[d][1,3]dioxol-5-yl)-N-(2-(cyclopentyloxy)ethyl)imidazo[1,2-b]pyridazin-6-amine | 366.4 | * | ** |
| 3,3-dimethyl-1-(4-(3-phenylimidazo[1,2-b]pyridazin-6-yl)piperazin-1-yl)butan-1-one | 377.5 | ** | *** |
| 4-((3-(4-(aminomethyl)phenyl)imidazo[1,2-b]pyridazin-6-yl)amino)-2-methylbutan-2-ol | 325.4 | ** | — |
| 4-(3-bromoimidazo[1,2-b]pyridazin-6-yl)-N-(tert-butyl)piperazine-1-carboxamide | 381.3 | ** | *** |
| 4-(6-((2-(N,3,3-trimethylbutanamido)ethyl)amino)imidazo[1,2-b]pyridazin-3-yl)benzamide | 408.5 | ** | — |
| 4-(6-((2-(tert-butoxy)ethyl)amino)imidazo[1,2-b]pyridazin-3-yl)benzamide | 353.4 | ** | — |
| 4-(6-((2-(tert-butoxy)ethyl)amino)imidazo[1,2-b]pyridazin-3-yl)-N-(2-(diethylamino)ethyl)benzamide | 452.6 | ** | — |
| 4-(6-((2-(tert-butoxy)ethyl)amino)imidazo[1,2-b]pyridazin-3-yl)-N-methylbenzamide | 367.4 | ** | — |
| 4-(6-((2-(trifluoromethoxy)phenethyl)amino)imidazo[1,2-b]pyridazin-3-yl)benzamide | 441.4 | *** | — |
| 4-(6-((2-ethoxyphenethyl)amino)imidazo[1,2-b]pyridazin-3-yl)-N-methylbenzamide | 415.5 | *** | — |
| 4-(6-((2-isobutoxyethyl)amino)imidazo[1,2-b]pyridazin-3-yl)-N-(2-(pyrrolidin-1-yl)ethyl)benzamide | 450.6 | ** | — |

TABLE 1-continued

| Compound | MW | CBA IC$_{50}$ | P81 IC$_{50}$ |
|---|---|---|---|
| 4-(6-((2-isopropoxyethyl)amino)imidazo[1,2-b]pyridazin-3-yl)-N-(2-(pyrrolidin-1-yl)ethyl)benzamide | 436.5 | ** | — |
| 4-(6-((2-methoxyphenethyl)amino)imidazo[1,2-b]pyridazin-3-yl)benzamide | 387.4 | *** | — |
| 4-(6-((3-(trifluoromethyl)phenethyl)amino)imidazo[1,2-b]pyridazin-3-yl)benzamide | 425.4 | ** | — |
| 4-(6-((3-methoxyphenethyl)amino)imidazo[1,2-b]pyridazin-3-yl)benzamide | 387.4 | ** | — |
| 4-(6-(butylamino)imidazo[1,2-b]pyridazin-3-yl)-2-fluoro-N-(2-(methylamino)ethyl)benzamide | 384.5 | ** | — |
| 4-(6-(butylamino)imidazo[1,2-b]pyridazin-3-yl)benzamide | 309.4 | ** | — |
| 4-(6-(butylamino)imidazo[1,2-b]pyridazin-3-yl)-N-(2-(diethylamino)ethyl)benzamide | 408.5 | *** | — |
| 4-(6-(butylamino)imidazo[1,2-b]pyridazin-3-yl)-N-(2-(dimethylamino)ethyl)benzamide | 380.5 | ** | — |
| 4-(6-(butylamino)imidazo[1,2-b]pyridazin-3-yl)-N-(2-(methylamino)ethyl)benzamide | 366.5 | ** | — |
| 4-(6-(butylamino)imidazo[1,2-b]pyridazin-3-yl)-N-(2-(pyrrolidin-1-yl)ethyl)benzamide | 406.5 | ** | — |
| 5-(6-((2-(cyclopentyloxy)ethyl)amino)imidazo[1,2-b]pyridazin-3-yl)thiophene-2-carbonitrile | 353.4 | ** | *** |
| 5-(6-(butylamino)imidazo[1,2-b]pyridazin-3-yl)thiophene-2-carboxamide | 315.4 | * | — |
| 5-(6-(propylamino)imidazo[1,2-b]pyridazin-3-yl)thiophene-2-carbaldehyde | 286.4 | * | — |
| 6-(butylamino)-N-(1H-pyrazol-4-yl)imidazo[1,2-b]pyridazine-3-carboxamide | 299.3 | * | — |
| 6-(butylamino)-N-(4-((2-(dimethylamino)ethyl)carbamoyl)phenyl)imidazo[1,2-b]pyridazine-3-carboxamide | 423.5 | ** | — |
| cyclopentyl (2-((3-(4-carbamoylphenyl)imidazo[1,2-b]pyridazin-6-yl)amino)ethyl)(isopropyl)carbamate | 450.5 | ** | — |
| ethyl (2-((3-(3-methoxypyridin-4-yl)imidazo[1,2-b]pyridazin-6-yl)amino)ethyl)(methyl)carbamate | 370.4 | *** | — |
| ethyl (2-((3-(4-(isopentylcarbamoyl)phenyl)imidazo[1,2-b]pyridazin-6-yl)amino)ethyl)(methyl)carbamate | 452.5 | ** | — |
| ethyl (2-((3-(4-(tert-butylcarbamoyl)phenyl)imidazo[1,2-b]pyridazin-6-yl)amino)ethyl)(methyl)carbamate | 438.5 | ** | — |
| ethyl (2-((3-(4-carbamoylphenyl)imidazo[1,2-b]pyridazin-6-yl)amino)ethyl)(methyl)carbamate | 382.4 | ** | — |
| ethyl (2-((3-(4-carbamoylphenyl)imidazo[1,2-b]pyridazin-6-yl)amino)ethyl)(isopropyl)carbamate | 410.5 | ** | — |
| ethyl (3-((3-(5-acetylthiophen-2-yl)imidazo[1,2-b]pyridazin-6-yl)amino)propyl)(methyl)carbamate | 401.5 | * | — |
| ethyl 4-((3-(4-(aminomethyl)phenyl)imidazo[1,2-b]pyridazin-6-yl)amino)butanoate | 353.4 | ** | — |
| ethyl 4-((3-(5-acetylthiophen-2-yl)imidazo[1,2-b]pyridazin-6-yl)amino)butanoate | 372.4 | ** | — |
| ethyl 4-(3-(methylcarbamoyl)imidazo[1,2-b]pyridazin-6-yl)piperazine-1-carboxylate | 332.4 | — | ** |
| ethyl 4-(3-phenylimidazo[1,2-b]pyridazin-6-yl)piperazine-1-carboxylate | 351.4 | ** | *** |
| ethyl isopropyl(2-((3-(3-methoxypyridin-4-yl)imidazo[1,2-b]pyridazin-6-yl)amino)ethyl)carbamate | 398.5 | *** | — |
| ethyl methyl(2-((3-(4-(methylcarbamoyl)phenyl)imidazo[1,2-b]pyridazin-6-yl)amino)ethyl)carbamate | 396.4 | ** | — |
| ethyl methyl(2-((3-(5-(methylcarbamoyl)thiophen-2-yl)imidazo[1,2-b]pyridazin-6-yl)amino)ethyl)carbamate | 402.5 | ** | — |
| isobutyl (2-((3-(4-carbamoylphenyl)imidazo[1,2-b]pyridazin-6-yl)amino)ethyl)(methyl)carbamate | 410.5 | ** | — |
| isobutyl isopropyl(2-((3-(3-methoxypyridin-4-yl)imidazo[1,2-b]pyridazin-6-yl)amino)ethyl)carbamate | 426.5 | ** | — |
| isobutyl methyl(2-((3-(4-(methylcarbamoyl)phenyl)imidazo[1,2-b]pyridazin-6-yl)amino)ethyl)carbamate | 424.5 | ** | — |
| isopropyl (2-((3-(1H-pyrazol-4-yl)imidazo[1,2-b]pyridazin-6-yl)amino)ethyl)(methyl)carbamate | 343.4 | ** | — |
| isopropyl (2-((3-(2,4-dimethylthiazol-5-yl)imidazo[1,2-b]pyridazin-6-yl)amino)ethyl)(methyl)carbamate | 388.5 | ** | — |
| isopropyl (2-((3-(2-aminopyridin-4-yl)imidazo[1,2-b]pyridazin-6-yl)amino)ethyl)(methyl)carbamate | 369.4 | ** | — |
| isopropyl (2-((3-(2-fluorophenyl)imidazo[1,2-b]pyridazin-6-yl)amino)ethyl)(methyl)carbamate | 371.4 | ** | — |
| isopropyl (2-((3-(2-methoxyphenyl)imidazo[1,2-b]pyridazin-6-yl)amino)ethyl)(methyl)carbamate | 383.4 | ** | — |
| isopropyl (2-((3-(3-methoxypyridin-4-yl)imidazo[1,2-b]pyridazin-6-yl)amino)ethyl)(methyl)carbamate | 384.4 | ** | — |

TABLE 1-continued

| Compound | MW | CBA IC$_{50}$ | P81 IC$_{50}$ |
|---|---|---|---|
| isopropyl (2-((3-(3-methoxypyridin-4-yl)imidazo[1,2-b]pyridazin-6-yl)amino)ethyl)carbamate | 370.4 | ** | — |
| isopropyl (2-((3-(4,5-difluoro-2-methoxyphenyl)imidazo[1,2-b]pyridazin-6-yl)amino)ethyl)(isopropyl)carbamate | 447.5 | ** | — |
| isopropyl (2-((3-(4-carbamoylphenyl)imidazo[1,2-b]pyridazin-6-yl)amino)ethyl)(isopropyl)carbamate | 424.5 | ** | — |
| isopropyl (2-((3-(4-carbamoylphenyl)imidazo[1,2-b]pyridazin-6-yl)amino)ethyl)(methyl)carbamate | 396.4 | *** | — |
| isopropyl (2-((3-(4-fluoro-2-methoxyphenyl)imidazo[1,2-b]pyridazin-6-yl)amino)ethyl)(methyl)carbamate | 401.4 | ** | — |
| isopropyl (2-((3-(5-fluoro-2-methoxyphenyl)imidazo[1,2-b]pyridazin-6-yl)amino)ethyl)(methyl)carbamate | 401.4 | *** | — |
| isopropyl (2-((3-(5-fluoro-2-methoxyphenyl)imidazo[1,2-b]pyridazin-6-yl)amino)ethyl)(isopropyl)carbamate | 429.5 | ** | — |
| isopropyl (3-((3-(4-(aminomethyl)phenyl)imidazo[1,2-b]pyridazin-6-yl)amino)propyl)(methyl)carbamate | 396.5 | ** | — |
| isopropyl (3-((3-(5-acetylthiophen-2-yl)imidazo[1,2-b]pyridazin-6-yl)amino)propyl)(methyl)carbamate | 415.5 | ** | — |
| isopropyl 4-(3-(2-(difluoromethoxy)phenyl)imidazo[1,2-b]pyridazin-6-yl)piperazine-1-carboxylate | 431.4 | ** | *** |
| isopropyl 4-(3-(2-(difluoromethoxy)pyridin-3-yl)imidazo[1,2-b]pyridazin-6-yl)piperazine-1-carboxylate | 432.4 | ** | *** |
| isopropyl 4-(3-(2,2-difluorobenzo[d][1,3]dioxol-4-yl)imidazo[1,2-b]pyridazin-6-yl)piperazine-1-carboxylate | 445.4 | * | *** |
| isopropyl 4-(3-(2,3-dihydrobenzofuran-7-yl)imidazo[1,2-b]pyridazin-6-yl)piperazine-1-carboxylate | 407.5 | ** | — |
| isopropyl 4-(3-(2,3-dimethoxyphenyl)imidazo[1,2-b]pyridazin-6-yl)piperazine-1-carboxylate | 425.5 | ** | *** |
| isopropyl 4-(3-(2,5-dimethoxyphenyl)imidazo[1,2-b]pyridazin-6-yl)piperazine-1-carboxylate | 425.5 | ** | *** |
| isopropyl 4-(3-(2-ethoxyphenyl)imidazo[1,2-b]pyridazin-6-yl)piperazine-1-carboxylate | 409.5 | ** | *** |
| isopropyl 4-(3-(2-fluoro-3-methoxyphenyl)imidazo[1,2-b]pyridazin-6-yl)piperazine-1-carboxylate | 413.4 | ** | *** |
| isopropyl 4-(3-(2-fluorophenyl)imidazo[1,2-b]pyridazin-6-yl)piperazine-1-carboxylate | 383.4 | ** | *** |
| isopropyl 4-(3-(2-methoxyphenyl)imidazo[1,2-b]pyridazin-6-yl)piperazine-1-carboxylate | 395.5 | *** | *** |
| isopropyl 4-(3-(2-methoxypyridin-3-yl)imidazo[1,2-b]pyridazin-6-yl)piperazine-1-carboxylate | 396.4 | *** | *** |
| isopropyl 4-(3-(2-methoxypyridin-4-yl)imidazo[1,2-b]pyridazin-6-yl)piperazine-1-carboxylate | 396.4 | ** | *** |
| isopropyl 4-(3-(2-oxo-1,2-dihydropyridin-3-yl)imidazo[1,2-b]pyridazin-6-yl)piperazine-1-carboxylate | 382.4 | ** | *** |
| isopropyl 4-(3-(3-chlorophenyl)imidazo[1,2-b]pyridazin-6-yl)piperazine-1-carboxylate | 399.9 | * | *** |
| isopropyl 4-(3-(3-methoxyphenyl)imidazo[1,2-b]pyridazin-6-yl)piperazine-1-carboxylate | 395.5 | ** | *** |
| isopropyl 4-(3-(3-methoxypyridin-4-yl)imidazo[1,2-b]pyridazin-6-yl)piperazine-1-carboxylate | 396.4 | *** | — |
| isopropyl 4-(3-(benzo[d][1,3]dioxol-4-yl)imidazo[1,2-b]pyridazin-6-yl)piperazine-1-carboxylate | 409.4 | ** | — |
| isopropyl 4-(3-(methylcarbamoyl)imidazo[1,2-b]pyridazin-6-yl)piperazine-1-carboxylate | 346.4 | ** | — |
| isopropyl 4-(3-(pyridin-4-yl)imidazo[1,2-b]pyridazin-6-yl)piperazine-1-carboxylate | 366.4 | ** | — |
| isopropyl 4-(3-phenylimidazo[1,2-b]pyridazin-6-yl)piperazine-1-carboxylate | 365.4 | ** | — |
| isopropyl ethyl(2-((3-(3-methoxypyridin-4-yl)imidazo[1,2-b]pyridazin-6-yl)amino)ethyl)carbamate | 398.5 | ** | — |
| isopropyl ethyl(2-((3-(4-(methylcarbamoyl)phenyl)imidazo[1,2-b]pyridazin-6-yl)amino)ethyl)carbamate | 424.5 | ** | — |
| isopropyl isopropyl(2-((3-(2-methoxyphenyl)imidazo[1,2-b]pyridazin-6-yl)amino)ethyl)carbamate | 411.5 | ** | — |
| isopropyl isopropyl(2-((3-(3-methoxypyridin-4-yl)imidazo[1,2-b]pyridazin-6-yl)amino)ethyl)carbamate | 412.5 | *** | — |
| isopropyl isopropyl(2-((3-(4-(methylcarbamoyl)phenyl)imidazo[1,2-b]pyridazin-6-yl)amino)ethyl)carbamate | 438.5 | ** | — |
| isopropyl isopropyl(2-((3-(pyridin-4-yl)imidazo[1,2-b]pyridazin-6-yl)amino)ethyl)carbamate | 382.5 | ** | — |
| isopropyl isopropyl(2-((3-phenylimidazo[1,2-b]pyridazin-6-yl)amino)ethyl)carbamate | 381.5 | ** | — |
| isopropyl methyl(2-((3-(4-(methylcarbamoyl)phenyl)imidazo[1,2-b]pyridazin-6-yl)amino)ethyl)carbamate | 410.5 | ** | — |

TABLE 1-continued

| Compound | MW | CBA IC$_{50}$ | P81 IC$_{50}$ |
|---|---|---|---|
| isopropyl methyl(2-((3-(4-(pyrrolidin-2-yl)phenyl)imidazo[1,2-b]pyridazin-6-yl)amino)ethyl)carbamate | 422.5 | *** | — |
| isopropyl methyl(2-((3-(thiazol-4-yl)imidazo[1,2-b]pyridazin-6-yl)amino)ethyl)carbamate | 360.4 | ** | — |
| methyl isopropyl(2-((3-(3-methoxypyridin-4-yl)imidazo[1,2-b]pyridazin-6-yl)amino)ethyl)carbamate | 384.4 | *** | — |
| N-((1R,2S)-2-aminocyclohexyl)-4-(6-(butylamino)imidazo[1,2-b]pyridazin-3-yl)benzamide | 406.5 | ** | — |
| N-(2-((3-(4-cyanophenyl)imidazo[1,2-b]pyridazin-6-yl)amino)ethyl)-N,3,3-trimethylbutanamide | 390.5 | ** | — |
| N-(2-((3-(4-cyanophenyl)imidazo[1,2-b]pyridazin-6-yl)amino)ethyl)-N-methylpivalamide | 376.5 | ** | — |
| N-(2-(cyclopentyloxy)ethyl)-3-(1H-pyrazol-3-yl)imidazo[1,2-b]pyridazin-6-amine | 312.4 | * | ** |
| N-(2-(cyclopentyloxy)ethyl)-3-(2-fluoropyridin-3-yl)imidazo[1,2-b]pyridazin-6-amine | 341.4 | * | *** |
| N-(2-(cyclopentyloxy)ethyl)-3-(2-methoxypyridin-3-yl)imidazo[1,2-b]pyridazin-6-amine | 353.4 | ** | — |
| N-(2-(cyclopentyloxy)ethyl)-3-(3-fluoropyridin-4-yl)imidazo[1,2-b]pyridazin-6-amine | 341.4 | ** | — |
| N-(2-(cyclopentyloxy)ethyl)-3-(3-methoxyphenyl)imidazo[1,2-b]pyridazin-6-amine | 352.4 | — | ** |
| N-(2-(cyclopentyloxy)ethyl)-3-(3-methoxypyridin-4-yl)imidazo[1,2-b]pyridazin-6-amine | 353.4 | * | — |
| N-(2-(cyclopentyloxy)ethyl)-3-(4-(pyrrolidin-2-yl)phenyl)imidazo[1,2-b]pyridazin-6-amine | 391.5 | ** | — |
| N-(2-(cyclopentyloxy)ethyl)-3-(4-methylthiophen-2-yl)imidazo[1,2-b]pyridazin-6-amine | 342.5 | — | ** |
| N-(2-(cyclopentyloxy)ethyl)-3-(5-methoxypyridin-3-yl)imidazo[1,2-b]pyridazin-6-amine | 353.4 | ** | *** |
| N-(2-(cyclopentyloxy)ethyl)-3-(5-methylthiophen-2-yl)imidazo[1,2-b]pyridazin-6-amine | 342.5 | — | ** |
| N-(2-(cyclopentyloxy)ethyl)-3-(pyridin-2-yl)imidazo[1,2-b]pyridazin-6-amine | 323.4 | ** | *** |
| N-(2-(cyclopentyloxy)ethyl)-3-(thiophen-2-yl)imidazo[1,2-b]pyridazin-6-amine | 328.4 | — | *** |
| N-(2-(cyclopentyloxy)ethyl)-3-(thiophen-3-yl)imidazo[1,2-b]pyridazin-6-amine | 328.4 | — | ** |
| N-(2-(diethylamino)ethyl)-4-(6-((2-isobutoxyethyl)amino)imidazo[1,2-b]pyridazin-3-yl)benzamide | 452.6 | ** | — |
| N-(2-(diethylamino)ethyl)-4-(6-((2-isopropoxyethyl)amino)imidazo[1,2-b]pyridazin-3-yl)benzamide | 438.6 | ** | — |
| N-(2-(methylamino)ethyl)-4-(6-((3-(N-methylpivalamido)propyl)amino)imidazo[1,2-b]pyridazin-3-yl)benzamide | 465.6 | * | — |
| N-(2-(tert-butoxy)ethyl)-3-(3-methoxypyridin-4-yl)imidazo[1,2-b]pyridazin-6-amine | 341.4 | ** | — |
| N-(2-(tert-butoxy)ethyl)-3-(4-(pyrrolidin-2-yl)phenyl)imidazo[1,2-b]pyridazin-6-amine | 379.5 | ** | — |
| N-(2-aminoethyl)-4-(6-((3-(tert-butoxy)propyl)amino)imidazo[1,2-b]pyridazin-3-yl)benzamide | 410.5 | * | — |
| N-(2-aminoethyl)-4-(6-((3,3-dimethylbutyl)amino)imidazo[1,2-b]pyridazin-3-yl)benzamide | 380.5 | * | — |
| N-(2-aminoethyl)-4-(6-((3-phenylpropyl)amino)imidazo[1,2-b]pyridazin-3-yl)benzamide | 414.5 | * | — |
| N-(2-aminoethyl)-4-(6-(butylamino)imidazo[1,2-b]pyridazin-3-yl)-2-methoxybenzamide | 382.5 | * | — |
| N-(2-aminoethyl)-4-(6-(butylamino)imidazo[1,2-b]pyridazin-3-yl)-2-fluorobenzamide | 370.4 | ** | — |
| N-(2-aminoethyl)-4-(6-(butylamino)imidazo[1,2-b]pyridazin-3-yl)-3-fluorobenzamide | 370.4 | * | — |
| N-(2-aminoethyl)-4-(6-(butylamino)imidazo[1,2-b]pyridazin-3-yl)benzamide | 352.4 | * | — |
| N-(2-aminopropyl)-4-(6-(butylamino)imidazo[1,2-b]pyridazin-3-yl)benzamide | 366.5 | * | — |
| N-(2-ethoxyphenethyl)-3-(3-methoxypyridin-4-yl)imidazo[1,2-b]pyridazin-6-amine | 389.5 | ** | — |
| N-(2-isobutoxyethyl)-3-(2-methoxyphenyl)imidazo[1,2-b]pyridazin-6-amine | 340.4 | * | — |
| N-(2-isobutoxyethyl)-3-(3-methoxypyridin-4-yl)imidazo[1,2-b]pyridazin-6-amine | 341.4 | ** | — |
| N-(2-isobutoxyethyl)-3-(pyridin-4-yl)imidazo[1,2-b]pyridazin-6-amine | 311.4 | * | — |
| N-(2-isopropoxyethyl)-3-(1H-pyrazol-3-yl)imidazo[1,2-b]pyridazin-6-amine | 286.3 | * | — |

TABLE 1-continued

| Compound | MW | CBA IC$_{50}$ | P81 IC$_{50}$ |
|---|---|---|---|
| N-(2-isopropoxyethyl)-3-(3-methoxypyridin-4-yl)imidazo[1,2-b]pyridazin-6-amine | 327.4 | *** | — |
| N-(2-isopropoxyethyl)-3-(4-(pyrrolidin-2-yl)phenyl)imidazo[1,2-b]pyridazin-6-amine | 365.5 | ** | — |
| N-(2-isopropoxyethyl)-3-(isothiazol-5-yl)imidazo[1,2-b]pyridazin-6-amine | 303.4 | ** | — |
| N-(2-isopropoxyethyl)-3-(thiazol-4-yl)imidazo[1,2-b]pyridazin-6-amine | 303.4 | * | — |
| N-(3-((3-(4-(aminomethyl)phenyl)imidazo[1,2-b]pyridazin-6-yl)amino)propyl)-N-methylpivalamide | 394.5 | * | — |
| N-(3-(6-((2-(cyclopentyloxy)ethyl)amino)imidazo[1,2-b]pyridazin-3-yl)phenyl)acetamide | 379.5 | ** | ** |
| N-(3-(tert-butoxy)propyl)-3-(3-methoxypyridin-4-yl)imidazo[1,2-b]pyridazin-6-amine | 355.4 | * | — |
| N-(3,3-dimethylbutyl)-3-(4-((2-(methylamino)ethoxy)methyl)phenyl)imidazo[1,2-b]pyridazin-6-amine | 381.5 | ** | — |
| N-(3,3-dimethylbutyl)-3-(4-(pyrrolidin-2-yl)phenyl)imidazo[1,2-b]pyridazin-6-amine | 363.5 | * | — |
| N-(3-aminopropyl)-4-(6-(butylamino)imidazo[1,2-b]pyridazin-3-yl)benzamide | 366.5 | * | — |
| N-(3-fluoropropyl)-3-(4-(pyrrolidin-2-yl)phenyl)imidazo[1,2-b]pyridazin-6-amine | 339.4 | ** | — |
| N-(3-phenylpropyl)-3-(4-(pyrrolidin-2-yl)phenyl)imidazo[1,2-b]pyridazin-6-amine | 397.5 | * | — |
| N-(4-(2-aminoethoxy)phenyl)-6-(butylamino)imidazo[1,2-b]pyridazine-3-carboxamide | 368.4 | * | — |
| N-(4-(aminomethyl)phenyl)-6-(butylamino)imidazo[1,2-b]pyridazine-3-carboxamide | 338.4 | * | — |
| N-(cyclopentylmethyl)-3-(3-methoxypyridin-4-yl)imidazo[1,2-b]pyridazin-6-amine | 323.4 | ** | — |
| N-(tert-butyl)-4-(3-phenylimidazo[1,2-b]pyridazin-6-yl)piperazine-1-carboxamide | 378.5 | ** | *** |
| N,N-dimethyl-3-(6-(4-(pyrrolidine-1-carbonyl)piperazin-1-yl)imidazo[1,2-b]pyridazin-3-yl)benzamide | 447.5 | ** | *** |
| N1-(3-(4-(aminomethyl)phenyl)imidazo[1,2-b]pyridazin-6-yl)-N2-methyl-N2-phenylethane-1,2-diamine | 372.5 | ** | — |
| N1-(3-(4-(aminomethyl)phenyl)imidazo[1,2-b]pyridazin-6-yl)-N3-methyl-N3-phenylpropane-1,3-diamine | 386.5 | ** | — |
| N1-(3-(5-(aminomethyl)thiophen-2-yl)imidazo[1,2-b]pyridazin-6-yl)-N3-methyl-N3-phenylpropane-1,3-diamine | 392.5 | * | — |
| N1-(4-(6-((3,3-dimethylbutyl)amino)imidazo[1,2-b]pyridazin-3-yl)benzyl)ethane-1,2-diamine | 366.5 | * | — |
| N1-(4-(6-(butylamino)imidazo[1,2-b]pyridazin-3-yl)benzyl)ethane-1,2-diamine | 338.4 | * | — |
| N1-(4-(6-(butylamino)imidazo[1,2-b]pyridazin-3-yl)benzyl)propane-1,3-diamine | 352.5 | * | — |
| N-butyl-3-(1H-pyrazol-3-yl)imidazo[1,2-b]pyridazin-6-amine | 256.3 | ** | — |
| N-butyl-3-(2,4-dimethylthiazol-5-yl)imidazo[1,2-b]pyridazin-6-amine | 301.4 | ** | — |
| N-butyl-3-(3-methoxypyridin-4-yl)imidazo[1,2-b]pyridazin-6-amine | 297.4 | ** | — |
| N-butyl-3-(4-((((tetrahydrofuran-2-yl)methyl)amino)methyl)phenyl)imidazo[1,2-b]pyridazin-6-amine | 379.5 | * | — |
| N-butyl-3-(4-(((2-methoxyethyl)amino)methyl)phenyl)imidazo[1,2-b]pyridazin-6-amine | 353.5 | * | — |
| N-butyl-3-(4-(((cyclopropylmethyl)amino)methyl)phenyl)imidazo[1,2-b]pyridazin-6-amine | 349.5 | * | — |
| N-butyl-3-(4-((isopropylamino)methyl)phenyl)imidazo[1,2-b]pyridazin-6-amine | 337.5 | * | — |
| N-butyl-3-(4-((propylamino)methyl)phenyl)imidazo[1,2-b]pyridazin-6-amine | 337.5 | * | — |
| N-butyl-3-(4-((tert-butylamino)methyl)-2-fluorophenyl)imidazo[1,2-b]pyridazin-6-amine | 369.5 | * | — |
| N-butyl-3-(4-((tert-butylamino)methyl)-3-fluorophenyl)imidazo[1,2-b]pyridazin-6-amine | 369.5 | ** | — |
| N-butyl-3-(4-(pyrrolidin-2-yl)phenyl)imidazo[1,2-b]pyridazin-6-amine | 335.4 | * | — |
| N-butyl-3-(isoindolin-5-yl)imidazo[1,2-b]pyridazin-6-amine | 307.4 | * | — |
| N-butyl-3-(isoquinolin-6-yl)imidazo[1,2-b]pyridazin-6-amine | 317.4 | ** | — |
| N-cyclohexyl-3-(3-methoxypyridin-4-yl)imidazo[1,2-b]pyridazin-6-amine | 323.4 | | *** |
| N-isopentyl-3-(3-methoxypyridin-4-yl)imidazo[1,2-b]pyridazin-6-amine | 311.4 | ** | — |

TABLE 1-continued

| Compound | MW | CBA IC$_{50}$ | P81 IC$_{50}$ |
|---|---|---|---|
| N-isopropyl-4-(3-(2-methoxyphenyl)imidazo[1,2-b]pyridazin-6-yl)-N-methylpiperazine-1-carboxamide | 408.5 | ** | *** |
| N-isopropyl-4-(3-(2-methoxyphenyl)imidazo[1,2-b]pyridazin-6-yl)piperazine-1-carboxamide | 394.5 | * | *** |
| N-isopropyl-4-(3-phenylimidazo[1,2-b]pyridazin-6-yl)piperazine-1-carboxamide | 364.4 | ** | *** |
| N-methyl-4-(6-((2-(trifluoromethoxy)phenethyl)amino)imidazo[1,2-b]pyridazin-3-yl)benzamide | 455.4 | *** | — |
| N-pentyl-3-(4-(pyrrolidin-2-yl)phenyl)imidazo[1,2-b]pyridazin-6-amine | 349.5 | * | — |
| piperidin-1-yl(4-(3-(pyridin-2-yl)imidazo[1,2-b]pyridazin-6-yl)piperazin-1-yl)methanone | 391.5 | ** | *** |
| propyl isopropyl(2-((3-(3-methoxypyridin-4-yl)imidazo[1,2-b]pyridazin-6-yl)amino)ethyl)carbamate | 412.5 | * | — |
| S-isopropyl 4-(3-phenylimidazo[1,2-b]pyridazin-6-yl)piperazine-1-carbothioate | 381.5 | * | *** |
| tert-butyl (1-(3-(2-methoxyphenyl)imidazo[1,2-b]pyridazin-6-yl)pyrrolidin-3-yl)(methyl)carbamate | 423.5 | * | *** |
| tert-butyl (1-(3-(2-methoxypyridin-3-yl)imidazo[1,2-b]pyridazin-6-yl)pyrrolidin-3-yl)(methyl)carbamate | 424.5 | ** | *** |
| tert-butyl (1-(3-(2-methoxypyridin-3-yl)imidazo[1,2-b]pyridazin-6-yl)azetidin-3-yl)(methyl)carbamate | 410.5 | — | * |
| tert-butyl (2-((3-(2-aminopyridin-4-yl)imidazo[1,2-b]pyridazin-6-yl)amino)ethyl)(methyl)carbamate | 383.4 | *** | — |
| tert-butyl (2-((3-(2-fluorophenyl)imidazo[1,2-b]pyridazin-6-yl)amino)ethyl)(methyl)carbamate | 385.4 | ** | — |
| tert-butyl (2-((3-(2-fluoropyridin-4-yl)imidazo[1,2-b]pyridazin-6-yl)amino)ethyl)(methyl)carbamate | 386.4 | ** | — |
| tert-butyl (2-((3-(2-methoxyphenyl)imidazo[1,2-b]pyridazin-6-yl)amino)ethyl)(methyl)carbamate | 397.5 | ** | — |
| tert-butyl (2-((3-(3-carbamoylphenyl)imidazo[1,2-b]pyridazin-6-yl)amino)ethyl)(methyl)carbamate | 410.5 | ** | — |
| tert-butyl (2-((3-(3-methoxyphenyl)imidazo[1,2-b]pyridazin-6-yl)amino)ethyl)(methyl)carbamate | 397.5 | ** | — |
| tert-butyl (2-((3-(3-methoxypyridin-4-yl)imidazo[1,2-b]pyridazin-6-yl)amino)ethyl)(methyl)carbamate | 398.5 | * | — |
| tert-butyl (2-((3-(4-(aminomethyl)phenyl)imidazo[1,2-b]pyridazin-6-yl)amino)ethyl)carbamate | 382.5 | ** | — |
| tert-butyl (2-((3-(4-(cyanomethyl)phenyl)imidazo[1,2-b]pyridazin-6-yl)amino)ethyl)(methyl)carbamate | 406.5 | ** | — |
| tert-butyl (2-((3-(4-carbamoylphenyl)imidazo[1,2-b]pyridazin-6-yl)amino)ethyl)(methyl)carbamate | 410.5 | ** | *** |
| tert-butyl (2-((3-(4-carbamoylphenyl)imidazo[1,2-b]pyridazin-6-yl)amino)ethyl)(isopropyl)carbamate | 438.5 | *** | — |
| tert-butyl (2-((3-(4-cyanophenyl)imidazo[1,2-b]pyridazin-6-yl)amino)ethyl)(methyl)carbamate | 392.5 | ** | — |
| tert-butyl (2-((3-(5-acetylthiophen-2-yl)imidazo[1,2-b]pyridazin-6-yl)amino)ethyl)(methyl)carbamate | 415.5 | *** | — |
| tert-butyl (3-((3-(4-(aminomethyl)phenyl)imidazo[1,2-b]pyridazin-6-yl)amino)propyl)(methyl)carbamate | 410.5 | ** | — |
| tert-butyl (3-((3-(5-acetylthiophen-2-yl)imidazo[1,2-b]pyridazin-6-yl)amino)propyl)(methyl)carbamate | 429.5 | ** | — |
| tert-butyl 2-(2-((3-(4-(aminomethyl)phenyl)imidazo[1,2-b]pyridazin-6-yl)amino)ethyl)pyrrolidine-1-carboxylate | 436.5 | *** | — |
| tert-butyl 2-(2-((3-(4-carbamoylphenyl)imidazo[1,2-b]pyridazin-6-yl)amino)ethyl)pyrrolidine-1-carboxylate | 450.5 | ** | — |
| tert-butyl 4-(3-methoxypyridin-4-yl)imidazo[1,2-b]pyridazin-6-yl)piperazine-1-carboxylate | 410.5 | *** | — |
| tert-butyl 4-(3-chloroimidazo[1,2-b]pyridazin-6-yl)piperazine-1-carboxylate | 337.8 | ** | — |
| tert-butyl 4-(3-iodoimidazo[1,2-b]pyridazin-6-yl)piperazine-1-carboxylate | 429.3 | ** | *** |
| tert-butyl 4-(3-phenylimidazo[1,2-b]pyridazin-6-yl)piperazine-1-carboxylate | 379.5 | ** | *** |
| tert-butyl isopropyl(2-((3-(3-methoxypyridin-4-yl)imidazo[1,2-b]pyridazin-6-yl)amino)ethyl)carbamate | 426.5 | ** | — |
| tert-butyl methyl(1-(3-phenylimidazo[1,2-b]pyridazin-6-yl)pyrrolidin-3-yl)carbamate | 393.5 | ** | ** |
| tert-butyl methyl(2-((3-(4-(methylcarbamoyl)phenyl)imidazo[1,2-b]pyridazin-6-yl)amino)ethyl)carbamate | 424.5 | ** | — |
| tert-butyl methyl(2-((3-(4-(pyrrolidin-2-yl)phenyl)imidazo[1,2-b]pyridazin-6-yl)amino)ethyl)carbamate | 436.5 | *** | — |
| tert-butyl methyl(2-((3-(pyridin-4-yl)imidazo[1,2-b]pyridazin-6-yl)amino)ethyl)carbamate | 368.4 | ** | — |
| tert-butyl methyl(2-((3-phenylimidazo[1,2-b]pyridazin-6-yl)amino)ethyl)carbamate | 367.4 | ** | — |

TABLE 1-continued

| Compound | MW | CBA IC$_{50}$ | P81 IC$_{50}$ |
|---|---|---|---|
| isopropyl 4-(3-(5-fluoro-2-methoxy-4-methylphenyl)imidazo[1,2-b]pyridazin-6-yl)piperazine-1-carboxylate | 427.5 | *** | *** |
| (S)-isopropyl 2-(((3-(2-methoxypyridin-3-yl)imidazo[1,2-b]pyridazin-6-yl)amino)methyl)pyrrolidine-1-carboxylate | 410.5 | *** | *** |
| (S)-isopropyl 2-(((3-(2-methoxypyridin-3-yl)imidazo[1,2-b]pyridazin-6-yl)(methyl)amino)methyl)pyrrolidine-1-carboxylate | 424.5 | *** | *** |
| (S)-isopropyl 2-(((3-(2-hydroxypyridin-3-yl)imidazo[1,2-b]pyridazin-6-yl)oxy)methyl)pyrrolidine-1-carboxylate | 397.4 | — | ** |
| (S)-isopropyl 2-(((3-(2-methoxypyridin-3-yl)imidazo[1,2-b]pyridazin-6-yl)oxy)methyl)pyrrolidine-1-carboxylate | 411.5 | — | ** |
| (S)-6-(3-(2-methoxyethoxy)pyrrolidin-1-yl)-3-(2-methoxypyridin-3-yl)imidazo[1,2-b]pyridazine | 369.4 | — | * |
| (S)-3-(2-methoxy-6-methylpyridin-3-yl)-6-(3-(2-methoxyethoxy)pyrrolidin-1-yl)imidazo[1,2-b]pyridazine | 383.4 | — | ** |
| (S)-3-(2-methoxy-5-methylpyridin-3-yl)-6-(3-(2-methoxyethoxy)pyrrolidin-1-yl)imidazo[1,2-b]pyridazine | 383.4 | — | * |
| (S)-1-(3-(2-methoxypyridin-3-yl)imidazo[1,2-b]pyridazin-6-yl)pyrrolidin-3-ol | 311.3 | — | * |
| (S)-ethyl (1-(3-(5-fluoro-2-methoxypyridin-3-yl)imidazo[1,2-b]pyridazin-6-yl)pyrrolidin-3-yl)(methyl)carbamate | 414.4 | ** | *** |
| (S)-ethyl (1-(3-(2-methoxy-6-methylpyridin-3-yl)imidazo[1,2-b]pyridazin-6-yl)pyrrolidin-3-yl)(methyl)carbamate | 410.5 | ** | — |
| (S)-ethyl (1-(3-(5-fluoro-2-methoxyphenyl)imidazo[1,2-b]pyridazin-6-yl)pyrrolidin-3-yl)(methyl)carbamate | 413.4 | ** | *** |
| (S)-ethyl (1-(3-(2,6-dimethoxypyridin-3-yl)imidazo[1,2-b]pyridazin-6-yl)pyrrolidin-3-yl)(methyl)carbamate | 426.5 | — | — |
| (S)-ethyl (1-(3-(2-methoxy-5-methylpyridin-3-yl)imidazo[1,2-b]pyridazin-6-yl)pyrrolidin-3-yl)(methyl)carbamate | 410.5 | ** | *** |
| (S)-isopropyl (1-(3-(5-fluoro-2-methoxypyridin-3-yl)imidazo[1,2-b]pyridazin-6-yl)pyrrolidin-3-yl)(methyl)carbamate | 428.5 | ** | *** |
| (S)-isopropyl (1-(3-(2,6-dimethoxypyridin-3-yl)imidazo[1,2-b]pyridazin-6-yl)pyrrolidin-3-yl)(methyl)carbamate | 440.5 | ** | *** |
| (S)-isopropyl (1-(3-(5-fluoro-2-methoxyphenyl)imidazo[1,2-b]pyridazin-6-yl)pyrrolidin-3-yl)(methyl)carbamate | 427.5 | *** | *** |
| (S)-isopropyl (1-(3-(2-methoxy-5-methylpyridin-3-yl)imidazo[1,2-b]pyridazin-6-yl)pyrrolidin-3-yl)(methyl)carbamate | 424.5 | ** | *** |
| isopropyl 4-(3-acetylimidazo[1,2-b]pyridazin-6-yl)piperazine-1-carboxylate | 331.4 | — | ** |
| (S)-isopropyl (1-(3-(1,6-dimethyl-2-oxo-1,2-dihydropyridin-3-yl)imidazo[1,2-b]pyridazin-6-yl)pyrrolidin-3-yl)(methyl)carbamate | 424.5 | — | ** |
| (S)-isopropyl (1-(3-(2-(tri-deuteromethoxy)pyridin-3-yl)imidazo[1,2-b]pyridazin-6-yl)pyrrolidin-3-yl)(methyl)carbamate | 413.4 | *** | *** |
| (S)-ethyl (1-(3-(2-(trideuteromethoxy)pyridin-3-yl)imidazo[1,2-b]pyridazin-6-yl)pyrrolidin-3-yl)(methyl)carbamate | 399.4 | ** | *** |
| isopropyl 4-(3-(4-(aminomethyl)phenyl)imidazo[1,2-b]pyridazin-6-yl)piperazine-1-carboxylate | 394.5 | *** | *** |
| (S)-2-amino-1-(4-(imidazo[1,2-b]pyridazin-6-yl)piperazin-1-yl)-4-methylpentan-1-one | 316.4 | — | * |
| (S)-2-amino-1-(4-(3-bromoimidazo[1,2-b]pyridazin-6-yl)piperazin-1-yl)-4-methylpentan-1-one | 395.3 | — | *** |
| (S)-2-amino-1-(4-(3-(2-methoxypyridin-3-yl)imidazo[1,2-b]pyridazin-6-yl)piperazin-1-yl)-4-methylpentan-1-one | 423.5 | *** | *** |
| (S)-2-amino-1-(4-(3-chloroimidazo[1,2-b]pyridazin-6-yl)piperazin-1-yl)-4-methylpentan-1-one | 350.8 | — | ** |
| (S)-2-amino-3-methyl-1-(4-(3-methylimidazo[1,2-b]pyridazin-6-yl)piperazin-1-yl)butan-1-one | 316.4 | — | *** |
| (S)-2-amino-4-methyl-1-(4-(3-methylimidazo[1,2-b]pyridazin-6-yl)piperazin-1-yl)pentan-1-one | 330.4 | — | ** |
| (S)-isopropyl (1-(3-(4-(aminomethyl)phenyl)imidazo[1,2-b]pyridazin-6-yl)pyrrolidin-3-yl)(methyl)carbamate | 408.5 | *** | *** |
| isopropyl 4-(3-(5-fluoro-2-methoxypyridin-3-yl)imidazo[1,2-b]pyridazin-6-yl)piperazine-1-carboxylate | 414.4 | *** | *** |
| isopropyl 4-(3-(2-methoxy-6-methylpyridin-3-yl)imidazo[1,2-b]pyridazin-6-yl)piperazine-1-carboxylate | 410.5 | *** | *** |
| isopropyl 4-(3-(5-fluoro-2-methoxyphenyl)imidazo[1,2-b]pyridazin-6-yl)piperazine-1-carboxylate | 413.4 | *** | *** |
| (S)-1-(4-(3-acetylimidazo[1,2-b]pyridazin-6-yl)piperazin-1-yl)-2-amino-3-methylbutan-1-one | 344.4 | ** | *** |
| 1-(6-(4-(1-aminocyclopentanecarbonyl)piperazin-1-yl)imidazo[1,2-b]pyridazin-3-yl)ethanone | 356.4 | — | ** |
| isopropyl 4-(3-(2-ethoxypyridin-3-yl)imidazo[1,2-b]pyridazin-6-yl)piperazine-1-carboxylate | 410.5 | *** | *** |

TABLE 1-continued

| Compound | MW | CBA IC$_{50}$ | P81 IC$_{50}$ |
|---|---|---|---|
| methyl 1-(3-bromoimidazo[1,2-b]pyridazin-6-yl)-1H-pyrazole-4-carboxylate | 322.1 | — | ** |
| methyl 1-(3-(2-methoxypyridin-3-yl)imidazo[1,2-b]pyridazin-6-yl)-1H-pyrazole-4-carboxylate | 350.3 | — | *** |
| 2-methoxyethyl 4-(3-(2-methoxypyridin-3-yl)imidazo[1,2-b]pyridazin-6-yl)piperazine-1-carboxylate | 412.4 | ** | *** |

5.6.170. Pharmacological Effects

Studies of AAK1 knockout mice showed that disruption of the AAK1 gene affects pain response as measured using the formalin paw test. See example 5.6.1, above. The same test was used to confirm that the administration of an AAK1 inhibitor can also affect pain response.

Mice were tested for nociception with Automatic Nociception Analyzers (purchased from the Ozaki lab at University of California, San Diego). A metal band was placed around the left hind paw of each mouse with superglue 30 minutes prior to testing. After the 30-minute acclimation period, 20 μl of 5% formalin was subcutaneously injected in the dorsal surface of the left hind paw. Mice were individually housed in cylindrical chambers for 45 minutes. Fresh 5% formalin solution was prepared by diluting formaldehyde (Formalde-fresh 20%, Fisher Scientific, Fair Lawn, N.J.) with distilled water. Investigatory compounds were administered 30 minutes prior to formalin injection.

A computer software recorded flinches per minute, total flinches for Phase I (acute phase=first 8 minutes), and total flinches for Phase II (tonic phase between 20-40 minutes) through an electromagnetic field. See Yaksh T L, Ozaki G, McCumber D, Rathbun M, Svensson C, Malkmus S, Yaksh M C. An automated flinch detecting system for use in the formalin nociceptive bioassay. *J Appl Physiol.*, 2001; 90:2386-402.

Various compounds of the invention were tested at different doses. Gabapentin and pregabalin were used as positive controls. Results are shown below in Table 2, wherein "*" means an effect equal to or greater than 50 percent of that of gabapentin at 200 mpk, "**" means an effect equal to or greater than 100 percent of that of gabapentin at 200 mpk, "sc" means subcutaneous administration, "ip" means in intraperitoneal administration, and "po" means oral administration.

TABLE 2

| Compound | Dose (mpk) | Effect |
|---|---|---|
| Gabapentin | 50 sc | * |
| Gabapentin | 200 sc | ** |
| Pregabalin | 50 sc | * |
| (S)-isopropyl (1-(3-(2-methoxypyridin-3-yl)imidazo[1,2-b]pyridazin-6-yl)pyrrolidin-3-yl)(methyl)carbamate | 10 po | * |
| (S)-isopropyl (1-(3-(2-methoxypyridin-3-yl)imidazo[1,2-b]pyridazin-6-yl)pyrrolidin-3-yl)(methyl)carbamate | 30 po | ** |
| (S)-isopropyl (1-(3-(2-methoxypyridin-3-yl)imidazo[1,2-b]pyridazin-6-yl)pyrrolidin-3-yl)(methyl)carbamate | 60 po | ** |
| (S)-tert-butyl 2-(((3-(4-(aminomethyl)phenyl)imidazo[1,2-b]pyridazin-6-yl)amino)methyl)pyrrolidine-1-carboxylate | 60 sc | ** |
| (S)-tert-butyl 2-(((3-bromoimidazo[1,2-b]pyridazin-6-yl)amino)methyl)pyrrolidine-1-carboxylate | 30 sc | ** |
| (S)-tert-butyl 2-(((3-bromoimidazo[1,2-b]pyridazin-6-yl)amino)methyl)pyrrolidine-1-carboxylate | 60 sc | ** |
| 3-(4-(1H-tetrazol-5-yl)phenyl)-N-butylimidazo[1,2-b]pyridazin-6-amine | 60 ip | ** |
| 3-(4-(aminomethyl)phenyl)-N-(2-(cyclopentyloxy)ethyl)imidazo[1,2-b]pyridazin-6-amine | 60 sc | ** |
| 3-(4-(aminomethyl)phenyl)-N-(2-(cyclopentyloxy)ethyl)imidazo[1,2-b]pyridazin-6-amine | 100 sc | ** |
| 3-(4-(aminomethyl)phenyl)-N-(2-(tert-butoxy)ethyl)imidazo[1,2-b]pyridazin-6-amine | 60 sc | ** |
| 3-(4-(aminomethyl)phenyl)-N-(3-(tert-butoxy)propyl)imidazo[1,2-b]pyridazin-6-amine | 60 sc | ** |
| 3-(4-(aminomethyl)phenyl)-N-(3-phenylpropyl)imidazo[1,2-b]pyridazin-6-amine | 30 ip | ** |
| isopropyl 4-(3-(2-methoxyphenyl)imidazo[1,2-b]pyridazin-6-yl)piperazine-1-carboxylate | 30 sc | ** |
| isopropyl 4-(3-(2-methoxyphenyl)imidazo[1,2-b]pyridazin-6-yl)piperazine-1-carboxylate | 60 sc | ** |
| N-(2-aminoethyl)-4-(6-(butylamino)imidazo[1,2-b]pyridazin-3-yl)benzamide | 30 ip | ** |

TABLE 2-continued

| Compound | Dose (mpk) | | Effect |
|---|---|---|---|
| tert-butyl (2-((3-(4-carbamoylphenyl)imidazo[1,2-b]pyridazin-6-yl)amino)ethyl)(methyl)carbamate | 100 | po | ** |
| tert-butyl (2-((3-(4-carbamoylphenyl)imidazo[1,2-b]pyridazin-6-yl)amino)ethyl)(methyl)carbamate | 60 | sc | ** |

These results demonstrate that AAK1 inhibitors can be used to treat pain.

All publications (e.g., patents and patent applications) cited above are incorporated herein by reference in their entireties.

What is claimed is:

1. A compound of the formula:

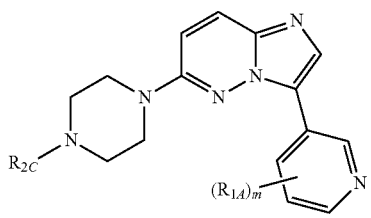

or a pharmaceutically acceptable salt thereof, wherein:
each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$;
each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo;
each $R_{1C}$ is independently hydrogen or optionally substituted $C_{1-12}$ hydrocarbyl or 2-12-membered heterocarbyl, which optional substitution is with one or more of cyano, halo or hydroxyl;
each $R_{2C}$ is independently —$OR_{2D}$, —$N(R_{2D})_2$, —$C(O)R_{2D}$, —$C(O)N(R_{2D})_2$, —$N(R_{2D})C(O)OR_{2D}$, cyano, halo, or optionally substituted $C_{1-12}$ hydrocarbyl or 2-12-membered heterocarbyl, which optional substitution is with one or more with one or more amino, cyano, halo, hydroxyl, or $R_{2D}$;
each $R_{2D}$ is independently hydrogen or optionally substituted $C_{1-12}$ hydrocarbyl or 2-12-membered heterocarbyl, which optional substitution is with one or more of amino, cyano, halo, hydroxyl; and
m is 0-3.

2. The compound of claim 1, which is of the formula:

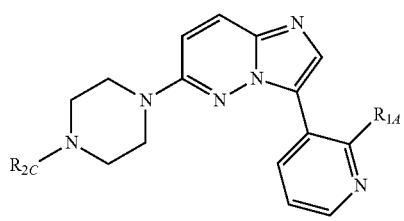

3. The compound of claim 1, which is of the formula:

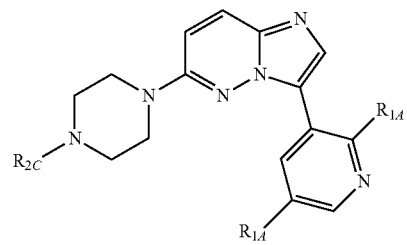

4. A compound of the formula:

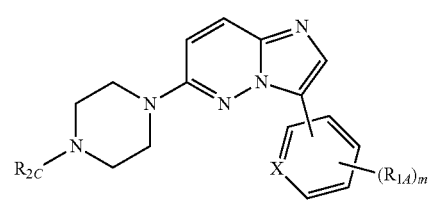

or a pharmaceutically acceptable salt thereof, wherein:
X is CH or N;
each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$;
each $R_{1B}$ is independently —$OR_{1C}$, —$N(R_{1C})_2$, $C(O)R_{1C}$, —$C(O)OR_{1C}$, —$C(O)N(R_{1C})_2$, —$N(R_{1C})C(O)OR_{1C}$, cyano or halo;
each $R_{1C}$ is independently hydrogen or optionally substituted $C_{1-12}$ hydrocarbyl or 2-12-membered heterocarbyl, which optional substitution is with one or more of cyano, halo or hydroxyl;
each $R_{2C}$ is independently —$C(O)OR_{2D}$, —$C(O)N(R_{2D})_2$, or —$N(R_{2D})C(O)OR_{2D}$, which optional substitution is with one or more with one or more amino, cyano, halo, hydroxyl, or $R_{2D}$;
$R_{2D}$ is 2-12-membered heterocarbyl comprising at least one nitrogen atom; and
m is 0-3.

5. A compound of the formula:

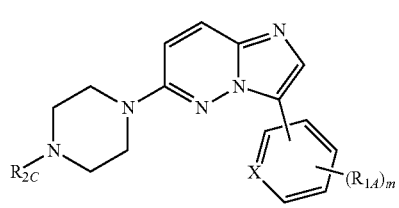

or a pharmaceutically acceptable salt thereof, wherein:
X is CH or N;
each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$;
each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo;
each $R_{1C}$ is independently hydrogen or optionally substituted $C_{1-12}$ hydrocarbyl or 2-12-membered heterocarbyl, which optional substitution is with one or more of cyano, halo or hydroxyl;
each $R_{2C}$ is independently —$C(O)R_{2D}$;
each $R_{2D}$ is 2-12-membered heterocarbyl comprising at least one nitrogen atom; and
m is 0-3.

* * * * *